US006884775B1

(12) United States Patent
Tabin et al.

(10) Patent No.: US 6,884,775 B1
(45) Date of Patent: Apr. 26, 2005

(54) METHODS AND COMPOSITIONS FOR REGULATING SKELETOGENIC FORMATION

(75) Inventors: Clifford J. Tabin, Cambridge, MA (US); Andrew P. McMahon, Lexington, MA (US); Philip W. Ingham, Summertown (GB); Andrea M. Vortkamp, Boston, MA (US)

(73) Assignees: President and Fellows of Harvard College, Cambridge, MA (US); Imperial Cancer Research Technology, Inc., London (GB)

( * ) Notice: Subject to any disclaimer, the term of this patent is extended or adjusted under 35 U.S.C. 154(b) by 0 days.

(21) Appl. No.: 08/905,572

(22) Filed: Aug. 1, 1997

Related U.S. Application Data

(63) Continuation-in-part of application No. 08/674,509, filed on Jul. 2, 1996, which is a continuation-in-part of application No. 08/462,386, filed on Jun. 5, 1995, which is a continuation-in-part of application No. 08/435,093, filed on May 4, 1995, now abandoned, which is a continuation-in-part of application No. 08/356,060, filed on Dec. 14, 1994, now Pat. No. 5,844,079, which is a continuation-in-part of application No. 08/176,427, filed on Dec. 30, 1993, now Pat. No. 5,789,543.

(51) Int. Cl.[7] .................... A61K 38/18; C07K 14/475
(52) U.S. Cl. .................... 514/12; 514/2; 530/300; 530/350; 536/23.1; 536/23.5; 435/69.1
(58) Field of Search .................... 514/2, 12; 424/143.1, 424/130.1; 530/350, 300; 536/23.1, 23.5

(56) References Cited

U.S. PATENT DOCUMENTS

| 5,223,408 A | 6/1993 | Goeddel et al. ........... 435/69.3 |
| 5,585,087 A | 12/1996 | Lustig et al. ................ 424/9.2 |
| 5,844,079 A | * 12/1998 | Ingham et al. |

FOREIGN PATENT DOCUMENTS

| WO | WO 90/02809 | 3/1990 |
| WO | WO 92/15679 | 9/1992 |

OTHER PUBLICATIONS

Vortkamp et al., Regulation of rate of cartilage differentiation by Indian hedgehog and PTH–related protein, Science, 273: 613–622 (Aug. 2, 1996).*
Iwamoto et al., Actions of hedgehog proteins on skeletal cells, Crit. Rev. Oral Biol. Med., 10(4):477–486, 1999 (abstract).*
Iwasake et al., Age–dependent effects of hedgehog protein on chondrocytes, J. Bone Joint Surg. Br., 81(6):1076–1082, Nov. 1999 (abstract).*
Katsuura et al., The NH2–terminal region of the active domain of sonic hedgehog is necessary for its signal transduction, FEBS Lett., 447(2–3):325–328, Mar. 1999 (abstract).*
Williams et al., Functiona antagonists of sonic hedgehog reveal the importance of the N terminus for activity, J. Cell Sci., 112(Pt 23):4405–4414, Dec. 1999 (abstract).*
Yuasa et al., Sonic hedgehog is involved in osteoblast differentiation by cooperating with BMP–2, J. Cell. Physiol. 193:225–232, 2002.*
Kraus et al., Some distal limb structures develop in mice lacking sonic hedgehog signaling, Mech. Dev. 100:45–58, 2001.*
Anderson, R. et al., "Maintenance of ZPA signaling in cultured mouse limb bud cells", Devel. 117:142–1433 (1993).
Angier, N. "Biologists find key genes that shape patterning of embryos", New York Times, Jan. 11, 1994, C–1.
Basler, K. and G. Struhl, "Compartment boundaries and the control of Drosophila limb pattern by hedgehog protein", Nature 368: 208–214 (1994).
Basler, K. et al., "Control of cell pattern in the neural Tube: Regulation of cell differentiation by dorsalin–1, a novel TGFβ family member", Cell 73:687–702 (1993).
Bass, S. et al., "Hormone phage: An Enrichment Method for Variant Proteins with Altered Binding Properties", PROTEINS: Structure, Function, and Genetics 8:309–314 (1990).
Bejsovec, A. and E. Wieschaus, "Segment polarity gene interactions modulate epidermal patterning in Drosophila embryos", Devel. 119:501–517 (1993).
Bienz, M., "Homeotic genes and positional signalling in the Drosophila viscera", TIG 10:22–26 (Jan. 1994).
Bitgood, M. and McMahon, A., "Hedgehog and Bmp Genes are Coexpressed at Many Diverse Sites of Cell–Cell Interaction in the Mouse Embryo", Dev. Biol. 172 (1):126–138 (1995).
Blair, S.S., "Hedgehog digs up an old friend", Nature 373:656–657 (Feb. 23, 1995).
Brand–Saberi, B. et al., "The ventralizing effect of the notochord on somite differentiation in chick embryos", Anat. Embryol. 188: 239–245 (1993).
Brockes, J., "We may not have a morphogen", Nature 350:15 (1991).
Bumcrot, D.A. and McMahon A. "Sonic Hedgehog: Making the gradient", Chem. Biol. 3 (1):13–16 (Jan. 1996).
Bumcrot, D.A. and McMahon, A., "Somite differentiation. Sonic signals somites", Curr. Biol. 5 (6):612–614 (Jun. 1995).

(Continued)

Primary Examiner—Lorraine Spector
Assistant Examiner—Claire M. Kaufman
(74) Attorney, Agent, or Firm—Ropes & Gray LLP

(57) ABSTRACT

The present application is directed to the discovery that hedgehog proteins, and agents which effect the activities thereof, can be used to control the formation and/or maintenance of cartilage and bone.

38 Claims, 18 Drawing Sheets

OTHER PUBLICATIONS

Bumcrot, D.A. et al., "Proteolytic processing yields two secreted forms of sonic hedgehog", *Mol. Cell. Biol.* 15 (4):2294–2303 (4/95).

Charité, J. et al., "Ectopic Expression of Hoxb–8 Causes Duplication of the ZPA in the Forelimb and Homeotic Transformation of Axial Structures", *Cell* 78:589–601 (1994).

Coffman et al., "Xotch, the Xenopus homolog of *Drosophila* notch", *Science* 249:1438–1441 (1990).

Concordet, J. and Ingham, P., "Developmental biology. Patterning goes sonic", *Nature* 375 (6529):279–280 (May 1995).

Currie et al., "Induction of a specific muscle cell type by a hedgehog–like protein in zebrafish", *Nature* 383:452–455 (1996).

Curry et al., "Sequence analysis reveals homology between two proteins of the flagellar radial spoke", *Mol. Cell. Biol.* 12:3967–3977 (1992).

Davidson, E.H., "How embryos work: a comparative view of diverse modes of cell fate specification", *Devel.* 108:365–389 (1990).

Davis, A.P. and M.R. Capecchi, "Axial homeosis and appendicular skeleton defects in mice with a targeted disruption of hoxd–1", *Devel.* 120:2187–2198 (1994).

Dickinson W. , "Molecules and morphology: Where's the homology", *TIG 11,* (4):119–120 (1995).

Dingemanse, M.A. et al., "The expression of liver–specific genes within rat embryonic hepatocytes is a discontinuous process", *Differentiation* 56:153–162 (1994).

Dollé, P. et al., "Coordinate expression of the murine Hox–5 complex homoeobox–containing genes during limb pattern formation", *Nature* 342:767–772 (1989).

Dollé, P. et al., "Disruption of the Hoxd–13 gene induces localized heterochrony leading to mice with neotenic limbs", *Cell* 75:431–441 (1993).

Echelard, Y. et al., "Sonic hedgehog, a member of a family of putative signaling molecules, is implicated in the regulation of CNS polarity", *Cell* 75:1417–1430 (1993).

Ekker, S. et al., "Distinct expression and shared activities of members of the hedgehog gene family of *xenopus laevis*", *Devel. 121* (8):2337–2347 (Aug. 1995).

Ericson, J. et al., "Sonic hedgehog induces the differentiation of ventral forebrain neurons: a common signal for ventral patterning within the neural tube", *Cell* 81 (5):747–756 (Jun. 1995).

Ettelaie, C. et al., "The effect of lipid peroxidation and lipolysis on the ability of lipoproteins to influence thromboplastin activity", *Biochim. Biophys. Acta.* 1257 (1):25–30 (Jun. 1995).

Fahrner, K. et al., "Transcription of H–2 and Qa genes in embryonic and adult mice", *EMBO J.* 6:1265–1271 (1987).

Fallon, J.F. et al., "FGF–2: Apical ectodermal ridge growth signal for chick limb development", *Science* 264:104–107 (1994).

Fan, C. et al., "Long–range sclerotome induction by sonic hedgehog: Direct role of the amino–terminal cleavage product and modulation by the cyclic AMP signaling pathway", *Cell* 81:457–465 (May 5, 1995).

Fietz, M. et al., "The hedgehog gene family in *Drosophila* and vertebrate development", *Devel. Supp:* 43–51 (1994).

Forbes, A.J. et al., "Genetic analysis of hedgehog signalling in the *Drosophila* embryo", *Devel. 119* (Supp.):115–124 (1993).

Francis, P.H. et al., "Bone morphogenetic proteins and a signalling pathway that controls patterning in the developing chick limb", *Devel. 120*:209–218 (1994).

Gallop, M. et al., "Applications of combinatorial technologies to drug discovery. 1. Background and peptide combinatorial libraries", *J. of Med. Chem.* 37 (9):1233–1251 (1994).

Gérard, M. et al., "Structure and activity of regulatory elements involved in the activation the the Hoxd–11 gene during late gastrulation", *EMBO J. 12*:3539–3550 (1993).

Gurdon, J.B., "The Generation of diversity and pattern in animal development", *Cell 68*:185–199 (1992).

Gustin, K. et al., "Characterization of the role of individual protein binding motifs within the hepatitis B virus enhancer 1 on X promoter activity using linker scanning mutageneis", *Virology* 193:653–660 (1993).

Hall, T., et al., "A potential catalytic site revealed by the 1.7–A crystal structure of the amino–terminal signalling domain of Sonic hedgehog", *Nature* 378 (6553):212–216 (Nov. 1995).

Halpern, M.E., et al., "Induction of muscle pioneers and floor plate is distinguished by the zebrafish no tail mutation", *Cell* 75:99–111 (1993).

Hamburger, V. and H.L. Hamilton, "A series of normal stages in the development of the chick embryo", *J. Morph.* 88:49–92 (1951).

Hammerschmidt, M. et al., "The world according to hedgehog", *TIG* 13(1):14–21 (1997).

Haramis, A. et al., "The limb deformity mutation disrupts the SHH/FGF–4 feedback loop and regulation of 5–HoxD genes during limb pattern formation", *Devel. 121* (12):4161–4170 (Dec. 1995).

Hardy, A., et al., "Gene expression, polarising activity and skeletal patterning in reaggregated hind limb mesenchyme", *Devel. 121* (12):4329–4337 (Dec. 1995).

Hatta, K. et al., "The cyclops mutation blocks specification of the floor plate of the zebrafish central nervous system", *Nature* 350:339–341 (1991).

Heberlein, U. et al., "The TGBβ homolog dpp and the segment polarity gene hedgehog are required for propagation of a morpho–genetic wave in the *Drosophila* retina", *Cell* 75:913–926 (1993).

Heemskerk, J. and S. DiNardo, "*Drosophila* hedgehog acts as a morphogen in cellular patterning", *Cell* 76:449–460 (1994).

Hidalgo, A. and P. Ingham, "Cell patterning in *Drosophila* segment: spatial regulation of the segment polarity gene patched", *Devel. 110*:291–301 (1990).

Hooper, J. and Scott, M., "The *Drosophila* patched gene encodes a putative membrane protein required for segmental patterning", *Cell* 59:751–765 (1989).

Hynes, R.O., "Integrins: A family of Cell Surface Receptors", *Cell 48*:549–554 (1987).

Hynes, M., et al., "Induction of midbrain dopaminergic neurons by Sonic hedgehog", *Neuron* 15(1):35–44 (Jul. 1995).

Ingham, P.W., "Signalling by hedgehog family proteins in *Drosophila* and vertebrate developmenr", *Curr. Opin. Genet. Dev.* 5(4):478–484 (Aug. 1995).

Ingham, P.W., "Hedgehog points the way", *Current Biology* 4(4):347–350 (1994).

Ingham, P.W., "Localized hedgehog activity controls spatial limits of wingless transcription in the *Drosophila* embryo", *Nature* 366:560–562 (1993).

Ingham, P.W. and A. Hidalgo, "Regulation of wingless transcription in the *Drosophila* embryo", *Devel.* 117:283–291 (1993).

Ingham, P.W. et al., "Role of the *Drosophila* patched gene in positional signalling", *Nature* 353:184–187 (1991).

Izpisúa–Belmonte, J.–C. et al., "Expression of the homeobox Hox–4 genes and the specification of position in chick wing development", *Nature* 350:585–589 (1991).

Izpisúa–Belmonte, J.–C. et al., "Expression of Hox–4 genes in the chick wings links pattern formation to the epithelial–mesenchymal interactions that mediate growth", *EMBO J.* 11:1451–1457 (1992).

Jiang, J. and Struhl, G., "Protein kinase A in hedgehog signalling in *Drosophila* limb development", *Cell* 80 (4):563–572 (Feb. 1995).

Jessel, T.M. and D.A. Melton, "Diffusible factors in vertebrate embryonic induction", *Cell* 68:257–270 (1992).

Johnson, R.L. and C. Tabin, "The long and short of hedgehog signaling", *Cell* 81:313–315 (May 5, 1995).

Johnson, R.L. et al., "Patched overexpression alters wing disc size and pattern: transcriptional and post–transcriptional effects on hedgehog targets", *Devel.* 121 (12):4237–4245 (Dec. 1995).

Johnson, R.L., et al., "Ectopic expression of Sonic hedgehog alters dorsal–ventral patterning of somosites", *Cell* 79 (7):1165–1173 (Dec. 1994).

Johnson, R.L. et al., "Mechanism of limb patterning", *Curr. Opin. Genet. Dev.* 4(4):535–542 (Aug. 1994).

Johnson, R.L. et al., "Sonic hedgehog: a key mediator of anterior–posterior patterning of the limb and dorso–ventral patterning of axial embryonic structures" *Biochem. Soc. Trans.* 22 (3):569–574 (Aug. 1994).

Jones, M. et al., "Involvement of bone morphogenetic protein–4 (BMP–4) and Vgr–L in morphogenesis and neurogenesis in the mouse", *Devel.* 111:531–542 (1991).

Kalderon, D., "Morphogenetic signaling. Responses to hedgehog" *Curr. Biol.* 5 (6):580–582 (Jun. 1995).

Koonin, E., "A protein splice–junction motif in hedgehog family proteins", *Trends in Biochem. Sci.* 20 (4):141–142 (Apr. 1995).

Kornblihtt, A.R. et al., "Primary structure of human fibronectin: differential splicing may generate at least 10 polypeptides from a single gene", *EMBO J.* 4:1755–1759 (1985).

Kornfeld, R. and S. Kornfeld, "Assembly of asparagine–Linked oligosaccharides", *Ann. Rev. Biochem.* 54:631–664 (1985).

Krauss, S. et al., "Expression of the zebrafish paired box gene pax[zf–b] during early neurogenesis", *Devel.* 113:1193–1206 (1991).

Krauss, S. et al., "A functionally conserved homolog of the *Drosophila* segment polarity gene hh Is expressed in tissues with polarizing activity in zebrafish embryos", *Cell* 75:1431–1444 (1993).

Lai, C. et al., "Patterning of the neural ectoderm of *Xenopus laevis* by the amino–terminal product of hedgehog autoproteolytic cleavage", *Devel.* 121 (8):2349–2360 (Aug. 1995).

Laufer, E. et al., "Sonic hedgehog and Fgf–4 acb through a signaling cascade and feedback loop to integrate growth and patterning of the developing limb Bud", *Cell* 79:993–1003 (Dec. 16, 1994).

Lee, J.J. et al., "Secretion and localized transcription suggest a role in positional signaling for products of the segmentation gene hedgehog", *Cell* 71:33–50 (1992).

Lee, J, et al., "Autoproteolysis in hedgehog protein biogenesis", *Science* 266 (5190):1528–1537 (Dec. 1994).

Levin, M. et al., "A molecular pathway determining left–right asymmetry in chick embryogenesis", *Cell* 82 (5):803–814 (Sep. 1995).

Li, W. et al., "Function of protein kinase A in hedgehog signal transduction and *Drosophila* imaginal disc development", *Cell* 80 (4):553–562 (Feb. 1995).

Lopez–Martinez, A. et al., "Limb–patterning activity and restricted posterior localization of the amino–terminal product of Sonic hedgehog cleavage", *Curr. Biol.* 5 (7):791–796 (Jul. 1995).

Lumsden, A. and Graham, A., "Neural patterning: A forward role for hedgehog", *Curr. Biol.* 5 (12):1347–1350 (Dec. 1995).

Ma, C. et al., "The segment polarity gene hedgehog is required for progression of the morphogenetic furrow in the developing *Drosophila* eye", *Cell* 75:927–938 (1993).

Ma, C. and Moses, K., "Wingless and patched are negative regulators of the morphogenetic furrow and can affect tissue polarity in the developing *Drosophila* compound eye", *Devel.* 121 (8) 2279–2289 (Aug. 1995).

Marigo, V. et al., "Biochemical evidence that patched is the hedgehog receptor", *Nature* 384: 176–179 (1996).

Maccabe, J.A. and B.W. Parker, "The target tissue of limb–bud polarizing activity in the induction of supernumerary structures", *J. Embryol. Exp. Morph.* 53:67–73 (1979).

Marti, E. et al., "Distribution of Sonic hedgehog peptides in the developing chick and mouse embryo", *Devel.* 121 (8):2537–2547 (Aug. 1995).

Marti, E. et al., "Requirement of 19K form of Sonic hedgehog for induction of distinct ventral cell types in CNS explants" *Nature* 375 (6529):322–325 (May 1995).

Mavillo, F. et al., "Activation of four homeobox gene clusters in human embryonal carcinoma cells induced to differentiate by retinoic acid", *Differentiation* 37:73–79 (1988).

McGinnis, W. and R. Krumlauf, "Homeobox genes and axial patterning", *Cell* 68:283–302 (1992).

Mohler, J., "Requirements for hedgehog, a segmental polarity gene, in patterning larval and adult cuticle of *Drosophila*", *Genetics* 120:1061–1072 (1988).

Mohler, J. and K. Vani, "Molecular organization and embryonic expression of the hedgehog gene involved in cell–cell communication in segmental patterning of *Drosophila*", *Devel.* 115:957–971 (1992).

Morgan, B.A. et al., "Targeted misexpression of Hox–4.6 in the avian limb bud causes apparent homeotic transformations", *Nature* 358:236–239 (1992).

Munsterberg A. et al., "Combinatorial signaling by Sonic hedgehog and Wnt family members induces myogenic bH1H gene expression in the somite", *Genes Dev.* 9 (23):2911–2922 (Dec. 1995).

Nakano, Y. et al., "A protein with several possible membrane–spanning domains encoded by the *Drosophila* segment polarity gene patched", *Nature* 341:508–513 (1989).

Ngo, J. et al., "The protein folding problem and tertiary structure prediction", Merz and LeGrand, ed. Birkhauser, Boston (1994).

Niswander, L. and G.R. Martin, "FGF–4 and BMP–2 have opposite effects on limb growth", *Nature* 361:68–71 (1993).

Niswander, L. et al., "A positive feedback loop coordinates growth and patterning in the vertebrate limb", *Nature* 371 (6498): 609–612 (Oct. 1994).

Nohno, T. et al., "Involvement of the Chox–4 chicken homeobox genes in determination of anteroposterior axial polarity during limb development", *Cell* 64:1197–1205 (1991).

Nohno, T. et al., "Involvement of the Sonic hedgehog gene in chick feather formation", *Biochem. Biophys. Res. Comm.* 206(1): 33–39 (Jan. 1995).

O'Farrell, P.H., "Unanimity waits in the wings", *Nature* 368:188–189 (1994).

Parr, B.A. et al., "Mouse Wnt genes exhibit discrete domains of expression in the early embryonic CNS and limb buds", *Devel.* 119:247–261 (1993).

Patel, N.H. et al., "The role of segment polarity genes during *Drosophila* neurogenesis", *Genes Devel.* 3:890–904 (1989).

Peifer, M., "The two faces of hedgehog", *Science* 266 (5190):1492–1493 (Dec. 1994).

Perrimon, N., "Hedgehog and beyond", *Cell* 80:517–520 (Feb. 24, 1995).

Pham, A. et al., "The suppressor of fused gene encodes a novel PEST protein involved in *Drosophila* segment polarity establishment", *Genetics* 140 (2):587–598 (Jun. 1995).

Placzek, M. et al., "Induction of floor plate differentiation by contact–dependent, homeogenetic signals", *Devel.* 117:205–218 (1993).

Placzek, M. et al., "Orientation of commissural axons in vitro in response to a floor plate–derived chemoattractant", *Devel.* 110:19–30 (1990).

Pollack, R.A. et al., "Altering the boundaries of Hox3.1 expression: Evidence for antipodal gene regulation", *Cell* 71:911–923 (1992).

Porter, J, et al., "The product of hedgehog autoproteolytic cleavage active in local and long–range signalling", *Nature* 374 (6520): 363–366 (Mar. 1995).

Reeck et al., "Homology in proteins and nucleic acids: A terminology muddle and a way out of it", *Cell* 50:667 (1987).

Rennie, J., "Super Sonic", *Scientific American* :20 (Apr. 1994).

Riddle, R.D. et al., "Sonic hedgehog Mediates the Polarizing Activity of the ZPA", *Cell* 75:1401–1416 (1993).

Riddle, R.D. et al., "Induction of the LIM homeobox gene Lmx1 by WNT7 a establishes dosoventral pattern in the vertebrate limb", *Cell* 83 (6553):212–216 (Nov. 1995).

Riley, B.B. et al., "Retroviral expression of FGF–2 (bFGF) affects patterning in chick limb bud", *Devel.* 118:95–104 (1993).

Roberts, D. et al., "Sonic hedgehog is an endothermal signal inducing Bmp–4 and Hox genes during induction and regionalization of the chick hindgut", *Devel.* 121 (10): 3163–74 (Oct. 1995).

Roelink, H. et al., "Floor plate and motor neuron Induction by different concentrations of the amino–terminal cleavage product of sonic hedgehog autoproteolysis", *Cell* 81:445–455 (May 5, 1995).

Roelink, H. et al., Floor plate and motor neuron induction by vhh–1, a Vertebrate Homolog of hedgehog expressed by the notochord, *Cell* 76:761–775 (1994).

Sambrook et al., *Molecular Cloning CSH:*11.47 (1989).

Sasaki, H. and B.L.M. Hogan, "Differential expression of multiple fork head related genes during gastrulation and axial pattern formation in the mouse embryo", *Devel.* 118:47–59 (1993).

Savage, M. et al., "Distribution of FGH–2 suggests it has a role in chick limb bud growth", *Devel. Dynamics* 198:159–170 (1993).

Schuske, K. et al., "Patched overexpression causes loss of wingless expression in *drosophila* embryos", *Devel. Biol.* 164:300–311 (1994).

Smith, J.C., "Hedgehog, the floor plate, and the zone of polarizing activity", *Cell* 76:193–196 (1994).

Stachel, S.E. et al., "Lithium perturbation and goosecoid expression identify a dorsal specification pathway in the pregastrula zebrafish", *Devel.* 117:1261–1274 (1993).

Stolow, M. and Shi, Y., Xenopus sonic hedgehog as a potential morphogen during embryogenesis and thyroid hormone–dependent metamorphosis, *Nucleic Acids Res.* 23 (13):2555–1562 (Jul. 1995).

Stratagene 1988 cDNA libraries.

Tabata, T. and T.B. Kornberg, "Hedgehog Is a signaling protein with a key Role in patterning *Drosophila* imaginal discs", *Cell* 76:89–102 (1994).

Tabata, T. et al., "The *Drosophila* hedgehog gene is expressed specifically in posterior compartment cells and is a target of engrailed regulation", *Genes Devel.* 6:2635–2645 (1992).

Tabin, C.J., "Retinoids, homeoboxes, and growth factors: Toward molecular models for limb development", *Cell* 66:199–217 (1991).

Tanebe, Y. et al., "Induction of motor neurons by Sonic hedgehog is independent of floor plate differentiation", *Curr. Biol.* 5 (6): 651–658 (Jun. 1995).

Tanaka, E. and Gann, A., "Limb development", *Curr. Biol.* 5(6):594–597 (Jun. 1995).

Tashiro, S. et al., "Structure and expression of hedgehog, a *Drosophila* segment–polarity gene required for cell–cell communication", *Gene* 124:183–189 (1993).

Taylor, A.M. et al., "Contrasting distributions of patched and hedgehog proteins in the *Drosophila* embryo", *Mech. Dev.* 42:89–96 (1993).

Thaller, C. and G. Eichele, "Identification and spatial distribution of retinoids in the developing chick limb bud", *Nature* 327:625–628 (1987).

Tickle, C. et al., "A Quantitative Analysis of the Effect of all–trans–Retinoic Acid on the Pattern of Chick Wing Development", *Devel. Biol.* 109:82–95 (1985).

Tickle, C., "Vertebrate limb development", *Curr. Opin. Genet. Dev.* 5(4):478–484 (Aug. 1995).

Tickle, C. and Eichele, G., "Vertebrate limb development", *Ann. Rev. Cell Biol.* 10:121–152 (1994).

van Straaten, H.W.M. et al., "Effect of the notochord on the differentiation of a floor plate area in the neural tube of the chick embryo," *Anat. Embryol.* 177:317–324 (1988).

Vogel, A. and C. Tickle, "FGF–4 maintains polarizing activity of posterior limb bud cells in vivo and in vitro", *Devel.* 119:199–206 (1993).

Wallace et al., "Oligonucleotide probes for the screening of recombinant DNA libraries", *Methods in Enzymology* 152:432 (1987).

Wanek, N. et al., "Conversion by retinoic acid of anterior cells into ZPA cells in the chick wing bud", *Nature* 350:81–83 (1991).-

Wang, M. et al., "Induction of dopaminergic neuron phenotype in the midbrain by Sonic hedgehog protein", *Nat. Med. 1* (11):1184–1188 (Nov. 1995).

Yamada, T. et al., "Control of cell pattern in the developing nervous system: Polarizing activity of the floor plate and notochord", *Cell 64*:635–647 (1991).

Yang, Y. and L. Niswander, "Interaction between the signalling molecules WNT7a and SHH during vertebrate limb development: Dorsal signals regulate anteroposterior patterning" *Cell 80*:939–947 (Mar. 1995).

Zappavigna et al., "Hox4 genes encode transcription factors with potential auto– and cross–regulatory capacities", *EMBO 10*:4177–4187 (1991).

Zardoya et al., "Evolution and orthology of hedgehog genes", TIG 12 (12):496–467 (199 ).

Zecca, M. et al., "Sequential organizing activities of engrailed, hedgehog and decapentaplegic in the *Drosophlia* wing", *Devel. 121* (8):2265–2278 (Aug. 1995).

* cited by examiner

METHODS AND COMPOSITIONS FOR REGULATING SKELETOGENIC FORMATION

RELATED APPLICATIONS

This application is a continuation-in-part of U.S. Ser. No. 08/674,509, filed Jul. 2, 1996, which is a continuation-in-part of U.S. Ser. No. 08/462,386, filed Jun. 5, 1995, which is a continuation-in-part of U.S. Ser. No. 08/435,093, filed May 4, 1995, which is a continuation-in-part of U.S. Ser. No. 08/356,060, filed Dec. 14, 1994, which is a continuation-in-part of U.S. Ser. No. 08/176,427 filed Dec. 30, 1993, the teachings each specification being hereby incorporated by reference herein.

FUNDING

Work described herein was supported by Grant Number HD 27222-01 awarded by the National Institutes of Health. The United States Government has certain rights in the invention.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation (Davidson, E., (1990) *Development* 108: 365–389; Gurdon, J. B., (1992) *Cell* 68: 185–199; Jessell, T. M. et al., (1992) *Cell* 68: 257–270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homoiogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68:185–199).

The process of bone formation (osteogenesis) involves three main steps: (i) production of the extracellular organic matrix (osteoid); (ii) mineralization of the matrix to form bone; and (iii) bone remodeling by resorption and reformation. The cellular activities of osteoblasts, osteocytes, and osteoclasts are essential to the process. Osteoblasts synthesize the collagenous precursors of bone matrix and also regulate its mineralization. As the process of bone formation progresses, the osteoblasts come to lie in tiny spaces (lacunae) within the surrounding mineralized matrix and are then called osteocytes. The cell processes of osteocytes occupy minute canals (canaliculi) which permit the circulation of tissue fluids. To meet the requirements of skeletal growth and mechanical function, bone undergoes dynamic remodeling by a coupled process of bone resorption by osteoclasts and reformation by osteoblasts.

Osteoblasts are cells of mesenchymal origin. They possess a single nucleus, have a shape that varies from flat to plump, reflecting their level of cellular activity, and in later stages of maturity line up along bone-forming surfaces. Osteoblasts synthesize and lay down precursors of collagen, which comprises 90–95% of the organic matrix of bone. Osteoblasts also produce the proteoglycans of ground substance and are rich in alkaline phosphatase, an organic phosphate-splitting enzyme. Osteoblasts have receptors for parathyroid hormone and possibly also for estrogen. Hormones, growth factors, physical activity, and other stimuli act through osteoblasts to bring about their effects on bone.

The collagen formed by osteoblasts is typically deposited in parallel or concentric layers to produce mature (lamellar) bone. But when bone is rapidly formed, as in the fetus or certain pathological conditions (fracture callus, fibrous dysplasia, hyperparathyroidism), the collagen is not deposited in a parallel array but in a basket-like weave and is called woven, immature, or primitive bone. In fully decalcified bone sections, the extracellular matrix stains pink with H+E, similar to collagen elsewhere but with a more homogeneous than fibrillar structure which latter is easily observed by polarizing microscopy.

The main mineral component of bone is an imperfectly crystalline hydroxyapatite $[Ca_{10}(PO_4)_6(OH)_2 1$ which comprises about ¼ the volume and ½ the mass of normal adult bone. The mineral crystals, as shown by electron microscopy, are deposited along, and in close relation to, the bone collagen fibrils. Calcium and phosphorus (Pi) are, of course, derived from the blood plasma and ultimately from nutritional sources. Vitamin D metabolites and parathormone (PTH) are important mediators of calcium regulation, and lack of the former or excess of the latter leads to bone mineral depletion.

The extracellular matrix of bone is mineralized soon after its deposition, but a very thin layer of unmineralized matrix is seen on the bone surface, and this is called the osteoid layer or osteoid seam. In some pathological conditions, the thickness and extent of the osteoid layer may be increased (hyperosteoidosis) or decreased. Hyperosteoidosis may be caused by conditions of delayed bone mineralization (as in osteomalacia/rickets resulting from vitamin D deficiency) or of increased bone formation (as in fracture callus, Paget's disease of bone, etc.).

Osteoclasts are multinucleated cells, apparently of monocyte-phagocyte origin, which adhere to the surface of bone undergoing resorption and lie in depressions termed Howship's lacunae or resorption bays. With remodeling, the resorptive surfaces become covered by osteoblasts which form new bone at the site. Several metabolic bone diseases (such as hyperparathyroidism, Paget's disease, and others) are characterized by increased modeling and increased osteoclastic activity. Osteoclasts are apparently activated by "signals" from osteoblasts. For example, osteoblasts have receptors for PTH whereas osteoclasts do not, and PTH-induced osteoclastic bone resorption is said not to occur in the absence of osteoblasts.

At an early stage of human embryonic development, a cartilage model of much of the skeleton (of extremities, trunk, and base of the skull) is formed from the mesenchyme. In the further fetal development of long bones, a rim of primitive bone is first laid down in layers over the middle of the shaft by osteoblasts arising from the overlying periosteum, and subperiosteal bone formed in this way soon extends up and down the shaft (diaphysis). The process by which bone tissue replaces membranous fibrous tissue is called intramembranous ossification. This is the process by which the diaphysis increases in width throughout postnatal growth. Some bones, such as the flat bones of the calvarium, are formed entirely, or in great part, by intramembranous ossification.

The cartilage cells of the core of the fetal shaft degenerate upon contact with penetrating buds of periosteal osteoblasts, the cartilage matrix becomes mineralized and resorbed, and the resulting surfaces and spaces are lined by osteoblasts which lay down woven bone and form primitive bone trabeculae. The process by which bone tissue replaces cartilage is called endochondral ossification and begins in the femur at about the ninth week of fetal life. Some of the trabeculae fuse with the subperiosteal new bone while others are resorbed to form a medullary cavity which will be occupied by hematopoietic tissue. Thus, the primitive bone shaft is formed and lies between the cartilaginous ends which become the epiphyses. In the later months of fetal life, the woven bone of the diaphysis will be replaced by lamellar bone of mature type. Over time, the bone cortex is thickened and remodeled to serve mechanical functions and is permeated by haversian systems (bone-forming units) of longitudinal, vascularized canals bounded by concentric lamellae of bone, culminating in the typical appearance of compact cortical bone as seen in the adult.

The longitudinal growth of the long bones occurs in the epiphysial (epiphyseal) growth plate as cartilage cells, arising from reserve cells, undergo mitosis and proliferate in orderly longitudinal columns. The proliferated cartilage cells vacuolate as they move toward the cartilage-bone junction (metaphysis), the cartilage matrix becomes mineralized, and buds of osteoblasts emerging from the metaphysis replace the mineralized cartilage with bone. This process of cartilage cell proliferation and endochondral ossification is repeated over and over, and the bones become longer and larger. Meanwhile, at age-related intervals, secondary centers of endochondral ossification ("radiologic epiphysis") begin to form on the articular side of the growth plate.

When skeletal maturity is reached, the cartilage cells of the growth plate cease to proliferate, the growth plate becomes thinner, is replaced by bone and disappears, and the epiphysis is "closed" or fused with the shaft.

The recent identification of the genetic basis of hereditary skeletal disorders, such as dwarfism and osteochondrodysplasias, is providing important insights into the intricate processes of skeletal formation, growth and homeostasis. These processes include patterning events during condensation and differentiation of mesenchymal cells to form cartilage precursors of the future bones, the replacement of cartilage by bones through endochondral ossification, the growth of long bones through proliferation and differentiation of chondrocytes in growth plates, and bone formation through differentiation of osteoblasts from mesenchymal cells in areas of intramembranous ossification. Defects in any of these processes can give rise to skeletal abnormalities. Mutations in transcription factors such as HOX and PAX and members of the TGFβ superfamily cause disorders associated with abnormal mesenchymal condensation, while defects in the transcription factor SOX-9 lead to abnormalities in chondrocyte differentiation.

SUMMARY OF THE INVENTION

One aspect of the present application relates to a method for promoting regulating the growth state of a chondrocytic cell, e.g., rates of proliferation and differentiation, by contacting the cells, in vitro or in vivo, with a hedgehog therapeutic or ptc therapeutic in an amount effective potentiate proliferation of the chondrocytes (a chondrogenic form of the therapeutic) or inhibiting proliferation and inducing differentiation of the cell, e.g., into a hypertrophic chondrocyte (an osteogenic form of the therapeutic) relative to the absence of administeration of the hedgehog therapeutic or ptc therapeutic.

Wherein the subject method is carried out using a hedgehog therapeutic, the hedgehog therapeutic preferably a polypeptide including a hedgehog portion comprising at least a bioactive extracellular portion of a hedgehog protein, e.g., the hedgehog portion includes at least 50, 100 or 150 amino acid residues of an N-terminal half of a hedgehog protein. In preferred embodiments, the hedgehog portion includes at least a portion of the hedgehog protein corresponding to a 19 kd fragment of the extracellular domain of a hedgehog protein.

In preferred embodiments, the hedgehog portion has an amino acid sequence at least 60, 75, 85, or 95 percent identical with a hedgehog protein of any of SEQ ID Nos. 10–18 or 20, though sequences identical to those sequence listing entries are also contemplated as useful in the present method. The hedgehog portion can be encoded by a nucleic acid which hybridizes under stringent conditions to a nucleic acid sequence of any of SEQ ID Nos. 1–9 or 19, e.g., the hedgehog portion can be encoded by a vertebrate hedgehog gene, especially a human hedgehog gene.

In other embodiments, the subject method can be carried out by administering a gene activation construct, wherein the gene activation construct is deigned to recombine with a genomic hedgehog gene of the patient to provide a heterologous transcriptional regulatory sequence operatively linked to a coding sequence of the hedgehog gene.

In still other embodiments, the subject method can be practiced with the administration of a gene therapy construct encoding a hedgehog polypeptide. For instance, the gene therapy construct can be provided in a composition selected from a group consisting of a recombinant viral particle, a liposome, and a poly-cationic nucleic acid binding agent.

In yet other embodiments, the subject method can be practiced with the administration of a ptc therapeutic. For instance, the ptc therapeutic can be a small molecule which inhibits ptc-mediated signal (mimics hedgehog) or potentiates ptc-mediated signals (antagonizes hedgehog).

DETAILED DESCRIPTION OF THE INVENTION

Figure 1A:
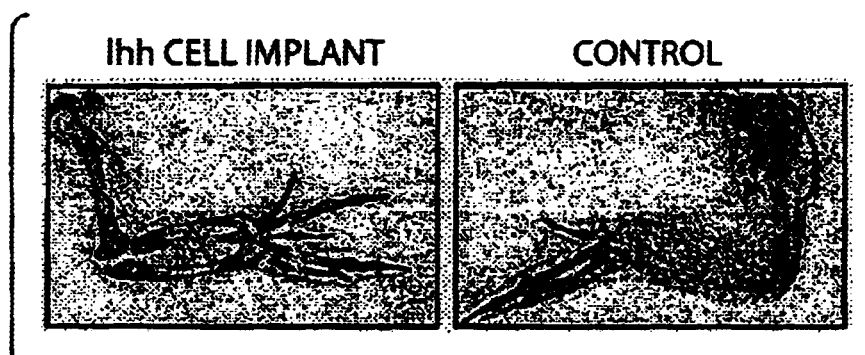
FIG. 1 (panels A–C): Ihh activates the Shh signaling pathway. (A) Anterior misexpression of Ihh induces duplication of posterior limb structures. Ihh-expressing cells (46) were implanted into the anterior mesenchyme HH stage 21 chicken wing bud. After 7 days of incubation, Alcian blue staining of the limbs revealed anterior duplications of the radius and digits II and III. (B and C) Anterior misexpression of Ihh induces expression of Shh target genes. HH stage 21 chicken limb buds were infected with an Ihh-expressing replication-competent retrovirus and analyzed by whole-mount in situ hybridization 40 to 48 hours later (46, 48). Hoxd-13 and Bmp-2, genes thought to be involved in patterning (B), and Ptc and Gli, genes believed to transduce the hedgehog signal (C), are induced by Ihh (C) in the anterior limb bud.

The morphogenesis of vertebrate long bones is a two-stage process: first, the formation of a cartilage model; second, the replacement of this cartilage by bone and marrow during endochondral ossification. The first process is one of cell differentiation and pattern formation. The second process is one of cartilage maturation (hypertrophy), matrix degradation, vascular invasion, and ossification.

Progress in understanding the developmental biology of bone has lagged behind that in other tissues. But over the past few years the key role played by locally produced growth factors including transforming growth factor-β and parathyroid hormone-related protein (PTHrP) has emerged. More recently, the importance of growth factors in human bone development has been dramatically confirmed by the finding that several dwarfisms are linked to growth-factor receptor mutations. Achondroplasia is linked to a hyperactivating mutation in the fibroblast growth factor-3 (FGF3) receptor, Crouzon's syndrome is linked to a mutation in the FGF2 receptor, and some people with Jansen-type metaphyseal chondrodysplasia have hyperactivating mutations in their PTHrP receptor (*New Eng J Med* (1996) 335:708–714).

I. Overview

The present application is directed to the discovery that preparations of hedgehog polypeptides can be used to control the formation and/or maintenance of cartilage and bone. As described in the appended examples, hedgehog proteins are implicated in the control of the growth state of chondrocytes, and apparently provide early signals that regulate the balance between proliferating chondrocytes and differentiation of the chondrocytes into hypertrophic chondrocytes. In particular, as described in the appended examples, we have defined a regulatory loop controlling bone development in which the growth factor parathyroid hormone-related protein (PTHrP) is a key component, and whereby a hedgehog protein couples the expression of PTHrP protein in a regulatory circuit controlling bone development.

As set out above, the genesis of long bones begins with the laying down of a cartilage mold that is gradually filled in and ossified by bone-making cells. The first step is chondrocyte differentiation. The chondrocytes stop dividing and swell to become hypertrophic chondrocytes, a process that induces vascularisation and the invasion of bone-forming cells. Cartilage differentiation proceeds as a linear wave moving out from the bone centre to the ends, but stopping short of the growth plate—a zone of undifferentiated, proliferating chondrocytes. It is the balance between the rate of chondrocyte growth and the rate of differentiation that determines the growth characteristics of the bone, whether it be the extraordinary growth rate seen during fetal life and infancy or the defective growth in disorders of endochondral bone.

As described in the examples below, the hedgehog protein Ihh (for Indian hedgehog) is expressed in the developing cartilage of long bones. In the developing chick wing, Ihh is transiently expressed by cells making the transition from proliferating to hypertrophic chondrocytes suggesting a regulatory function for Ihh. To investigate what that function might be, we overdosed developing wing buds by injecting them with a retrovirus carrying the Ihh gene. At the time when normal wings were largely ossified, injected wing bones were still made of a continuous, undifferentiated cartilage core. These results indicate that Ihh is inhibiting chondrocyte differentiation.

We observed that Gli and Patched were present in the perichondrium, a sheath of cells surrounding the cartilage, and have developed a model whereby Ihh, a secreted protein, regulates the growth state of chondrocytes by direct and indirect mechanisms, the latter involving activation of cells in the perichondrium, which, in turn, produce an inhibitory signal to cells in the growth plate that inhibit their differentiation.

The art had already established that PTHrP is produced by the perichondrial cells, and PTHrP has been strongly implicated in cartilage differentiation, e.g., there is premature differentiation of long bones in genetically engineered mice lacking either the PTHrP gene or its receptor. As described in the appended examples, to establish that PTHrP was involved in Ihh signaling Ihh was injected into chick wing buds and it was observed that expression of PTHrP was induced in the periarticular perichondrium. The examples also show that Ihh is unable to completely arrest premature differentiation in limb explants from transgenic mice which lacked the gene for PTHrP. The examples also demonstrate that the cells affected by Ihh and PTHrP, e.g., the chondrocytes of the growth plate, express receptors for PTHrP. Mouse limb explants which lacked the PTHrP receptor had diminished responses to both Ihh or PTHrP.

The data provided in the appended examples establish an apparent negative feedback loop controlling the rate of cartilage differentiation and bone growth. It is believed that Ihh, released by cells as they become committed to differentiation, serves as a sensor within the skeletal element to regulate the number of cells committed to the process. An Ihh signals to the dividing, growth-plate cells (via PTHrP) that no more cells should become committed to differentiation. As Ihh concentrations fall, more chondrocytes are able to enter the differentiation pathway, again signaling their intent by expressing Ihh.

While not wishing to be bound by any particular theory, we speculate that controlled changes in this cycle may cause the more gradual deceleration of bone growth in children. The findings also suggest that if chondrocyte differentiation proceeds too quickly or too slowly, abnormalities of the long bones can result, such as those in some forms of dwarfism. Accordingly, the present findings have implications for both treatment and diagnosis of skeletal disorders.

Based at least in part one these findings, the present invention provides methods and compositions for healing or preventing defects in bone or other osseous structures, e.g., in the treatment of skeletal tissue deficiencies. In general, the method of the present invention comprises administering to an animal a hedgehog therapeutic composition (defined infra) in an amount effective to induce formation of normal, adult bone or to maintain such bone. The present invention particularly contemplates the use of hedgehog agonists which maintain a skeletogenic activity, such as an ability to induce chondrogenesis and/or osteogenesis. For example, hedgehog polypeptides of the present invention can be used as part of a protocol to control the de novo formation of cartilage and endochondral bone, including regulation of proliferation and differentiation of progenitor cells into chondrocytes and osteoblasts, including appropriate mineralization and bone remodeling, and formation of appropriate bone vascular supply. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions.

The subject method can be employed for the generation of bone (osteogenesis) at a site in the animal where such skeletal tissue is deficient. In one aspect, the present invention provides pharmaceutical preparations and methods for controlling the formation of bone utilizing, as an active ingredient, a hedgehog polypeptide or a mimetic thereof. For instance, as described in Example 10, hedgehog polypeptides can induce endochondral bone formation in mammals when implanted subcutaneously in association with a suitable matrix material, using a standard in vivo bone assay.

Regulatory signals produced by Indian hedgehog are particularly associated with the balance between proliferative chondrocytes and hypertrophic chondrocytes. For instance, administration of a hedgehog therapeutic can be employed as part of a method for treating bone loss in a subject, e.g. to prevent and/or reverse osteoporosis and other osteopenic disorders, as well as to regulate bone growth and maturation. For example, preparations comprising hedgehog agonists can be employed, for example, to induce endochondral ossification, at least so far as to facilitate the formation of cartilaginous tissue precursors to form the "model" for ossification.

The hedgehog formulations of the present invention may be used as part of regimens in the treatment of disorders of, or surgical or cosmetic repair of, e.g., endochondral and/or intramembraneous bone. The methods and compositions disclosed herein provide for the treatment or prevention of a variety of bone disorders and surgical procedures. Examples of indications where the subject method can be used to promote bone repair at a skeletal site include periodontal disease where root socket healing is desired (tooth socket sites); fractures, including bone and joint fractures, e.g., such as non-unions and delayed unions; bony defects caused by trauma or surgery (e.g., resections for cancer, cranial defects, spinal (vertebral) fusions, correction of scoliosis by surgical alignment, spinal fractures, etc.); stabilization and enhanced fixation of artificial prostheses and spacer bars, oral joints, bone replacements and the like; percutaneous arthrodesis; pseudo-arthrosis; bone defects resulting from congenital defects, trauma, tumor infection, degenerative disease and other causes of loss of skeletal tissue; as well as bone grafting.

The subject method can be used in plastic and reconstructive surgery, e.g., the subject method is useful for prosthesis stability, enhancement of osseointegration of implant materials used for internal fixation procedures, stabilization of dental implant materials, healing acceleration of ligament insertion, and spine and other joint fusion procedures. For instance, it may be used as part of a protocol for fixation of permanent dentures, enhanced fixation of accepted joint prosthesis, e.g., hips, knees, and shoulders. The subject method can also be used in limb salvage procedures (such as may be associated with removal of cancerous bone tissue).

Therapeutic compositions of hedgehog can be supplemented, if required, with osteoinductive factors, such as bone growth factors (e.g. TGF-β factors, such as the bone morphogenetic factors BMP-2 and BMP-4, as well as activin), and may also include, or be administered in combination with, inhibitors of bone resorption such as estrogen, bisphosphonate, sodium fluoride, calcitonin, or tamoxifen, or related compounds.

The subject hedgehog treatments are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats.

In preferred embodiments, the type of bone treated by the present invention is endochondral bone, e.g., long bones, vertebrae, and other bones forming the basic skeletal frame, as well as bones of the feet and hands and paws as the case may be.

Without wishing to be bound by any particular theory, the ability of hedgehog to regulate the growth and differentiation of chondrocytes may be due at least in part to the ability of hedgehog proteins to antagonize (directly or indirectly) patched-mediated regulation of gene expression and other physiological effects mediated by that protein. Moreover, patched expression in proliferating chondrocytes was also observed. The patched gene product, a cell surface protein, is understood to signal through a pathway which causes transcriptional repression of members of the Wnt and Dpp/BMP families of morphogens, proteins which impart positional information. In development of the CNS and patterning of limbs in vertebrates, the introduction of hedgehog relieves (derepresses) this inhibition conferred by patched, allowing expression of particular gene programs.

Recently, it has been reported that mutations in the human version of patched, a gene first identified in a fruit fly developmental pathway, cause a hereditary skin cancer and may contribute to sporadic skin cancers. See, for example, Hahn et al. (1996) *Cell* 86:841–851; and Johnson et al. (1996) *Science* 272:1668–1671. The demonstration that nevoid basal-cell carcinoma (NBCC) results from mutations in the human patched gene provided an example of the roles patched plays in post-embryonic development. These observations have led the art to understand one activity of patched to be a tumor suppressor gene, which may act by inhibiting proliferative signals from hedgehog. Our observations set forth below reveal potential new roles for the hedgehog/patched pathway in maintenance of chondrocyte cell proliferation and differentiation by regulating, inter alia, the expression of PTHrP by perichondrial cells and/or directly acting on chondrocytes. Accordingly, the present invention contemplates the use of other agents which are capable of mimicking the effect of the hedgehog protein on patched signaling, e.g., as may be identified from the drug screening assays described below, and which accordingly can induce the expression of PTHrP by (perichondrial) cells.

II. Definitions

For convenience, certain terms employed in the specification, examples, and appended claims are collected here.

The term "hedgehog therapeutic" refers to various forms of hedgehog polypeptides, as well as peptidomimetics, which can modulate the proliferation/differentiation state of chondrocytes directly or indirectly. For instance, the hedgehog therapeutic may interact chondrocytes or progenitors thereof to effect their proliferative state. The hedgehog therapeutic may also function by inducing or inhibiting, as will be clear from the context of individual examples, expression of a parathyroid hormone-related protein. The term includes naturally occurring forms of hedgehog proteins, as well as modified or mutant forms generated by molecular biological techniques, chemical synthesis, etc. While in preferred embodiments the hedgehog polypeptide is derived from a vertebrate homolog, cross species reported in the literature supports the use of hedgehog polypeptides from invertebrate organisms as well. Naturally and non-naturally occurring hedgehog therapeutics referred to herein as "agonists" mimic or potentiate (collectively "agonize") the effects of a naturally-occurring hedgehog protein on bone formation, chondrocyte proliferation, etc. The hedgehog therapeutic may alternatively inhibit (antagonize), the effects of a naturally-occurring hedgehog protein. In addition, the term "hedgehog therapeutic" includes molecules which can activate expression of an endogenous hedgehog gene. The term also includes gene therapy constructs for causing expression of hedgehog polypeptides in vivo, as for example, expression constructs encoding recombinant hedgehog polypeptides as well as trans-activation constructs for altering the regulatory sequences of an endogenous hedgehog gene by homologous recombination.

In particular, the term "hedgehog polypeptide" encompasses preparations of hedgehog proteins and peptidyl fragments thereof, both agonist and antagonist forms as the specific context will make clear.

As used herein the term "bioactive fragment of a hedgehog protein" refers to a fragment of a full-length hedgehog polypeptide, wherein the fragment specifically agonizes or antagonizes inductive events mediated by wild-type hedgehog proteins. The hedgehog bioactive fragment preferably is a soluble extracellular portion of a hedgehog protein, where solubility is with reference to physiologically compatible solutions. Exemplary bioactive fragments are described in PCT publications WO 95/18856 and WO 96/17924 and U.S. application Ser. Nos. 08/674,509, 08/460,900, 08/462,386, 08/435,093, 08/356,060 and 08/176,427, each of which is expressly incorporated by reference herein.

The term "ptc therapeutic" refers to agents which either (i) mimic the effect of hedgehog proteins on patched signaling e.g., which induce expression of PTHrP, or (ii) activate or potentiate patched signaling and thereby repress hedgehog-mediated expression of PTHrP. The ptc therapeutic can be, e.g., a peptide, a nucleic acid, a carbohydrate, a small organic molecule, or natural product extract (or fraction thereof).

A "chondroinductive" hedgehog or ptc therapeutic is one which ultimately (noncytotoxically) inhibits the differentiation of chondrocytes into hypertrophic chondrocytes, such as by inducing expression of PTHrP, e.g., by perichondrial cells. The term also includes induction of proliferation of chondrocytes. In contrast, an "osteoinductive" hedgehog or ptc therapeutic is one which promotes differentiation of chondrocytes into hypertrophic chondrocytes, such as by inhibiting the direct effect of a hedgehog protein on a chondrocyte or hedgehog-mediated expression of expression of PTHrP, e.g., such as agents which competitively inhibit a wild-type Ihh protein from binding to patched.

As used herein, "proliferating" and "proliferation" refer to cells undergoing mitosis.

A "patient" or "subject" to be treated by the subject method can mean either a human or non-human animal.

An "effective amount" of, e.g., a hedgehog therapeutic, with respect to the subject method of treatment, refers to an amount of, e.g., a hedgehog polypeptide, which when applied as part of a desired dosage regimen brings about a change in the rate of proliferation and/or the state of differentiation of a chondrocyte cell to clinically acceptable standards for the disorder to be treated.

"Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. An "unrelated" or "non-homologous" sequence shares less than 40 percent identity, though preferably less than 25 percent identity, with a hedgehog sequence of the present invention.

The term "corresponds to", when referring to a particular polypeptide or nucleic acid sequence is meant to indicate that the sequence of interest is identical or homologous to the reference sequence to which it is said to correspond.

The terms "recombinant protein", "heterologous protein" and "exogenous protein" are used interchangeably throughout the specification and refer to a polypeptide which is produced by recombinant DNA techniques, wherein generally, DNA encoding the polypeptide is inserted into a suitable expression construct which is in turn used to transform a host cell to produce the heterologous protein. That is, the polypeptide is expressed from a heterologous nucleic acid.

A "chimeric protein" or "fusion protein" is a fusion of a first amino acid sequence encoding a hedgehog polypeptide with a second amino acid sequence defining a domain foreign to and not substantially homologous with any domain of hh protein. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula $(X)_n$—$(hh)_m$—$(Y)_n$, wherein hh represents all or a portion of the hedgehog protein, X and Y each independently represent an amino acid sequences which are not naturally found as a polypeptide chain contiguous with the hedgehog sequence, m is an integer greater than or equal to 1, and each occurrence of n is, independently, 0 or an integer greater than or equal to 1 (n and m are preferably no greater than 5 or 10).

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding one of the vertebrate hh polypeptides of the present invention, including both exon and (optionally) intron sequences. A "recombinant gene" refers to nucleic acid encoding a vertebrate hh polypeptide and comprising vertebrate hh-encoding exon sequences, though it may optionally include intron sequences which are either derived from a chromosomal vertebrate hh gene or from an unrelated chromosomal gene. Exemplary recombinant genes encoding the subject vertebrate hh polypeptide are represented by SEQ ID No:1, SEQ ID No:2, SEQ ID No:3, SEQ ID No:4, SEQ ID No:5, SEQ ID No:6 or SEQ ID No:7. The term "intron" refers to a DNA sequence present in a given vertebrate hh gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a vertebrate hh polypeptide or, where anti-sense expression occurs from the transferred gene, the expression of a naturally-occurring form of the vertebrate hh protein is disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the recombinant vertebrate hedgehog genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of hedgehog proteins.

As used herein, the terms "transforming growth factor-beta" and "TGF-β" denote a family of structurally related paracrine polypeptides found ubiquitously in vertebrates, and prototypic of a large family of metazoan growth, differentiation, and morphogenesis factors (see, for review, Massaque et al. (1990) *Ann Rev Cell Biol* 6:597–641; and Sporn et al. (1992) *J Cell Biol* 119:1017–1021). Included in this family are the "bone morphogenetic proteins" or "BMPs", which refers to proteins isolated from bone, and fragments thereof and synthetic peptides which are capable of inducing bone deposition alone or when combined with appropriate cofactors. Preparation of BMPs, such as BMP-1, -2, -3, and 4, is described in, for example, PCT publication WO 88/00205. Wozney (1989) *Growth Fact Res* 1:267–280 describes additional BMP proteins closely related to BMP-2, and which have been designated BMP-5, -6, and -7. PCT publications WO89/09787 and WO89/09788 describe a protein called "OP-1," now known to be BMP-7. Other BMPs are known in the art.

As used herein the term "approximately 19 kDa" with respect to N-terminal bioactive fragments of a hedgehog protein, refers to a polypeptide which can range in size from 16 kDa to 22 kDa, more preferably 18–20 kDa. In a preferred embodiment, "approximately 19 kDa" refers to a mature form of the peptide after the cleavage of the signal sequence and proteolysis to release an N-terminal portion of the mature protein. For instance, in the case of the Sonic hedgehog polypeptide, a fragment of approximately 19 kDa is generated when the mature polypeptide is cleaved at a proteolytic processing site which is located in the region between Ala-169 and Gly-178 of SEQ ID No:15, e.g., corresponding approximately to a fragment from Cys-1 to Gly-174 of SEQ ID No:15.

III. Exemplary Modes for the Modulating Bone Growth and Cartilage Growth

In one embodiment, the subject hedgehog and ptc therapeutics can be used to augment the treatment of a bone fracture. A fracture is the most common bone lesion and is defined as a break in the continuity of a bone or a part of its mineralized structure caused by a traumatic physical force. The subject method can be used to treat fractures which may be the result of an excessive impact, rotation, bending, or other mechanical force acting on previously normal bone or may be the consequence of an unnoticed or trivial injury of previously diseased bone (pathologic or spontaneous fracture). The method of the present invention may also be used as part of a treatment of a pathologic fracture, e.g., a fracture which develops in bone that is weakened by disease, such as: metastatic carcinoma, multiple myeloma, osteoporosis or other metabolic bone disease, primary tumor, and tumor-like disorders.

A fracture is described as complete or incomplete, simple (closed) or compound (open) if contiguous to an open external or internal wound, and comminuted if the bone is grossly splintered. A stress fracture is one that is caused by the cumulative effect of repeated episodes of physical stress on previously normal bone. Fracture healing may be complicated by delayed union, non-union, formation of false joint (pseudarthrosis), necrosis, infection, and underlying bone disease (pathologic fracture). The subject method can be used, in part, to alleviate this complicating conditions.

The process of fracture repair normally proceeds both internally (endosteally) and externally (subperiosteally) and, while continuous, is arbitrarily divisible into three stages occurring at approximately the following time intervals: by the second or third day, organization of hematoma and exudate by granulation tissue; by the fifth or sixth day, beginning formation of primitive or woven bone around the fracture (primary callus) which bridges the gap between the bone fragments and immobilizes them; by six weeks and beyond, replacement of callus by mature lamellar bone (secondary callus) and establishment of bony union.

Soon after injury, activated osteoblasts, derived from precursor cells in the elevated periosteum, the cortical surface, and the trabeculae on either side of the fracture, begin to deposit osteoid on the existing cortex and trabeculae or other solid tissue base. The osteoid becomes mineralized and forms primitive (woven) bone which surrounds the fracture, bridges the fracture gap, plugs the medullary cavity, and immobilizes the bone fragments. At this stage, a periosteal shell of mineralized callus may first appear in the clinical x-ray film. Small islands of cartilage may also be formed in the repair process, more so apparently in less vascularized or poorly immobilized regions of the fracture.

Next, the bulky external and internal callus of woven bone is slowly decreased in size and replaced by strong lamellar bone, and firm bony union is established. The process of bone remodeling by osteoclastic resorption and osteoblastic reformation takes place over subsequent weeks or months. The final result of fracture healing in a setting of good alignment, close positioning, and firm immobilization of bone fragments is to attain a normal anatomical and functional reconstitution of the bone cortex and medulla.

The application of hedgehog or ptc therapeutics at the fracture site may accordingly be varied depending on the stage of the healing process. For instance, it is expected that higher concentrations of the subject therapeutic compositions would be useful in the early stages of fracture healing, e.g., in order to augment the reformation of a cartilage model and production of the extracellular organic matrix. The administration of the hedgehog or ptc therapeutic can be tapered off as the healing process reaches those stages marked by secondary callus formation, e.g., when endochondral ossification rather than chondocyte proliferation is desired.

A contributory factor in delayed or non-union of fractures includes interposition of soft tissues between bone fragments. Under such circumstances, fibrous and fibrocartilaginous tissue formation may predominate in the repair process, resulting in fibrous union of the fracture or in the development of a false joint surfaced by fibrocartilage where the bone ends meet. In such instances, the use of bone inductive hedgehog or ptc therapeutics may be useful to enhance the ossification process rather than the proliferation of chondrocytes.

Many factors influence fracture repair, among them: the severity of injury; type of fracture; vascular damage; method of treatment; infection; age of patient; hormonal and nutritional factors; and systemic disease. Accordingly, the dosage, frequency of administration, supplementation with other agents and/or chondrocytes, and the like will vary from patient to patient, but will, however, be readily ascertainable by the skilled artisan.

The potential utility of an osteogenic device capable of inducing endochondral bone formation in vivo has been recognized widely. For instance, the present uses contemplated in the art for such devices include certain types of plastic surgery, and various periodontal and craniofacial reconstructive procedures. Thus, the present invention also relates to osteogenic devices, and more specifically to synthetic implants which induce osteogenesis in vivo, which are charged with a hedgehog or ptc therapeutic. More particularly, this invention relates to biocompatible, bioresorbable, synthetic matrices which promote endochondral bone growth in vivo.

It has been discovered that osteogenic protein dispersed within a porous, bioresorbable matrix including collagen and glycosaminoglycan is capable of inducing osteogenesis in vivo. This knowledge can be exploited in the present invention to develop osteogenic devices including hedgehog or ptc therapeutic formulations which induce the formation of endochondral bone in a mammalian host in a shape conforming substantially to the shape of the device. The devices may also be used as a surface coating for implantable prosthetic devices to promote cellular ingrowth.

In one embodiment, a porous matrix of the osteogenic device includes a cross-linked polymer of collagen and glycosaminoglycan with the hedgehog or ptc therapeutic dispersed within the porous matrix. Collagen is a major protein constituent of connective tissue in vertebrates and invertebrates. Type I collagen, Type II collagen, or mixtures thereof are preferable as the matrix material of the osteogenic device. Preferably collagen comprises about 80–95% by weight of the matrix. Glycosaminoglycans (GAGs) are mucopolysaccharides of animal origin. They are made up of residues of hexosamines glycosidically bound and alternating in a more-or-less regular manner with either hexuronic acid or hexose moieties. GAGs preferably make up at least about 5%, and more preferably, from about 6% to about 15% by weight of the polymer. Useful GAGs include those comprising sulfate groups such as chondroitin 4-sulfate, chondroitin 6-sulfate, hyaluronic acid, dermatan sulfate, keratan sulfate, heparin, heparan sulfate and combinations thereof. Preferably the matrix includes chondroitin 6-sulfate.

The collagen-GAG polymer is cross-linked to control the solubility and mechanical properties of the matrix. It is believed that cross-linking the matrix to an M[c]value (the average molecular weight between cross-links) of about 800 to about 60,000, and preferably to an M[c]of between 5,000 and 10,000, is preferred for the osteogenic device.

The invention is embodied as a method of growing bone by conduction including contacting a viable mammalian bone with, e.g., a hedgehog-doped cross-linked collagen-GAG matrix. Bone conduction is the growth of bone from existing viable bone, and involves the migration of osteoblasts from the bone to an area immediately adjacent the bone. In one aspect of the invention the matrix material is provided as a coating on an implant placed in contact with viable bone. Useful implants are composed of an inert material such as ceramic, metal, or polymer. In another aspect of the invention, conductive bone growth is induced from a viable mammalian bone by contacting the bone with matrix material into which has been dispersed a glue in an amount sufficient to solidify the matrix when implanted in a mammal or when placed at 37° C. A useful glue is methyl cellulose or other glue which may be compatible with the particular hedgehog or ptc therapeutic used in the implant. The matrix solidifies substantially in the shape of the implanted matrix.

Another aspect of this invention involves methods of producing the osteogenic device which contains a hedgehog or ptc therapeutic. The method includes providing a porous matrix comprising a polymer of collagen and GAG cross-linked, e.g., to an M[c] value of about 800 to about 60,000; and dispersing within the matrix a hedgehog or ptc therapeutic in an amount sufficient to induce endochondral bone formation substantially in the shape of the matrix when implanted in a host.

The dispersing step may include dispersing the hedgehog or ptc therapeutic in a solvent such as buffered saline or acetonitrile. If insoluble collagen is to be incorporated into the matrix, it, too, may be dispersed in the solvent. In one aspect of the invention, the solvent is an acidified, aqueous solution containing about 30% to about 55% acetonitrile, and preferably about 50% acetonitrile. The dispersion step may be conducted by dehydrating a mixture including the hedgehog or ptc therapeutic and particles of the collagen-GAG polymer. Alternatively, the dispersing step may be accomplished by lyophilizing the mixture. Lyophilization is dehydration of frozen material under vacuum.

Prior to the dispersing step, the matrix may be preequilibrated with the solvent in which the hedgehog or ptc therapeutic has been dispersed. The method may further include the steps of forming the product of the dispersion step into a shape with predetermined dimensions; and implanting the formed product into a mammal. Implantation of the device results in the induction of endochondral bone having essentially the shape of the formed product.

The method of the present invention can also be used in the treatment of congenital and hereditary bone disorders. For instance, it can be used as part of a therapy for treating achondroplasia. Briefly, achondroplasia is a congenital and often hereditary (autosomal dominant) skeletal disorder characterized by a unique form of dwarfism and bone deformity resulting in a disproportionate shortness of the extremities relative to the trunk. Achondroplasia is caused by a failure of proliferation and column formation of epiphysial cartilage cells, that is, by a defect in endochondral bone formation which impairs the longitudinal growth of the tubular bones.

Achondroplasia shows various degrees of expression. The severest cases result in fetal or neonatal death, and milder cases survive and comprise the commonest type of adult dwarfism. The adult height in achondroplasia is usually less than four feet. The extremities (legs, arms, fingers, toes) are very short (micromelia) relative to the trunk which is only slightly shortened. Intramembraneous ossification is not affected. The head (cranial vault) is large. The root of the nose is depressed. The skeletal deformities just noted along with normal intelligence and sexual development distinguish achondroplasia from dwarfism resulting from endocrine and nutritional deficiencies and other causes.

The microscopic changes in achondroplasia are best shown by a section of the epiphysis of a long bone during the neonatal period. The epiphysial growth plate is thin. There are few cells in the zone of proliferating cartilage. The hypertrophic cartilage cells form extremely irregular columns, if any, and as a result the zone of provisionally calcified cartilage is small and does not provide an adequate scaffolding for bone matrix deposition by metaphysical osteoblasts. Periosteal new-bone formation by osteoblasts is not impaired.

The subject method can be used, in various forms of this disease, to induce the proliferation of chondrocytes which ultimately become available to produce hypertrophic chondrocytes, e.g., to provide an adequate scaffolding for bone matrix deposition.

In yet another embodiment, the subject method can be used in the treatment of osteopetrosis (Marble Bone Disease, Osteosclerosis). Osteopetrosis is a hereditary, usually congenital, disorder of skeletal development characterized by massive but fragile bones, with marked thickening of cortical and medullary bone and concomitant reduction of the marrow space, and resulting in some cases in severe, even fatal, anemia and in blindness and deafness. The cause of osteopetrosis is unknown but the pathogenesis appears to be related to a defect in the function of osteoclasts in bone resorption and remodeling.

Radiographically and pathologically, all bones are affected, but the most significant changes in osteopetrosis occur in the bones which are preformed in cartilage. The long bones of the extremities, vertebrae, pelvic bones, and base of the skull show a great increase in the density and thickness of the cortex, an increase in the number and size of bony trabeculae, and a marked reduction or obliteration of the marrow spaces and haversian systems. The reduction in the total amount of bone marrow leads to anemia and extramedullary hemopoiesis, resulting in enlargement of the spleen, liver, and lymph nodes. Bone overgrowth at the base of the cranium causes narrowing of the optic foramina and pressure on the optic nerves, resulting in primary optic atrophy and blindness.

In addition to the increased density and mass of the long bones, the most characteristic microscopic change in medullary and cortical bone is the presence and persistence into adult life of spicules of calcified cartilage which normally would have been resorbed, replaced, and remodeled preparatory to endochondral ossification. These changes apparently reflect a basic defect in the function of osteoclasts in the resorption and remodeling of mineralized epiphysial cartilage. Osteoclasts and active osteoblasts are few in number. The bone tissue formed is largely woven bone, and very little of it is remodeled and replaced by lamellar bone. Although massive, the bone structure is of poor structure and easily fractured.

The subject method, such as may be carried out using hedgehog or ptc therapeutics which inhibit chodrocyte differentiation, can be used to manage osteopetrosis.

In other embodiments, the subject method can be used as part of a therapy to treat tumors and tumor-like lesions of bone. Primary bone tumors, either benign or malignant, may originate in cartilage cells, osteoblastic (osteoid- or bone-forming) cells, fibroblastic cells as well as primitive mesenchymal cells. For instance, the subject method can be used in treatment of both focal and diffuse lesions, e.g., such as solitary bone cysts, nonossifying fibromas, osteoporosis fibrous dysplasias, aneurysmal bone cysts, osteomalacia eosinophilic granulomas, exuberant fracture calluses, bone lesions resulting from hyperparathyroidism, myositis ossificans, Paget's disease of bone, and Gaucher's disease.

The subject method can also be used in the treatment of benign neoplasms of bone, such as enchondroma, osteochondroma, osteoid osteoma, osteoblastoma, giant cell tumor and chondroblastoma. Likewise, hedgehog and ptc therapeutics can be applied opportunely in the treatment of such malignant neoplasms of bone as, for example, chondrosarcomas, osteogenic sarcomas, medullary fibrosarcomas, multiple myelomas, metastatic carcinomas, Ewing's sarcomas, and metastatic carcinoma.

In choosing whether to use a osteoinductive or chondroinductive hedgehog or ptc therapeutic, as well as determining the dosage regimen and duration for administering a particular hedgehog or ptc therapeutic, there are many features of tumor and tumor-like bone lesion to be considered. Among these considerations are the presence or absence of mineralization of the tumor matrix; whether the lesion causes bone destruction (osteolytic lesion) or bone production (osteosclerotic lesion); presence of reactive periosteal new bone formation; destruction of cortex and extracortical tumor extension. Where the neoplasm is marked by unwanted proliferation of chondrocytes, osteoinductive forms of hedgehog and ptc therapeutics can be used, e.g., which inhibit expression of PTHrP or other proteins which may be providing proliferative paracrine signals to the chondrocytes. In this manner, the osteoinductive of the subject therapeutics can promote terminal differentiation of the hyperproliferative chondrocytes. Likewise, where the neoplastic tissue is bone-like in morphology, chondroinductive forms of hedgehog and ptc therapeutics can be used to inhibit differentiation of chondrocytes into hypertrophic cells which can contribute to the tumor mass. In this manner, the subject method can be use as part of a therapy to manage such proliferative disorders, e.g., as part of a broader therapeutic approach.

In a preferred embodiment, the subject method can be used in the treatment of cartilaginous tumor, such as osteochondroma (osteocartilaginous exostosis). Osteochondroma is the most common of the benign tumors or tumor-like lesions of bone, may occur in almost any bone preformed in cartilage, particularly long tubular bones, and presents as a solitary cartilage-capped bony outgrowth protruding from the bone surface near the metaphysis. Solitary osteochondroma most commonly occurs in children and shows no notable difference in sex incidence. An osteochondroma is quite as much an anomaly of skeletal development as a neoplasm. It grows by the aberrant proliferation of epiphysial cartilage cells and resulting endochondral ossification, and its growth ceases at, or prior to, the time of skeletal maturation. The most common location of an osteochondroma is in the region of the knee, particularly the lower metaphysis of the femur or the upper metaphysis of the tibia.

Microscopically, an osteochondroma has a cap of mature cartilage beneath which, if the lesion is actively growing, are proliferating cartilage cells growing in columns and undergoing endochondral ossification, much as seen in the epiphysial growth plate.

The subject method, employing osteoinductive forms of hedgehog or ptc therapeutic, may cause differentiation of the proliferating chondrocytes, e.g., and can inhibit further growth of the osteochondroma by differentiation therapy. In other embodiments, a PTHrP antagonist can be used to inhibit proliferation of the chondrocytes.

In other embodiments, the subject method can be used to treat enchondromas of bone. An enchondroma is a benign tumor which is composed of mature hyaline cartilage and develops in the medullary cavity of a single bone. This tumor usually occurs in the third to sixth decades of life, with the average age of occurrence between 30 and 40 years. The most common location is in the bones of the hand: about one-third of all cases occur in the phalanges. The bones of the foot, a long tubular bone such as the humerus or femur, and the pelvic and shoulder girdles are sometimes involved. The typical x-ray picture of an enchondroma shows a central, or slightly eccentric, well-circumscribed or "bubbly" radiolucent lesion, finely or densely stippled with calcification, and located in the interior of a short or long tubular bone.

As an enchondroma of a phalanx enlarges, it may cause thinning, bulging, or pathological fracture of the overlying cortex. Although usually seen in the metaphysis near the epiphysis, an enchondroma may extend to the end of an ossified epiphysis. The subject method, by utilizing an osteoinductive hedgehog or ptc therapeutic, or PTHrP antagonist, can be used to inhibit proliferation of the neoplastic cartilage cells of an enchondroma.

The subject method can also be used in the treatment of chondrosarcomas of bone, a malignant cartilaginous tumor in which the basic neoplastic component is cartilage, without tumor osteoid or bone being formed by the sarcomatous stroma. Chondrosarcoma usually occurs in the third to sixth decades of life (average age of 45 years) and is slightly more common in males than females. Chondrosarcomas are most commonly located in the flat bones of the pelvis, the large limb bones, and the ribs. Approximately 25% of cases occur in the femur; the ribs and the humerus are the next most common sites. Grossly, a central chondrosarcoma of a long bone is composed of confluent lobules of glistening white hyaline cartilage with dull grey gritty areas of calcification. The tumor infiltrates the medullary cavity, erodes and penetrates the cortex, and expands into the surrounding soft tissue. In the art, chondrosarcomas are treated by major surgery, such as amputation, chest wall resection, and hemipelvectomy. With surgery, the five year survival rate is approximately 40%. The subject method can be used in place of surgical resection, or to augment such approaches.

In another embodiment, the subject method can be used in the treatment of osteogenic sarcoma (OSA), which is a malignant tumor of bone in which the proliferating malignant spindle-cell stroma directly produces osteoid or immature bone. OSA is clinically subdivided into primary OSA which is the most common and arises de novo in the absence of preexisting bone disease and secondary OSA which is a complication of some other bone disease or process. Excluding multiple myeloma, OSA is the most common primary malignant bone tumor.

OSA occurs most often in young people under 20 years of age, with a peak incidence in the second decade of life (corresponding to the adolescent growth phase) and a male to female incidence ratio of about 2:1. Overall, OSA has a bimodal age distribution with the first peak as mentioned and a second, but lesser, peak beyond 40 years of age, developing secondary to preexisting disease, such as Paget's disease (Paget's sarcoma), previous radiation (irradiation sarcoma), or other conditions. OSA may occur in virtually any bone, but the most frequent location is near the knee (~50–60% of cases), most commonly in the distal end of the femur followed, in order of frequency, by the upper end of the tibia, upper end of the humerus, pelvis, and upper end of the femur. Less common examples of OSA reveal mainly destructive (osteolytic) lesions with a "moth eaten" appearance of the cortex.

The cause of OSA is not known but, as with most other human cancers, may involve genetic, environmental, and other factors. Notably, OSA develops most often in places of most active bone growth, such as the long bones near the knees in adolescence or a site of Paget's disease in older persons. Grossly, a typical OSA is composed of gritty to hard tumor tissue which involves the entire width of the medullary canal, erodes and penetrates the cortex, and extends into the neighboring soft tissues. Microscopically, an OSA is characterized and defined by proliferating malignant spindle-cell stroma which directly forms osteoid or immature bone.

As appropriate an osteoinductive form of the subject hedgehog or ptc therapeutic can be used to induce differentiation of the proliferating chondrocytes.

The subject method can also be used in treatment of various different metabolic bone disorders. Bone turnover and remodeling occurs throughout life and involves the two coupled processes of bone formation by osteoblasts and bone resorption by osteoclasts and perhaps osteolytic osteocytes. The metabolic bone diseases may reflect disturbances in the organic matrix, the mineral phase, the cellular processes of remodeling, and the endocrine, nutritional, and other factors which regulate skeletal and mineral homeostasis. These disorders may be hereditary or acquired and usually affect the entire bony skeleton. The acquired metabolic bone diseases are the more common and include: osteoporosis, osteomalacia, the skeletal changes of hyperparathyroidism and chronic renal failure (renal osteodystrophy), and osteitis deformans (Paget's disease of bone).

Osteoporosis is defined as a decrease in bone density (mass per unit volume) of normally mineralized bone, resulting in thinning and increased porosity of the bone cortices and trabeculae. The bone that is lost in osteoporosis existed at a previous time. The bone that remains, although diminished in amount, is normally mineralized and lacks the wide osteoid seams which are typical of osteomalacia and other disorders of bone mineralization. Osteoporosis is also a broadly used clinical term for a generalized loss of bone density resulting in skeletal fragility, bone pain, and pathological fractures (of the spine, wrist, hip, and ribs), particularly in postmenopausal women and both sexes with increasing age. The subject method, particularly when combined with addition of chondrocytes to a lesion, can be used in the treatment of osteoporosis.

Moreover, although not the only factor in pathogenesis, sex-hormone deficiency is involved in the development of postmenopausal and senile osteoporosis. Briefly, estrogens apparently react with osteoblasts via high-affinity estrogen receptors. In women with a balanced state of the bone mass, estrogen-mediated bone formation by osteoblasts offsets parathyroid hormone (PTH)-mediated bone resorption by osteoclasts. With withdrawal of estrogen (or of androgen in men), PTH-mediated osteoclast activity predominates, resulting in increased resorption and loss of bone. Accordingly, the subject method can be carried out with conjoint administration of estrogen or other suitable analog thereof.

Likewise, the subject method can be used in the treatment of osteopenia. Osteopenia ("too little" bone) is a descriptive term for a loss of bone density observed radiologically. Osteopenia may be local (as in disuse atrophy of an immobilized limb) or generalized. There are many causes of generalized osteopenia, among them: osteoporosis unrelated to other disease, endocrinopathies (hypercortisolism, hypogonadism, hyperparathyroidism, hyperthyroidism), deficiency states (rickets/osteomalacia, scurvy, malnutrition), neoplastic diseases (multiple myeloma, metastatic carcinoma, leukemia), chronic diseases (malabsorption syndromes, chronic renal failure), drugs (glucocorticoids, heparin, alcohol), and hereditary diseases (osteogenesis imperfecta, homocystinuria).

The subject method can also be used as part of a therapy for the treatment of such disorders as rickets and osteomalacia. The diseases resulting from vitamin D deficiency are rickets in infants and growing children and osteomalacia in adult life. The bone changes in both conditions are characterized by inadequate mineralization, resulting in a deficient amount of the mineral phase of bone and an excess of unmineralized osteoid. The osteoid excess is caused by a failure of the process of mineralization to keep up with the new formation of osteoid during bone formation and remodeling. In rickets, which mainly affects children between the ages of 6–30 months, inadequate mineralization occurs not only in bone but also in epiphysial cartilage at sites of endochondral ossification, resulting in growth disturbances, skeletal deformities, and susceptibility to fractures. Presenting symptoms of osteomalacia ("softness of bone") include diffuse skeletal pain, bone tenderness, and muscular weakness. As part of a treatment protocol, the subject method can provide a means for augmenting formation of normal, mature bone in patients being treated for rickets or osteomalacia.

In still another embodiment, the subject method can be used to treat bone changes accompanying hyperparathyroidism (e.g., generalized osteitis, fibrosa cystica, von Recklinghausen's disease of Bone). The skeletal changes in hyperparathyroidism are characterized by diffuse or focal resorptive loss and fibrous replacement of bone due to an excess of osteoclastic over osteoblastic activity and caused by an over-production of parathormone (PTH) in primary or secondary hyperparathyroidism.

In yet another embodiment, the subject method can be used to treat Paget's disease of bone (Osteitis Deformans). Paget's disease of bone (osteitis deformans) is a localized, although sometimes multifocal, skeletal disorder of unknown cause and is characterized by abnormal bone remodeling brought about by waves of bone resorption and reformation. The skeletal involvement may be limited to a single bone (monostotic) or affect many bones (polyostotic), notably the pelvis, femur, tibia, spine, and skull. The affected bones may be weakened by resorption or enlarged by reparative, although defective, new-bone formation. In the final stage of the disease, dense bone is formed, but it is poorly organized and predisposed to fracture and deformity. The subject method can be carried out using either a osteogenic or a chrondogenic form of a hedgehog or ptc therapeutic, depending on whether the disease is manifest with weakened or enlarged bone deformities.

IV. Exemplary Hedgehog Therapeutic Compounds.

The hedgehog therapeutic compositions of the subject method can be generated by any of a variety of techniques, including purification of naturally occurring proteins, recombinantly produced proteins and synthetic chemistry. Polypeptide forms of the hedgehog therapeutics are preferably derived from vertebrate hedgehog proteins, e.g., have sequences corresponding to naturally occurring hedgehog proteins, or fragments thereof, from vertebrate organisms. However, it will be appreciated that the hedgehog polypeptide can correspond to a hedgehog protein (or fragment thereof) which occurs in any metazoan organism.

The various naturally-occurring hedgehog proteins from which the subject therapeutics can be derived are characterized by a signal peptide, a highly conserved N-terminal region, and a more divergent C-terminal domain. In addition to signal sequence cleavage in the secretory pathway (Lee, J. J. et. al. (1992) Cell 71:33–50; Tabata, T. et al. (1992) Genes Dev. 2635–2645; Chang, D. E. et al (1994) Development 120:3339–3353), hedgehog precursor proteins naturally undergo an internal autoproteolytic cleavage which depends on conserved sequences in the C-terminal portion (Lee et al. (1994) Science 266:1528–1537; Porter et al. (1995) Nature 374:363–366). This autocleavage leads to a 19 kD N-terminal peptide and a C-terminal peptide of 26–28 kD (Lee et al. (1992) supra; Tabata et al. (1992) supra; Chang et al. (1994) supra; Lee et al. (1994) supra; Bumcrot, D. A., et al. (1995) Mol. Cell. Biol. 15:2294–2303; Porter et al. (1995) supra; Ekker, S. C. et al. (1995) Curr. Biol. 5:944–955; Lai, C. J. et al. (1995) Development 121:2349–2360). The N-terminal peptide stays tightly associated with the surface of cells in which it was synthesized, while the C-terminal peptide is freely diffusible both in vitro and in vivo (Lee et al. (1994) supra; Bumcrot et al. (1995) supra; Mart', E. et al (1995) Development 121:2537–2547; Roelink, H. et al (1995) Cell 81:445–455). Cell surface retention of the N-terminal peptide is dependent on autocleavage, as a truncated form of hedgehog encoded by an RNA which terminates precisely at the normal position of internal cleavage is diffusible in vitro (Porter et a. (1995) supra) and in vivo (Porter, J. A. et al. (1996) Cell 86, 21–34). Biochemical studies have shown that the autoproteolytic cleavage of the hedgehog precursor protein proceeds through an internal thioester intermediate which subsequently is cleaved in a nucleophilic substitution. It is suggested that the nucleophile is a small lipophilic molecule, more particularly cholesterol, which becomes covalently bound to the C-terminal end of the N-peptide (Porter et al. (1996) supra), tethering it to the cell surface.

Moreover, mutagenesis can be used to create modified hh polypeptides, e.g., for such purposes as enhancing therapeutic or prophylactic efficacy, or stability (e.g., ex vivo shelf life and resistance to proteolytic degradation in vivo). Such modified forms of the polypeptides can also be used to generate antagonist forms of the protein, e.g., which bind to a receptor for hedgehog proteins, but do not induce singling by the receptor to the extent a naturally occurring hedgehog protein would, and which competitively inhibit the binding of a naturally occurring hedgehog polypeptide to the receptor. Such modified peptides can be produced, for instance, by amino acid substitution, deletion, or addition. Modified hedgehog polypeptides can also include those with altered post-translational processing relative to a naturally occurring hedgehog protein, e.g., altered glycosylation, cholesterolization, prenylation and the like.

The vertebrate family of hedgehog genes includes at least four members, e.g., paralogs of the single drosophila hedgehog gene (SEQ ID No. 19). Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. According to the appended sequence listing, (see also Table 1) a chicken Shh polypeptide is encoded by SEQ ID No:1; a mouse Dhh polypeptide is encoded by SEQ ID No:2; a mouse Ihh polypeptide is encoded by SEQ ID No:3; a mouse Shh polypeptide is encoded by SEQ ID No:4 a zebrafish Shh polypeptide is encoded by SEQ ID No:5; a human Shh polypeptide is encoded by SEQ ID No:6; a human Ihh polypeptide is encoded by SEQ ID No:7; a human Dhh polypeptide is encoded by SEQ ID No. 8; and a zebrafish Thh is encoded by SEQ ID No. 9.

TABLE 1

Guide to hedgehog sequences in Sequence Listing

|  | Nucleotide | Amino Acid |
| --- | --- | --- |
| Chicken Shh | SEQ ID No. 1 | SEQ ID No. 10 |
| Mouse Dhh | SEQ ID No. 2 | SEQ ID No. 11 |
| Mouse Ihh | SEQ ID No. 3 | SEQ ID No. 12 |
| Mouse Shh | SEQ ID No. 4 | SEQ ID No. 13 |
| Zebrafish Shh | SEQ ID No. 5 | SEQ ID No. 14 |
| Human Shh | SEQ ID No. 6 | SEQ ID No. 15 |
| Human Ihh | SEQ ID No. 7 | SEQ ID No. 16 |
| Human Dhh | SEQ ID No. 8 | SEQ ID No. 17 |
| Zebrafish Thh | SEQ ID No. 9 | SEQ ID No. 18 |
| Drosophila HH | SEQ ID No. 19 | SEQ ID No. 20 |

In addition to the sequence variation between the various hedgehog homologs, the hedgehog proteins are apparently present naturally in a number of different forms, including a pro-form, a full-length mature form, and several processed fragments thereof. The pro-form includes an N-terminal signal peptide for directed secretion of the extracellular domain, while the full-length mature form lacks this signal sequence. Further processing of the mature form occurs in some instances to yield biologically active fragments of the protein. For instance, sonic hedgehog undergoes additional proteolytic processing to yield two peptides of approximately 19 kDa and 27 kDa, the 19 kDa fragment corresponding to an proteolytic N-terminal portion of the mature protein. In addition to proteolytic fragmentation, the vertebrate hedgehog proteins can also be modified post-translationally, such as by glycosylation and/or addition of cholesterol, though bacterially produced (e.g. unglycosylated/uncholesterolized) forms of the proteins still maintain certain of the bioactivities of the native protein. Bioactive fragments of hedgehog polypeptides of the present invention have been generated and are described in great detail in, e.g., PCT publications WO 95/18856 and WO 96/17924.

In one embodiment, the hedgehog therapeutic is a polypeptide encodable by a nucleotide sequence that hybridizes under stringent conditions to a hedgehog coding sequence represented in one or more of SEQ ID Nos:1–9. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

As described in the literature, genes for other hedgehog proteins, e.g., from other animals, can be obtained from mRNA or genomic DNA samples using techniques well known in the art. For example, a cDNA encoding a hedgehog protein can be obtained by isolating total mRNA from a cell, e.g. a mammalian cell, e.g. a human cell, including embryonic cells. Double stranded cDNAs can then be prepared from the total mRNA, and subsequently inserted into a suitable plasmid or bacteriophage vector using any one of a number of known techniques. The gene encoding a hedgehog protein can also be cloned using established polymerase chain reaction techniques.

Homologs of naturally occurring hedgehog proteins can be generated by mutagenesis, such as by discrete point mutation(s), or by truncation. For instance, mutation can give rise to homologs which retain substantially the same, or merely a subset, of the biological activity of the hedgehog polypeptide from which it was derived. Alternatively, antagonistic forms of the protein can be generated which are able to inhibit the function of the naturally occurring form of the protein, such as by competitively binding to an hedgehog receptor.

Preferred nucleic acids encode a hedgehog polypeptide comprising an amino acid sequence at least 60% homologous, more preferably 70% homologous and most preferably 80% homologous with an amino acid sequence selected from the group consisting of SEQ ID Nos:8–14. Nucleic acids which encode polypeptides at least about 90%, more preferably at least about 95%, and most preferably at least about 98–99% homology with an amino acid sequence represented in one of SEQ ID Nos:8–14 are also within the scope of the invention.

Hedgehog polypeptides preferred by the present invention, in addition to native hedgehog proteins, are at least 60% homologous, more preferably 70% homologous and most preferably 80% homologous with an amino acid sequence represented by any of SEQ ID Nos:8–14. Polypeptides which are at least 90%, more preferably at least 95%, and most preferably at least about 98–99% homologous with a sequence selected from the group consisting of SEQ ID Nos:8–14 are also within the scope of the invention, or by competitively inhibiting a wild-type hedgehog protein from inducing expression of PTHrP.

The term "recombinant protein" refers to a polypeptide of the present invention which is produced by recombinant DNA techniques, wherein generally, DNA encoding a hedgehog polypeptide is inserted into a suitable expression vector which is in turn used to transform a host cell to produce the heterologous protein. Moreover, the phrase "derived from", with respect to a recombinant hedgehog gene, is meant to include within the meaning of "recombinant protein" those proteins having an amino acid sequence of a native hedgehog protein, or an amino acid sequence similar thereto which is generated by mutations including substitutions and deletions (including truncation) of a naturally occurring form of the protein.

The method of the present invention can also be carried out using variant forms of the naturally occurring hedgehog polypeptides, e.g., mutational variants.

As is known in the art, hedgehog polypeptides can be produced by standard biological techniques. For example, a host cell transfected with a nucleic acid vector directing expression of a nucleotide sequence encoding the subject polypeptides can be cultured under appropriate conditions to allow expression of the peptide to occur. The polypeptide hedgehog may be secreted and isolated from a mixture of cells and medium containing the recombinant hedgehog polypeptide. Alternatively, the peptide may be retained cytoplasmically by removing the signal peptide sequence from the recombinant hedgehog gene and the cells harvested, lysed and the protein isolated. A cell culture includes host cells, media and other byproducts. Suitable media for cell culture are well known in the art. The recombinant hedgehog polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant hedgehog polypeptide is a fusion protein containing a domain which facilitates its purification, such as an hedgehog/GST fusion protein. The host cell may be any prokaryotic or eukaryotic cell.

Recombinant hedgehog genes can be produced by ligating nucleic acid encoding an hedgehog protein, or a portion thereof, into a vector suitable for expression in either prokaryotic cells, eukaryotic cells, or both. Expression vectors for production of recombinant forms of the subject hedgehog polypeptides include plasmids and other vectors. For instance, suitable vectors for the expression of a hedgehog polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used. In an illustrative embodiment, an hedgehog polypeptide is produced recombinantly utilizing an expression vector generated by sub-cloning the coding sequence of one of the hedgehog genes represented in SEQ ID Nos:1–9.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art.

For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

In some instances, it may be desirable to express the recombinant hedgehog polypeptide by the use of a baculovirus expression system. Examples of such baculovirus expression systems include pVL-derived vectors (such as pVL1392, pVL1393 and pVL941), pAcUW-derived vectors (such as pAcUWI), and pBlueBac-derived vectors (such as the β-gal containing pBlueBac III).

When it is desirable to express only a portion of an hedgehog protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) PNAS 84:2718–1722). Therefore, removal of an N-terminal methionine, if desired, can be achieved either in vivo by expressing hedgehog-derived polypeptides in a host which produces MAP (e.g., *E. coli* or CM89 or *S. cerevisiae*), or in vitro by use of purified MAP (e.g., procedure of Miller et al., supra).

Alternatively, the coding sequences for the polypeptide can be incorporated as a part of a fusion gene including a nucleotide sequence encoding a different polypeptide. It is widely appreciated that fusion proteins can also facilitate the expression of proteins, and accordingly, can be used in the expression of the hedgehog polypeptides of the present invention. For example, hedgehog polypeptides can be generated as glutathione-S-transferase (GST-fusion) proteins. Such GST-fusion proteins can enable easy purification of the hedgehog polypeptide, as for example by the use of glutathione-derivatized matrices (see, for example, Current Protocols in Molecular Biology, eds. Ausubel et al. (N.Y.: John Wiley & Sons, 1991)). In another embodiment, a fusion gene coding for a purification leader sequence, such as a poly-(His)/enterokinase cleavage site sequence, can be used to replace the signal sequence which naturally occurs at the N-terminus of the hedgehog protein (e.g. of the pro-form, in order to permit purification of the poly(His)-hedgehog protein by affinity chromatography using a $Ni^{2+}$ metal resin. The purification leader sequence can then be subsequently removed by treatment with enterokinase (e.g., see Hochuli et al. (1987) *J. Chromatography* 411:177; and Janknecht et al. PNAS 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Hedgehog polypeptides may also be chemically modified to create hedgehog derivatives by forming covalent or aggregate conjugates with other chemical moieties, such as glycosyl groups, cholesterol, isoprenoids, lipids, phosphate, acetyl groups and the like. Covalent derivatives of hedgehog proteins can be prepared by linking the chemical moieties to functional groups on amino acid sidechains of the protein or at the N-terminus or at the C-terminus of the polypeptide.

For instance, hedgehog proteins can be generated to include a moiety, other than sequence naturally associated with the protein, that binds a component of the extracellular matrix and enhances localization of the analog to cell surfaces. For example, sequences derived from the fibronectin "type-III repeat", such as a tetrapeptide sequence R-G-D-S (Pierschbacher et al. (1984) *Nature* 309:30–3; and Komblihtt et al. (1985) *EMBO* 4:1755–9) can be added to the hedgehog polypeptide to support attachment of the chimeric molecule to a cell through binding ECM components (Ruoslahti et al. (1987) *Science* 238:491–497; Pierschbacher et al. (1987) J. Biol. Chem. 262:17294–8; Hynes (1987) *Cell* 48:549–54; and Hynes (1992) *Cell* 69:11–25).

In preferred embodiment, the hedgehog polypeptide is isolated from, or is otherwise substantially free of, other cellular proteins, especially other extracellular or cell surface associated proteins which may normally be associated with the hedgehog polypeptide. The term "substantially free of other cellular or extracellular proteins" (also referred to herein as "contaminating proteins") or "substantially pure or purified preparations" are defined as encompassing preparations of hedgehog polypeptides having less than 20% (by dry weight) contaminating protein, and preferably having less than 5% contaminating protein. By "purified", it is meant that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

As described above for recombinant polypeptides, isolated hedgehog polypeptides can include all or a portion of the amino acid sequences represented in any of SEQ ID Nos: 10–18 or 20, or a homologous sequence thereto. Preferred fragments of the subject hedgehog proteins correspond to the N-terminal and C-terminal proteolytic fragments of the mature protein. Bioactive fragments of hedgehog polypeptides are described in great detail in PCT publications WO 95/18856 and WO 96/17924.

With respect to bioactive fragments of hedgehog polypeptide, preferred hedgehog therapeutics include at least 50 amino acid residues of a hedgehog polypeptide, more preferably at least 100, and even more preferably at least 150.

Another preferred hedgehog polypeptide which can be included in the hedgehog therapeutic is an N-terminal fragment of the mature protein having a molecular weight of approximately 19 kDa.

Preferred human hedgehog proteins include N-terminal fragments corresponding approximately to residues 24–197 of SEQ ID No. 15, 28–202 of SEQ ID No. 16, and 23–198 of SEQ ID No. 17. By "corresponding approximately" it is meant that the sequence of interest is at most 20 amino acid residues different in length to the reference sequence, though more preferably at most 5, 10 or 15 amino acid different in length.

Still other preferred hedgehog polypeptides includes an amino acid sequence represented by the formula A-B wherein: (i) A represents all or the portion of the amino acid sequence designated by residues 1–168 of SEQ ID No:21; and B represents at least one amino acid residue of the amino acid sequence designated by residues 169–221 of SEQ ID No:21; (ii) A represents all or the portion of the amino acid sequence designated by residues 24–193 of SEQ ID No:15; and B represents at least one amino acid residue of the amino acid sequence designated by residues 194–250 of SEQ ID No:15; (iii) A represents all or the portion of the amino acid sequence designated by residues 25–193 of SEQ ID No:13; and B represents at least one amino acid residue of the amino acid sequence designated by residues 194–250 of SEQ ID No: 13; (iv) A represents all or the portion of the amino acid sequence designated by residues 23–193 of SEQ ID No: 11; and B represents at least one amino acid residue of the amino acid sequence designated by residues 194–250 of SEQ ID No: 11; (v) A represents all or the portion of the amino acid sequence designated by residues 28–197 of SEQ ID No:12; and B represents at least one amino acid residue of the amino acid sequence designated by residues 198–250 of SEQ ID No: 12; (vi) A represents all or the portion of the amino acid sequence designated by residues 29–197 of SEQ ID No:16; and B represents at least one amino acid residue of the amino acid sequence designated by residues 198–250 of SEQ ID No:16; or (vii) A represents all or the portion of the amino acid sequence designated by residues 23–193 of SEQ ID No. 17, and B represents at least one amino acid residue of the amino acid sequence designated by residues 194–250 of SEQ ID No. 17. In certain preferred embodiments, A and B together represent a contiguous polypeptide sequence designated sequence, A represents at least 25, 50, 75, 100, 125 or 150 amino acids of the designated sequence, and B represents at least 5, 10, or 20 amino acid residues of the amino acid sequence designated by corresponding entry in the sequence listing, and A and B together preferably represent a contiguous sequence corresponding to the sequence listing entry. Similar fragments from other hedgehog also contemplated, e.g., fragments which correspond to the preferred fragments from the sequence listing entries which are enumerated above. Isolated peptidyl portions of hedgehog proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a hedgehog polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") hedgehog protein. For example, Roman et al. (1994) *Eur J Biochem* 222:65–73 describe the use of competitive-binding assays using short, overlapping synthetic peptides from larger proteins to identify binding domains.

The recombinant hedgehog polypeptides of the present invention also include homologs of the authentic hedgehog proteins, such as versions of those protein which are resistant to proteolytic cleavage, as for example, due to mutations which alter potential cleavage sequences or which inactivate an enzymatic activity associated with the protein. Hedgehog homologs of the present invention also include proteins which have been post-translationally modified in a manner different than the authentic protein. Exemplary derivatives of hedgehog proteins include polypeptides which lack N-glycosylation sites (e.g. to produce an unglycosylated protein), which lack sites for cholesterolization, and/or which lack N-terminal and/or C-terminal sequences.

Modification of the structure of the subject hedgehog polypeptides can also be for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the hedgehog polypeptides described in more detail herein. Such modified peptides can be produced, for instance, by amino acid substitution, deletion, or addition.

It is well known in the art that it one reasonably expect that certain isolated replacements of amino acids, e.g., replacement of an amino acid residue with another related amino acid (i.e. isosteric and/or isoelectric mutations), can be carried out without major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (I) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide= asparagine, glutamine; and (6) sulfur-containing=cysteine and methionine. (see, for example, *Biochemistry*, 2nd ed., Ed. by L. Stryer, WH Freeman and Co.: 1981). Whether a change in the amino acid sequence of a peptide results in a functional hedgehog homolog (e.g. functional in the sense that it acts to mimic or antagonize the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

It is specifically contemplated that the methods of the present invention can be carried using homologs of naturally occurring hedgehog proteins. In one embodiment, the invention contemplates using hedgehog polypeptides generated by combinatorial mutagenesis. Such methods, as are known in the art, are convenient for generating both point and truncation mutants, and can be especially useful for identifying potential variant sequences (e.g. homologs) that are functional in binding to a receptor for hedgehog proteins. The purpose of screening such combinatorial libraries is to generate, for example, novel hedgehog homologs which can act as either agonists or antagonist. To illustrate, hedgehog homologs can be engineered by the present method to provide more efficient binding to a cognate receptor, such as patched, yet still retain at least a portion of an activity associated with hedgehog. Thus, combinatorially-derived homologs can be generated to have an increased potency relative to a naturally occurring form of the protein. Likewise, hedgehog homologs can be generated by the present combinatorial approach to act as antagonists, in that they are able to mimic, for example, binding to other extracellular matrix components (such as receptors), yet not induce any biological response, thereby inhibiting the action of authentic hedgehog or hedgehog agonists. Moreover, manipulation of certain domains of hedgehog by the present method can provide domains more suitable for use in fusion proteins, such as one that incorporates portions of other proteins which are derived from the extracellular matrix and/or which bind extracellular matrix components.

To further illustrate the state of the art of combinatorial mutagenesis, it is noted that the review article of Gallop et al. (1994) *J Med Chem* 37:1233 describes the general state of the art of combinatorial libraries as of the earlier 1990's. In particular, Gallop et al state at page 1239 "[s]creening the analog libraries aids in determining the minimum size of the active sequence and in identifying those residues critical for binding and intolerant of substitution". In addition, the Ladner et al. PCT publication WO90/02809, the Goeddel et al. U.S. Pat. No. 5,223,408, and the Markland et al. PCT publication WO92/15679 illustrate specific techniques which one skilled in the art could utilize to generate libraries of hedgehog variants which can be rapidly screened to identify variants/fragments which retained a particular activity of the hedgehog polypeptides. These techniques are exemplary of the art and demonstrate that large libraries of related variants/truncants can be generated and assayed to isolate particular variants without undue experimentation. Gustin et al. (1993) *Virology* 193:653, and Bass et al. (1990) *Proteins: Structure, Function and Genetics* 8:309–314 also describe other exemplary techniques from the art which can be adapted as means for generating mutagenic variants of hedgehog polypeptides.

Indeed, it is plain from the combinatorial mutagenesis art that large scale mutagenesis of hedgehog proteins, without any preconceived ideas of which residues were critical to the biological function, and generate wide arrays of variants having equivalent biological activity. Indeed, it is the ability of combinatorial techniques to screen billions of different variants by high throughout analysis that removes any requirement of a priori understanding or knowledge of critical residues.

To illustrate, the amino acid sequences for a population of hedgehog homologs or other related proteins are aligned, preferably to promote the highest homology possible. Such a population of variants can include, for example, hedgehog homologs from one or more species. Amino acids which appear at each position of the aligned sequences are selected to create a degenerate set of combinatorial sequences. In a preferred embodiment, the variegated library of hedgehog variants is generated by combinatorial mutagenesis at the nucleic acid level, and is encoded by a variegated gene library. For instance, a mixture of synthetic oligonucleotides can be enzymatically ligated into gene sequences such that the degenerate set of potential hedgehog sequences are expressible as individual polypeptides, or alternatively, as a set of larger fusion proteins (e.g. for phage display) containing the set of hedgehog sequences therein.

As illustrated in PCT publication WO 95/18856, to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial.

In an illustrative embodiment, alignment of exons 1, 2 and a portion of exon 3 encoded sequences (e.g. the N-terminal approximately 221 residues of the mature protein) of each of the Shh clones produces a degenerate set of Shh polypeptides represented by the general formula:

C-G-P-G-R-G-X(1)-G-X(2)-R-R-H-P-K-K-L-T-P-L-A-Y-K-Q-F-I-P-N-V-A-E-

K-T-L-G-A-S-G-R-Y-E-G-K-I-X(3)-R-N-S-E-R-F-K-E-L-T-P-N-Y-N-P-D-I-I-F-

K-D-E-E-N-T-G-A-D-R-L-M-T-Q-R-C-K-D-K-L-N-X(4)-L-A-I-S-V-M-N-X(5)-

W-P-G-V-X(6)-L-R-V-T-E-G-W-D-E-D-G-H-H-X(7)-E-E-S-L-H-Y-E-G-R-A-

V-D-I-T-T-S-D-R-D-X(8)-S-K-Y-G-X(9)-L-X(10)-R-L-A-V-E-A-G-F-D-W-V-

Y-Y-E-S-K-A-H-I-H-C-S-V-K-A-E-N-S-V-A-A-K-S-G-G-C-F-P-G-S-A-X(11)-

V-X(I 2)-L-X(13)-X(14)-G-G-X(15)-K-X-(16)-V-K-D-L-X(17)-P-G-D-X(I 8)-V-

L-A-A-D-X(19)-X(20)-G-X(21)-L-X(22)-X(23)-S-D-F-X(24)-X(25)-F-X(26)-D-

R (SEQ ID No: 21), wherein each of the degenerate positions "X" can be an amino acid which occurs in that position in one of the human, mouse, chicken or zebrafish Shh clones, or, to expand the library, each X can also be selected from amongst amino acid residue which would be conservative substitutions for the amino acids which appear naturally in each of those positions. For instance, Xaa(1) represents Gly, Ala, Val, Leu, Ile, Phe, Tyr or Trp; Xaa(2) represents Arg, His or Lys; Xaa(3) represents Gly, Ala, Val, Leu, Ile, Ser or Thr; Xaa(4) represents Gly, Ala, Val, Leu, Ile, Ser or Thr; Xaa(5) represents Lys, Arg, His, Asn or Gin; Xaa(6) represents Lys, Arg or His; Xaa(7) represents Ser, Thr, Tyr, Trp or Phe; Xaa(8) represents Lys, Arg or His; Xaa(9) represents Met, Cys, Ser or Thr; Xaa(10) represents Gly, Ala, Val, Leu, Ile, Ser or Thr; Xaa(11) represents Leu, Val, Met, Thr or Ser; Xaa(12) represents His, Phe, Tyr, Ser, Thr, Met or Cys; Xaa(13) represents Gin, Asn, Glu, or Asp; Xaa(14) represents His, Phe, Tyr, Thr, Gin, Asn, Glu or Asp; Xaa(15) represents Gin, Asn, Glu, Asp, Thr, Ser, Met or Cys; Xaa(16) represents Ala, Gly, Cys, Leu, Val or Met; Xaa(17) represents Arg, Lys, Met, Ile, Asn, Asp, Glu, Gin, Ser, Thr or Cys; Xaa(18) represents Arg, Lys, Met or Ile; Xaa(19) represents Ala, Gly, Cys, Asp, Glu, Gin, Asn, Ser, Thr or Met; Xaa(20) represents Ala, Gly, Cys, Asp, Asn, Glu or Gin; Xaa(21) represents Arg, Lys, Met, Ile, Asn, Asp, Glu or Gin; Xaa(22) represent Leu, Val, Met or Ile; Xaa(23) represents Phe, Tyr, Thr, His or Trp; Xaa(24) represents Ile, Val, Leu or Met; .Xaa(25) represents Met, Cys, Ile, Leu, Val, Thr or Ser; Xaa(26) represents Leu, Val, Met, Thr or Ser. In an even more expansive library, each X can be selected from any amino acid.

In similar fashion, alignment of each of the human, mouse, chicken and zebrafish hedgehog clones, can provide a degenerate polypeptide sequence represented by the general formula:

C-G-P-G-R-G-X(1)-X(2)-X(3)-R-R-X(4)-X(5)-X(6)-P-K-X(7)-L-X(8)-P-L-X(9)-

Y-K-Q-F-X(10)-P-X(11)-X(12)-X(13)-E-X(14)-T-L-G-A-S-G-X(15)-X(16)-E-G-

X(17)-X(18)-X(19)-R-X(20)-S-E-R-F-X(21)-X(22)-L-T-P-N-Y-N-P-D-I-I-F-K-

D-E-E-N-X(23)-G-A-D-R-L-M-T-X(24)-R-C-K-X(25)-X(26)-X(27)-N-X(28)-L-

A-I-S-V-M-N-X(29)-W-P-G-V-X(30)-L-R-V-T-E-G-X(31)-D-E-D-G-H-H-

X(32)-X(33)-X(34)-S-L-H-Y-E-G-R-A-X(35)-D-I-T-T-S-D-R-D-X(36)-X(37)-K-

Y-G-X(38)-L-X(39)-R-L-A-V-E-A-G-F-D-W-V-Y-Y-E-S-X(40)-X(41)-H-X(42)-

H-X(43)-S-V-K-X(44)-X(45) (SEQ ID No:22), wherein, as above, each of the degenerate positions "X" can be an amino acid which occurs in a corresponding position in one of the wild-type clones, and may also include amino acid residue which would be conservative substitutions, or each X can be any amino acid residue. In an exemplary embodiment, Xaa(1) represents Gly, Ala, Val, Leu, Ile, Pro, Phe or Tyr; Xaa(2) represents Gly, Ala, Val, Leu or Ile; Xaa(3) represents Gly, Ala, Val, Leu, Ile, Lys, His or Arg; Xaa(4) represents Lys, Arg or His; Xaa(5) represents Phe, Trp, Tyr or an amino acid gap; Xaa(6) represents Gly, Ala, Val, Leu, Ile or an amino acid gap; Xaa(7) represents Asn, Gin, His, Arg or Lys; Xaa(8) represents Gly, Ala, Val, Leu, Ile, Ser or Thr; Xaa(9) represents Gly, Ala, Val, Leu, Ile, Ser or Thr; Xaa(10) represents Gly, Ala, Val, Leu, Ile, Ser or Thr; Xaa(11) represents Ser, Thr, Gln or Asn; Xaa(12) represents Met, Cys, Gly, Ala, Val, Leu, Ile, Ser or Thr; Xaa(13) represents Gly, Ala, Val, Leu, Ile or Pro; Xaa(14) represents Arg, His or Lys; Xaa(15) represents Gly, Ala, Val, Leu, Ile, Pro, Arg, His or Lys; Xaa(16) represents Gly, Ala, Val, Leu, Ile, Phe or Tyr; Xaa(17) represents Arg, His or Lys; Xaa(18) represents Gly, Ala, Val, Leu, Ile, Ser or Thr; Xaa(19) represents Thr or Ser; Xaa(20) represents Gly, Ala, Val, Leu, Ile, Asn or Gin; Xaa(21) represents Arg, His or Lys; Xaa(22) represents Asp or Glu; Xaa(23) represents Ser or Thr; Xaa(24) represents Glu, Asp, Gin or Asn; Xaa(25) represents Glu or Asp; Xaa(26) represents Arg, His or Lys; Xaa(27) represents Gly, Ala, Val, Leu or Ile; Xaa(28) represents Gly, Ala, Val, Leu, Ile, Thr or Ser; Xaa(29) represents Met, Cys, Gin, Asn, Arg, Lys or His; Xaa(30) represents Arg, His or Lys; Xaa(31) represents Trp, Phe, Tyr, Arg, His or Lys; Xaa(32) represents Gly, Ala, Val, Leu, Ile, Ser, Thr, Tyr or Phe; Xaa(33) represents Gin, Asn, Asp or Glu; Xaa(34) represents Asp or Glu; Xaa(35) represents Gly, Ala, Val, Leu, or Ile; Xaa(36) represents Arg, His or Lys; Xaa(37) represents Asn, Gin, Thr or Ser; Xaa(38) represents Gly, Ala, Val, Leu, Ile, Ser, Thr, Met or Cys; Xaa(39) represents Gly, Ala, Val, Leu, Ile, Thr or Ser; Xaa(40) represents Arg, His or Lys; Xaa(41) represents Asn, Gin, Gly, Ala, Val, Leu or Ile; Xaa(42) represents Gly, Ala, Val, Leu or Ile; Xaa(43) represents Gly, Ala, Val, Leu, Ile, Ser, Thr or Cys; Xaa(44) represents Gly, Ala, Val, Leu, Ile, Thr or Ser; and Xaa(45) represents Asp or Glu.

There are many ways by which the library of potential hedgehog homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential hedgehog sequences. The synthesis of degenerate oligonucleotides is well known in the art (see for example, Narang, SA (1983) *Tetrahedron* 39:3; Itakura et al. (1981) *Recombinant DNA, Proc* 3rd *Cleveland Sympos. Macromolecules*, ed. AG Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of hedgehog homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate hedgehog sequences created by combinatorial mutagenesis techniques.

In one embodiment, the combinatorial library is designed to be secreted (e.g. the polypeptides of the library all include a signal sequence but no transmembrane or cytoplasmic domains), and is used to transfect a eukaryotic cell that can be co-cultured with perichondrial cells. A functional hedgehog protein secreted by the cells expressing the combinatorial library will diffuse to neighboring perichondrial cells and induce a particular biological response, such as expression of PTHrP. The pattern of detection of proliferation will resemble a gradient function, and will allow the isolation (generally after several repetitive rounds of selection) of cells producing hedgehog homologs active as inducers of PTHrP expression. Likewise, hedgehog antagonists can be selected in similar fashion by the ability of the cell producing a functional antagonist to protect neighboring cells (e.g., to inhibit proliferation) from the effect of wild-type hedgehog added to the culture media.

To illustrate, target perichondrial cells are cultured in 24-well microtitre plates. Other eukaryotic cells are transfected with the combinatorial hedgehog gene library and cultured in cell culture inserts (e.g. Collaborative Biomedical Products, Catalog #40446) that are able to fit into the wells of the microtitre plate. The cell culture inserts are placed in the wells such that recombinant hedgehog homologs secreted by the cells in the insert can diffuse through the porous bottom of the insert and contact the target cells in the microtitre plate wells. After a period of time sufficient for functional forms of a hedgehog protein to produce a measurable response in the target cells, such as PTHrP expression, the inserts are removed and the effect of the variant hedgehog proteins on the target cells determined. Cells from the inserts corresponding to wells which score positive for activity can be split and re-cultured on several inserts, the process being repeated until the active clones are identified. In similar fashion, the activity of hedgehog variants on the proliferation of chondrocytes can be directly detected on chondrocytes in culture.

In yet another screening assay, the candidate hedgehog gene products are displayed on the surface of a cell or viral particle, and the ability of particular cells or viral particles to associate with a hedgehog-binding moiety (such as the patched protein or other hedgehog receptor) via this gene product is detected in a "panning assay". Such panning steps can be carried out on cells cultured from embryos, perichondrial cells or other cells expressing, e.g., patched. For instance, the gene library can be cloned into the gene for a surface membrane protein of a bacterial cell, and the resulting fusion protein detected by panning (Ladner et al., WO 88/06630; Fuchs et al. (1991) Bio/Technology 9:1370–1371; and Goward et al. (1992) TIBS 18:136–140). In a similar fashion, fluorescently labeled molecules which bind hedgehog can be used to score for potentially functional hedgehog homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, large number of phage can be screened at one time. Second, since each infectious phage displays the combinatorial gene product on its surface, if a particular phage is recovered from an affinity matrix in low yield, the phage can be amplified by another round of infection. The group of almost identical E. coli filamentous phages M13, fd, and fl are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) J. Biol. Chem. 267:16007–16010; Griffths et al. (1993) EMBO J. 12:725–734; Clackson et al. (1991) Nature 352:624–628; and Barbas et al. (1992) PNAS 89:4457–4461).

In an illustrative embodiment, the recombinant phage antibody system (RPAS, Pharamacia Catalog number 27-9400-01) can be easily modified for use in expressing and screening hedgehog combinatorial libraries. For instance, the pCANTAB 5 phagemid of the RPAS kit contains the gene which encodes the phage gIII coat protein. The hedgehog combinatorial gene library can be cloned into the phagemid adjacent to the gIII signal sequence such that it will be expressed as a gIII fusion protein. After ligation, the phagemid is used to transform competent E. coli TG1 cells. Transformed cells are subsequently infected with M13KO7 helper phage to rescue the phagemid and its candidate hedgehog gene insert. The resulting recombinant phage contain phagemid DNA encoding a specific candidate hedgehog, and display one or more copies of the corresponding fusion coat protein. The phage-displayed candidate hedgehog proteins which are capable of binding an hedgehog receptor are selected or enriched by panning. For instance, the phage library can be applied to cells which express the patched protein and unbound phage washed away from the cells. The bound phage is then isolated, and if the recombinant phage express at least one copy of the wild type gIII coat protein, they will retain their ability to infect E. coli. Thus, successive rounds of reinfection of E. coli, and panning will greatly enrich for hedgehog homologs, which can then be screened for further biological activities in order to differentiate agonists and antagonists.

Combinatorial mutagenesis has a potential to generate very large libraries of mutant proteins, e.g., in the order of 10$^{26}$ molecules. Combinatorial libraries of this size may be technically challenging to screen even with high throughput screening assays such as phage display. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, PNAS USA 89:7811–7815; Yourvan et al., 1992, Parallel Problem Solving from Nature, 2., In Maenner and Manderick, eds., Elsevir Publishing Co., Amsterdam, pp.401–410; Delgrave et al., 1993, Protein Engineering 6(3):327–331).

Subsequent testing of the hedgehog analogs, e.g., to discern between agonists and antagonist of chondrocyte proliferation and bone formation, can be carried using any of a wide range of bioassays known in the art. For example, the candidate agonist or antagonist can be implanted in an animal, and the degree of endochondral bone formation measured. The endochondral bone formation stages include:

(1) leukocytes on day one;
(2) mesenchymal cell migration and proliferation on days two and three;
(3) chondrocyte appearance on days five and six;
(4) cartilage matrix formation on day seven;
(5) cartilage calcification on day eight;
(6) vascular invasion, appearance of osteoblasts, and formation of new bone on days nine and ten;
(7) appearance of osteoblastic and bone remodeling and dissolution of the implanted matrix on days twelve to eighteen; and
(8) hematopoietic bone marrow differentiation in the ossicle on day twenty-one.

In addition to histological evaluation, biological markers may be used as a marker for tissue morphogenesis. Useful markers include tissue-specific enzymes whose activity may be assayed (e.g., spectrophotometrically) after homogenization of the implant. These assays may be useful for quantitation and for obtaining an estimate of tissue formation quickly after the implants are removed from the animal. For example, alkaline phosphatase activity may be used as a marker for osteogenesis.

The invention also provides for reduction of the hedgehog protein to generate mimetics, e.g. peptide or non-peptide agents, which are able to disrupt binding of a hedgehog polypeptide of the present invention with an hedgehog receptor. Thus, such mutagenic techniques as described above are also useful to map the determinants of the hedgehog proteins which participate in protein—protein interactions involved in, for example, binding of the subject hedgehog polypeptide to other extracellular matrix components. To illustrate, the critical residues of a subject hedgehog polypeptide which are involved in molecular recognition of an hedgehog receptor such as patched can be determined and used to generate hedgehog-derived peptidomimetics which competitively inhibit binding of the authentic hedgehog protein with that moiety. By employing, for example, scanning mutagenesis to map the amino acid residues of each of the subject hedgehog proteins which are involved in binding other extracellular proteins, peptidomimetic compounds can be generated which mimic those residues of the hedgehog protein which facilitate the interaction. Such mimetics may then be used to interfere with the normal function of a hedgehog protein. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) Biochem Biophys Res Commun 134:71).

Recombinantly produced forms of the hedgehog proteins can be produced using, e.g., expression vectors containing a nucleic acid encoding a hedgehog polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of a hedgehog polypeptide. Accordingly, the term transcriptional regulatory sequence includes promoters, enhancers and other expression control elements. Such regulatory Academic Press, San Diego, Calif. (1990). For instance, any of a wide variety of expression control sequences, sequences that control the expression of a DNA sequence when operatively linked to it, may be used in these vectors to express DNA sequences encoding hedgehog polypeptide. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

In addition to providing a ready source of hedgehog polypeptides for purification, the gene constructs of the present invention can also be used as a part of a gene therapy protocol to deliver nucleic acids encoding either an agonistic or antagonistic form of a hedgehog polypeptide. Thus, another aspect of the invention features expression vectors for in vivo transfection of a hedgehog polypeptide in particular cell types so as cause ectopic expression of a hedgehog polypeptide in chondrocytes, perichondrial cells or other cells native or ectopically added to a bone matrix.

Formulations of such expression constructs may be administered in any biologically effective carrier, e.g. any formulation or composition capable of effectively delivering the recombinant gene to cells in vivo. Approaches include insertion of the hedgehog coding sequence in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of hedgehog expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA, encoding the particular form of the hedgehog polypeptide desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a hedgehog polypeptide and renders the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include Crip, Cre, 2 and Am. Retroviruses have been used to introduce a variety of genes into many different cell types, in vitro and/or in vivo (see for example Eglitis, et al. (1985) *Science* 230:1395–1398; Danos and Mulligan (1988) *Proc. Natl. Acad. Sci. USA*

85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868, 116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) PNAS 86:9079–9083; Julan et al. (1992) *J. Gen Virol* 73:3251–3255; and Goud et al. (1983) *Virology* 163:251–254); or coupling cell surface receptor ligands to the viral env proteins (Neda et al. (1991) *J Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the hedgehog gene of the retroviral vector.

Another viral gene delivery system useful in the present method utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in Methods in Molecular Biology, E. J. Murray, Ed. (Humana, Clifton, N.J., 1991) vol. 7. pp. 109–127). Expression of the inserted hedgehog gene can be under control of, for example, the E1A promoter, the major late promoter (MLP) and associated leader sequences, the E3 promoter, or exogenously added promoter sequences.

In addition to viral transfer methods, such as those illustrated above, non-viral methods can also be employed to cause expression of a hedgehog polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the hedgehog polypeptide gene by the targeted cell. Exemplary gene delivery systems of this type include liposomal derived systems, poly-lysine conjugates, and artificial viral envelopes.

In clinical settings, the gene delivery systems for the therapeutic hedgehog gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057). A hedgehog expression construct can be delivered in a gene therapy construct to dermal cells by, e.g., electroporation using techniques described, for example, by Dev et al. ((1994) *Cancer Treat Rev* 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

In yet another embodiment, the hedgehog or ptc therapeutic can be a "gene activation" construct which, by homologous recombination with a genomic DNA, alters the transcriptional regulatory sequences of an endogenous gene. For instance, the gene activation construct can replace the endogenous promoter of a hedgehog gene with a heterologous promoter, e.g., one which causes consitutive expression of the hedgehog gene or which causes inducible expression of the gene under conditions different from the normal expression pattern of the gene. Other genes in the patched signaling pathway can be similarly targeted. A vareity of different formats for the gene activation constructs are available. See, for example, the Transkaryotic Therapies, Inc PCT publications WO93/09222, WO95/31560, WO96/29411, WO95/31560 and WO94/12650.

In preferred embodiments, the nucleotide sequence used as the gene activation construct can be comprised of (1) DNA from some portion of the endogenous hedgehog gene (exon sequence, intron sequence, promoter sequences, etc.)

which direct recombination and (2) heterologous transcriptional regulatory sequence(s) which is to be operably linked to the coding sequence for the genomic hedgehog gene upon recombination of the gene activation construct.

The gene activation construct is inserted into a cell, and integrates with the genomic DNA of the cell in such a position so as to provide the heterologous regulatory sequences in operative association with the native hedgehog gene. Such insertion occurs by homologous recombination, i.e., recombination regions of the activation construct that are homologous to the endogenous hedgehog gene sequence hybridize to the genomic DNA and recombine with the genomic sequences so that the construct is incorporated into the corresponding position of the genomic DNA.

The terms "recombination region" or "targeting sequence" refer to a segment (i.e., a portion) of a gene activation construct having a sequence that is substantially identical to or substantially complementary to a genomic gene sequence, e.g., including 5' flanking sequences of the genomic gene, and can facilitate homologous recombination between the genomic sequence and the targeting transgene construct.

As used herein, the term "replacement region" refers to a portion of a activation construct which becomes integrated into an endogenous chromosomal location following homologous recombination between a recombination region and a genomic sequence.

The heterologous regulatory sequences, e.g., which are provided in the replacement region, can include one or more of a variety elements, including: promoters (such as constitutive or inducible promoters), enhancers, negative regualtory elements, locus control regions, transcription factor binding sites, or combinations thereof. Promoters/enhancers which may be used to control the expression of the targeted gene in vivo include, but are not limited to, the cytomegalovirus (CMV) promoter/enhancer (Karasuyarna et al., 1989, *J. Exp. Med.*, 169:13), the human β-actin promoter (Gunning et al. (1987) *PNAS* 84:4831–4835), the glucocorticoid-inducible promoter present in the mouse mammary tumor virus long terminal repeat (MMTV LTR) (Klessig et al. (1984) *Mol. Cell Biol.* 4:1354–1362), the long terminal repeat sequences of Moloney murine leukemia virus (MuLV LTR) (Weiss et al. (1985) *RNA Tumor Viruses*, Cold Spring Harbor Laboratory, Cold Spring Harbor, N.Y.), the SV40 early or late region promoter (Bemoist et al. (1981) *Nature* 290:304–310; Templeton et al. (1984) *Mol. Cell Biol.*, 4:817; and Sprague et al. (1983) *J Virol*, 45:773), the promoter contained in the 3' long terminal repeat of Rous sarcoma virus (RSV) (Yamamoto et al., 1980, *Cell*, 22:787–797), the herpes simplex virus (HSV) thymidine kinase promoter/enhancer (Wagner et al. (1981) *PNAS* 82:3567–71), and the herpes simplex virus LAT promoter (Wolfe et al. (1992) *Nature Genetics*, 1:379–384).

In an exemplary embodiment, portions of the 5' flanking region of the human Shh gene are amplified using primers which add restriction sites, to generate the following fragments 5'-gcgcgcttcgaaGCGAGGCAGCCAGCGAGGGAGAGA GCGAGCGGGCGAGCCGGAGCGAG-GAAatcgatgcgcgc (primer 1)

5'-gcgcgcagatctGGGAAAGCGCAAGAGAGAGCGCAC ACGCACACACCCGCCGCGCGCACTCGg-gatccgcgcgc (primer 2).

As illustrated, primer 1 includes a 5' non-coding region of the human Shh gene and is flanked by an AsuII and ClaI restriction sites. Primer 2 includes a portion of the 5' non-coding region immediately 3' to that present in primer 1. The hedgehog gene sequence is flanked by XhoII and BamHI restriction sites. The purified amplimers are cut with each of the enzymes as appropriate.

The vector pCDNA1.1 (Invitrogen) includes a CMV promoter. The plasmid is cut with with AsuII, which cleaves just 3' to the CMV promoter sequence. The AsuII/ClaI fragment of primer 1 is ligated to the AsuII cleavage site of the pcDNA vector. The ClaI/AsuII ligation destroys the AsuII site at the 3' end of a properly inserted primer 1.

The vector is then cut with BamHI, and an XhoII/BamHI fragment of primer 2 is ligated to the BamHI cleavage site. As above, the BamHI/XhoII ligation destroys the BamHI site at the 5' end of a properly inserted primer 2.

Individual colonies are selected, cut with AsuII and BamHI, and the size of the AsuII/BamHI fragment determined. Colonies in which both the primer 1 and primer 2 sequences are correctly inserted are further amplified, an cut with AsuII and BamHI to produce the gene activation construct

```
cgaagcgaggcagccagcgagggagagagcgagcgggcgagccggagcgaggaaATCGAAGGTTC
GAATCCTTCCCCCACCACCATCACTTTCAAAAGTCCGAAAGAATCTGCTCCCTGCTTGTGTGTTG
GAGGTCGCTGAGTAGTGCGCGAGTAAAATTTAAGCTACAACAAGGCAAGGCTTGACCGACAATTG
CATGAAGAATCTGCTTAGGGTTAGGCGTTTTGCGCTGCTTCGCGATGTACGGGCCAGATATACGC
GTTGACATTGATTATTGACTAGTTATTAATAGTAATCAATTACGGGGTCATTAGTTCATAGCCCA
TATATGGAGTTCCGCGTTACATAACTTACGGTAAATGGCCCGCCTGGCTGACCGCCCAACGACCC
CCGCCCATTGACGTCAATAATGACGTATGTTCCCATAGTAACGCCAATAGGGACTTTCCATTGAC
GTCAATGGGTGGACTATTTACGGTAAACTGCCCACTTGGCAGTACATCAAGTGTATCATATGCCA
AGTACGCCCCCTATTGACGTCAATGACGGTAAATGGCCCGCCTGGCATTATGCCCAGTACATGAC
CTTATGGGACTTTCCTACTTGGCAGTACATCTACGTATTAGTCATCGCTATTACCATGGTGATGC
GGTTTTGGCAGTACATCAATGGGCGTGGATAGCGGTTTGACTCACGGGGATTTCCAAGTCTCCAC
CCCATTGACGTCAATGGGAGTTTGTTTTGGCACCAAAATCAACGGGACTTTCCAAAATGTCGTAA
```

```
                            -continued
CAACTCCGCCCCATTGACGCAAATGGGCGGTAGGCGTGTACGGTGGGAGGTCTATATAAGCAGAG

CTCTCTGGCTAACTAGAGAACCCACTGCTTACTGGCTTATCGAAATTAATACGACTCACTATAGG

GAGACCCAAGCTTGGTACCGAGCTCGGATCgatctgggaaagcgcaagagagagcgcacacgcac acaccgccgcgcgcactcgg
```

In this construct, the flanking primer 1 and primer 2 sequences provide the recombination region which permits the insertion of the CMV promoter in front of the coding sequence for the human Shh gene. Other heterologous promoters (or other transcriptional regulatory sequences) can be inserted in a genomic hedgehog gene by a similar method.

In still other embodiments, the replacement region merely deletes a negative transcriptional control element of the native gene, e.g., to activate expression, or ablates a positive control element, e.g., to inhibit expression of the targeted gene.

V. Exemplary ptc Therapeutic Compounds.

In another embodiment, the subject method is carried out using a ptc therapeutic composition. Such compositions can be generated with, for example, compounds which bind to patched and alter its signal transduction activity, compounds which alter the binding and/or enzymatic activity of a protein (e.g., intracellular) involved in patched signal pathway, and compounds which alter the level of expression of a hedgehog protein, a patched protein or a protein involved in the intracellular signal transduction pathway of patched.

The availability of purified and recombinant hedgehog polypeptides facilitates the generation of assay systems which can be used to screen for drugs, such as small organic molecules, which are either agonists or antagonists of the normal cellular function of a hedgehog and/or patched protein, particularly their role in the pathogenesis of gene expression ultimately leading to control of chondrocyte proliferation and/or differentiation. In one embodiment, the assay evaluates the ability of a compound to modulate binding between a hedgehog polypeptide and a hedgehog receptor such as patched. In other embodiments, the assay merely scores for the ability of a test compound to alter the signal transduction acitity of the patched protein. In this manner, a variety of hedgehog and/or ptc therapeutics, both osteogenic and chondrogenic in activity, can be identified. A variety of assay formats will suffice and, in light of the present disclosure, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with receptor proteins.

Accordingly, in an exemplary screening assay for ptc therapeutics, the compound of interest is contacted with a mixture including a hedgehog receptor protein (e.g., a cell expressing the patched receptor) and a hedgehog protein under conditions in which it is ordinarily capable of binding the hedgehog protein. To the mixture is then added a composition containing a test compound. Detection and quantification of receptor/hedgehog complexes provides a means for determining the test compound's efficacy at inhibiting (or potentiating) complex formation between the receptor protein and the hedgehog polypeptide. The efficacy of the compound can be assessed by generating dose response curves from data obtained using various concentrations of the test compound. Moreover, a control assay can also be performed to provide a baseline for comparison. In the control assay, isolated and purified hedgehog polypeptide is added to the receptor protein, and the formation of receptor/hedgehog complex is quantitated in the absence of the test compound.

In other embodiments, a ptc therapeutic of the present invention is one which disrupts the association of patched with smoothened.

Agonist and antagonists of hedgehog-mediated chondrocyte proliferation can be distinguished, and the efficacy of the compound can be assessed, by subsequent testing with chondrocytic cultures.

In an illustrative embodiment, the polypeptide utilized as a hedgehog receptor can be generated from the patched protein. Accordingly, an exemplary screening assay includes all or a suitable portion of the patched protein which can be obtained from, for example, the human patched gene (GenBank U43148) or other vertebrate sources (see GenBank Accession numbers U40074 for chicken patched and U46155 for mouse patched), as well as from *drosophila* (GenBank Accession number M28999) or other invertebrate sources. The patched protein can be provided in the screening assay as a whole protein (preferably expressed on the surface of a cell), or alternatively as a fragment of the full length protein which binds to hedgehog polypeptides, e.g., as one or both of the substantial extracellular domains (e.g. corresponding to residues Asn120-Ser438 and/or Arg770-Trp1027 of the human patched protein). For instance, the patched protein can be provided in soluble form, as for example a preparation of one of the extracellular domains, or a preparation of both of the extracellular domains which are covalently connected by an unstructured linker (see, for example, Huston et al. (1988) PNAS 85:4879; and U.S. Pat. No. 5,091,513). In other embodiments, the protein can be provided as part of a liposomal preparation or expressed on the surface of a cell. The patched protein can derived from a recombinant gene, e.g., being ectopically expressed in a heterologous cell. For instance, the protein can be expressed on oocytes, mammalian cells (e.g., COS, CHO, 3T3 or the like), or yeast cell by standard recombinant DNA techniques. These recombinant cells can be used for receptor binding, signal transduction or gene expression assays. Marigo et al. (1996) *Development* 122:1225–1233 illustrates a binding assay of human hedgehog to chick patched protein ectopically expressed in *Xenopus laevis* oocytes. The assay system of Marigo et al. can be adapted to the present drug screening assays. As illustrated in that reference, Shh binds to the patched protein in a selective, saturable, dose-dependent manner, thus demonstrating that patched is a receptor for Shh.

Complex formation between the hedgehog polypeptide and a hedgehog receptor may be detected by a variety of techniques. For instance, modulation of the formation of complexes can be quantitated using, for example, detectably labelled proteins such as radiolabelled, fluorescently labelled, or enzymatically labelled hedgehog polypeptides, by immunoassay, or by chromatographic detection.

Typically, for cell-free assays, it will be desirable to immobilize either the hedgehog receptor or the hedgehog polypeptide to facilitate separation of receptor/hedgehog complexes from uncomplexed forms of one of the proteins, as well as to accommodate automation of the assay. In one embodiment, a fusion protein can be provided which adds a domain that allows the protein to be bound to a matrix. For example, glutathione-S-transferase/receptor (GST/receptor) fusion proteins can be adsorbed onto glutathione sepharose beads (Sigma Chemical, St. Louis, Mo.) or glutathione derivatized microtitre plates, which are then combined with the hedgehog polypeptide, e.g. an $^{35}$S-labeled hedgehog polypeptide, and the test compound and incubated under conditions conducive to complex formation, e.g. at physiological conditions for salt and pH, though slightly more stringent conditions may be desired. Following incubation, the beads are washed to remove any unbound hedgehog polypeptide, and the matrix bead-bound radiolabel determined directly (e.g. beads placed in scintillant), or in the supernatant after the receptor/hedgehog complexes are dissociated. Alternatively, the complexes can be dissociated from the bead, separated by SDS-PAGE gel, and the level of hedgehog polypeptide found in the bead fraction quantitated from the gel using standard electrophoretic techniques.

Other techniques for immobilizing proteins on matrices are also available for use in the subject assay. For instance, soluble portions of the hedgehog receptor protein can be immobilized utilizing conjugation of biotin and streptavidin. For instance, biotinylated receptor molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the hedgehog receptor but which do not interfere with hedgehog binding can be derivatized to the wells of the plate, and the receptor trapped in the wells by antibody conjugation. As above, preparations of a hedgehog polypeptide and a test compound are incubated in the receptor-presenting wells of the plate, and the amount of receptor/hedgehog complex trapped in the well can be quantitated. Exemplary methods for detecting such complexes, in addition to those described above for the GST-immobilized complexes, include immunodetection of complexes using antibodies reactive with the hedgehog polypeptide, or which are reactive with the receptor protein and compete for binding with the hedgehog polypeptide; as well as enzyme-linked assays which rely on detecting an enzymatic activity associated with the hedgehog polypeptide. In the instance of the latter, the enzyme can be chemically conjugated or provided as a fusion protein with the hedgehog polypeptide. To illustrate, the hedgehog polypeptide can be chemically cross-linked or genetically fused with alkaline phosphatase, and the amount of hedgehog polypeptide trapped in the complex can be assessed with a chromogenic substrate of the enzyme, e.g. paranitrophenylphosphate. Likewise, a fusion protein comprising the hedgehog polypeptide and glutathione-S-transferase can be provided, and complex formation quantitated by detecting the GST activity using l-chloro-2,4-dinitrobenzene (Habig et al (1974) *J Biol Chem* 249:7130).

For processes which rely on immunodetection for quantitating one of the proteins trapped in the complex, antibodies against the protein, such as the anti-hedgehog antibodies described herein, can be used. Alternatively, the protein to be detected in the complex can be "epitope tagged" in the form of a fusion protein which includes, in addition to the hedgehog polypeptide or hedgehog receptor sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150–21157) which includes a 10-residue sequence from c-myc, as well as the pFLAG system (International Biotechnologies, Inc.) or the pEZZ-protein A system (Pharamacia, NJ).

Where the desired portion of the hedgehog receptor (or other hedgehog binding molecule) cannot be provided in soluble form, liposomal vesicles can be used to provide manipulatable and isolatable sources of the receptor. For example, both authentic and recombinant forms of the patched protein can be reconstituted in artificial lipid vesicles (e.g. phosphatidylcholine liposomes) or in cell membrane-derived vesicles (see, for example, Bear et al. (1992) *Cell* 68:809–818; Newton et al. (1983) *Biochemistry* 22:6110–6117; and Reber et al. (1987) *J Biol Chem* 262:11369–11374).

In addition to cell-free assays, such as described above, the readily available source of hedgehog proteins provided by the art also facilitates the generation of cell-based assays for identifying small molecule agonists/antagonists and the like. Analogous to the cell-based assays described above for screening combinatorial libraries, cells which are sensitive to hedgehog induction, e.g. chondrocytes, perichondrial cells or other patched-expressing cells sensitive to hedgehog induction, can be contacted with a hedgehog protein and a test agent of interest, with the assay scoring for anything from simple binding to the cell to modulation in hedgehog inductive responses by the target cell in the presence and absence of the test agent. As with the cell-free assays, agents which produce a statistically significant change in hedgehog activities (either inhibition or potentiation) can be identified.

In other emdodiments, the cell-based assay scores for agents which disrupt association of patched and smoothened proteins, e.g., in the cell surface membrane or liposomal preparation.

In addition to characterizing cells that naturally express the patched protein, cells which have been genetically engineered to ectopically express patched can be utilized for drug screening assays. As an example, cells which either express low levels or lack expression of the patched protein, e.g. *Xenopus laevis* oocytes, COS cells or yeast cells, can be genetically modified using standard techniques to ectopically express the patched protein. (see Marigo et al., supra).

The resulting recombinant cells, e.g., which express a functional patched receptor, can be utilized in receptor binding assays to identify agonist or anatagonsts of hedgehog binding. Binding assays can be performed using whole cells. Furthermore, the recombinant cells of the present invention can be engineered to include other heterolgous genes encoding proteins involved in hedgehog-dependent siganl pathways. For example, the gene products of one or more of smoothened, costal-2 and/or fused can be co-expressed with patched in the reagent cell, with assays being sensitive to the functional reconstituion of the hedgehog signal transduction cascade.

Alternatively, liposomal preparations using reconstituted patched protein can be utilized. Patched protein purified from detergent extracts from both authentic and recombinant origins can be reconstituted in in artificial lipid vesicles (e.g. phosphatidylcholine liposomes) or in cell membrane-derived vesicles (see, for example, Bear et al. (1992) *Cell* 68:809–818; Newton et al. (1983) *Biochemistry* 22:6110–6117; and Reber et al. (1987) *J Biol Chem* 262:11369–11374). The lamellar structure and size of the resulting liposomes can be characterized using electron microscopy. External orientation of the patched protein in the reconstituted membranes can be demonstrated, for example, by immunoelectron microscopy. The hedgehog protein binding activity of liposomes containing patched and liposomes without the protein in the presence of candidate agents can be compared in order to identify potential modulators of the hedgehog-patched interaction.

The hedgehog protein used in these cell-based assays can be provided as a purified source (natural or recombinant in origin), or in the form of cells/tissue which express the protein and which are co-cultured with the target cells. As in the cell-free assays, where simple binding (rather than induction) is the hedgehog activity scored for in the assay, the protein can be labelled by any of the above-mentioned techniques, e.g., fluorescently, enzymatically or radioactively, or detected by immunoassay.

In addition to binding studies, functional assays can be used to identified modulators, i.e., agonists or antagonists, of hedgehog or patched activities. By detecting changes in intracellular signals, such as alterations in second messengers or gene expression, in patched-expressing cells contacted with a test agent, candidate agonists and antagonists to patched signaling can be identified.

A number of gene products have been implicated in patched-mediated signal transduction, including patched, the transcription factor *cubitus interruptus* (ci), the serine/threonine kinase fused (fu) and the gene products of costal-2, smoothened and suppressor of fused.

The interaction of a hedgehog protein with patched sets in motion a cascade involving the activation and inhibition of downstream effectors, the ultimate consequence of which is, in some instances, a detectable change in the transcription or translation of a gene. Potential transcriptional targets of patched signaling are the patched gene itself (Hidalgo and Ingham, 1990 *Development* 110, 291–301; Marigo et al., 1996) the vertebrate homologs of the *drosophila* cubitus interruptus gene, the GLI genes (Hui et al. (1994) *Dev Biol* 162:402–413), and the gene encoding parathyroid hormone-related protein (see Example 1 and 2 below). Patched gene expression has been shown to be induced in cells of the limb bud and the neural plate that are responsive to hedgehog. (Marigo et al. (1996) *Development* 122:1225–1233). The GLI genes encode putative transcription factors having zinc finger DNA binding domains (Orenic et al. (1990) *Genes & Dev* 4:1053–1067; Kinzler et al. (1990) *Mol Cell Biol* 10:634–642). Transcription of the GLI gene has been reported to be upregulated in response to hedgehog in limb buds, while transcription of the GLI3 gene is downregulated in response to hedgehog induction (Marigo et al. (1996) Development 122:1225–1233). Likewise, the appended examples demonstrate that expression of the PTHrP gene can be upregulated in response to Ihh signalling.

By selecting transcriptional regulatory sequences from such target genes, e.g. from patched, GLI or PTHrP genes, that are responsible for the up- or down regulation of these genes in response to patched signalling, and operatively linking such promoters to a reporter gene, one can derive a transcription based assay which is sensitive to the ability of a specific test compound to modify patched signalling pathways. Expression of the reporter gene, thus, provides a valuable screening tool for the development of compounds that act as agonists or antagonists of ptc induction of PTHrP expression.

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on ptc signaling. To identify potential regulatory elements responsive to ptc signaling present in the transcriptional regulatory sequence of a target gene, nested deletions of genomic clones of the target gene can be constructed using standard techniques. See, for example, *Current Protocols in Molecular Biology*, Ausubel, F. M. et al. (eds.) Greene Publishing Associates, (1989); U.S. Pat. No. 5,266,488; Sato et al. (1995) *J Biol Chem* 270:10314–10322; and Kube et al. (1995) *Cytokine* 7:1–7. A nested set of DNA fragments from the gene's 5'-flanking region are placed upstream of a reporter gene, such as the luciferase gene, and assayed for their ability to direct reporter gene expression in patched expressing cells. Host cells transiently transfected with reporter gene constructs can be scored for the induction of expression of the reporter gene in the presence and absence of hedgehog to determine regulatory sequences which are responsice to patched-dependent signalling.

In practicing one embodiment of the assay, a reporter gene construct is inserted into the reagent cell in order to generate a detection signal dependent on second messengers generated by induction with hedgehog protein. Typically, the reporter gene construct will include a reporter gene in operative linkage with one or more transcriptional regulatory elements responsive to the hedgehog activity, with the level of expression of the reporter gene providing the hedgehog-dependent detection signal. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic activity. The amount of expression from the reporter gene is then compared to the amount of expression in either the same cell in the absence of the test compound (or hedgehog) or it may be compared with the amount of transcription in a substantially identical cell that lacks the target receptor protein. Any statistically or otherwise significant difference in the amount of transcription indicates that the test compound has in some manner altered the signal transduction of the patched protein, e.g., the test compound is a potential ptc therapeutic.

As described in further detail below, in preferred embodiments the gene product of the reporter is detected by an intrinsic activity associated with that product. For instance, the reporter gene may encode a gene product that, by enzymatic activity, gives rise to a detection signal based on color, fluorescence, or luminescence. In other preferred embodiments, the reporter or marker gene provides a selective growth advantage, e.g., the reporter gene may enhance cell viability, relieve a cell nutritional requirement, and/or provide resistance to a drug.

Preferred reporter genes are those that are readily detectable. The reporter gene may also be included in the construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101), human placental secreted alkaline phosphatase (Cullen and Malim (1992) Methods in Enzymol. 216:362–368).

Transcriptional control elements which may be included in a reporter gene construct include, but are not limited to, promoters, enhancers, and repressor and activator binding sites. Suitable transcriptional regulatory elements may be derived from the transcriptional regulatory regions of genes whose expression is induced after modulation of a patched signal transduction pathway. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

In yet other embodiments, second messenger generation can be measured directly in the detection step, such as mobilization of intracellular calcium, phospholipid metabolism or adenylate cyclase activity are quantitated, for instance, the products of phospholipid hydrolysis $IP_3$, DAG or cAMP could be measured For example, recent studies have implicated protein kinase A (PKA) as a possible component of hedgehog/patched signaling (Hammerschmidt et al. (1996) Genes & Dev 10:647). High PKA activity has been shown to antagonize hedgehog signaling in these systems. Conversely, inhibitors of PKA will mimic and/or potentiate the action of hedgehog. Although it is unclear whether PKA acts directly downstream or in parallel with hedgehog signaling, it is possible that hedgehog signalling occurs via inhibition of PKA activity. Thus, detection of PKA activity provides a potential readout for the instant assays.

In a preferred embodiment, the ptc therapeutic is a PKA inhibitor. A variety of PKA inhibitors are known in the art, including both peptidyl and organic compounds. For instance, the ptc therapeutic can be a 5-isoquinolinesulfonamide, such as represented in the general formula:

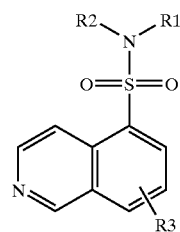

wherein, $R_1$ and $R_2$ each can independently represent hydrogen, and as valence and stability permit a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, $-(CH_2)_m-R_8$, $-(CH_2)_m-OH$, $-(CH_2)_m-$O-lower alkyl, $-(CH_2)_m-$O-lower alkenyl, $-(CH_2)_n-O-(CH_2)_m-R_8$, $-(CH_2)_m-SH$, $-(CH_2)_m-$S-lower alkyl, $-(CH_2)_m-$S-lower alkenyl, $-(CH_2)_n-S-(CH_2)_m-R_8$, or $R_1$ and $R_2$ taken together with N form a heterocycle (substituted or unsubstituted);

$R_3$ is absent or represents one or more substitutions to the isoquinoline ring such as a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, $-(CH_2)_m-R_8$, $-(CH_2)_m-OH$, $-(CH_2)_m-$O-lower alkyl, $-(CH_2)_m-$O-lower alkenyl, $-(CH_2)_n-O-(CH_2)_m-R_8$, $-(CH_2)_m-SH$, $-(CH_2)_m-$S-lower alkyl, $-(CH_2)_m-$S-lower alkenyl, $-(CH_2)_n-S-(CH_2)_m-R_8$;

$R_8$ represents a substituted or unsubstituted aryl, aralkyl, cycloalkyl, cycloalkenyl, or heterocycle; and n and m are independently for each occurrence zero or an integer in the range of 1 to 6.

In a preferred embodiment, the PKA inhibitor is N-[2-((p-bromocinnamyl)amino)ethyl]-5-isoquinolinesulfonamide (H-89; Calbiochem Cat. No. 371963), e.g., having the formula:

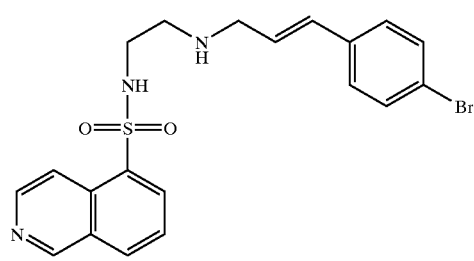

In another embodiment, the PKA inhibitor is 1-(5-isoquinolinesulfonyl)-2-methylpiperazine (H-7; Calbiochem Cat. No. 371955), e.g., having the formula:

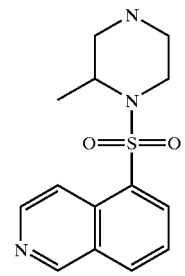

In still other embodiments, the PKA inhibitor is KT5720 (Calbiochem Cat. No. 420315), having the structure

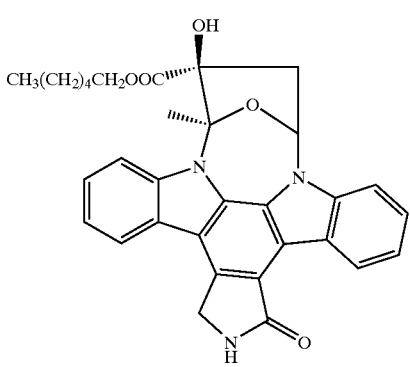

A variety of nucleoside analogs are also useful as PKA inhibitors. For example, the subject method can be carried out cyclic AMP analogs which inhibit the kinase activity of PKA, as for example, 8-bromo-cAMP or dibutyryl-cAMP

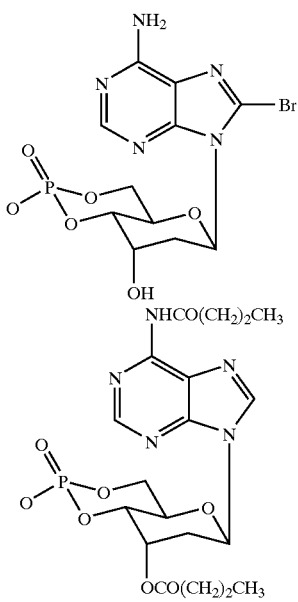

Exemplary peptidyl inhibitors of PKA activity include the PKA Heat Stable Inhibitor (isoform α; see, for example, Calbiochem Cat. No. 539488, and Wen et al. (1995) *J Biol Chem* 270:2041).

Certain hedgehog receptors may stimulate the activity of phospholipases. Inositol lipids can be extracted and analyzed using standard lipid extraction techniques. Water soluble derivatives of all three inositol lipids ($IP_1$, $IP_2$, $IP_3$) can also be quantitated using radiolabelling techniques or HPLC.

The mobilization of intracellular calcium or the influx of calcium from outside the cell may be a response to hedgehog stimulation or lack there of. Calcium flux in the reagent cell can be measured using standard techniques. The choice of the appropriate calcium indicator, fluorescent, bioluminescent, metallochromic, or $Ca^{++}$-sensitive microelectrodes depends on the cell type and the magnitude and time constant of the event under study (Borle (1990) *Environ Health Perspect* 84:45–56). As an exemplary method of $Ca^+$ detection, cells could be loaded with the $Ca^{++}$ sensitive fluorescent dye fira-2 or indo-1, using standard methods, and any change in $Ca^{++}$ measured using a fluorometer.

In certain embodiments of the assay, it may be desirable to screen for changes in cellular phosphorylation. As an example, the *drosophila* gene fused (fu) which encodes a serine/threonine kinase has been identified as a potential downstream target in hedgehog signaling. (Preat et al., 1990 *Nature* 347, 87–89; Therond et al. 1993, *Mech. Dev.* 44.65–80). The ability of compounds to modulate serine/threonine kinase activation could be screened using colony immunoblotting (Lyons and Nelson (1984) *Proc. Natl. Acad. Sci. USA* 81:7426–7430) using antibodies against phosphorylated serine or threonine residues. Reagents for performing such assays are commercially available, for example, phosphoserine and phosphothreonine specific antibodies which measure increases in phosphorylation of those residues can be purchased from comercial sources.

In yet another embodiment, the ptc therapeutic is an antisense molecule which inhibits expression of a protein involved in a patched-mediated signal transduction pathway. To illustrate, by inhibiting the expression of a protein involved in patched signals, such as fused, costal-2, smoothened and/or Gli genes, or patched itself, the ability of the patched signal pathway(s) to alter the ability of, e.g., a dopaminergic or GABAergic cell to maintain its differentiated state can be altered, e.g., potentiated or repressed.

As used herein, "antisense" therapy refers to administration or in situ generation of oligonucleotide probes or their derivatives which specifically hybridize (e.g. bind) under cellular conditions with cellular mRNA and/or genomic DNA encoding a hedgehog protein, patched, or a protein involved in patched-mediated signal transduction. The hybridization should inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the target cellular mRNA. Alternatively, the antisense construct is an oligonucleotide probe which is generated ex vivo and which, when introduced into the cell causes inhibition of expression by hybridizing with the mRNA and/or genomic sequences of a target gene. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256, 775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668.

Several considerations should be taken into account when constructing antisense oligonucleotides for the use in the methods of the invention: (1) oligos should have a GC content of 50% or more; (2) avoid sequences with stretches of 3 or more G's; and (3) oligonucleotides should not be longer than 25–26 mers. When testing an antisense oligonucleotide, a mismatched control can be constructed. The controls can be generated by reversing the sequence order of the corresponding antisense oligonucleotide in order to conserve the same ratio of bases.

In an illustrative embodiment, the ptc therapeutic can be an antisense construct for inhibiting the expression of patched, e.g., to mimic the inhibition of patched by hedgehog. Exemplary antisense constructs include:
5'-GTCCTGGCGCCGCCGCCGCCGTCGCC
5'-TTCCGATGACCGGCCTTTCGCGGTGA
5'-GTGCACGGAAAGGTGCAGGCCACACT VI. Exemplary Pharmaceutical Preparations of Hedgehog and ptc Therapeutics The source of the hedgehog and ptc therapeutics to be formulated will depend on the particular form of the agent. Small organic molecules and peptidyl fragments can be chemically synthesized and provided in a pure form suitable for pharmaceutical/cosmetic usage. Products of natural extracts can be purified according to techniques known in the art. For example, the Cox et al. U.S. Pat. No. 5,286,654 describes a method for purifying naturally occurring forms of a secreted protein and can be adapted for purification of hedgehog polypeptides. Recombinant sources of hedgehog polypeptides are also available. For example, the gene encoding hedgehog polypeptides, are known, inter alia, from PCT publications WO 95/18856 and WO 96/17924.

Those of skill in treating epithelial tissues can determine the effective amount of an hedgehog or ptc therapeutic to be formulated in a pharmaceutical or cosmetic preparation.

The hedgehog or ptc therapeutic formulations used in the method of the invention are most preferably applied in the form of appropriate compositions. As appropriate compositions there may be cited all compositions usually employed for systemically or topically administering drugs. The pharmaceutically acceptable carrier should be substantially inert, so as not to act with the active component. Suitable inert carriers include water, alcohol polyethylene glycol, mineral oil or petroleum gel, propylene glycol and the like.

To prepare the pharmaceutical compositions of this invention, an effective amount of the particular hedgehog or ptc therapeutic as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represents the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositons suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

In addition to the direct topical application of the preparations they can be topically administered by other methods, for example, encapsulated in a temperature and/or pressure sensitive matrix or in film or solid carrier which is soluble in body fluids and the like for subsequent release, preferably sustained-release of the active component.

As appropriate compositions for topical application there may be cited all compositions usually employed for topically administering therapeuitcs, e.g., creams, gellies, dressings, shampoos, tinctures, pastes, ointments, salves, powders, liquid or semiliquid formulation and the like. Application of said compositions may be by aerosol e.g. with a propellent such as nitrogen carbon dioxide, a freon, or without a propellent such as a pump spray, drops, lotions, or a semisolid such as a thickened composition which can be applied by a swab. In particular compositions, semisolid compositions such as salves, creams, pastes, gellies, ointments and the like will conveniently be used.

It is especially advantageous to formulate the subject compositions in dosage unit form for ease of administration and uniformity of dosage. Dosage unit form as used in the specification and claims herein refers to physically discreate units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powders packets, wafers, injectable solutions or suspensions, teaspoonfuls, tablespoonfuls and the like, and segregated multiples thereof.

The pharmaceutical preparations of the present invention can be used, as stated above, for the many applications whcih can be considered cosmetic uses. Cosmetic compositions known in the art, preferably hypoallergic and pH controlled are especially preferred, and include toilet waters, packs, lotions, skin milks or milky lotions. The preparations contain, besides the hedgehog or ptc therapeutic, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflammatory agents, antibacterials, antifungals, disinfectants, vitamins, sunscreens, antibiotics, or other anti-acne agents.

Examples of oils comprise fats and oils such as olive oil and hydrogenated oils; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate. As examples of surfactants there may be cited anionic surfactants such as sodium stearate, sodium cetylsulfate, polyoxyethylene laurylether phosphate, sodium N-acyl glutamate; cationic surfactants such as stearyldimethylbenzylammonium chloride and stearyltrimethylammonium chloride; ampholytic surfactants such as alkylaminoethylglycine hydrocloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxypropylene glycol (e.g. the materials sold under the trademark "Pluronic"), polyoxyethylene castor oil, and polyoxyethylene lanolin. Examples of humectants include glycerin, 1,3-butylene glycol, and propylene glycol; examples of lower alcohols include ethanol and isopropanol; examples of thickening agents include xanthan gum, hydroxypropyl cellulose, hydroxypropyl methyl cellulose, polyethylene glycol and sodium carboxymethyl cellulose; examples of antioxidants comprise butylated hydroxytoluene, butylated hydroxyanisole, propyl gallate, citric acid and ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid.

For preparing ointments, creams, toilet waters, skin milks, and the like, typically from 0.01 to 10% in particular from 0.1 to 5% and more in particular from 0.2 to 2.5% of the active ingredient, e.g., of the hedgehog or ptc therapeutic, will be incorporated in the compositions. In ointments or creams, the carrier for example consists of 1 to 20%, in particular 5 to 15% of a humectant, 0.1 to 10% in particular from 0.5 to 5% of a thickener and water; or said carrier may consist of 70 to 99%, in particular 20 to 95% of a surfactant, and 0 to 20%, in particular 2.5 to 15% of a fat; or 80 to 99.9% in particular 90 to 99% of a thickener; or 5 to 15% of a surfactant, 2–15% of a humectant, 0 to 80% of an oil, very small (<2%) amounts of preservative, coloring agent and/or perfume, and water. In a toilet water, the carrier for example consists of 2 to 10% of a lower alcohol, 0.1 to 10% or in particular 0.5 to 1% of a surfactant, 1 to 20%, in particular 3 to 7% of a humectant, 0 to 5% of a buffer, water and small amounts (<2%) of preservative, dyestuff and/or perfume. In a skin milk, the carrier typically consists of 10–50% of oil, 1 to 10% of surfactant, 50–80% of water and 0 to 3% of preservative and/or perfume. In the aforementioned preparations, all % symbols refer to weight by weight percentage.

Particular compositions for use in the method of the present invention are those wherein the hedgehog or ptc therapeutic is formulated in liposome-containing compositions. Liposomes are artificial vesicles formed by amphiphatic molecules such as polar lipids, for example, phosphatidyl cholines, ethanolamines and serines, sphingomyelins, cardiolipins, plasmalogens, phosphatidic acids and cerebiosides. Liposomes are formed when suitable amphiphathic molecules are allowed to swell in water or aqueous solutions to form liquid crystals usually of multilayer structure comprised of many bilayers separated from each other by aqueous material (also referred to as coarse liposomes). Another type of liposome known to be consisting of a single bilayer encapsulating aqueous material is referred to as a unilamellar vesicle. If water-soluble materials are included in the aqueous phase during the swelling of the lipids they become entrapped in the aqueous layer between the lipid bilayers.

Water-soluble active ingredients such as, for example, various salt forms of a hedgehog polypeptide, are encapsulated in the aqueous spaces between the molecular layers. The lipid soluble active ingredient of hedgehog or ptc therapeutic, such as an organic mimetic, is predominantly incorporated into the lipid layers, although polar head groups may protude from the layer into the aqueous space. The encapsulation of these compounds can be achieved by a number of methods. The method most commonly used involves casting a thin film of phospholipid onto the walls of a flask by evaporation from an organic solvent. When this film is dispersed in a suitable aqueous medium, multilamellar liposomes are formed. Upon suitable sonication, the coarse liposomes form smaller similarly closed vesicles.

Water-soluble active ingredients are usually incorporated by dispersing the cast film with an aqueous solution of the compound. The unencapsulated compound is then removed by centrifugation, chromatography, dialysis or other art-known suitable procedures. The lipid-soluble active ingredient is usually incorporated by dissolving it in the organic solvent with the phospholipid prior to casting the film. If the solubility of the material in the lipid phase is not exceeded or the amount present is not in excess of that which can be bound to the lipid, liposomes prepared by the above method usually contain most of the material bound in the lipid bilayers; separation of the liposomes from unencapsulated material is not required.

A particularly convenient method for preparing liposome formulated forms of hedgehog and ptc therapeutics is the method described in EP-A-253,619, incorporated herein by reference. In this method, single bilayered liposomes containing encapsulated active ingredients are prepared by dissolving the lipid component in an organic medium, injecting the organic solution of the lipid component under pressure into an aqueous component while simultaneously mixing the organic and aqueous components with a high speed homogenizer or mixing means, whereupon the liposomes are formed spontaneously.

The single bilayered liposomes containing the encapsulated hedgehog or ptc therapeutic can be employed directly or they can be employed in a suitable pharmaceutically acceptable carrier for topical administration. The viscosity of the liposomes can be increased by the addition of one or more suitable thickening agents such as, for example xanthan gum, hydroxypropyl cellulose, hydroxypropyl methylcellulose and mixtures thereof. The aqueous component may consist of water alone or it may contain electrolytes, buffered systems and other ingredients, such as, for example, preservatives. Suitable electrolytes which can be employed include metal salts such as alkali metal and alkaline earth metal salts. The preferred metal salts are calcium chloride, sodium chloride and potassium chloride. The concentration of the electrolyte may vary from zero to 260 mM, preferably from 5 mM to 160 mM. The aqueous component is placed in a suitable vessel which can be adapted to effect homogenization by effecting great turbulence during the injection of the organic component. Homogenization of the two components can be accomplished within the vessel, or, alternatively, the aqueous and organic components may be injected separately into a mixing means which is located outside the vessel. In the latter case, the liposomes are formed in the mixing means and then transferred to another vessel for collection purpose.

The organic component consists of a suitable non-toxic, pharmaceutically acceptable solvent such as, for example ethanol, glycerol, propylene glycol and polyethylene glycol, and a suitable phospholipid which is soluble in the solvent. Suitable phospholipids which can be employed include lecithin, phosphatidylcholine, phosphatydylserine, phosphatidylethanolamine, phosphatidylinositol, lysophosphatidylcholine and phospha-tidyl glycerol, for example. Other lipophilic additives may be employed in order to selectively modify the characteristics of the liposomes. Examples of such other additives include stearylamine, phosphatidic acid, tocopherol, cholesterol and lanolin extracts.

In addition, other ingredients which can prevent oxidation of the phospholipids may be added to the organic component. Examples of such other ingredients include tocopherol, butylated hydroxyanisole, butylated hydroxytoluene, ascorbyl palmitate and ascorbyl oleate. Preservatives such as benzoic acid, methyl paraben and propyl paraben may also be added.

Apart from the above-described compositions, use may be made of covers, e.g. plasters, bandages, dressings, gauze pads and the like, containing an appropriate amount of a hedgehog or ptc therapeutic. In some cases use may be made of plasters, bandages, dressings, gauze pads and the like which have been impregnated with a topical formulation containing the therapeutic formulation.

EXEMPLIFICATION

The invention, now being generally described, will be more readily understood by reference to the following examples, which are included merely for purposes of illustration of certain aspects and embodiments of the present invention and are not intended to limit the invention.

Example 1

Cloning and Expression of Chick Sonic Hedgehog
(i) Experimental Procedures

Using degenerate PCR primers, vHH50 (SEQ ID No:23), vHH30 (SEQ ID No:24) and vHH31 (SEQ ID No:25) corresponding to a sequence conserved between Drosophila hedgehog (SEQ ID No:19) (Lee, J. J. et al. (1992) *Cell* 71: 33–50; Mohler, J. et al., (1992) *Development* 115: 957–971) and mouse Indian hedgehog (Ihh) (SEQ ID No:3), a 220 base pair (bp) fragment was amplified from chicken genomic DNA. From 15 isolates, two distinct sequences were cloned, each highly homologous to mouse Ihh. A probe made from isolate pCHA did not detect expression in embryonic tissues. Isolate pCHB, however, detected a 4 kb message in RNA prepared from embryonic head, trunk, or limb bud RNA. This cloned PCR fragment was therefore used as a probe to screen an unamplified cDNA library prepared from Hamburger Hamilton stage 22 (Hamburger, W. et al., (1951) *J. Morph.* 88: 49–92) limb bud RNA as described below.

A single 1.6 kilobase (kb) cDNA clone, pHH-2, was selected for characterization and was used in all subsequent analyses. The gene encoding for this cDNA was named Sonic Hedgehog (after the Sega computer game cartoon character). Sequencing of the entire cDNA confirmed the presence of a single long open reading frame potentially encoding for a protein of 425 amino acids (aa). The clone extends 220 bp upstream of the predicted initiator methionine and approximately 70 bp beyond the stop codon. No consensus polyadenylation signal could be identified in the 3' untranslated region. A second potential initiator methionine occurs at amino acid residue 4. The putative translation initiation signals surrounding both methionines are predicted to be equally efficient (Kozak, M., (1987) *Nuc. Acids Res.* 15: 8125–8132). When the pHH-2 Sonic cDNA is used to probe a northern blot of stage 24 embryonic chick RNA, a single mRNA species of approximately 4 kb is detected in both limb and trunk tissue. The message size was predicted by comparing it to the position of 18S and 28S ribosomal RNA. Hybridized mRNA was visualized after a two day exposure to a phosphoscreen. Because the Sonic cDNA clone pHH-2 is only 1.6 kb, it is likely to be missing approximately 2.4 kb of untranslated sequence.

PCR Cloning

All standard cloning techniques were performed according to Ausubel et. al. (1989), and all enzymes were obtained from Boehringer Mannheim Biochemicals. Degenerate oligonucleotides corresponding to amino acid residues 161 to 237 of the *Drosophila* hedgehog protein (Lee, J. J. et. al., (1992) *Cell* 71: 33–50) were synthesized. These degenerate oligonucleotides, vHH50, vHH30, and vHH31 also contained Eco RI, Cla I, and Xba I sites, respectively, on their 5' ends to facilitate subcloning. The nucleotide sequence of these oligos is given below:

vHH5O: 5'-GGAATTCCCAG(CA)GITG(CT)AA(AG)GA (AG)(CA)(AG)I(GCT)IAA-3' (SEQ ID No: 23)

vHH3O: 5'-TCATCGATGGACCCA(GA)TC(GA) AAICCIGC(TC)TC-3' (SEQ ID No: 24)

vHH3I: 5'-GCTCTAGAGCTCIACIGCIA(GA)IC(GT)IGC-3' (SEQ ID No: 25).

where I represents inosine. Nested PCR was performed by first amplifying chicken genomic DNA using the vHH50 and vHH30 primer pair and then further amplifying that product using the vHH50 and vHH3]primer pair. In each case the reaction conditions were: initial denaturation at 93° C. for 2.5 min., followed by 30 cycles of 94° C. for 45 s, 50° C. for 1 min., 72° C. for 1, and a final incubation of 72° C. for 5 min. The 220 bp PCR product was subcloned into pGEM7zf (Promega).

DNA Sequence Analysis

Nucleotide sequences were determined by the dideoxy chain termination method (Sanger, F. et al., (1977) *Proc. Natl. Acad. Sci. USA* 74: 5463–5467) using Sequenase v2.0 T7 DNA polymerase (US Biochemicals). 5' and 3' nested deletions of pHH-2 were generated by using the nucleases Exo III and SI (Erase a Base, Promega) and individual subclones sequenced. DNA and amino acid sequences were analyzed using both GCG (Devereux, J. et al., (1984) *Nuc. Acids Res.* 12: 387–394) and DNAstar software. Searches for related sequences were done through the BLAST network service (Altschul, S. F. et al., (1990) *J. Mol. Biol* 215: 403–410) provided by the National Center for Biotechnology Information.

Southern Blot Analysis

Five (5) µg of chick genomic DNA was digested with Eco RI and/or Bam HI, fractionated on a 1% agarose gel, and transferred to a nylon membrane (Genescreen, New England Nuclear). The filters were probed with $^{32}$P-labeled hha or hhb at 42° C. in hybridization buffer (0.5% BSA, 500 mM NaHPO$_4$, 7% SDS, 1 mM EDTA, pH 7.2; Church, G. M. et al., (1984) Proc. Natl. Acad. Sci. USA 81: 1991–1995). The blots were washed at 63° C. once in 0.5% bovine serum albumin, 50 mM NaHPO$_4$ (pH 7.2), 5% SDS, 1 mM EDTA and twice in 40 mM NaHPO$_4$ (pH 7.2), 1% SDS, 1 mM EDTA, and visualized on Kodak XAR-5 film.

Isolation Of Chicken Sonic cDNA Clones

A stage 22 limb bud cDNA library was constructed in λgt10 using Eco RI/NotI linkers. Unamplified phage plaques (10$^6$) were transferred to nylon filters (Colony/Plaque screen, NEN) and screened with α$^{32}$P-labelled pooled inserts from PCR clones pCHA and pCHB. Hybridization was performed at 42° C. in 50% formamide 2×SSC, 10% dextran sulfate, % SDS and washing as described in the Southern Blot procedure. Eight positive plaques were identified, purified and their cDNA inserts excised with EcoRI and subcloned into pBluescript SK+ (Stratagene). All eight had approximately 1.7 kb inserts with identical restriction patterns. One, pHH-2, was chosen for sequencing and used in all further manipulations.

Preparation Of Digoxigenin-Labeled Riboprobes

Plasmid pHH-2 was linearized with Hind III and transcribed with T3 RNA polymerase (for antisense probes) or with Bam HI and transcribed with T7 RNA polymerase according to the manufacturers instructions for the preparation of non-radioactive digoxigenin transcripts. Following the transcription reaction, RNA was precipitated, and resuspended in RNAse-free water.

Whole Mount In Situ Hybridization

Whole-mount in situ hybridization was performed using protocols modified from Parr, B. A. et al. (1993) *Development* 119: 247–261; Sasaki, H. et al. (1993) *Development* 118: 47–59; Rosen, B. et al. (1993) *Trends Genet.* 9: 162–167. Embryos from incubated fertile White Leghorn eggs (Spafas) were removed from the egg and extra-embryonic membranes dissected in calcium/magnesium-free phosphate-buffered saline (PBS) at room temperature. Unless otherwise noted, all washes are for five minutes at room temperature. Embryos were fixed overnight at 4° C. with 4% paraformaldehyde in PBS, washed twice with PBT (PBS with 0.1% Tween-20) at 4° C., and dehydrated through an ascending methanol series in PBT (25%, 50%, 75%, 2×100% methanol). Embryos were stored at −20° C. until further use.

Both pre-limb bud and limb bud stage embryos were rehydrated through an descending methanol series followed by two washes in PBT. Limb bud stage embryos were bleached in 6% hydrogen peroxide in PBT, washed three times with PBT, permeabilized with proteinase K (Boehringer, 2 µg/ml) for 15 minutes, washed with 2 mg/ml glycine in PBT for 10 minutes, and twice with PBT. Pre-limb bud stage embryos were permealibized (without prior incubation with hydrogen peroxide) by three 30 minute washes in RIPA buffer (150 mM NaCl, 1% NP-40, 0.5% Deoxycholate, 0.1% SDS, 1 mM EDTA, 50 mM Tris-HCl, pH 8.0). In all subsequent steps, pre-limb bud and limb bud stage embryos were treated equivalently. Embryos were fixed with 4% paraformaldehyde/0.2% gluteraldehyde in PBT, washed four times with PBT, once with pre-hybridization buffer (50% formamide, 5×SSC, 1% SDS, 50 µg/ml total yeast RNA, 50 µg/ml heparin, pH 4.5), and incubated with fresh pre-hybridization buffer for one hour at 70° C. The pre-hybridization buffer was then replaced with hybridization buffer (pre-hybridization buffer with digoxigenin labeled riboprobe at 1 µg/ml) and incubated overnight at 70° C.

Following hybridization, embryos were washed 3×30 minutes at 70° C. with solution 1 (50% formamide, 5×SSC, 1% SDS, pH 4.5), 3×30 minutes at 70° C. with solution 3 (50% formamide, 2×SSC, pH 4.5), and three times at room temperature with TBS (Tris-buffered saline with 2 mM levamisole) containing 0.1% Tween-20. Non-specific binding of antibody was prevented by preblocking embryos in TBS/0.1% Tween-20 containing 10% heat-inactivated sheep serum for 2.5 hours at room temperature and by pre-incubating anti-digoxigenin Fab alkaline-phosphatase conjugate (Boehringer) in TBS/0.1% Tween-20 containing heat inactivated 1% sheep serum and approximately 0.3% heat inactivated chick embryo powder. After an overnight incubation at 4° C. with the pre-adsorbed antibody in TBS/0.1% Tween-20 containing 1% sheep serum, embryos were washed 3×5 minutes at room temperature with TBS/0.1% Tween-20, 5×1.5 hour room temperature washes with TBS/1% Tween-20, and overnight with TBS/1% Tween-20 at 4° C. The buffer was exchanged by washing 3×10 minutes with NTMT (100 mM NaCl, 100 mM Tris-HCl, 50 mM MgCl2, 0.1% Tween-20, 2 mM levamisole). The antibody detection reaction was performed by incubating embryos with detection solution (NTMT with 0.25 mg/ml NBT and 0.13 mg/ml X-Phos). In general, pre-limb bud stage embryos were incubated for 5–15 hours and limb bud stage embryos 1–5 hours. After the detection reaction was deemed complete, embryos were washed twice with NTMT, once with PBT (pH 5.5), postfixed with 4% paraformaldehyde/0.1% gluteraldehyde in PBT, and washed several times with PBT. In some cases embryos were cleared through a series of 30%, 50%, 70%, and 80% glycerol in PBT. Whole embryos were photographed under transmitted light using a Nikon zoom stereo microscope with Kodak Ektar 100 ASA film. Selected embryos were processed for frozen sections by dehydration in 30% sucrose in PBS followed by embedding in gelatin and freezing. 25 µm cryostat sections were collected on superfrost plus slides (Fisher), rehydrated in PBS, and mounted with gelvatol. Sections were photographed with Nomarski optics using a Zeiss Axiophot microscope and Kodak Ektar 25 ASA film.

(ii) Sequence Homolgy Comparison Between Chicken Sonic hh And *Drosophila* hh And Other Vertebrate Sonic hh Proteins The deduced Sonic amino acid sequence (SEQ ID No:1) was compared to the *Drosophila* hedgehog protein (SEQ ID No:20). Over the entire open reading frame the two proteins are 48% homologous at the amino acids level. The predicted *Drosophila* protein extends 62 aa beyond that of Sonic at its amino terminus. This N-terminal extension precedes the putative signal peptide (residues 1–26) of the fly protein, and has been postulated to be removed during processing of the secreted form of *Drosophila* hedgehog (Lee, J. J. et al., (1992) *Cell* 71: 33–50). The sequence of residues 1–26 of the chicken Sonic protein matches well with consensus sequences for eukaryotic signal peptides (Landry, S. J. et al., (1993) *Trends. Biochem. Sci.* 16: 159–163) and is therefore likely to serve that function for Sonic. A hydropathy plot (Kyte, J. et al., (1982) *J. Mol. Biol.* 157: 133–148) indicates that residues 1–26 of the Sonic protein exhibit a high hydrophobic moment in accord with identified eukaryotic signal peptides. Cleavage of the putative signal sequence should occur C-terminal to residue 26 according to the predictive method of von Henjie, G. (1986) *Nucl. Acid. Res.* 11: 1986. A single potential N-linked glycosylation site is located at amino acid residue 282 of the Sonic protein. The predicted Sonic protein does not contain any other strong consensus motifs, and is not homologous to any other proteins outside of the Hedgehog family.

The mouse (SEQ ID No:4) and zebrafish (SEQ ID No 5) homologs of Sonic have also been isolated. All of the vertebrate proteins have a similar predicted structure: a putative signal peptide at their amino terminus, followed by an extraordinarily similar 182 amino acid region (99% identity in chicken versus mouse and 95% identity in chicken versus zebrafish) and a less well conserved carboxy-terminal region.

(iii) At Least Three Hedgehog Homologues are Present in the Chicken Genome

Since two distinct PCR products encoding for chicken hedgehogs were amplified from genomic DNA, the total number of genes in the chicken hedgehog family needed to be estimated. The two PCR clones pCHA and pCHB were used to probe a genomic Southern blot under moderately stringent conditions as described in the above Experimental Procedures. The blot was generated by digesting 5 µg of chick chromosomal DNA with EcoRI and BamHI alone and together. Each probe reacted most strongly with a distinct restriction fragment. For example, the blot probed with pCHA, shows three bands in each of the Barn HI lanes, one strong at 6.6 kb and two weak at 3.4 and 2.7 kb. The blot probed with pCHB, shows the 2.7 kb band as the most intense, while the 3.4 and 6.6 kb bands are weaker. A similar variation of intensities can also be seen in the Bam HI/Eco RI and EcoRI lanes. Exposure times were 72 hr. This data indicates that each probe recognizes a distinct chicken hedgehog gene, and that a third as yet uncharacterized chicken hedgehog homolog exists in the chicken genome.

(iv) Northern Analysis Defining Sites of Sonic Transcription

Northern analysis was performed which confirmed that Sonic is expressed during chick development. The spatial and temporal expression of Sonic in the chick embryo from gastrulation to early organogenesis was determined by whole mount in situ hybridization using a riboprobe corresponding to the full-length Sonic cDNA (SEQ ID No:1).

20 μg total RNA isolated from stage 24 chick leg buds or bodies (without heads or limbs) was fractionated on a 0.8% agarose formaldehyde gel and transferred to a nylon membrane (Hybond N, Amersham). The blot was probed with the 1.6 kb EcoRI insert from pHH-2. Random-primed $\alpha^{32}$P-labelled insert was hybridized at 42° C. hybridization buffer (1% BSA, 500 mM NaHPO$_4$, 7% SDS, 1 mM EDTA, pH 7.2) and washed at 63° C. once in 0.5% bovine serum albumin, 50 mM NaHPO4 (pH 7.2), 5% SDS, 1 mM EDTA and once in 40 mM NaHPO4 (pH 7.2), 1% SDS, 1 mM EDTA. The image was visualized using a phosphoimager (Molecular Dynamics) and photographed directly from the video monitor.

(v) Expression Of Sonic During Mid-Gastrulation

Sonic message is detected in the gastrulating blastoderm at early stage 4, the earliest stage analyzed. Staining is localized to the anterior end of the primitive streak in a region corresponding to Hensen's node. As gastrulation proceeds, the primitive streak elongates to its maximal cranial-caudal extent, after which Hensen's node regresses caudally and the primitive streak shortens. At an early point of node regression, Sonic mRNA can be detected at the node and in midline cells anterior to the node. By late stage 5, when the node has migrated approximately one-third of the length of the fully elongated primitive streak, prominent Sonic expression is seen at the node and in the midline of the embryo, reaching its anterior limit at the developing head process. Sections at a cranial level show that Sonic mRNA is confined to invaginated axial mesendoderm, tissue which contributes to foregut and notochord. More caudally, but still anterior to Hensen's node, staining of axial mesoderm is absent and Sonic expression is confined to the epiblast. At the node itself, high levels of Sonic message are observed in an asymmetric distribution extending to the left of and posterior to the primitive pit. This asymmetric distribution is consistently observed (6/6 embryos from stages 5–7) and is always located to the left of the primitive pit. At the node, and just posterior to the node, Sonic expression is restricted to the epiblast and is not observed in either mesoderm or endoderm. The expression of Sonic in the dorsal epiblast layer without expression in underlying axial mesoderm contrasts markedly with later stages where Sonic expression in underlying mesoderm always precedes midline neural tube expression.

(vi) Expression Of Sonic During Head Fold Stages

During the formation and differentiation of the head process, Sonic mRNA is detected in midline cells of the neural tube, the foregut, and throughout most of the axial mesoderm. At stage 7, Sonic message is readily detected asymmetrically at the node and in ventral midline cells anterior to the node. The rostral limit of Sonic expression extends to the anterior-most portions of the embryo where it is expressed in the foregut and prechordal mesoderm (Adelmann, H. B., (1932) *Am. J. Anat.* 31, 55–101). At stage 8, expression of Sonic persists along the entire ventral midline anterior to Hensen's node, while the node region itself no longer expresses Sonic. Transverse sections at different axial levels reveal that at stage 8 Sonic is coexpressed in the notochord and the overlying ventromedial neuroectoderm from anterior to Hensen's node to the posterior foregut. The levels of Sonic message are not uniform in the neural tube: highest levels are found at the presumptive mid- and hindbrain regions with progressively lower levels anterior and posterior. The increasing graded expression in the neural tube from Hensen's node to the rostral brain may reflect the developmental age of the neuroectoderm as differentiation proceeds from posterior to anterior. At the anterior-most end of the embryo, expression is observed in midline cells of the dorsal and ventral foregut as well as in prechordal mesoderm. Although the prechordal mesoderm is in intimate contact with the overlying ectoderm, the latter is devoid of Sonic expression.

(vii) Expression of Sonic During Early CNS Differentiation

At stages 10 through 14, Sonic expression is detected in the notochord, ventral neural tube (including the floor plate), and gut precursors. By stage 10, there is a marked expansion of the cephalic neuroectoderm, giving rise to the fore- mid- and hind-brain. At stage 10, Sonic mRNA is abundantly expressed in the ventral midline of the hindbrain and posterior midbrain. This expression expands laterally in the anterior midbrain and posterior forebrain. Expression does not extend to the rostral forebrain at this or later stages. Sections reveal that Sonic is expressed in the notochord, the prechordal mesoderm, and the anterior midline of the foregut. Expression in the neuroepithelium extends from the forebrain caudally. In the posterior-most regions of the embryo which express Sonic, staining is found only in the notochord and not in the overlying neurectoderm. This contrasts with earlier expression in which the posterior domains of Sonic expression contain cells are located in the dorsal epiblast, but not in underlying mesoderm or endoderm. Midgut precursors at the level of the anterior intestinal portal also show weak Sonic expression.

At stage 14, expression continues in all three germ layers. The epithelium of the closing midgut expresses Sonic along with portions of the pharyngeal endoderm and anterior foregut. Ectoderm lateral and posterior to the tail bud also exhibits weak expression. At this stage, Sonic is also expressed along entire length of the notochord which now extends rostrally only to the midbrain region and no longer contacts the neuroepithelium at the anterior end of the embryo. Expression in head mesenchyme anterior to the notochord is no longer observed. In the neural tube Sonic is found along the ventral midline of the fore- mid- and hindbrain and posteriorly in the spinal cord. In the forebrain, ex pr ession is expanded laterally relative to the hindbrain. At midgut levels, expression of Sonic in the neural tube appears to extend beyond the floor plate into more lateral regions. As observed at stage 10, Sonic at stage 14 is found in the notochord, but not in the ventral neural tube in posterior-most regions of the embryo. When neuroectodermal expression is first observed in the posterior embryo, it is located in midline cells which appear to be in contact with the notochord. At later stages, expression continues in areas which show expression at stage 14, namely the CNS, gut epithelium including the allantoic stalk, and axial mesoderm.

(viii) Sonic Is Expressed In Posterior Limb Bud Mesenchyme

The limb buds initially form as local thickenings of the lateral plate mesoderm. As distal outgrowth occurs during stage 17, Sonic expression becomes apparent in posterior regions of both the forelimb a nd the hindlimb. Sections through a stage 21 embryo at the level of the forelimbs reveal th at expression of Sonic in limb buds is limited to mesenchymal tissue. A more detailed expression pro file of Sonic during limb development is discussed below in Example 3. Briefly, as the limb bud grows out, expression of Sonic narrows along the anterior-posterior axis to become a thin stripe along the posterior margin closely apposed to the ectoderm. Expression is not found at more proximal regions of the bud. High levels of Sonic expression are maintained until around stage 25/26 when staining becomes weaker. Expression of Sonic is no longer observed in wing buds or leg buds after stage 28.

Example 2

Mouse Sonic Hedgehog Is Implicated in the Regulation of CNS and Limb Polarity (i) Experimental Procedures Isolation of Hedgehog Phage Clones The initial screen for mammalian hh genes was performed, as above, using a 700 bp PCR fragment encompassing exons 1 and 2 of the *Drosophila* hh gene. Approximately one million plaques of a 129/Sv Lambda Fix II genomic library (Stratagene) were hybridized with an a $^{32}$P dATP labeled probe at low stringency (55° C. in 6×SSC, 0.5% SDS, 5× Denhardt's; final wash at 60° C. in 0.5×SSC, 0.1% SDS for 20'). Five cross hybridizing phage plaques corresponding to the Dhh gene were purified. Restriction enzyme analysis indicated that all clones were overlapping. Selected restriction enzyme digests were then performed to map and subclone one of these. Subclones in pGEM (Promega) or Bluescript (Stratagene) which crosshybridized with the *Drosophila* hh fragment where sequenced using an ABI automatic DNA sequencer.

Mouse Ihh and Shh were identified by low stringency hybridization (as described above) with a chick Shh cDNA clone to one million plaques of an 8.5 day λgt10 mouse embryo cDNA library (Fahrner, K. et al., (1987) *EMBO J.* 6: 1265–1271). Phage plaques containing a 1.8 kb Ihh and 0.64 and 2.8 kb Shh inserts were identified. Inserts were excised and subcloned into Bluescript (Stratagene) for dideoxy chain termination sequencing using modified T7 DNA polymerase (USB). The larger Shh clone contained a partially processed cDNA in which intron splicing at the exon 1/2 junction had not occurred.

To screen for additional Ihh and Shh cDNA clones, an 8.5 day λZAPII cDNA library was probed at high stringency (at 65° C. in 6×SSC, 0.5% SDS, 5× Denhardt's; final wash at 65° C. in 0.1×SSC, 0.1% SDS for 30') with the Ihh and Shh mouse cDNA clones. No additional Ihh clones were identified. However several 2.6 kb, apparently full length, Shh clones were isolated. The DNA sequence of the additional 5' coding region not present in the original 0.64 and 2.8 kb Shh clones was obtained by analysis of one of the 2.6 kb inserts.

Northern Blot Analysis

Expression of Shh was investigated by RNA blot analysis using 20 μg of total RNA from adult brain, spleen, kidney, liver, lung, 16.5 dpc brain, liver and lung; 9.5 dpc to 17.5 dpc whole embryo; 9.5 dpc forebrain, midbrain and 10.5 dpc brain. RNA samples were electrophoretically separated on a 1.2% agarose gel, transferred and u.v. crosslinked to Genescreen (DuPont) and probed with 2×10$^6$ cpm/ml of an α$^{32}$P-dATP labeled mouse Shh probe (2.8 kb insert from λgt 10 screen). Hybridization was performed at 42° C. in 50% formamide 5× Denhardt's, 5×SSPE, 0.1% SDS, 6.5% dextran, 200 μg/ml salmon sperm DNA. Final wash was at 55° C. in 0.1×SSC, 0.1% SDS. The blot was exposed for 6 days in the presence of an intensifying screen.

In Situ Hybridization, β-Galactosidase Staining And Histological Analysis

Embryos from 7.25 to 14.5 dpc were analyzed for either Shh or HNF-3β expression by whole mount in situ hybridization to digoxygenin labeled RNA probes as described in Wilkinson, (1992) *In situ Hybridization: A Practical Approach*. Oxford; Parr et al., (1993) *Development* 119:247–261. The mouse Shh probe was either a 2.8 kb or 0.6 kb RNA transcript generated by T7 (2.8 kb) or T3 (0.6 kb) transcription of XbaI and HindIII digests of Bluescript (Stratagene) subclones of the original Shh cDNA inserts. The HNF-3β probe was generated by HindIII linearization of a HNF-3β cDNA clone (Sasaki, H. et al., (1993) *Development* 118: 47–59) and T7 polymerase transcription of 1.6 kb transcript. Embryos were photographed on an Olympus-SZH photomicroscope using Kodak Ektachrome EPY 64T color slide film.

Sections through wild type and WEXP2—CShh transgenic embryos were prepared and hybridized with $^{35}$S-UIP labeled RNA probes (Wilkinson, D. G. et al., (1987) *Development* 99: 493–500). Sections were photographed as described in McMahon, A. P. et al., (1992) *Cell* 69: 581–595.

β Staining of WEXP2-lacZ embryos with βwas performed according to Whiting, J. et al., (1991) *Genes & Dev.* 5: 2048–2059. General histological analysis of wildtype and WEXP2-CShh transgenic embryos was performed on paraffin sections of Bouin's fixed embryos counterstained with haematoxylin and eosin. Histological procedures were as described by Kaufman, M. H. (1992) *The Atlas of Mouse Development*, London: Academic Press. Sections were photographed on a Leitz Aristoplan compound microscope using Kodak EPY 64T color slide film.

DNA Constructs For Transgenics

Genomic Wnt-1 fragments were obtained by screening a λGEM12 (Promega) 129/Sv mouse genomic library with a 375 bp MluI-BglII fragment derived from the fourth exon of the murine Wnt-1 gene. One of the clones (W1-15.1) was used in this study.

As an initial step towards the generation of the pWEXP2 expression vector, W1-15.1 was digested to completion with restriction enzymes AatII and ClaI, and a 2774 bp AatII-ClaI fragment isolated. This fragment was ligated into AatII and ClaI cut pGEM-7Zf vector (Promega), generating pW1-18. This plasmid was digested with HindIII and ligated to annealed oligonucleotides lad (SEQ ID No:26) and lac2 (SEQ ID No:27) generating pW1-18S* which has a modified polylinker downstream of the ClaI restriction site. This construct (pW1-18S*) was digested with ClaI and BglII and ligated with both the 2.5 kb 3' ClaI-BglII exon-intron region and 5.5 kb 3' BglII—BglII Wnt-1 enhancer, generating pWRES4. This construct contains a 10.5 kb genomic region which starts upstream of the Wnt-1 translation initiation codon (at an AatII site approximately 1.0 kb from the ATG) and extends to a BglII site 5.5 kb downstream of the Wnt-1 polyadenylation signal. This plasmid also contains a 250 bp region of the neomycin phosphotransferase (neo) gene inserted in inverse orientation in the 3' transcribed but untranslated region. Finally, to generate the WEXP2 expression vector, a 2 kb Sfi I fragment was amplified from pWRES4 using Sf-1 (SEQ ID No:28) and Sf-2 (SEQ ID No:29) oligonucleotides. This amplified fragment was digested with Sfi I and inserted into Sfi I linearised pWRES4, generating pWEXP2. This destroys the Wnt-1 translation initiation codon, and replaces it by a polylinker containing Nru I, Eco RV, Sac II, and Bst BI restriction sites, which are unique in pWEXP2.

The WEXP2—lacZ construct was obtained by inserting an end-filled Bgl II-Xho I lacZ fragment isolated from the pSDKlacZpA vector in the Nru I cut pWEXP2 expression vector. Similarly, the WEXP2—CShh construct was obtained by inserting an end-filled XbaI cDNA fragment containing the full Chick Shh coding sequence (SEQ ID No:1) into the Nru I cut WEXP2 expression vector.
Oligonucleotide sequences are as follows:
lac: 5'-AGCTGTCGACGCGGCCGCTACGTAGGTT ACCGACGTCAAGCTTAGATCTC-3'
lac2: 5'-AGCTGAGATCTAAGCTTGACGTCGGTAA CCTACGTAGCGGCCGCGTCGAC-3'
Sf-1: 5'-GATCGGCCAGGCAGGCCTCGCGATATCG TCACCGCGGTATTCGAA-3'
Sf-2: 5'-AGTGCCAGTCGGGGCCCCCAGGGCCG CGCC-3'

Production And Genotyping Of Transgenic Embryos

Transgenic mouse embryos were generated by microinjection of linear DNA fragments into the male pronucleus of B6CBAFI/J (C57BL/6J×CBA/J) zygotes. CD-I or B6CBAFI/J females were used as recipients for injected embryos. Go mice embryos were collected at 9.5, 10.5, and 11.5 dpc, photographed using an Olympus SZH stereophotomicroscope on Kodak EPY-64T color slide film, then processed as described earlier.

WEXP2-lacZ and WEXP2—CShh transgenic embryos were identified by PCR analysis of proteinase-K digests of yolk sacs. Briefly, yolk sacs were carefully dissected free from maternal and embryonic tissues, avoiding cross-contamination between littermates, then washed once in PBS. After overnight incubation at 55° C. in 50 μl of PCR proteinase-K digestion buffer (McMahon, A. P. et al., (1990) Cell 62: 1073–1085). 1 μl of heat-inactivated digest was subjected to polymerase chain reaction (PCR) in a 20 μl volume for 40 cycles as follows: 94° C. for 30 seconds, 55° C. for 30 seconds, 72° C. for 1 minute, with the reaction ingredients described previously (McMahon, A. P. et al., (1990) Cell 62: 1073–1085)). In the case of the WEXP2-lacZ transgenic embryos, oligonucleotides 137 (SEQ ID No:30) and 138 (SEQ ID No:31) amplify a 352 bp lacZ specific product. In the case of the WEXP2—CShh embryos, oligonucleotides WPR2 (Wnt-1-specific) (SEQ ID No:32) and 924 (Chick Shh-specific) (SEQ ID No:33) amplify a 345 bp fragment spanning the insertion junction of the Chick-Shh cDNA in the WEXP2 expression vector. Table 2 summarizes the results of WEXP2—C-Shh transgenic studies.
Oligonucleotide sequences are as follows:
137: 5'-TACCACAGCGGATGGTTCGG-3'
138: 5'-GTGGTGGTTATGCCGATCGC-3'
WPR2: 5'-TAAGAGGCCTATAAGAGGCGG-3'
924: 5'-AAGTCAGCCCAGAGGAGACT-3'

(ii) Mouse hh Genes

The combined screening of mouse genomic and 8.5 day post coitum (dpc) cDNA libraries identified three mammalian hh counterparts which herein will be referred to as Desert, Indian and Sonic hedgehog (Dhh, Ihh and Shh, respectively). Sequences encoding Dhh (SEQ ID No:2) were determined from analysis of clones identified by low stringency screening of a mouse genomic library. DNA sequencing of one of five overlapping lambda phage clones identified three homologous regions encoding a single open reading frame interrupted by introns in identical position to those of the Drosophila hh gene). Splicing across the exon 1/2 boundary was confirmed by polymerase chain reaction (PCR) amplification of first strand cDNA generated from adult testicular RNA. A partial sequence of Ihh (SEQ ID No:3) and the complete sequence of Shh (SEQ ID No:4) coding regions were determined from the analysis of overlapping cDNA clones isolated from 8.5 dpc cDNA libraries. The longest Shh clone, 2.6 kb, appears to be full length when compared with the Shh transcript present in embryonic RNAs. The 1.8 kb partial length Ihh cDNA is complete at the 3' end, as evidenced by the presence of a polyadenylation consensus sequence and short poly A tail.

Alignment of the predicted Drosophila hh protein sequence with those of the mouse Dhh, Ihh and Shh, and chick Shh and zebrafish Shh, reveals several interesting features of the hh-family. All the vertebrate hh-proteins contain an amino terminal hydrophobic region of approximately 20 amino acids immediately downstream of the initiation methionine. It is likely that this region constitutes a signal peptide and vertebrate hhs are secreted proteins. Signal peptide cleavage is predicted to occur (von Heijne, G., (1986) Nucleic Acids Research 14: 4683–4690) just before an absolutely conserved six amino acid stretch, CGPGRG (SEQ ID No:34) (corresponding to residues 85–90), in all hh proteins. This generates processed mouse Dhh and Shh proteins of 41 and 44 kd, respectively. Interestingly, Drosophila hh is predicted to contain a substantial amino terminal extension beyond the hydrophobic domain suggesting that the Drosophila protein enters the secretory pathway by a type II secretory mechanism. This would generate a transmembrane tethered protein which would require subsequent cleavage to release a 43 kd secreted form of the protein. In vitro analysis of Drosophila hh is consistent with this interpretation (Lee, J. J. et al., (1992) Cell 71: 33–50). However, there also appears to be transitional initiation at a second methionine (position 51 of SEQ ID No:20) just upstream of the hydrophobic region (Lee, J. J. et al., (1992) Cell 71: 33–50), suggesting that Drosophila hh, like its vertebrate counterparts, may also be secreted by recognition of a conventional amino terminal signal peptide sequence.

Data base searches for protein sequences related to vertebrate hh's failed to identify any significant homologies, excepting Drosophila hh. In addition, searching the "PROSITE" data bank of protein motifs did not reveal any peptide motifs which are conserved in the different hh proteins. Thus, the hhs represent a novel family of putative cell signaling molecules.

One feature of the amino acid alignment is the high conservation of hh sequences. Vertebrate hhs share 47 to 51% amino acid identity with Drosophila hh throughout the predicted processed polypeptide sequence. Dhh has a slightly higher identity than that of Ihh and Shh suggesting that Dhh may be the orthologue of Drosophila hh. Conservation is highest in the amino terminal half of the proteins, indeed, from position 85 (immediately after the predicted shared cleavage site) to 249, 62% of the amino acids are completely invariant amongst the Drosophila and vertebrate proteins. Comparison of mouse Dhh, Ihh and Shh where their sequences overlap in this more conserved region, indicates that Ihh and Shh are more closely related (90% amino acid identity; residues 85 to 266) than with the Dhh sequence (80% amino acid identity; residues 85 to 266). Thus, Ihh and Shh presumably resulted from a more recent gene duplication event.

Comparison of cross species identity amongst Shh proteins reveals an even more striking sequence conservation. Throughout the entire predicted processed sequence mouse and chick Shh share 84% of amino acid residues. However, in the amino terminal half (positions 85 to 266) mouse and chick are 99% and mouse and zebrafish 94% identical in an 180 amino acid stretch. Conservation falls off rapidly after position 266. SEQ ID No:21 shows the consensus sequence in the amino terminal half of all vertebrate Shh genes (human, mouse, chicken and zebrafish) identified to date. SEQ ID No:22 shows the consensus sequence in the amino terminal half of vertebrate hedgehog genes (Shh, Ihh, and Dhh) identified to date in different species (mouse, chicken, human and zebrafish).

In summary, hh family members are secreted proteins consisting of a highly conserved amino terminal and more divergent carboxyl terminal halves. The extreme interspecies conservation of the vertebrate Shh protein points to likely conservation of Shh function across vertebrate species.

(iii) Expression of Mouse Shh at the Axial Midline

Expression of Shh in the mouse was examined in order to explore the role of mouse Shh (SEQ ID No:13) in vertebrate development. Northern blots of embryonic and adult RNA samples were probed with a radiolabelled mouse Shh cDNA probe. An Shh transcript of approximately 2.6 kb was detected in 9.5 dpc whole embryo RNA, and 9.5 and 10.5 dpc brain RNA fractions. No expression was detected in total RNA samples from later embryonic stages.

Of the late fetal and adult tissue RNAs examined Shh expression was only detected in 16.5 dpc and adult lung.

To better define the precise temporal and spatial expression of Shh an extensive series of whole mount and serial section in situ hybridizations were performed using digoxygenin and 10 $^{35}$S-radiolabelled RNA probes, respectively, to mouse embryo samples from 7.25 dpc (mid streak egg cylinder stage of gastrulation) to 13.5 dpc. No Shh expression is detected at mid-gastrulation stages (7.25 dpc) prior to the appearance of the node, the mouse counterpart of the amphibian organizer and chick Hensen's node. When the primitive streak is fully extended and the midline mesoderm of the head process is emerging from the node (7.5 to 7.75 dpc), Shh is expressed exclusively in the head process. At late head fold stages, Shh is expressed in the node and midline mesoderm of the head process extending anteriorly under the presumptive brain. Just prior to somite formation, Shh extends to the anterior limit of the midline mesoderm, underlying the presumptive midbrain. As somites are formed, the embryonic axis extends caudally. The notochord, which represents the caudal extension of the head process, also expresses Shh, and expression is maintained in the node.

Interestingly, by 8 somites (8.5 dpc) strong Shh expression appears in the CNS. Expression is initiated at the ventral midline of the midbrain, above the rostral limit of the head process. By 10 somites CNS expression in the midline extends rostrally in the forebrain and caudally into the hindbrain and rostral spinal cord. Expression is restricted in the hindbrain to the presumptive floorplate, whereas midbrain expression extends ventro-laterally. In the forebrain, there is no morphological floor plate, however ventral Shh expression here is continuous with the midbrain. By 15 somites ventral CNS expression is continuous from the rostral limit of the diencephalon to the presumptive spinal cord in somitic regions. Over the next 18 to 24 hrs, to the 25–29 somite stage, CNS expression intensifies and forebrain expression extends rostral to the optic stalks. In contrast to all other CNS regions, in the rostral half of the diencephalon, Shh is not expressed at the ventral midline but in two strips immediately lateral to this area which merge again in the floor of the forebrain at its rostral limit. Expression of Shh in both the notochord and floorplate is retained until at least 13.5 dpc.

Several groups have recently reported the cloning and expression of vertebrate members of a family of transcription factors, related to the *Drosophila* forkhead gene. One of these, HNF-3 $\mu$l shows several similarities in expression to Shh (Sasaki, H. et al., (1993) Development 118: 47–59) suggesting that HNF-3β may be a potential regulator of Shh. To investigate this possibility, direct comparison of HNF-3β and Shh expression was undertaken. HNF-3β transcripts are first detected in the node (as previously reported by Sasaki, H. et al., (1993) supra), prior to the emergence of the head process and before Shh is expressed. From the node, expression proceeds anteriorly in the head process, similar to Shh expression. Activation of HNF-3β within the CNS is first observed at 2–3 somites, in the presumptive mid and hindbrain, prior to the onset of Shh expression. By 5 somites, expression in the midbrain broadens ventrolaterally, extends anteriorly into the forebrain and caudally in the presumptive floor plate down much of the neuraxis in the somitic region. Strong expression is maintained at this time in the node and notochord. However, by 10 somites expression in the head process is lost and by 25–29 somites notochordal expression is only present in the most extreme caudal notochord. In contrast to the transient expression of HNF-3β in the midline mesoderm, expression in the floor plate is stably retained until at least 11.5 dpc. Thus, there are several spatial similarities between the expression of HNF-3β and Shh in both the midline mesoderm and ventral CNS and it is likely that both genes are expressed in the same cells. However, in both regions, HNF-3β expression precedes that of Shh. The main differences are in the transient expression of HNF-3β in the head process and notochord and Shh expression in the forebrain. Whereas HNF-3β and Shh share a similar broad ventral and ventral lateral midbrain and caudal diencephalic expression, only Shh extends more rostrally into the forebrain. In general, these results are consistent with a model in which initial activation of Shh expression may be regulated by HNF-3β.

The similarity in Shh and HNF-3β expression domains is also apparent in the definitive endoderm which also lies at the midline. Broad HNF-3β expression in the foregut pocket is apparent at 5 somites as previously reported by Sasaki, H. et al., (1993) supra. Shh is also expressed in the endoderm, immediately beneath the forebrain. Both genes are active in the rostral and caudal endoderm from 8 to 11 somites. Whereas HNF-3β is uniformly expressed, Shh expression is initially restricted to two ventro-lateral strips of cells. Ventral restricted expression of Shh is retained in the most caudal region of the presumptive gut until at least 9.5 dpc whereas HNF-3β is uniformly expressed along the dorso-ventral axis. Both genes are expressed in the pharyngeal ectoderm at 9.5 dpc and expression is maintained in the gut until at least 11.5 dpc. Moreover, expression of Shh in the embryonic and adult lung RNA suggests that endodermal expression of Shh may continue in, at least some endoderm derived organs.

(iv) Expression of Shh In The Limb

Expression of Shh is not confined to midline structures. By 30–35 somites (9.75 dpc), expression is detected in a small group of posterior cells in the forelimb bud. The forelimb buds form as mesenchymal outpocketings on the flanks, opposite somites 8 to 12, at approximately the 17 to 20 somite stage. Shh expression is not detectable in the forelimbs until about 30–35 somites, over 12 hours after the initial appearance of the limbs. Expression is exclusively posterior and restricted to mesenchymal cells. By 10.5 dpc, both the fore and hindlimbs have elongated substantially from the body flank. At this time Shh is strongly expressed in the posterior, distal aspect of both limbs in close association with the overlying ectoderm. Analysis of sections at this stage detects Shh expression in an approximately six cell wide strip of posterior mesenchymal cells. In the forelimb, Shh expression ceases by 11.5 dpc. However, posterior, distal expression is still detected in the hindlimb. No limb expression is detected beyond 12.5 dpc.

(v) Ectopic Expression Of Shh

Grafting studies carried out principally in the chick demonstrate that cell signals derived from the notochord and floor plate pattern the ventral aspect of the CNS (as described above). In the limb, a transient signal produced by a group of posterior cells in both limb buds, the zone of polarizing activity (ZPA), is thought to regulate patterning across the anterior-posterior axis. Thus, the sequence of Shh, which predicts a secreted protein and the expression profile in midline mesoderm, the floor plate and in the limb, suggest that Shh signaling may mediate pattern regulation in the ventral CNS and limb.

To determine whether Shh may regulate ventral development in the early mammalian CNS, a Wnt-1 enhancer was used to alter its normal domain of expression. Wnt-1 shows a dynamic pattern of expression which is initiated in the presumptive midbrain just prior to somite formation. As the neural folds elevate and fuse to enclose the neural tube, Wnt-1 expression in the midbrain becomes restricted to a tight circle, just anterior of the midbrain, the ventral midbrain and the dorsal midline of the diencephalon, midbrain, myelencephalon and spinal cord (Wilkinson, D. G. et al., (1987) *Cell* 50: 79–88; McMahon, A. P. et al., (1992) *Cell* 69: 581–595; Parr, B. A. et al., (1993) *Development* 119: 247–261).

It was determined that essentially normal expression of lacZ reporter constructs within the Wnt-1 expression domain is dependent upon a 5.5 kb enhancer region which lies downstream of the Wnt-1 polyadenylation sequence. A construct was generated for ectopic expression of cDNA clones in the Wnt-1 domain and tested in transgenics using a lacZ reporter (pWEXP-lacZ). Two of the four $G_O$ transgenic embryos showed readily detectable β-galactosidase activity, and in both expression occurred throughout the normal Wnt-1 expression domain. More extensive studies with a similar construct also containing the 5.5 kb enhancer gave similar frequencies. Some ectopic expression was seen in newly emerging neural crest cells, probably as a result of perdurance of β-galactosidase RNA or protein in the dorsally derived crest. Thus, the Wnt-1 expression construct allows the efficient ectopic expression of cDNA sequences in the midbrain and in the dorsal aspect of much of the CNS.

An Shh ectopic expression construct (pWEXP-CShh) containing two tandem head to tail copies of a chick Shh cDNA was generated. By utilizing this approach, ectopic expression of the chick Shh is distinguishable from that of the endogenous mouse Shh gene. Chick Shh shows a high degree of sequence identity and similar expression to the mouse gene. Thus, it is highly likely that Shh function is widely conserved amongst vertebrates, a conclusion further supported by studies of the same gene in zebrafish.

Table 2 shows the results of several transgenic experiments in which the Go population was collected at 9.5 to 11.5 dpc. Approximately half of the transgenic embryos identified at each stage of development had a clear, consistent CNS phenotype. As we expect, on the basis of 1 control studies using the 5.5 kb Wnt-I enhancer, that only half the transgenics will express the transgene, it is clear that in most embryos ectopically expressing chick Shh, an abnormal phenotype results.

TABLE 2

Summary of WEXP2-Chick Shh transgenic studies

| Age (dpc) | Number of Embryos | Number of Transgenics | Number of Embryos with CNS phenotype[a] |
|---|---|---|---|
| 9.5 | 37 | 11 | 6 (54.5%) |
| 10.5 | 59 | 16 | 8 (50%) |
| 11.5 | 33 | 7 | 3 (42.9%) |

Figures in parentheses, refer to the percentage of transgenic embryos with a CNS phenotype
[a]In addition one 9.5 pc and two 10.5 pc transgenic embryos showed non-specific growth retardation, as occurs at low frequency in transgenic studies. These embryos were excluded from further analysis.

At 9.5 dpc, embryos with a weaker phenotype show an open neural plate from the mid diencephalon to the myelencephalon. In embryos with a stronger phenotype at the same stage, the entire diencephalon is open and telencephalic and optic development is morphologically abnormal. As the most anterior diencephalic expression of Wnt-I is lower than that in more caudal regions, the differences in severity may relate to differences in the level of chick Shh expression in different Go embryos. At the lateral margins of the open neural folds, where Wnt-1 is normally expressed, there is a thickening of the neural tissue extending from the diencephalon to myelencephalon. The cranial phenotype is similar at 10.5 and 11.5 dpc. However, there appears to be a retardation in cranial expansion of the CNS at later stages.

In addition to the dorsal cranial phenotype, there is a progressive dorsal phenotype in the spinal cord. At 9.5 dpc, the spinal cord appears morphologically normal, except at extreme rostral levels. However by 10.5 dpc, there is a dorsal dysmorphology extending to the fore or hindlimbs. By 11.5 dpc, all transgenic embryos showed a dorsal phenotype along almost the entire spinal cord. Superficially, the spinal cord had a rippled, undulating appearance suggestive of a change in cell properties dorsally. This dorsal phenotype, and the cranial phenotype were examined by histological analysis of transgenic embryos.

Sections through a 9.5 dpc embryo with an extreme CNS phenotype show a widespread dorsal perturbation in cranial CNS development. The neural/ectodermal junction in the diencephalon is abnormal. Neural tissue, which has a columnar epithelial morphology quite distinct from the squamous epithelium of the surface ectoderm, appears to spread dorsolaterally. The myelencephalon, like the diencephalon and midbrain, is open rostrally. Interestingly, there are discontinuous dorso-lateral regions in the myelencephalon with a morphology distinct from the normal roof plate regions close to the normal site of Wnt-1 expression. These cells form a tight, polarized epithelium with basely located nuclei, a morphology similar to the floor plate and distinct from other CNS regions. Differentiation of dorsally derived neural crest occurs in transgenic embryos as can be seen from the presence of cranial ganglia. In the rostral spinal cord, the neural tube appeared distended dorso-laterally which may account for the superficial dysmorphology.

By 11.5 dpc, CNS development is highly abnormal along the entire dorsal spinal cord to the hindlimb level. The dorsal half of the spinal cord is enlarged and distended. Dorsal sensory innervation occurs, however, the neuronal trajectories are highly disorganized. Most obviously, the morphology of dorsal cells in the spinal cord, which normally are elongated cells with distinct lightly staining nuclei and cytoplasm, is dramatically altered. Most of the dorsal half of the spinal cord consists of small tightly packed cells with darkly staining nuclei and little cytoplasm. Moreover, there appears to be many more of these densely packed cells, leading to abnormal outgrowth of the dorsal CNS. In contrast, ventral development is normal, as are dorsal root ganglia, whose origins lie in neural cells derived from the dorsal spinal cord.

(vi) Ectopic Shh Expression Activates Floor Plate Gene Expression

To determine whether ectopic expression of chick Shh results in inappropriate activation of a ventral midline development in the dorsal CNS, expression of two floor plate expressed genes, HNF-3β and mouse Shh, were examined. Whole mounts of 9.5 dpc transgenic embryos show ectopic expression of HNF-3β throughout the cranial Wnt-1 expression domain. In addition to normal expression at the ventral midline, HNF-3β transcripts are expressed at high levels, in a circle just rostral to the mid/hindbrain junction, along the dorsal (actually lateral in unfused brain folds) aspects of the midbrain and, more weakly, in the roof plate of the myelencephalon. No expression is observed in the metencephalon which does not express Wnt-1. Thus, ectopic expression of Shh leads to the activation of HNF-3β throughout the cranial Wnt-1 expression domain.

The relationship between chick Shh expression and the expression of HNF-3β in serial sections was also examined. Activation of HNF-3β in the brain at 9.5 and 10.5 dpc is localized to the dorsal aspect in good agreement with the observed ectopic expression of chick Shh. Interestingly mouse Shh is also activated dorsally. Thus, two early floor plate markers are induced in response to chick Shh.

From 9.5 dpc to 11.5 dpc, the spinal cord phenotype becomes more severe. The possibility that activation of a floor plate pathway may play a role in the observed phenotype was investigated. In contrast to the brain, where ectopic HNF-3β and Shh transcripts are still present, little or no induction of these floor plate markers is observed. Thus, although the dorsal spinal cord shows a widespread transformation in cellular phenotype, this does not appear to result from the induction of floor plate development.

Example 3

Chick Sonic Hedgehog Mediates ZPA Activity (i) Experimental Procedures

Retinoic Acid Bead Implants

Fertilized white Leghorn chicken eggs were incubated to stage 20 and then implanted with AG1-X2 ion exchange beads (Biorad) soaked in 1 mg/ml retinoic acid (RA, Sigma) as described by Tickle, C. et al., (1985) Dev. Biol 109: 82–95. Briefly, the beads were soaked for 15 min in 1 mg/ml RA in DMSO, washed twice and implanted under the AER on the anterior margin of the limb bud. After 24 or 36 hours, some of the implanted embryos were harvested and fixed overnight in 4% paraformaldehyde in PBS and then processed for whole mount in situ analysis as previously described. The remainder of the animals were allowed to develop to embryonic day 10 to confirm that the dose of RA used was capable of inducing mirror image duplications. Control animals were implanted with DMSO soaked beads and showed no abnormal phenotype or gene expression.

Plasmids

Unless otherwise noted, all standard cloning techniques were performed according to Ausubel, F. M. et al., (1989) Current Protocols in Molecular Biology (N.Y.: Greene Publishing Assoc. and Wiley Inerscience), and all enzymes were obtained from Boehringer Mannheim Biochemicals. pHH-2 is a cDNA contain the entire coding region of chicken Sonic hedgehog (SEQ ID No:1). RCASBP(A) and RCASBP(E) are replication-competent retroviral vectors which encode viruses with differing host ranges. RCANBP(A) is a variant of RCASBP(A) from which the second splice acceptor has been removed. This results in a virus which can not express the inserted gene and acts as a control for the effects of viral infection (Hughes, S. H. et al., (1987) J. Virol. 61: 3004–3012; Fekete, D. et al., (1993) Mol Cell. Biol. 13: 2604–2613). RCASBP/AP(E) is version of RCASBP(E) containing a human placental alkaline phosphatase cDNA (Fekete, D. et al., (1993b) Proc. Natl. Acad. Sci. USA 90: 2350–2354). SLAX13 is a pBluescript SK+ derived plasmid with a second Cla I restriction site and the 5' untranslated region of v-src (from the adaptor plasmid CLA12-Nco, Hughes, S. H. et al., (1987) J. Virol. 61: 3004–3012) cloned 5' of the EcoRI (and ClaI) site in the pBluescript polylinker. RCASBP plasmids encoding Sonic from either the first (M1) or second (M2) methionine (at position 4) were constructed by first shuttling the 1.7 kb Sonic fragment of pHH-2 into SLAX-13 using oligonucleotides to modify the 5' end of the cDNA such that either the first or second methionine is in frame with the NcoI site of SLAX-13. The amino acid sequence of Sonic is not mutated in these constructs. The M1 and M2 Sonic ClaI fragments (v-src 5'UTR:Sonic) were each then subcloned into RCASBP(A), RCANBP(A) and RCASBP(E), generating Sonic/RCAS-A1, Sonic/RCAS-A2, Sonic/RCAN-A1, Sonic/RCAN-A2, Sonic/RCAS-E1 and Sonic/RCAS-E2.

Chick Embryos, Cell Lines And Virus Production

All experimental manipulations were performed on standard specific-pathogen free White Leghorn chick embryos (S-SPF) from closed flocks provided fertilized by SPAFAS (Norwich, Conn.). Eggs were incubated at 37.5° C. and staged according to Hamburger, V. et al., (1951) J Exp. Morph 88: 49–92. All chick embryo fibroblasts (CEF) were provided by C. Cepko. S-SPF embryos and CEFs have previously been shown to be susceptible to RCASBP(A) infection but resistant to RCASBP(E) infection (Fekete, D. et al., (1993b) Proc. Natl. Acad. Sci. USA 90: 2350–2354). Line 15b CEFs are susceptible to infection by both RCASBP (A) and (E). These viral host ranges were confirmed in control experiments. CEF cultures were grown and transfected with retroviral vector DNA as described (Morgan, B. A. et al., (1993) Nature 358: 236–239; Fekete, D. et al., (1993b) Proc. Natl. Acad. Sci. USA 90: 2350–2354). All viruses were harvested and concentrated as previously described (Morgan, B. A. et al., (1993) Nature 358: 236–239; Fekete, D. et al., (1993b) Proc. Natl. Acad. Sci. USA 90: 2350–2354) and had titers of approximately 108 cfu/ml.

Cell Implants

A single 60 mm dish containing line 15b CEFs which had been infected with either RCASBP/AP(E), Sonic/RCAS-E1 or Sonic/RCAS-E2 were grown to 50–90% confluence, lightly trypsinized and then spun at 1000 rpm for 5 min in a clinical centrifuge. The pellet was resuspended in 1 ml media, transferred to a microcentrifuge tube and then microcentrifuged for 2 min at 2000 rpm. Following a 30 min incubation at 37° C., the pellet was respun for 2 min at 2000 rpm and then lightly stained in media containing 0.01% nile blue sulfate. Pellet fragments of approximately 300 μm×100 μm×50 μm were implanted as a wedge to the anterior region of hh stage 19–23 wing buds (as described by Riley, B. B. et al., (1993) Development 118: 95–104). At embryonic day 10, the embryos were harvested, fixed in 4% paraformaldehyde in PBS, stained with alcian green, and cleared in methyl salicylate (Tickle, C. et al., (1985) Dev. Biol 109: 82–95).

Viral Infections

Concentrated Sonic/RCAS-A2 or Sonic/RCAN-A2 was injected under the AER on the anterior margin of stage 20–22 wing buds. At 24 or 36 hours post-infection, the embryos were harvested, fixed in 4% paraformaldehyde in PBS and processed for whole mount in situ analysis as previously described.

(ii) Co-Localization of Sonic Expression and Zpa Activity

ZPA activity has been carefully mapped both spatially and temporally within the limb bud (Honig, L. S. et al., (1985) *J. Embryol. exp. Morph.* 87: 163–174). In these experiments small blocks of limb bud tissue from various locations and stages of chick embryogenesis (Hamburger, V et al., (1951) *J. Exp. Morph.* 88: 49–92) were grafted to the anterior of host limb buds and the strength of ZPA activity was quantified according to degrees of digit duplication. Activity is first weakly detected along the flank prior to limb bud outgrowth. The activity first reaches a maximal strength at stage 19 in the proximal posterior margin of the limb bud. By stage 23 the activity extends the full length of the posterior border of the limb bud. The activity then shifts distally along the posterior margin so that by stage 25 it is no longer detectable at the base of the flank. The activity then fades distally until it is last detected at stage 29.

This detailed map of endogenous polarizing activity provided the opportunity to determine the extent of the correlation between the spatial pattern of ZPA activity and Sonic expression over a range of developmental stages. Whole mount in situ hybridization was used to assay the spatial and temporal pattern of Sonic expression in the limb bud. Sonic expression is not detected until stage 17, at the initiation of limb bud formation, at which time it is weakly observed in a punctate pattern reflecting a patchy expression in a few cells. From that point onwards the Sonic expression pattern exactly matches the location of the ZPA, as determined by Honig, L. S. et al., (1985) *J. Embryol. exp. Morph.* 87: 163–174, both in position and in intensity of expression.

(iii) Induction of Sonic Expression By Retinoic Acid

A source of retinoic acid placed at the anterior margin of the limb bud will induce ectopic tissue capable causing mirror-image duplications (Summerbell, D. et al., (1983) *In Limb Development and Regeneration* (N.Y.: Ala R. Liss) pp. 109–118; Wanek, N. et al., (1991) *Nature* 350: 81–83). The induction of this activity is not an immediate response to retinoic acid but rather takes approximately 18 hours to develop (Wanek, N. et al., (1991) *Nature* 350: 81–83). When it does develop, the polarizing activity is not found surrounding the implanted retinoic acid source, but rather is found distal to it in the mesenchyme along the margin of the limb bud (Wanek, N. et al., (1991) *Nature* 350: 81–83).

If Sonic expression is truly indicative of ZPA tissue, then it should be induced in the ZPA tissue which is ectopically induced by retinoic acid. To test this, retinoic acid-soaked beads were implanted in the anterior of limb buds and the expression of Sonic after various lengths of time using whole-mount in situ hybridization was assayed. As the limb bud grows, the bead remains imbedded proximally in tissue which begins to differentiate. Ectopic Sonic expression is first detected in the mesenchyme 24 hours after bead implantation. This expression is found a short distance from the distal edge of the bead. By 36 hours Sonic is strongly expressed distal to the bead in a stripe just under the anterior ectoderm in a mirror-image pattern relative to the endogenous Sonic expression in the posterior of the limb bud.

(iv) Effects of Ectopic Expression of Sonic On Limb Patterning

The normal expression pattern of Sonic, as well as that induced by retinoic acid, is consistent with Sonic being a signal produced by the ZPA. To determine whether Sonic expression is sufficient for ZPA activity, the gene was ectopically expressed within the limb bud. In most of the experiments we have utilized a variant of a replication-competent retroviral vector called RCAS (Hughes, S. H. et al., (1987) *J. Virol.* 61: 3004–3012)) both as a vehicle to introduce the Sonic sequences into chick cells and to drive their expression. The fact that there exists subtypes of avian retroviruses which have host ranges restricted to particular strains of chickens was taken advantage of to control the region infected with the Sonic/RCAS virus (Weiss, R. (et al.) (1984) *RNA Tumor Viruses,* Vol. 1 Weiss et al. eds., (N.Y.: Cold Spring Harbor Laboratories) pp. 209–260); Fekete, D. et al., (1993a) *Mol. Cell. Biol.* 13: 2604–2613). Thus a vector with a type E envelope protein (RCAS-E, Fekete, D. et al., (1993b) *Proc. Natl. Acad. Sci. USA* 90: 2350–2354) is unable to infect the cells of the SPAFAS outbred chick embryos routinely used in our lab. However, RCAS-E is able to infect cells from chick embryos of line 15b. In the majority of experiments, primary chick embryo fibroblasts (CEFs) prepared from line 15b embryos in vitro were infected. The infected cells were pelleted and implanted into a slit made in the anterior of S-SPF host limb buds. Due to the restricted host range of the vector, the infection was thus restricted to the graft and did not spread through the host limb bud.

To determine the fate of cells implanted and to control for any effect of the implant procedure, a control RCAS-E vector expressing human placental alkaline phosphatase was used. Alkaline phosphatase expression can be easily monitored histochemically and the location of infected cells can thus be conveniently followed at any stage. Within 24 hours following implantation the cells are dispersed proximally and distally within the anterior margin of the limb bud. Subsequently, cells are seen to disperse throughout the anterior portion of the limb and into the flank of the embryo.

Limb buds grafted with alkaline phosphatase expressing cells or uninfected cells give rise to limbs with structures indistinguishable from unoperated wild type limbs. Such limbs have the characteristic anterior-to-posterior digit pattern 2-3-4. ZPA grafts give rise to a variety of patterns of digits depending on the placement of the graft within the bud (Tickle, C. et al., (1975) *Nature* 254: 199–202) and the amount of tissue engrafted (Tickle, C. (1981) *Nature* 289: 295–298). In some instances the result can be as weak as the duplication of a single digit 2. However, in optimal cases the ZPA graft evokes the production of a full mirror image duplication of digits 4-3-2-2-3-4 or 4-3-2-3-4. A scoring system has been devised which rates the effectiveness of polarizing activity on the basis of the most posterior digit duplicated: any graft which leads to the development of a duplication of digit 4 has been defined as reflecting 100% polarizing activity (Honig, L. S. et al., (1985) *J. Embryol. Exp. Morph.* 87: 163–174).

Grafts of 15b fibroblasts expressing Sonic resulted in a range of ZPA-like phenotypes. In some instances the resultant limbs deviate from the wild type solely by the presence of a mirror-image duplication of digit 2. The most common digit phenotype resulting from grafting Sonic-infected CEF cells is a mirror-image duplication of digits 4 and 3 with digit 2 missing: 4-3-3-4. In many such cases the two central digits appear fused in a 4-3/3-4 pattern. In a number of the cases the grafts induced full mirror-image duplications of the digits equivalent to optimal ZPA grafts 4-3-2-2-3-4. Besides the digit duplications, the ectopic expression of Sonic also gave rise to occasional duplications of proximal elements including the radius or ulna, the humerus and the coracoid. While these proximal phenotypes are not features of ZPA grafts, they are consistent with an anterior-to-posterior respecification of cell fate. In some instances, most commonly when the radius or ulna was duplicated, more complex digit patterns were observed. Typically, an additional digit 3 was formed distal to a duplicated radius.

The mirror-image duplications caused by ZPA grafts are not limited to skeletal elements. For example, feather buds are normally present only along the posterior edge of the limb. Limbs exhibiting mirror-image duplications as a result of ectopic Sonic expression have feather buds on both their anterior and posterior edges, similar to those observed in ZPA grafts.

While ZPA grafts have a powerful ability to alter limb pattern when placed at the anterior margin of a limb bud, they have no effect when placed at the posterior margin (Saunders, J. W. et al., (1968) *Epithelial-Mesenchymal Interaction*, Fleischmayer and Billingham, eds. (Baltimore: Williams and Wilkins) pp. 78–97). Presumably, the lack of posterior effect is a result of polarizing activity already being present in that region of the bud. Consistent with this, grafts of Sonic expressing cells placed in the posterior of limb buds never result in changes in the number of digits. Some such grafts did produce distortions in the shape of limb elements, the most common being a slight posterior curvature in the distal tips of digits 3 and 4 when compared to wild type wings.

(v) Effect Of Ectopic Sonic Expression On Hoxd Gene Activity

The correct expression of Hoxd genes is part of the process by which specific skeletal elements are determined (Morgan, B. A. et al., (1993) Nature 358: 236–239). A transplant of a ZPA into the anterior of a chick limb bud ectopically activates sequential transcription of Hoxd genes in a pattern which mirrors the normal sequence of Hoxd gene expression (Nohno, T. et al., (1991) *Cell* 64: 1197–1205; Izpisua-Belmonte, J. C. et al., (1991) *Nature* 350: 585–589). Since ectopic Sonic expression leads to the same pattern duplications as a ZPA graft, we reasoned that Sonic would also lead to sequential activation of Hoxd genes.

To test this hypothesis, anterior buds were injected with Sonic/RCAS-A2, a virus which is capable of directly infecting the host strains of chicken embryos. This approach does not strictly limit the region expressing Sonic (being only moderately controlled by the timing, location and titer of viral injection), and thus might be expected to give a more variable result. However, experiments testing the kinetics of viral spread in infected limb buds indicate that infected cells remain localized near the anterior margin of the bud for at least 48 hours. Hoxd gene expression was monitored at various times post infection by whole mount in situ hybridization. As expected, these genes are activated in a mirror-image pattern relative their expression in the posterior of control limbs. For example, after 36 hours Hoxd-13 is expressed in a mirror-image symmetrical pattern in the broadened distal region of infected limb buds. Similar results were obtained with other Hoxd genes (manuscript in preparation).

Example 4

A Functionally Conserved Homolog of *Drosophila* Hedgehog is Expressed in Tissues With Polarizing Activity in Zebrafish Embryos (i) Experimental Procedures Cloning and Sequencing Approximately $1.5 \times 10^6$ plaques of a 33 h zebrafish embryonic λgt11 cDNA library were screened by plaque hybridization at low stringency (McGinnis, W. et al., (1984) *Nature* 308: 428433) using a mix of two hh sequences as a probe: a *Drosophila* hh 400 bp EcoRI fragment and a murine Ihh 264 bp BamHI-EcoRI exon 2 fragment. Four clones were isolated and subcloned into the EcoRI sites of pUC18 T3T7 (Pharmacia). Both strands of clone 8.3 were sequenced using nested deletions (Pharmacia) and internal oligonucleotide primers. DNA sequences and derived amino acid sequences were analyzed using "Geneworks" (Intelligenetics) and the GCG software packages.

PCR amplification

Degenerate oligonucleotides hh5.1 (SEQ ID No:35) and hh3.3 (SEQ ID No:36) were used to amplify genomic zebrafish DNA hh 5.1: AG(CA)GITG(CT)AA(AG)GA(AG)(CA)(AG)I (GCT)IAA hh 3.3: CTCIACIGCIA(GA)ICK=(GT)IGCIA PCR was performed with an initial denaturation at 94° C. followed by 35 cycles of 47° C. for 1 min, 72° C. for 2 min and 94° C. for 1 min with a final extension at 72° C. Products were subcloned in pUC18 (Pharmacia).

In Situ Hybridization

In situ hybridizations of zebrafish embryos were performed as described in Oxtoby, E. et al., (1993) *Nuc. Acids REs*. 21: 1087–1095 with the following modifications: Embryos were rehydrated in ethanol rather than methanol series; the proteinase K digestion was reduced to 5 min and subsequent washes were done in PBTw without glycine; the antibody was preadsorbed in PBTw, 2 mg/ml BSA without sheep serum; and antibody incubation was performed in PBTw, 2 mg/ml BSA. *Drosophila* embryos were processed and hybridized as previously described.

Histology

Stained embryos were dehydrated through ethanol:butanol series, as previously described (Godsave, S. F. et al., (1988) *Development* 102: 555–566), and embedded in Fibrowax. 8 μm sections were cut on an Anglian rotary microtome.

RNA Probe Synthesis

For analysis of Shh expression, two different templates were used with consistent results; (i) phh[c] 8.3 linearized with Bgl II to transcribe an antisense RNA probe that excludes the conserved region, and (ii) phh[c] 8.3 linearized with Hind III to transcribe an antisense RNA that covers the complete cDNA. All in situ hybridizations were performed with the latter probe which gives better signal. Other probes were as follows: Axial Dral-linearised p6TIN (Strähle, U. et al., (1993) *Genes & Dev.* 7: 1436–1446) using T3 RNA polymerase. gsc linearized with EcoRI and transcribed with T7: pax 2 Bam HI-linearized pcF16 (Krauss, S. et al., (1991) *Development* 113: 1193–1206) using T7 RNA polymerase. In situ hybridizations were performed using labelled RNA at a concentration of 1 ng/ml final concentration. Antisense RNA probes were transcribed according to the manufacturer's protocol (DIG RNA Labelling Kit, BCL).

Zebrafish Strains

Wild type fish were bred from a founder population obtained from the Goldfish Bowl, Oxford. The mutant cyclops strain b16 and the mutant notail strains b160 and b195 were obtained from Eugene, Oreg. Fish were reared at 28° C. on a 14 h light/I Oh dark cycle.

RNA Injections

The open reading frame of Shh was amplified by PCR, using oligonucleotides 5'-CTGCAGGGATCC ACCATGCGGCTTTTGACGAG-3' (SEQ ID No:37), which contains a consensus Kozak sequence for translation initiation, and 5'-CTGCAGGGATCCTTATT CCACACGAGGGATT-3' (SEQ ID No:38), and subcloned into the BglII site of pSP64T (Kreig, P. A. et al., (1984) *Nuc. Acids Res.* 12: 7057–7070). This vector includes 5' and 3' untranslated *Xenopus* β-Globin sequences for RNA stabilization and is commonly used for RNA injections experiments in *Xenopus*. In vitro transcribed Shh RNA at a concentration of approximately 100 μg/ml was injected into a single cell of naturally spawned zebrafish embryos at one-cell to 4-cell stages using a pressure-pulsed Narishige microinjector. The injected volume was within the picolitre range. Embryos were fixed 20 to 27 hrs after injection in BT-Fix (Westerfield, M. (1989) *The Zebrafish Book*, (Eugene: The University of Oregon Press)) and processed as described above for whole-mount in situ hybridizations with the axial probe.

Transgenic *Drosophila*

An EcoRI fragment, containing the entire Shh ORF, was purified from the plasmid phh[c]8.3 and ligated with phosphatased EcoRI digested transformation vector pCaSpeRhs (Thummel, C. S. et al., (1988) *Gene* 74: 445–456). The recombinant plasmid, pHS Shh containing the Shh ORF in the correct orientation relative to the heat shock promoter, was selected following restriction enzyme analysis of miniprep DNA from transformed colonies and used to transform *Drosophila* embryos using standard microinjection procedures (Roberts, D. B. (1986), *Drosophila, A Practical Approach*, Roberts, D. B., ed., (Oxford: IRL Press) pp. 1–38).

Ectopic Expression In *Drosophila* Embryos

Embryos carrying the appropriate transgenes were collected over 2 hr intervals, transferred to thin layers of 1% agarose on glass microscope slides and incubated in a plastic Petri dish floating in a water bath at 37° C. for 30 min intervals. Following heat treatment, embryos were returned to 25° C. prior to being fixed for in situ hybridization with DIG labelled single stranded Shh, wg or ptc RNA probes as previously described (Ingham et al., (1991) *Curr. Opin. Genet. Dev.* 1: 261–267).

(ii) Molecular Cloning Of Zebrafish Hedgehog Homologues

In an initial attempt to isolate sequences homologous to *Drosophila* hh, a zebrafish genomic DNA library was screened at reduced stringency with a partial cDNA, hhPCR4.1, corresponding to the first and second exons of the *Drosophila* gene (Mohler, J. et al., (1992) *Development* 115: 957–971). This screen proved unsuccessful; however, a similar screen of a mouse genomic library yielded a single clone with significant homology to hh., subsequently designated Ihh. A 264 bp BamHI-EcoRI fragment from this lambda clone containing sequences homologous to the second exon of the *Drosophila* gene was subcloned and, together with the *Drosophila* partial cDNA fragment, used to screen a λgt11 zebrafish cDNA library that was prepared from RNA extracted from 33 h old embryos. This screen yielded four clones with overlapping inserts the longest of which is 1.6 kb in length, herein referred to as Shh (SEQ ID No:5).

(iii) A Family Of Zebrafish Genes Homologous To The *Drosophila* Segment Polarity Gene, Hedgehog Alignment of the predicted amino acid sequences of Shh (SEQ ID No:14) and hh (SEQ ID No:20) revealed an identity of 47%, confirming that Shh is a homolog of the *Drosophila* gene. A striking conservation occurs within exon 2: an 80 amino acid long domain shows 72% identity between Shh and *Drosophila* hh. This domain is also highly conserved in all hh-related genes cloned so far and is therefore likely to be essential to the function of hh proteins. A second domain of approximately 30 amino acids close to the carboxy-terminal end, though it shows only 61% amino-acid identity, possesses 83% similarity between Shh and hh when allowing for conservative substitutions and could also, therefore, be of functional importance. Although putative sites of post-translational modification can be noted, their position is not conserved between Shh and hh.

Lee, J. J. et al., (1992) *Cell* 71: 33–50, identified a hydrophobic stretch of 21 amino acids flanked downstream by a putative site of signal sequence cleavage (predicted by the algorithm of von Heijne, G. (I 986) *Nuc. Acids Res.* 11) close to the amino-terminal end of hh. Both the hydrophobic stretch and the putative signal sequence cleavage sites of hh, which suggest it to be a signaling molecule, are conserved in Shh. In contrast to hh, Shh does not extend N-terminally to the hydrophobic stretch.

Using degenerate oligonucleotides corresponding to amino-acids flanking the domain of high homology between *Drosophila* hh and mouse Ihh exons 2 described above, fragments of the expected size were amplified from zebrafish genomic DNA by PCR. After subcloning and sequencing, it appeared that three different sequences were amplified, all of which show high homology to one another and to *Drosophila* hh. One of these corresponds to Shh therein referred to as 2-hh(a) (SEQ ID No:39) and 2hh(b) (SEQ ID No:40), while the other two represent additional zebrafish hh homologs. cDNAs corresponding to one of these additional homologs have recently been isolated, confirming that it is transcribed. Therefore, Shh represents a member of a new vertebrate gene family.

(iv) Shh Expression In The Developing Zebrafish Embryo Gastrula Stages

Shh expression is first detected at around the 60% epiboly stage of embryogenesis in the dorsal mesoderm. Transcript is present in a triangular shaped area, corresponding to the embryonic shield, the equivalent of the amphibian organizer, and is restricted to the inner cell layer, the hypoblast. During gastrulation, presumptive mesodermal cells involute to form the hypoblast, and converge towards the future axis of the embryo, reaching the animal pole at approximately 70% epiboly. At this stage, Shh-expressing cells extend over the posterior third of the axis, and the signal intensity is not entirely homogeneous, appearing stronger at the base than at the apex of the elongating triangle of cells.

This early spatial distribution of Shh transcript is reminiscent of that previously described for axial, a forkhead-related gene; however, at 80% epiboly, axial expression extends further towards the animal pole of the embryo and we do not see Shh expression in the head area at these early developmental stages.

By 100% epiboly, at 9.5 hours of development, the posterior tip of the Shh expression domain now constitutes a continuous band of cells that extends into the head. To determine the precise anterior boundary of Shh expression, embryos were simultaneously hybridized with probes of Shh and pax-2 (previously pax[b]), the early expression domain of which marks the posterior midbrain (Krauss, S. et al. (1991) *Development* 113: 1193–1206). By this stage, the anterior boundary of the Shh expression domain is positioned in the centre of the animal pole and coincides approximately with that of axial. At the same stage, prechordal plate cells expressing the homeobox gene goosecoid (gsc) overlap and underlay the presumptive forebrain (Statchel, S. E. et al., (1993) *Development* 117: 1261–1274). Whereas axial is also thought to be expressed in head mesodermal tissue at this stage, we cannot be certain whether Shh is expressed in the same cells. Sections of stained embryos suggest that in the head Shh may by this stage be expressed exclusively in neuroectodermal tissue.

(v) Somitogenesis

By the onset of somitogenesis (approximately 10.5 h of development), Shh expression in the head is clearly restricted to the ventral floor of the brain, extending from the tip of the diencephalon caudally through the hindbrain. At this stage, expression of axial has also disappeared from the head mesoderm and is similarly restricted to the floor of the brain; in contrast to Shh, however, it extends only as far as the anterior boundary of the midbrain. At this point, gsc expression has become very weak and is restricted to a ring of cells that appear to be migrating away from the dorsal midline.

As somitogenesis continues, Shh expression extends in a rostral-caudal progression throughout the ventral region of the central nervous system (CNS). Along the spinal cord, the expression domain is restricted to a single row of cells, the floor plate, but gradually broadens in the hindbrain and midbrain to become 5–7 cells in diameter, with a triangular shaped lateral extension in the ventral diencephalon and two strongly staining bulges at the tip of the forebrain, presumably in a region fated to become hypothalamus.

As induction of Shh in the floor plate occurs, expression in the underlying mesoderm begins to fade away, in a similar manner to axial (Strähle, U. et al., (1993) Genes & Dev. 7: 1436–1446). This downregulation also proceeds in a rostral to caudal sequence, coinciding with the changes in cell shape that accompany notochord differentiation. By the 22 somite stage, mesodermal Shh expression is restricted to the caudal region of the notochord and in the expanding tail bud where a bulge of undifferentiated cells continue to express Shh at relatively high levels. Expression in the midbrain broadens to a rhombic shaped area; cellular rearrangements that lead to the 90° kink of forebrain structures, position hypothalamic tissue underneath the ventral midbrain. These posterior hypothalamic tissues do not express Shh. In addition to Shh expression in the ventral midbrain, a narrow stripe of expressing cells extends dorsally on either side of the third ventricle from the rostral end of the Shh domain in the ventral midbrain to the anterior end of, but not including, the epiphysis. The most rostral Shh expressing cells are confined to the hypothalamus. In the telencephalon, additional Shh expression is initiated in two 1-2 cell wide stripes.

By 36 hours of development, Shh expression in the ventral CNS has undergone further changes. While expression persists in the floor plate of the tailbud, more rostrally located floor plate cells in the spinal cord cease to express the gene. In contrast, in the hindbrain and forebrain Shh expression persists and is further modified.

At 26–28 h, Shh expression appears in the pectoral fin primordia, that are visible as placode like broadenings of cells underneath the epithelial cell layer that covers the yolk. By 33 hrs of development high levels of transcript are present in the posterior margin of the pectoral buds; at the same time, expression is initiated in a narrow stripe at the posterior of the first gill. Expression continues in the pectoral fin buds in lateral cells in the early larva. At this stage, Shh transcripts are also detectable in cells adjacent to the lumen of the foregut.

(vi) Expression of Shh in Cyclops and Notail Mutants

Two mutations affecting the differentiation of the Axial tissues that express Shh have been described in zebrafish embryos homozygous for the cyclops (cyc) mutation lack a differentiated floorplate (Hatta, K. et al., (1991) Nature 350: 339–341). By contrast, homozygous notail (ntl) embryos are characterized by a failure in notochord maturation and a disruption of normal development of tail structures (Halpern, M. E. et al., (1993) Cell 75: 99–111).

A change in Shh expression is apparent in cyc embryos as early as the end of gastrulation; at this stage, the anterior limit of expression coincides precisely with the two pax-2 stripes in the posterior midbrain. Thus, in contrast to wild-type embryos, no Shh expression is detected in midline structures of the midbrain and forebrain. By the 5 somite stage, Shh transcripts are present in the notochord which at this stage extends until rhombomere 4; however, no expression is detected in more anterior structures. Furthermore, no Shh expression is detected in the ventral neural keel, in particular in the ventral portions of the midbrain and forebrain.

At 24 hours of development, the morphologically visible cyc phenotype consists of a fusion of the eyes at the midline due to the complete absence of the ventral diencephalon. As at earlier developmental stages, Shh expression is absent from neural tissue. Shh expression in the extending tail bud of wild-type embryos is seen as a single row of floor plate cells throughout the spinal cord. In a cyc mutant, no such Shh induction occurs in cells of the ventral spinal cord with the exception of some scattered cells that show transient expression near the tail. Similarly, no Shh expression is seen rostrally in the ventral neural tube. However, a small group of Shh expressing cells is detected underneath the epiphysis which presumably correspond to the dorsal-most group of Shh expressing cells in the diencephalon of wild-type embryos.

In homozygous notail (ntl) embryos, no Shh staining is seen in mesodermal tissue at 24 hours of development, consistent with the lack of a notochord in these embryos; by contrast, expression throughout the ventral CNS is unaffected. At the tail bud stage, however, just prior to the onset of somitogenesis, Shh expression is clearly detectable in notochord precursor cells.

(vii) Injection of Synthetic Shh Transcripts into Zebrafish Embryos Induces Expression of a Floor Plate Marker To investigate the activity of Shh in the developing embryo, an over-expression strategy, similar to that employed in the analysis of gene function in Xenopus, was adopted. Newly fertilized zebrafish eggs were injected with synthetic Shh RNA and were fixed 14 or 24 hours later. As an assay for possible changes in cell fate consequent upon the ectopic activity of Shh, we decided to analyze Axial expression, since this gene serves as a marker for cells in which Shh is normally expressed. A dramatic, though highly localized ectopic expression of Axial in a significant proportion (21/80) of the injected embryos fixed after 24 hours of development is observed. Affected embryos show a broadening of the Axial expression domain in the diencephalon and ectopic Axial expression in the midbrain; however, in no case has ectopic expression in the telencephalon or spinal cord been observed. Many of the injected embryos also showed disturbed forebrain structures, in particular smaller ventricles and poorly developed eyes. Amongst embryos fixed after 14 h, a similar proportion (8/42) exhibit the same broadening and dorsal extension of the Axial stripe in the diencephalon as well as a dorsal extension of Axial staining in the midbrain; again, no changes in Axial expression were observed caudal to the hindbrain with the exception of an increased number of expressing cells at the tip of the tail.

(viii) Overexpression of Shh in Drosophila Embryos Activates the hh-Dependent Pathway In order to discover whether the high degree of structural homology between the Drosophila and zebrafish hh genes also extends to the functional level, an overexpression system was used to test the activity of Shh in flies. Expression of *Drosophila* hh driven by the HSP70 promoter results in the ectopic activation of both the normal targets of hh activity; the wg transcriptional domain expands to fill between one third to one half of each parasegment whereas ptc is ectopically activated in all cells except those expressing en (Ingham, P. W. (1993) *Nature* 366:560–562). To compare the activities of the fly and fish genes, flies transgenic for a HS Shh construct were generated described above and subjected to the same heat shock regime as H Shh transgenic flies. HS Shh embryos fixed immediately after the second of two 30 min heat shocks exhibit ubiquitous transcription of the Shh cDNA. Similarly treated embryos were fixed 30 or 90 min after the second heat shock and assayed for wg or ptc transcription. Both genes were found to be ectopically activated in a similar manner to that seen in heat shocked H Shh embryos; thus, the zebrafish Shh gene can activate the same pathway as the endogenous hh gene.

Example 5

Cloning, Expression and Localization of Human Hedgehogs
(i) Experimental Procedures
Isolation of Human Hedgehog Cdna Clones.

Degenerate nucleotides used to clone chick Shh (Riddle et al., (1993) *Cell* 75:1401–1416) were used to amplify by nested PCR human genomic DNA, e.g., primers shown in SEQ ID Nos: 23–25).

The expected 220 bp PCR product was subcloned into pGEM7zf (Promega) and sequenced using Sequenase v2.0 (U.S. Biochemicals). One clone showed high nucleotide similarity to mouse Ihh and mouse Shh sequence (Echelard et al., (1993) *Cell* 75:1417–1430) and it was used for screening a human fetal lung 5'-stretch plus cDNA library (Clontech) in λgt10 phage. The library was screened following the protocol suggested by the company and two positive plaques were identified, purified, subcloned into pBluescript SK+ (Stratagene) and sequenced, identifying them as the human homologues of Shh (SEQ ID NO:6) and Ihh (SEQ ID NO:7).

One clone contained the full coding sequence of a human homolog of Shh as well as 150 bp of 5' and 36 bp of 3' untranslated sequence. The other clone, which is the human homolog of Ihh, extends from 330 bp 3' of the coding sequence to a point close to the predicted boundary between the first and second exon. The full-length sequence, shown in SEQ ID No: 7, was ultimately obtained by primers based on the mouse Ihh sequence. The identity of these clones was determined by comparison to the murine and chick genes. The protein encoded by human Shh has 92.4% overall identity to the mouse Shh, including 99% identity in the amino-terminal half. The carboxyl-terminal half is also highly conserved, although it contains short stretches of 16 and 11 amino acids not present in the mouse Shh. The human Ihh protein is 96.8% identical to the mouse Ihh. The two predicted human proteins are also highly related, particularly in their amino-terminal halves where they are 91.4% identical. They diverge significantly in their carboxyl halves, where they show only 45.1% identity. The high level of similarity in the amino portion of all of these proteins implies that this region encodes domains essential to the activity of this class of signaling molecules.

Northern blotting

Multiple Tissue Northern Blot (Clontech) prepared from poly A+ RNA isolated from human adult tissues was hybridized with either full length $^{32}$P-labeled human Shh clone or $^{32}$P labeled human Ihh clone following the protocol suggested by the company.

Digoxigenin in situ Hybridization.

Sections: tissues from normal human second trimester gestation abortus specimens were washed in PBS and fixed overnight at 4° C. paraformaldehyde in PBS, equilibrated 24 hours at 4° C. in 50% sucrose in PBS and then placed in 50% sucrose in oct for one hour before embedding in oct. Cryostat sections (10–25 mm) were collected on superfrost plus slides (Fisher) and frozen at −80° C. until used. Following a postfixation in 4% paraformaldehyde the slides were processed as in Riddle et al., (1993) *Cell* 75:1401–1416 with the following alterations: proteinase K digestion was performed at room temperature from 1–15 minutes (depending on section thickness), prehybridization, hybridization and washes time was decreased to ⅒ of time.

Whole-mounts: tissues from normal second trimester human abortus specimens were washed in PBS, fixed overnight at 4° C. in 4% paraformaldehyde in PBS and then processed as in Riddle et al., (1993) *Cell* 75:1401–1416.
Isolation of an Shh P1 Clone.

The human Shh gene was isolated on a P1 clone from a P1 library (Pierce and Sternberg, 1992) by PCR (polymerase chain reaction) screening. Two oligonucleotide primers were derived from the human Shh sequence. The two olignucleotide primers used for PCR were:
SHHF5'-ACCGAGGGCTGGGACGAAGATGGC-3' (SEQ ID NO:41)
SHR5'-CGCTCGGTCGTACGGCATGAACGAC-3' (SEQ ID NO:42).
The PCR reaction was carried using standard conditions as described previously (Thierfelder et al., 1994) except that the annealing temperature was 65° C. These primers amplified a 119 bp fragment from human and P1 clone DNA. The P1 clone was designated SHHP1. After the P1 clone was isolated these oligonucleotides were used as sequencing primers. A 2.5 KbEcoRI fragment that encoded a CA repeat was subcloned from this P1 clone using methods described previously (Thierfelder et al. 1994). Oligonucleotide primers that amplified this CA repeat sequence were fashioned from the flanking sequences:
SHHCAF5'-ATGGGGATGTGTGTGGTCAAGTGTA-3' (SEQ ID NO:43)
SHHCAR5'-TTCACAGACTCTCAAAGTGTATTTT-3' (SEQ ID NO:44).
Mapping the human Ihh and Shh genes.

The human Ihh gene was mapped to chromosome 2 using somatic cell hybrids from NIGMS mapping pannel 2 (GM10826B).

The Shh gene was mapped to chromosome 7 using somatic cell hybrids from NIGMS mapping panel 2 (GM10791 and GM10868).

Linkage between the limb deformity locus on chromosome 7 and the Shh gene was demonstrated using standard procedures. Family LD has been described previously (Tkukurov et al., (1994) *Nature Genet.* 6:282–286). A CA repeat bearing sequence near the Shh gene was amplified from the DNA of all members of Family LD by PCR using the SHHCAF and SHHCAR primers. Linkage between the CA repeat and the LD disease gene segregating in Family LD was estimated by the MLINK program (October 1967). Penetrance was set at 100% and the allele frequencies were determined using unrelated spouses in the LD family.
Interspecific Backcross Mapping.

Interspecific backcross progeny were generated by mating (C57BL/6J×*M. spretus*) F1 females and C57BL/6J males as described (Copeland and Jenkins, (1991) *Trends Genet.* 7:113–118). A total of 205 N2 mice were used to map the Ihh and Dhh loci. DNA isolation, restriction enzyme digestions, agarose gel electrophoresis, Southern blot transfer and hybridization were performed essentially as described (Jenkins et al., (1982) *J. Virol.* 43:26–36). All blots were prepared with Hybond-N+nylon membrane (Amersham). The probe, an ~1.8 kb EcoRI fragment of mouse cDNA, detected a major fragment of 8.5 kb in C57BL/6j (B) DNA and a major fragment 6.0 kb in *M. sprelus* (S) DNA following digestion with BglII. The Shh probe, an ~900 bp SmaI fragment of mouse cDNA, detected HincII fragments of 7.5 and 2.1 kb (B) as well as 4.6 and 2.1 (S). The Dhh probe, and ~800 bp BamHi/EcoRI fragment of mouse genomic DNA, detected major fragments of 4.7 and 1.3 kb (B) and 8.2 and 1.3 kb (S) following digestion with SphI. The presence or absence of *M. spretus* specific fragments was followed in backcross mice.

A description of the probes and RFLPs for loci used to position the Ihh, Shh and Dhh loci in the interspecific backcross has been reported. These include: Fnl, Vil and Acrg, chromosome 1 (Wilkie et al., (1993) *Genomics* 18:175–184), Gnail, En2, 116, chromosomes 5 (Miao et al., (1994) *PNAS USA* 91:11050–11054) and Pdgfb, Gdcl and Rarg, chromosome 15 (Brannan et al., (1992) *Genomics* 13:1075–1081). Recombination distances were calculated as described (Green, (1981) Linkage, recombination and mapping. In *"Genetics and Probability in Animal Breeding Experiments"*, pp. 77–113, Oxford University Press, NY) using the computer program SPRETUS MADNESS. Gene order was determined by minimizing the number of recombination events required to explain the allele distribution patterns.

(ii) Expression of Human Shh and Ihh

To investigate the tissue distribution of Shh and Ihh expression, poly(A)+ RNA samples from various adult human tissues were probed with the two cDNA clones. Of the tissues tested, an Ihh-specific message of ~2.7 kb is only detected in liver and kidney. Shh transcripts was not detected in the RNA from any of the adult tissues tested. All the samples contained approximately equal amounts of intact RNA, as determined by hybridization with a control probe.

The hedgehog family of genes were identified as mediators of embryonic patterning in flies and vertebrates. No adult expression of these genes had previously been reported. These results indicate that Ihh additionally plays a role in adult liver and kidney. Since the hedgehog genes encode intercellular signals, Ihh may function in coordinating the properties of different cell types in these organs. Shh may also be used as a signaling molecule in the adult, either in tissues not looked at here, or at levels too low to be detected under these conditions.

In situ hybridization was used to investigate the expression of Shh in various mid-gestational human fetal organs. Shh expression is present predominantly in endoderm derived tissues: the respiratory epithelium, collecting ducts of the kidney, transitional epithelium of the ureter, hepatocytes, and small intestine epithelium. Shh was not detectable in fetal heart or placental tissues. The intensity of expression is increased in primitive differentiating tissues (renal blastema, base villi, branching lung buds) and decreased or absent in differentiated tissues (e.g. glomeruli). Shh expression is present in the mesenchyme immediately abutting the budding respiratory tubes. The non-uniform pattern of Shh expression in hepatocytes is consistent with expression of other genes in adult liver (Dingemanse et al., (1994) *Differentiation* 56:153–162). The base of villi, the renal blastema, and the lung buds are all regions expressing Shh and they are areas of active growth and differentiation, suggesting Shh is important in these processes.

(iii) The Chromosomal Map Location of Human Shh and Ihh.

Since Shh is known to mediate patterning during the development of the mouse and chick and the expression of Shh and Ihh are suggestive of a similar role in humans, mutations in these genes would be expected to lead to embryonic lethality or congenital defects. One way of investigating this possibility is to see whether they are genetically linked to any known inherited disorders.

Shh- and Ihh-specific primers were designed from their respective sequences and were used in PCR reactions on a panel of rodent-human somatic cell hybrids. Control rodent DNA did not amplify specific bands using these primers. In contrast, DNA from several rodent-human hybrids resulted in PCR products of the appropriate size allowing us to assign Shh to chromosome 7q and Ihh to chromosome 2.

One of the central roles of chick Shh is in regulating the anterior-posterior axis of the limb. A human congenital polysyndactyly has recently been mapped to chromosome 7q36 (Tsukurov et al., (1994) *Nature Genet.* 6:282–286; Heutink et al., (1994) *Nature Genet.* 6:287–291). The phenotype of this disease is consistent with defects that might be expected from aberrant expression of Shh in the limb. Therefore, the chromosomal location of Shh was mapped more precisely, in particular in relation to the polysyndactyly locus.

A P1 phage library was screened using the Shh specific primers for PCR amplification and clone SHHP1 was isolated. Clone SHHP1 contained Shh sequence. A Southern blot of an EcoRi digest of this phage using [CA]/[GT] probe demonstrated that a 2.5 Kb EcoRi fragment contained a CA repeat. Nucleotide sequence analysis of this subcloned EcoRI fragment demonstrated that the CA repeat lay near the EcoRI sites. Primers flanking the CA repeat were designed and used to map the location of Shh relative to other markers on 7q in individuals of a large kindred with complex polysyndactyly (Tsukurov et al., (1994) *Nature Genet.* 6:282–286). Shh maps close to D75550 on 7q36, with no recombination events seen in this study. It is also extremely close to, but distinct from, the polysyndactyly locus with one recombination event observed between them (maximum lod score=4.82, Θ=0.05). One unaffected individual (pedigree ID V-10 in Tsukurov et al., (1994) *Nature Genet.* 6:282–286) has the Shh linked CA repeat allele found in all affected family members. No recombination was observed between the locus En2 and the Shh gene (maximum lod score=1.82, Θ=0.0).

(iv) Chromosomal mapping of the Murine Ihh, Shh and Dhh genes.

The murine chromosomal location of Ihh, Shh and Dhh was determined using an interspecific backcross mapping panel derived from crosses of [(C57BL/6J×*M. spetrus*)F1 X C57BL/J)] mice. cDNA fragments from each locus were used as probes in Southern blot hybridization analysis of C57BL/6J and *M. spretus* genomic DNA that was separately digested with several different restriction enzymes to identify informative restriction fragment length polymorphisms (RFLPs) useful for gene mapping. The strain distribution pattern of each RFLP in the interspecific backcross was then determined by following the presence or absence of RFLPs specific for *M. spretus* in backcross mice.

Ihh mapped to the central region of mouse chromosome 1, 2.7 cM distal of Fnl and did not recombine with Vil in 190 animals typed in common, suggesting that the two loci are within 1.6 cM (upper 95% confidence level). Shh mapped to the proximal region of mouse chromosome 5, 0.6 cM distal of En2 and 1.9 cM proximal of 116 in accordance to Chang et al., (1994) *Development* 120:3339–3353. Dhh mapped to the very distal region of mouse chromosome 15, 0.6 cM distal of Gdcl and did not recombine with Rarg in 160 animals typed in common, suggesting that the two loci are within 1.9 cM of each other (upper 95% confidence level).

Interspecific maps of chromosome 1, 5 and 15 were compared with composite mouse linkage maps that report the map location of many uncloned mouse mutations (compiled by M. T. Davisson, T. H. Roderick, A. L. Hillyard and D. P. Doolittle and provided from GBASE, a computerized database maintained at The Jackson Laboratory, Bar Harbor, Me.). The hemimelic extra-toe (Hx) mouse mutant maps 1.1 cM distal to En2 on chromosome 5 (Martin et al., (1990) *Genomics* 6:302–308), a location in close proximity to where Shh has been positioned. Hx is a dominant mutation which results in preaxial polydactyly and hemimelia affecting all four limbs (Dickie, (1968) *Mouse News Lett* 38:24; Knudsen and Kochhar, (1981) *J. EmbryoL. Exp. Morph.* 65: Suppl. 289–307). Shh has previously been shown to be expressed in the limb (Echelard et al., (1993) *Cell* 75:1417–1430). To determine whether Shh and Hx are tightly linked we followed their distribution in a backcross panel in which Hx was segregating. Two recombinants between Shh and Hx were identified, thus excluding the possibility that the two loci are allelic and these observations are again consistent with those of Chang et al., (1994) *Development* 120:3339–3353. While there are several other mutations in the vicinity of Ihh and Dhh, none is an obvious candidate for an alteration in the corresponding gene.

The central region of mouse chromosome 1 shares homology with hum an chromosome 2q. Placement of Ihh in this interval suggests the human homolog of Ihh will reside on 2q, as well. Similarly, it is likely th at human homolog of Dhh will reside on human chromosome 12q.

Example 6

Proteolytic Processing Yields Two Secreted Forms of Sonic Hedgehog (i) Experimental Procedures In vitro Translation and Processing Mouse and chick sonic hedgehog coding sequences were inserted into the vector pSP64T (kindly provided by D. Melton) which contains an SP6 phage promoter and both 5' and 3' untranslated sequences derived from the *Xenopus laevis* β-Globin gene. After restriction endonuclease digestion with Sal I to generate linear templates, RNA was trans cribed in vitro using SP6 RNA polymerase (Promega, Inc.) in the presence of 1 mM cap structure analog (m$^7$G(5')ppp (5')Gm; Boehringer-Mannheim, Inc.) Following digestion with RQ1 DNase I (Promega, Inc.) to remove the DNA template, transcripts were purified by phenol:choloroform extraction and ethanol precipitation.

Rabbit reticulocyte lysate (Promega, Inc.) was used according to the manufacturer's instructions. For each reaction, 12.5 μl of lysate was programmed with 0.5–2.0 μg of in vitro transcribed RNA. The reactions contained 20 μCi of Express labeling mix (NEN/DuPont, Inc.) were included. To address processing and secretion in vitro, 1.0–2.0 μl of canine pancreatic microsomal membranes (Promega, Inc.) were included in the reactions. The final reaction volume of 25 μl was incubated for one hour at 30° C. Aliquots of each reaction (between 0.25 and 3.0 μl) were boiled for 3 minutes in Laemmli sample buffer (LSB: 125 mM Tris-Hcl [pH 6.8]; 2% SDS; 1% 2-mercaptoethanol; 0.25 mg/ml bromophenol blue) before separating on a 15% polyacrylamide gel. Fixed gels were processed for fluorography using EnHance (NEN/DuPont, Inc.) as described by the manufacturer.

Glycosylation was addressed by incubation with Endoglycosidase H (Endo H; New England Biolabs, Inc.) according to the manufacturer's directions. Reactions were carried out for 1–2 hr at 37° C. before analyzing reaction products by polyacrylamide gel electrophoresis (PAGE).

*Xenopus* Oocyte Injection and Labeling

Oocytes were enzymatically defolliculated and rinsed with OR2 (50 mM HEPES [pH 7.2], 82 mM NaCl, 2.5 mM KCl, 1.5 mM Na2HPO4). Healthy stage six oocytes were injected with 30 ng of in vitro transcribed, capped mouse Shh RNA (prepared as described above). Following a 2 hr recovery period, healthy injected oocytes and uninjected controls were cultured at room temperature in groups of ten in 96-well dishes containing 0.2 ml of OR2 (supplemented with 0.1 mg/ml Gentamicin and 0.4 mg/ml BSA) per well. The incubation medium was supplemented with 50 μCi of Express labeling mix. Three days after injection, the culture media were collected and expression of Shh protein analyzed by immunoprecipitation. Oocytes were rinsed several times in OR2 before lysing in TENT (20 mM Tris-HCl [pH 8.0]; 150 mM NaCl, 2mM EDTA; 1% Triton-X-100; 10 μl/oocyte) supplemented with 1 μg/ml aprotinin, 2 μg/ml leupeptin and 1 mM phenylmethylsufonylfluoride (PMSF). After centrifugation at 13000×g for 10 minutes at 4° C., soluble protein supernatants were recovered and analyzed by immunoprecipitation (see below).

Cos Cell Transfection and Labeling

Cos cells were cultured in Dulbecco's Modified Eagle Medium (DMEM; Sigma, Inc.) supplemented with 10% fetal bovine serum (Gibco/BRL), 2 mM L-Glutamine (Gibco/BRL) and 50 mU/ml penicillin and 50 μg/ml streptomycin (Gibco/BRL). Subconfluent cos cells in 35 mm or 60 mm dishes (Falcon, Inc.) were transiently transfected with 2 mg or 6 mg supercoiled plasmid DNA, respectively. Between 42 and 44 hr post-transfection, cells were labeled for 4–6 hr in 0.5 ml (35 mm dishes) or 1.5 ml (60 mm dishes) serum-free DMEM lacking Cysteine and Methionine (Gibco/BRL) and supplemented with 125 μCi/ml each of Express labeling mix and L-35S-Cysteine (NEN/DuPont). After labeling, media were collected and used for immunoprecipitation. Cells were rinsed with cold PBS and lysed in the tissue culture dishes by the addition of 0.5 ml (35 mm dishes) or 1.5 ml (60 mm dishes) TENT (with protease inhibitors as described above) and gentle rocking for 30 minutes at 4° C. Lysates were cleared by centrifugation (13000×g for 5 min. at 4° C.) and the supernatants were analyzed by immunoprecipitation (see below).

Baculovirus Production and Infection

A recombinant baculovirus expressing mouse sonic hedgehog with a myc epitope tag inserted at the carboxy terminus was generated using the Baculogold kit (Pharmingen, Inc.). The initial virus production used Sf 9 cells, followed by two rounds of amplification in High Five cells (Invitrogen, Inc.) in serum-free medium (ExCell 401; Invitrogen, Inc.). A baculovirus lacking Shh coding sequences was also constructed as a control. For protein induction, High Five cells were infected at a multiplicity of approximately 15. Three days later, medium and cells were collected by gentle pipetting. Cells were collected by centrifugation (1000×g) and the medium was recovered for Western blot analysis. Cell pellets were washed twice in cold PBS and lysed in TENT plus protease inhibitors (see above) by rotating for 30 minutes at 4° C. in a microcentrifuge tube. The lysate was cleared as described above prior to Western blotting.

Western Blotting

For Western blotting, 0.25 ml samples of media (1% of the total) were precipitated with TCA and redissolved in 15 μl of LSB. Cell lysate samples (1% of total) were brought to a final volume of 15 μl with water and concentrated (5×) LSB. Samples were boiled S minutes prior to separation on a 15% acrylamide gel. Proteins were transferred to PVDF membrane (Immobilon-P; Millipore, Inc.) and blocked in BLOTTO (5% w/v non-fat dried milk in PBS) containing 0.2% Tween-20. Hybridoma supernatant recognizing the human c-myc epitope (9E10; Evan, G. I. et al., (1985) *Mol. Cell. Biol.* 5:3610–3616) was added at a dilution of 1:200 for one hour followed by a 1:5000 dilution of Goat anti-Mouse-Alkaline phosphatase conjugate (Promega, Inc.) for 30 minutes. Bands were visualized using the Lumi-Phos 530 reagent (Boehringer-Mannheim) according to the manufacturer's directions.

For Western blotting of COS cell material, cleared media (see above) were precipitated with TCA in the presence of 4 μg of BSA per ml as a carrier the protein pellets were dissolved in 20 μl of LSB. Dissolved medium protein and cell lysates (see above) were boiled for 5 min, and 10 μl (50%) of each medium sample and 1011 (10%) of each cell lysate were separated on a 15% acrylamide gel. The gel was blotted to a polyvinylidene difluoride membrane as described above. The membrane was blocked as described above and incubated in a 1:200 dilution of affinity-purified Shh antiserum (see below) and then in a 1:5,000 dilution of horseradish peroxidase-conjugated donkey anti-rabbit immunoglobulin g (IgG; Jackson Immuno research, Inc.). Bands were visualized with the Enhanced Chemiluminescence kit (Amersham, Inc.) according to the manufacturer's instructions.

For Western blotting of mouse and chicken embryonic tissue lysates, 60 μg of each sample was separated on 15% acrylamide gels. Blotting and probing with affinity-purified Shh antiserum as well as chemiluminescence detection were carried out as described above for the COS cell material.

Immunoprecipitation

Cell lysates (*Xenopus* oocytes or cos cells) were brought to 0.5 ml with TENT (plus protease inhibitors as above). Media samples (OR2 or DMEM) were cleared by centrifugation at 13000×g for 5 min. (4° C.) and 10× TENT was added to a final concentration of IX (final volume: 0.5–1.5 ml). The c-myc monoclonal antibody hybridoma supernatant was added to $\frac{1}{20}$ of the final volume. Samples were rotated for 1 hr at 4° C., then 0.1 ml of 10% (v/v) protein A-Sepharose CL-4B (Pharmacia, Inc.) was added. Samples were rotated an additional 14–16 h. Immune complexes were washed 4 times with 1.0 ml TENT. Immunoprecipitated material was eluted and denatured by boiling for 10 minutes in 25 μl IX LSB. Following centrifugation, samples were separated on 15% acrylamide gels and processed for fluorography as described previously. Samples for Endo H digestion were eluted and denatured by boiling for 10 minutes in the provided denaturation buffer followed by digestion with Endo H for 1–2 hr at 37° C. Concentrated (SX) LSB was added and the samples were processed for electrophoresis as described.

For immunoprecipitation with the anti-mouse Shh serum, samples (Cos cell lysates and DMEM) were precleared by incubating 1 hr on ice with 3 μl pre-immune serum, followed by the addition of 0.1 ml 10% (v/v) Protein A-Sepharose. After rotating for 1 hr at 4 C, supernatants were recovered and incubated for 1 hr on ice with 311 depleted anti-mouse Shh serum (see below). Incubation with Protein A-Sepharose, washing, elution and electrophoresis were then performed as described above.

Immunofluorescent Staining of Cos Cells

Twenty-four hours after transfection, cells were transferred to 8-chamber slides (Lab-Tek, Inc.) and allowed to attach an additional twenty-four hours. Cells were fixed in 2% paraformaldehyde/0.1% glutaraldehyde, washed in PBS and permeabilized in 1% Triton-X-100 (Munro, S. and Pelham, H. R. B., (1987) *Cell* 48:899–907). After washing in PBS, cells were treated for 10 minutes in 1 mg/ml sodium borohydride. Cells were incubated with the c-myc monoclonal antibody hybridoma supernatant (diluted 1:10) and the affinity purified mouse Sonic hedgehog antiserum (diluted 1:4) for 45 minutes followed by incubation in 1:100 Goat-anti Mouse IgG-RITC plus 1:100 Goat anti Rabbit IgG FITC (Southern Biotechnology Associates, Inc.) for 45 minutes. DAPI (Sigma, Inc.) was included at 0.3 μg/ml The slides were mounted in Slo-Fade (Molecular Probes, Inc.) and photographed on a Leitz DMR compound microscope.

Embryonic Tissue Dissection and Lysis

Mouse forebrain, midbrain, hindbrain, lung, limb, stomach, and liver tissues form 15.5-day-postcoitum Swiss Webster embryos were dissected into cold PBS, washed several times in PBS, and then lysed by trituraton and gentle sonication in LSB lacking bromophenol blue. Lysates were cleared by brief centrifugation, and protein concentrations were determined by the Bradford dye-binding assay.

To obtain chicken CNS and limb bud tissue, fertilized eggs (Spafas, Inc.) were incubated at 37° C. until the embryos reached stages 20 and 25, respectively (Hamburg and Hamilton (1951) *J. Exp. Morphol.* 88:49–92). By using sharp tungsten needles, dorsal and ventral pieces of the anterior CNS were obtained from the stage 15 embryos, and limb buds from the stage 25 embryos were cut into anterior and posterior halves. Tissues were lysed, and protein concentrations were determined as described above. Prior to electrophoresis of the mouse and chicken proteins (see above), samples were brought to 20 μl with LSB containing bromophenol blue and boiled for 5 minutes.

Antibody Production and Purification

A PCR fragment encoding amino acids 44–143 of mouse Sonic hedgehog was cloned in frame into the Eco RI site of pGEX-2T (Pharmacia, Inc.). Transformed bacteria were induced with IPTG and the fusion protein purified on a Glutathione-Agarose affinity column (Pharmacia, Inc.) according to the manufacturer's instructions. Inoculation of New Zealand White rabbits, as well as test and production bleeding were carried out at Hazelton Research Products, Inc.

To deplete the serum of antibodies against Glutathione-S-transferase (GST) and bacterial proteins, a lysate of *E. coli* transformed with pGEX-2T and induced with IPTG was coupled to Affi-Gel 10 (Bio-Rad, Inc.) The serum was incubated in batch for two hours with the depletion matrix before centrifugation (1000×g for 5 min.) and collection of the supernatant. To make an affinity matrix, purified bacterially expressed protein corresponding to the amino terminal two-thirds of mouse Sonic hedgehog was coupled to Affi-Gel 10 (Bio-Rad, Inc.). The depleted antiserum was first adsorbed to this matrix in batch, then transferred to a column. The matrix was washed with TBST (25 mM Tris-HCl [pH 7.5], 140 mM NaCl, 5 mM KCl, 0.1% Triton-X-100), and the purified antibodies were eluted with ten bed volumes of 0.15 M Glycine [pH 2.5]. The solution was neutralized with one volume of 1 M Tris-HCl [pH 8.0], and dialyzed against 160 volumes of PBS.

Other antibodies have been generated against hedgehog proteins and three polyclonal rabbit antisera obtained to hh proteins can be characterized as follows:Ab77-reacts only with the carboxylprocessed chick Shh peptide (27 kd); Ab79-reacts with amino processed chick, mouse and human Shh peptide (19 kd). Weakly reacts with 27 kd peptide from chick and mouse. Also reacts with mouse Ihh; and Ab80-reacts with only amino peptide (19 kd) of chick, mouse and human.

(ii) In Vitro Translated Sonic Hedgehog is Proteolytically Processed and Glycosylated The open reading frames of chick and mouse Shh encode primary translation products of 425 and 437 amino acids, respectively, with predicted molecular masses of 46.4 kilodaltons (kDa) and 47.8 kDa (Echelard, Y. et al., (1993) *Cell* 75:1417–1430; Riddle, RD. et al., (1993) *Cell* 75:1401–1416). Further examination of the protein sequences revealed a short stretch of amino terminal residues (26 for chick, 24 for mouse) that are highly hydrophobic and are predicted to encode signal peptides. Removal of these sequences would generate proteins of 43.7 kDa (chick Shh) and 45.3 kDa (mouse Shh). Also, each protein contains a single consensus site for N-linked glycosylation (Tarentino, A. L. et al., (1989) *Methods Cell Biol.* 32:111–139) at residue 282 (chick) and 279 (mouse).

A rabbit reticulocyte lysate programmed with in vitro translated messenger RNA encoding either chick or mouse Shh synthesizes proteins with molecular masses of 46 kDa and 47 kDa, respectively. These values are in good agreement with those predicted by examination of the amino acid sequences. To examine posttranslational modifications of Shh proteins, a preparation of canine pancreatic microsomal membranes was included in the translation reactions. This preparation allows such processes as signal peptide cleavage and core glycosylation. When the Shh proteins are synthesized in the presence of these membranes, two products with apparent molecular masses of approximately 19 and 28 kDa (chick), or 19 and 30 kDa (mouse) are seen in addition to the 46 kDa and 47 kDa forms. When the material synthesized in the presence of the membranes is digested with Endoglycosidase H (Endo H), the mobilities of the two larger proteins are increased. The apparent molecular masses of the Endo H digested forms are 44 kDa and 26 kDa for chick Shh, and 45 kDa and 27 kDa for mouse Shh. The decrease in the molecular masses of the largest proteins synthesized in the presence of the microsomal membranes after Endo H digestion is consistent with removal of the predicted signal peptides. The mobility shift following Endo H treatment indicates that N-linked glycosylation occurs, and that the 26 kDa (chick) and 27 kDa (mouse) proteins contain the glycosylation sites.

The appearance of the two lower molecular weight bands (hereafter referred to as the "processed forms") upon translation in the presence of microsomal membranes suggests that a proteolytic event in addition to signal peptide cleavage takes place. The combined molecular masses of the processed forms (19 kDa and 26 kDa for chick; 19 kDa and 27 kDa for mouse) add up to approximately the predicted masses of the signal peptide cleaved proteins (44 kDa for chick and 45 kDa for mouse) suggesting that only a single additional cleavage occurs.

The mouse Shh protein sequence is 12 amino acid residues longer than the chick sequence (437 versus 425 residues). Alignment of the chick and mouse Shh protein sequences reveals that these additional amino acids are near the carboxy terminus of the protein (Echelard, Y. et al., (1993) *Cell* 75:1417–1430). Since the larger of the processed forms differ in molecular mass by approximately 1 kDa between the two species, it appears that these peptides contain the carboxy terminal portions of the Shh proteins. The smaller processed forms, whose molecular masses are identical, presumably consist of the amino terminal portions.

(iii) Secretion of Shh Peptides

To investigate the synthesis of Shh proteins in vivo, the mouse protein was expressed in several different eukaryotic cell types. In order to detect synthesized protein, and to facilitate future purification, the carboxy terminus was engineered to contain a twenty-five amino acid sequence containing a recognition site for the thrombin restriction protease followed by a ten amino acid sequence derived from the human c-myc protein and six consecutive histidine residues. The c-myc sequence serves as an epitope tag allowing detection by a monoclonal antibody (9E10; Evan, G. I. et al., (1985) *Mol. Cell Biol.* 5:3610–3616). The combined molecular mass of the carboxy terminal additions is approximately 3 kDa.

*Xenopus laevis* oocytes

Immunoprecipitation with the c-myc antibody detects several proteins in lysates of metabolically labeled *Xenopus laevis* oocytes injected with Shh mRNA. Cell lysates and medium from $^{35}S$ labeled oocytes injected with RNA encoding mouse Shh with the c-myc epitope tag at the at the carboxy terminus, or from control oocytes were analyzed by immunoprecipitation with c-myc monoclonal antibody. A band of approximately 47 kDa is seen, as is a doublet migrating near 30 kDa. Treatment with Endo H increases the mobility of the largest protein, and resolves the doublet into a single species of approximately 30 kDa. These observations parallel the behaviors seen in vitro. Allowing for the added mass of the carboxy terminal additions, the largest protein would correspond to the signal peptide cleaved form, while the doublet would represent the glycosylated and unglycosylated larger processed form. Since the epitope tag was placed at the carboxy terminus of the protein, the identity of the 30 kDa peptide as the carboxy terminal portion of Shh is confirmed. Failure to detect the 19 kDa species supports its identity as an amino terminal region of the protein.

To test whether Shh is secreted by *Xenopus* oocytes, the medium in which the injected oocytes were incubated was probed by immunoprecipitation with the c-myc antibody. A single band migrating slightly more slowly than the glycosylated larger processed form was observed. This protein is insensitive to Endo H. This result is expected since most secreted glycoproteins lose sensitivity to Endo H as they travel through the Golgi apparatus and are modified by a series of glycosidases (Komfeld, R. and Komfeld, S., (1985) *Annu. Rev. Biochem.* 54:631–664). The enzymatic maturation of the Asn-linked carbohydrate moiety could also explain the slight decrease in mobility of the secreted larger protein versus the intracellular material. Following Endo H digestion, a band with a slightly lower mobility than the signal peptide cleaved protein is also apparent, suggesting that some Shh protein is secreted without undergoing proteolytic processing. Failure to detect this protein in the medium without Endo H digestion suggests heterogeneity in the extent of carbohydrate modification in the Golgi preventing the material from migrating as a distinct band. Resolution of this material into a single band following Endo H digestion suggests that the carbohydrate structure does not mature completely in the Golgi apparatus. Structural differences between the unprocessed protein and the larger processed form could account for this observation (Komfeld, R. and Komfeld, S., (1985) *Annu. Rev. Biochem.* 54:631–664).

Cos cells

The behavior of mouse Shh in a mammalian cell type was investigated using transfected cos cells. Synthesis and secretion of the protein was monitored by immunoprecipitation using the c-myc antibody. Transfected cos cells express the same Sonic hedgehog species that were detected in the injected *Xenopus* oocytes, and their behavior following Endo H digestion is also identical. Furthermore, secretion of the 30 kDa glycosylated form is observed in cos cells, as well as the characteristic insensitivity to Endo H after secretion. Most of the secreted protein co-migrates with the intracellular, glycosylated larger processed form, but a small amount of protein with a slightly lower mobility is also detected in the medium. As in the *Xenopus* oocyte cultures, some Shh which has not undergone proteolytic processing is evident in the medium, but only after Endo H digestion.

Baculovirus infected cells

To examine the behavior of the mouse Shh protein in an invertebrate cell type, and to potentially purify Shh peptides, a recombinant baculovirus was constructed which placed the Shh coding sequence, with the carboxy terminal tag, under the control of the baculoviral Polyhedrin gene promoter. When insect cells were infected with the recombinant baculovirus, Shh peptides could be detected in cell lysates and medium by Western blotting with the c-myc antibody.

The Shh products detected in this system were similar to those described above. However, virtually no unprocessed protein was seen in cell lysates, nor was any detected in the medium after Endo H digestion. This suggests that the proteolytic processing event occurs more efficiently in these cells than in either of the other two cell types or the in vitro translation system. A doublet corresponding to the glycosylated and unglycosylated 30 kDa forms is detected, as well as the secreted, Endo I resistant peptide as seen in the other expression systems. Unlike the other systems, however, all of the secreted larger processed form appears to comigrate with the glycosylated intracellular material.

(iv) Secretion of a Highly Conserved Amino Terminal Peptide

To determine the behavior of the amino terminal portion of the processed Sonic hedgehog protein, the c-myc epitope tag was positioned 32 amino acids after the putative signal peptide cleavage site. Cos cells were transfected with Shh expression constructs containing the c-myc tag at the carboxy terminus or near the amino terminus. When this construct was expressed in cos cells, both the full length protein and the smaller processed form (approximately 20 kDa due to addition of the c-myc tag) were detected by immunoprecipitation of extracts from labeled cells. However, the 20 kDa product is barely detected in the medium. In cells transfected in parallel with the carboxy terminal c-myc tagged construct, the full length and 30 kDa products were both precipitated from cell lysates and medium as described earlier.

As the amino terminal c-myc tag may affect the secretion efficiency of the smaller processed form, the expression of this protein was examined in cos cells using an antiserum directed against amino acids 44 through 143 of mouse Shh. After transfection with the carboxy-terminal c-myc tagged construct, immunoprecipitation with the anti-Shh serum detected a very low level of the smaller processed form in the medium despite a strong signal in the cell lysate. This recapitulates the results with the myc antibody.

To examine the subcellular localization of Shh proteins, cos cells were transfected with the carboxy terminal tagged Shh construct and plated on multi-chamber slides, fixed and permeabilized. The cells were incubated simultaneously with the anti-Shh serum and the c-myc antibody followed by FITC conjugated Goat anti-Rabbit-IgG and RITC conjugated Goat anti-Mouse-IgG. DAPI was included to stain nuclei. Strong perinuclear staining characteristic of the Golgi apparatus was observed with the anti-Shh serum. The same subcellular region was also stained using the c-myc antibody. The coincidence of staining patterns seen with the two antibody preparations suggest that the low level of the smaller processed form detected in the medium is not due to its retention in the endoplasmic reticulum, since both processed forms traffic efficiently to the Golgi apparatus.

One explanation for the failure to detect large amounts of the smaller processed form in the culture medium could that this protein associates tightly with the cell surface or ECM. To examine this, cells were treated with the polyanionic compounds herparin and suramin. These compounds have been shown to increase the levels of some secreted proteins in culture medium, possibly by displacing them from cell surface or ECM components or by directly binding the proteins and perhaps protecting them from proteolytic degradation (Bradley and Brown (1990) *EMBO J.* 9:1569–1575; Middaugh et al. (1992) *Biochem.* 31:90169024; Smolich et al. (1993) *Mol. Biol. Cell* 4:1267–1275). The 19-kDa amino-terminal form of Shh is barely detectable in the medium of transfected COS cells, despite its obvious presence in the cell lysate. However, in the presence of 10 mg of heparin per ml, this peptide is readily detected in the medium. The addition of 10 mM suramin to the medium has an even greater effect. Since the concentrations used where those previously determined to elicit maximal responses, it is clear that suramin is more active than heparin in this assay.

The ability of heparin and suramin to increase the amount of the smaller processed form in the medium of transfected cells implies that this peptide may be tightly associated with the cell surface of ECM. As a first step toward determining which region(s) of the Shh protein may be responsible for this retention, a truncated form of mouse Shh deleted of all sequence downstream of amino acid 193 was expressed in COS cells. This protein contains all of the sequences encode by exons one and two, as well as five amino acids derived for exon three. Since its predicted molecular mass (19.2 kDa) is very close to the observed molecular mass of the smaller processed form, the behavior of this protein would be expected to mimic that of the smaller processed form. This protein is detected at a very high level in the medium, even in the absence of heparin or suramin, and migrates at a position indistinguishable form that of the amino-terminal cleavage product generated from the full-length protein. In fact, virtually no protein is seen in the cell lysates, suggesting nearly quantitative release of the protein into the medium. This raises the possibility that the actual amino terminally processed form may extend a short distance beyond amino acid 193 and that these additional amino acids contain a cell surface-ECM retention signal.

The influence of sequences located at the extreme amino and carboxy termini of mouse Shh on the behavior of the protein in transfected cells was examined using the amino terminus-specific antiserum. Expression of a mouse Shh construct lacking a signal peptide results in the accumulation of approximately 28-kDa protein, as well as a small amount of protein which comigrates with the smaller processed form. This implies that correct cleavage of Shh requires targeting of the protein to the endoplasmic reticulum, since the bulk of the processed form of Shh expressed in the cytoplasm is cleaved at a new position that is approximately 9 kDa carboxy after amino acid 428 (lacking nine carboxy-terminal amino acids [ΔCt]) results in the expected amino-terminal cleavage product; however, the efficiency of cleavage is significantly decreased compared with that seen with the wild-type protein. Therefore, sequences located at a distance from the proteolytic processing site are able to affect the efficiency of processing.

(v) Sonic hedgehog processing in embryonic tissues

In order to determine whether the proteolytic processing of Shh observed in the different expression systems reflects the behavior of the protein in embryos, the amino terminus-specific mouse Shh antiserum was used to probe Western blots of various chicken and mouse embryonic tissues. A protein with an electrophoretic mobility identical to that of COS cell-synthesized amino terminally processed form is detected at a substantial level in the stomach and lung tissue and at a markedly lower level in the forebrain, midbrain, and hindbrain tissues of 15.5-day-postcoitum mouse embryos. These tissues have all been shown to express Shh RNA. The 19 kDa peptide is not detected in liver or late limb tissues, which do not express Shh RNA. Thus, the proteolytic processing of Shh observed in cell culture also occurs in embryonic mouse tissue.

The cross-reactivity of the amino terminus-specific mouse Shh antiserum with chicken Shh protein allowed for examination of expression of Shh in chicken embryonic tissue. The antiserum detects the 19-kDa amino terminally processed form of chicken Shh in transfected COS cells, as well as in two tissues which have been shown by whole-mount in situ hybridization and antiserum staining to express high levels of Shh RNA and protein, i.e., the posterior region of the limb bud and the ventral region of the anterior CNA (Riddle et al. (1993) *Cell* 75:1401–1416). Therefore, the expected proteolytic processing of Shh occurs in chicken embryonic tissues, and diffusion of the 19-kDa protein does not extend into the anterior limb buds and dorsal CNS.

(v) Hedgehog Processing

In summary, the results discussed above demonstrate that the mouse and chick Shh genes encode secreted glycoproteins which undergo additional proteolytic processing. Data indicate that this processing occurs in an apparently similar fashion in a variety of cell types suggesting that it is a general feature of the Shh protein, and not unique to any particular expression system. For mouse Shh, data indicate that both products of this proteolytic processing are secreted.

It was observed that the 19 kDa amino peptide accumulates to a lower level in the medium than the 27 kDa carboxyl peptide. This may reflect inefficient secretion or rapid turnover of this species once secreted. Alternatively, the smaller form may associate with the cell surface or extracellular matrix components making it difficult to detect in the medium. The insensitivity of the secreted, larger form to Endo H is a common feature of secreted glycoproteins. During transit through the Golgi apparatus, the Asn-linked carbohydrate moiety is modified by a series of specific glycosidases (reviewed in Komfeld, R. and Komfeld, S., (1985) *Annu. Rev. Biochem* 54:631–664; Tarentino, A. L. et al., (1989) *Methods Cell Biol.* 32:111–139). These modifications convert the structure from the immature "high mannose" to the mature "complex" type. At one step in this process, a Golgi enzyme, α-mannosidase II, removes two mannose residues from the complex rendering it insensitive to Endo H (Komfeld, R. and Komfeld, S., (1985)Annu. Rev. Biochem 54:631–664).

The biochemical behavior of mouse Shh appears to be quite similar to that described for the *Drosophila* Hedgehog (Dros-HH) protein (Lee, J. L. et al., (1992) *Cell* 71:33–50; Tabata, T. et al., (1992) *Genes & Dev.* 6:2635–2645). In vitro translation of *Drosophila* hh mRNA, in the presence of microsomes, revealed products with molecular masses corresponding to full length protein, as well as to the product expected after cleavage of the predicted internal (Type II) signal peptide (Lee, J. L. et al., (1992) *Cell* 71:33–50). Interestingly, no additional, processed forms were observed. However, such forms could have been obscured by breakdown products migrating between 20 and 30 kDa. When an RNA encoding a form of the protein lacking the carboxy-terminal 61 amino acids was translated, no breakdown products were seen, but there is still no evidence of the proteolytic processing observed with mouse Shh. A similar phenomenon has been observed in these experiments. A reduction in the extent of proteolytic processing is seen when a mouse Shh protein lacking 10 carboxy-terminal amino acids is translated in vitro or expressed in cos cells (data not shown). This suggests that sequences at the carboxy termini of Hh proteins act at a distance to influence the efficiency of processing.

Recently, Lee et al. (Science 266:1528–1537, 1994) described the biochemical behavior of the *Drosophila* HH protein. Using region-specific antisera, they detected similar processed forms of HH in embryonic tissues, thus confirming studies in which processing of HH was observed in embryos forced to express high levels of HH from a heat shock promoter (Tabata and Komberg (1994) *Cell* 76:89–102). Thus, *Drosophila* HH is processed to yield a 19 kDa amino-terminal peptide and a 25 kDa carboxy-terminal peptide. Furthermore, Lee et al. concluded that the production of the processed forms occurs via an autocatalytic mechanism and identified a conserved histidine residue (at position 329, according to Lee et al. (Science 266:1528–1537, 1994)) which is required for self-cleavage of HH protein in vitro and in vivo. The significance of the proteolytic processing is demonstrated by the inability of self-processing-either because of mutation of this histidine residue or because of truncation of sequences at the extreme carboxy terminus-to carry out HH functions in *Drosophila* embryos.

Their studies of the biochemical behavior of mouse and chicken Shh and mouse Ihh proteins correlate well with the *Drosophila* studies of Lee et al. (*Science* 266:1528–1537, 1994) in that the similar proteolytic processing of endogenous vertebrate proteins in embryonic tissues was demonstrated. Furthermore, it was demonstrated that the efficiency of processing depends on sequences located at the extreme carboxy terminus of mouse Shh. Interestingly, it has also been shown that he specificity of mouse Shh cleavage may depend on targeting of the protein to the secretory pathway, since a form lacing a signal peptide is processed into an approximately 28-kDa amino-terminal form. A similar protein is observed as the predominant species when it was attempted to express full-length mouse Shh in bacteria (data no shown). Lee et al. (*Science* 266:1528–1537, 1994) have demonstrated that two zebra fish hedgehog proteins undergo proteolytic processing when translated in vitro, even in the absence of microsomal membranes. The electrophoretic mobilities of the processed peptides are consistent with cleavage occurring at a position similar to that of the *Drosophila* HH cleavage site. Furthermore, they showed that the cleavage fails to occur if the conserved histidine residue is mutated, arguing for an autoproteolytic mechanism similar to that of the *Drosophila* protein. However, the processing of mouse or chicken Shh protein translated in vitro was not detected unless microsomal membrane are included. Therefore, it is possible that correct proteolytic processing of vertebrate hedgehog proteins is dependent on specific incubation conditions or may require cellular factors in addition to Shh itself.

An additional correlation between the work presented here and that of Lee et al. (*Science* 266:1528–1537, 1994) concerns the different behaviors of the amino (smaller) and carboxy (larger) terminally processed forms of the hedgehog proteins. The evidence is presented that the 27 kDa carboxy-terminal form diffuses more readily from expressing cells than the 19 kDa amino-terminal form, which seems to be retained near the cell surface. The polyanions heparin and suramin appear capable of releasing the amino peptide into the medium. Similarly, the amino-terminal form of *Drosophila* HH is more closely associated with the RNA expression domain in embryonic segments than is the carboxy-terminal form, and the amino-terminal form binds to heparin agarose beads. Therefore, the distinct behaviors of the different hedgehog peptides have been conserved across phyla.

The observed molecular masses of the amino terminally processed forms of mouse and chicken Shh, mouse Ihh proteins, and *Drosophila* HH are between 19 and 20 kDa. Therefore, the predicted secondary proteolytic cleavage site would be located near the border of the sequences encoded by the second and third exons. Interestingly, the region marks the end of the most highly related part of the hedgehog proteins. The amino terminal (smaller) form would contain the most highly conserved portion of the protein. In fact, the amino acids encoded by exons one and two (exclusive of sequences upstream of the putative signal peptide cleavage sites) share 69/o identity between *Drosophila* Hh and mouse Shh, and 99% identity between chick and mouse Shh. Amino acid identity in the region encoded by the third exon is much lower 30% mouse to *Drosophila* and 71% mouse to chick (Echelard, Y. et al., (1993) *Cell* 75:1417–1430).

However, the boundary between sequences encoded by exons 2 and 3 is unlikely to be the actual proteolytic processing site, because a *Drosophila* HH protein containing a large deletion which extends three amino acids beyond this boundary is still cleaved at the expected position in vitro (Lee et al. (1994) *Science* 266:1528–1537). Moreover, the analysis of an amino-terminal mouse Shh peptide truncated at amino acid 193 (the fourth amino acid encoded by exon 3, described below) suggests that normal cleavage must occur downstream of this position. Close examination of hedgehog protein sequences reveals that strong sequence conservation between the *Drosophila* and vertebrate proteins continues for only a short distance into the third exon. If it is assumed that cleavage will generate an amino terminal product of no greater than 20 kDa, given the resolution of analysis, all of the data would indicate that cleavage occurs at 1 of the 10 amino acids within the mouse Shh positions 194–203, according to Echelard et al. (*Cell* 75:1417–1430,1993).

(vi) Hedgehog Signalling

In order to satisfy the criteria for intercellular signaling, hedgehog proteins must be detected outside of their domains of expression. This has been clearly demonstrated for *Drosophila* HH. Using an antiserum raised against nearly full length Dros-HH protein, Tabata and Komberg (Tabata, T. and Komberg, T. B., (1992) *Cell* 76:89–102) detect the protein in stripes that are slightly wider than the RNA expression domains in embryonic segments, and just anterior to the border of the RNA expression domain in wing imaginal discs. Similarly, Taylor, et. al., (1993) *Mech. Dev.* 42:89–96, detected HH protein in discrete patches within cells adjacent to those expressing hh RNA in embryonic segments using an antiserum directed against an amino-terminal portion of Hh which, based on the proteolytic processing data (Tabata, T. et al., (1992) *Genes & Dev.* 6:2635–2645), is not likely to recognize the carboxyl cleavage product.

The detection of Hh beyond cells expressing the hh gene is consistent with the phenotype of hh mutants. In these animals, cellular patterning in each embryonic parasegment in disrupted resulting in an abnormal cuticular pattern reminiscent of that seen in wg mutants. Further analysis has revealed that the loss of hh gene function leads to loss of wg expression in a thin stripe of cells just anterior to the hh expression domain (Ingham, P. W. and Hidalgo, A., (1993) *Development* 117:283–291). This suggests that Hh acts to maintain wg expression in neighboring cells. The observation that ubiquitously expressed Hh leads to ectopic activation of wg supports this model (Tabata, T. and Komberg, T. B., (1992) *Cell* 76:89–102). In addition to these genetic studies, there is also indirect evidence that Hh acts at a distance from its site of expression to influence patterning of the epidermis (Heemskerk, J. and DiNardo, S., (1994) *Cell* 76:449–460).

The apparent effect of *Drosophila* Hh on neighboring cells, as well as on those located at a distance from the site of hh expression is reminiscent of the influence of the notochord and floor plate on the developing vertebrate CNS, and of the ZPA in the limb. The notochord (a site of high level Shh expression) induces the formation of the floor plate in a contact dependent manner, while the notochord and floor plate (another area of strong Shh expression) are both capable of inducing motomeurons at a distance (Placzek, M. et al., (1993) *Development* 117:205–218; Yamada, T. et al., (1993) *Cell* 73:673–686).

Moreover ZPA activity is required not only for patterning cells in the extreme posterior of the limb bud where Shh is transcribed, but also a few hundred microns anterior of this zone. Several lines of evidence indicate that Shh is able to induce floor plate (Echelard, Y. et al., (1993) *Cell* 75:1417–1430; Roelink, H. et al., (1994) *Cell* 76:761–775) and mediate the signaling activity of the ZPA (Riddle, R. D. et al., (1993) *Cell* 75:1401–1416). Since it has been shown that Shh is cleaved, it can be speculated that the processed peptides may have distinct activities. The smaller amino terminal form, which appears to be more poorly secreted, less stable or retained at the cell surface or in the extracellular matrix, may act locally. In contrast, the larger carboxy terminal peptide could possibly function at a distance. In this way, Shh peptides may mediate distinct signaling functions in the vertebrate embryo. Alternatively, the carboxy-terminal peptide may be necessary only for proteolytic processing, with all signaling activity residing in the amino-terminal peptide.

Example 7

Sonic Hedgehog and Fgf-4 Act Through a Signaling Cascade and Feedback Loop to Integrate Growth and Patterning of the Developing Limb Bud (i) Experimental Procedures Cloning of Chicken Fgf-4 and Bmp-2

A 246 bp fragment of the chicken Fg-4 gene was cloned by PCR from a stage 22 chicken limb bud library. Degenerate primers were designed against previously cloned Fgf-4 and Fgf-6 genes: fgf5' (sense) AAA AGC TTT AYT GYT AYG TIG GIA THG G (SEQ ID No:45) and fgf3' (antisense) AAG AAT TCT AIG CRT TRT ART TRT TIG G (SEQ ID No:46). Denaturation was at 94° C. for 2 min, followed by 30 cycles of 94° C. for 30 sec, 50° C. for 60 sec, and 72° C. for 30 sec, with a final extension at 72° C. for 5 min. The PCR product was subcloned into the Bluescript SK+ vector. A clone was sequenced and confirmed as Fgf-4 by comparison with previously published Fgf-4 genes and a chicken Fgf-4 gene sequence kindly provided by Lee Niswander.

BMP-related sequences were amplified from a stage 22 posterior limb bud cDNA library prepared in Bluescript using primers and conditions as described by Basler, et al. (1993). Amplified DNAs were cloned and used to screen a stage 22 limb bud library prepared in λ-Zap (Stratagene). Among the cDNAs isolated was chicken Bmp-2. Its identity was confirmed by sequence comparison to the published clones (Francis, et al., (1994) *Developmeni* 120:209–218) and by its expression patterns in chick embryos.

Chick Surgeries and Recombinant Retroviruses

All experimental manipulations were performed on White Leghorn chick embryos (S—SPF) provided by SPAFAS (Norwich, Conn.). Eggs were staged according to Hamburger and Hamilton (1951) *J. Exp. Morph.* 88:49–92.

Viral supernatants of Sonic/RCAS-A2 or a variant containing an influenza hemaglutinin epitope tag at the carboxyl terminus of the hedgehog protein (Sonic7. I/RCAS-A2, functionally indistinguishable from Sonic/RCAS-A2), were prepared as described (Hughes, et al., (1987) *J. Virol.* 61:3004–13; Fekete and Cepko, (1993) *Mol. & Cell. Biol.* 13:2604–13; Riddle, et al., (1993) *Cell* 75:1401–16). For focal injections the right wings of stage 18–21 embryos were transiently stained with nile blue sulfate (0.01 mg/ml in Ringer's solution) to reveal the AER. A trace amount of concentrated viral supernatant was injected beneath the AER.

The AER was removed using electrolytically sharpened tungsten wire needles. Some embryos had a heparin-acrylic bead soaked in FGF-4 solution (0.8 mg/ml; a gift from Genetics Institute) or PBS stapled to the limb bud with a piece of 0.025 mm platinum wire (Goodfellow, Cambridge UK) essentially as described by Niswander et al, (1993) *Cell* 75:579–87.

Limbs which were infected with Sonic/RCAS virus after AER removal were infected over a large portion of the denuded mesoderm to ensure substantial infection. Those embryos which received both an Fgf-4 soaked bead and virus were infected only underneath the bead.

In Situ Hybridizations and Photography

Single color whole mount in situ hybridizations were performed as described (Riddle, et al., (1993) *Cell* 75:1401–16). Two color whole mount in situ hybridizations were performed essentially as described by Jowett and Lettice (1994) *Trends Genet.* 10:73–74. The second color detection was developed using 0.125 mg/ml magenta-phos (Biosynth) as the substrate. Radioactive in situ hybridizations on 5 μm sections was performed essentially as described by Tessarollo, et al. (1992) *Development* 115:11–20.

The following probes were used for whole mount and section in situ hybridizations: Sonic: 1.7 kb fragment of pHH2 (Riddle, et al., (1993) *Cell* 75:1401–16). Bmp-2: 1.5 kb fragment encoding the entire open reading frame. Fgf-4: 250 bp fragment described above. Hox d-11: a 600 bp fragment, Hoxd-13: 400 bp fragment both including 5' untranslated sequences and coding sequences upstream of the homeobox. RCAS: 900 bp SalI-ClaI fragment of RCAS (Hughes et al., (1987) *J. Virol.* 61:3004–12).

(ii) Relationship of Sonic to Endogenous Bmp-2 and Hoxd Gene Expression

The best candidates for genes regulated by Sonic in vivo are the distal members of the Hoxd gene cluster, Hoxd-9 through -13, and Bmp-2. Therefore, the relationships of the expression domains of these genes in a staged series of normal chick embryos were analyzed. Hoxd-9 and Hoxd-10 are expressed throughout the presumptive wing field at stage 16 (Hamburger and Hamilton, (1951) *J. Exp. Morph.* 88:49–92), prior to the first detectable expression of Sonic at early stage 18. Hoxd-11 expression is first detectable at early stage 18, the same time as Sonic, in a domain coextensive with Sonic. Expression of Hoxd-12 and Hoxd-13 commence shortly thereafter. These results suggest that Sonic might normally induce, directly or indirectly, the expression of only the latter three members of the cluster, even though all five are nested within the early limb bud.

As limb outgrowth proceeds Sonic expression remains at the posterior margin of the bud. In contrast the Hoxd gene expression domains, which are initially nested posteriorly around the Sonic domain, are very dynamic and lose their concentric character. By stage 23 the Hoxd-11 domain extends anteriorly and distally far beyond that of Sonic, while Hoxd-13 expression becomes biased distally and displaced from Sonic.

While it is not clear whether Bmp-2 is expressed before Sonic (see Francis et. al., (1994) *Development* 120:209–218) Bmp-2 is expressed in a mesodermal domain which apparently overlaps and surrounds that of Sonic at the earliest stages of Sonic expression. As the limb bud develops, the mesodermal expression of Bmp-2 remains near the posterior limb margin, centered around that of Sonic, but in a larger domain than Sonic. This correspondence between Sonic and Bmp-2 expression lasts until around stage 25, much longer than the correspondence between Sonic and Hoxd gene expression. After stage 25 Bmp-2 expression shifts distally and is no longer centered on Sonic.

(iii) Relationship of Sonic to Induced Bmp-2 and Hoxd Gene Expression

The fact that the expression domains of the Hoxd genes diverge over time from that of Sonic hedgehog implies that Sonic does not directly regulate their later patterns of expression. This does not preclude the possibility that the later expression domains are genetically downstream of Sonic. If this were the case, exogenously expressed Sonic would be expected to initiate a program of Hoxd gene expression which recapitulates that seen endogenously. Therefore, the spatial distribution of Hoxd gene expression at various times following Sonic misexpression was compared. The anterior marginal mesoderm of early bud (Stage 18–20) wings was injected at a single point under the AER with a replication competent virus that expresses a chicken Sonic cDNA. Ectopic Sonic expressed by this protocol leads to both anterior mesodermal outgrowth and anterior extension of the AFR.

The Sonic and Hoxd gene expression domains in the infected limbs were analyzed in sectioned and intact embryos. Viral Sonic message is first detected approximately 18 hours after infection at the anterior margin, at the same time as, and approximately coextensively with, induced Hoxd-11. This suggests that Sonic can rapidly induce Hoxd-11 expression and that the lag after injection represents the time required to achieve Sonic expression. By 35 hours post infection distal outgrowth of infected cells combined with lateral viral spread within the proliferating cells leads to viral expression in a wedge which is broadest at the distal margin and tapers proximally. By this time, Hoxd-11 expression has expanded both antero-proximally and distally with respect to the wedge of Sonic-expressing cells, into a domain which appears to mirror the more distal aspects of the endogenous Hoxd-11 domain. Weak Hoxd-13 expression is also detected at 35 hours in a subset of the Sonic expressing domain at its distal margin. 51 hours after infection the relationship of Sonic and Hoxd-11 expression is similar to that seen at 35 hours, while the induced Hoxd-13 expression has reached wild type levels restricted to the distal portions of the ectopic growth. Thus the ectopic Hoxd expression domains better reflect the endogenous patterns of expression than they do the region expressing Sonic. This suggests that there are multiple factors regulating Hoxd expression but their actions lie downstream of Sonic.

Since the endogenous Bmp-2 expression domain correlates well with that of Sonic, and Bmp-2 is induced by ZPA grafts, it was looked to see if Bmp-2 is also induced by Sonic. Bmp-2 is normally expressed in two places in the early limb bud, in the posterior mesoderm and throughout the AER (Francis, et al., (1994) *Development* 120:209–218). In injected limb buds additional Bmp-2 expression is seen in both the anterior mesoderm and in the anteriorly extended AER. The domain of Bmp-2 expression is slightly more restricted than that of viral expression, suggesting a delay in Bmp-2 induction. Bmp-2 expression in both the mesoderm and ectoderm is thus a downstream target of Sonic activity in the mesoderm. In contrast to the expression domains of the Hoxd genes, the endogenous and ectopic Bmp-2 expression domains correlate well with that of Sonic. This suggests that Bmp-2 expression is regulated more directly by Sonic than is expression of the Hoxd genes.

(iv) The AER and Competence to Respond to Sonic

Ectopic activation of Hoxd gene expression is biased distally in virally infected regions, suggesting that ectodermal factors, possibly from the AER, are required for Hoxd gene induction by Sonic. To test this, Sonic virus was injected into the proximal, medial mesoderm of stage 2.1 limb buds, presumably beyond the influence of the AER Although the level of Sonic expression was comparable to that observed in distal injections, proximal misexpression of Sonic did not result in ectopic induction of the Hoxd genes or Bmp-2, nor did it result in any obvious morphological effect (data not shown). The lack of gene induction following proximal misexpression of Sonic suggests that exposure to Sonic alone is insufficient to induce expression of these genes.

This was tested more rigorously by injection of Sonic virus into the anterior marginal mesoderm of stage 20/21 limb buds after the anterior half of the AER had been surgically removed. Embryos were allowed to develop for a further 36 to 48 hours before harvesting. During this time the AER remaining on the posterior half of the limb bud promotes almost wild type outgrowth and patterning of the bud. Gene expression was monitored both in sectioned and intact embryos. In the presence of the AFR, Sonic induces both anterior mesodermal proliferation and expression of Hoxd-11, Hoxd-13 and Bmp-2. In the absence of the overlying AER, Sonic does not induce either mesodermal proliferation or expression of these genes above background. Signals from the AER are thus required to allow both the proliferative and patterning effects of Sonic on the mesoderm.

Since application of FGF protein can rescue other functions of the AER such as promoting PD outgrowth and patterning, it was sought to determine whether FGFs might also promote mesodermal competence to respond to Sonic. FGF-4-soaked beads were stapled to AER-denuded anterior mesoderm which was infected with Sonic virus. Gene expression and mesodermal outgrowth were monitored as described previously. In the presence of both Sonic virus and FGF-4 protein, Hoxd-11, Hoxd-13 and Bmp-2 expression are all induced. The express ion levels of the induced genes are similar to or greater than the endogenous expression levels, and are equivalent in magnitude to their induction in the presence of the AER. Thus Fgf-4 can induce the competence of the mesoderm to respond to Sonic.

Sonic alone is insufficient to induce either gene expression or mesodermal proliferation in the absence of the AER, while the combination of Sonic and FGF-4 induces both proliferation and gene expression. It was than asked whether FGF-4 alone has any effect on gene induction or mesodermal proliferation. Application of FGF-4 in the absence of Sonic virus does not induce Hoxd or Bmp-2 gene expression above control levels, however FGF-4 alone induces mesodermal outgrowth. These results suggest that mesodermal gene activation requires direct action of Sonic 110 on the mesoderm and that proliferative response to Sonic is indirect, due to the induction of FGFs.

(v) Sonic Induces Polarized Fgf-4 Expression in the AER

Fgf-4 is expressed in a graded fashion in the AER of the mouse limb bud, with maximal expression at the posterior region of the AER tapering to undetectable levels in the anterior ridge (Niswander and Martin, (1992) *Development* 114:755–68). Therefore, it was appropriate to investigate whether Fgf-4 is asymmetrically expressed in the chick AER, and whether its expression is induced by Sonic. A fragment of the chicken Fgf-4 gene was cloned from a stage 22 chicken limb library by PCR using degenerate primers designed from mouse Fgf-4 and *Xenopus* e-Fgf sequence; based on information provided by L. Niswander and G. Martin. Assignment of gene identity was based on primary sequence as well as comparison of expression patterns with that of murine Fgf-4 (Niswander and Martin, (1992) *Development* 114:755–68). Whole mount in situ hybridization analysis showed strong limb expression of chick Fgf-4 in the AER. Fgf-4, like Bmp-2, is expressed all the way to the posterior border of the AER, but its anterior domain ends before the morphological end of the AER creating a posterior bias that has also been observed by Niswander et al., (1994) *Nature* (in press). Expression is first detected in the distal AER at about stage 18. As outgrowth proceeds the posterior bias develops. Expression peaks around stage 24/25 and then fades by stage 28/29.

The expression domain of Fgf-4 becomes posteriorly biased as Sonic is expressed in the posterior mesoderm. This observation is consistent with Sonic influencing the expression of Fgf-4 in the posterior AER. To test the effect of Sonic on Fgf-4 expression in the AER, stage 18–20 embryos were infected with Sonic virus in a single point at their anterior margin beyond the anterior limit of the AER. The embryos were harvested one to two days later, when an extension of the anterior AER became apparent. The expression of Fgf-4 was analyzed by in situ hybridization. Fgf-4 expression is induced in the anteriormost segment of the AER, in a region which is discontinuous with the endogenous expression domain, and overlies the domain of viral Sonic infection. This result contrasts with the Bmp-2 expression induced in the extended AER, which is always continuous with the endogenous expression domain. The asymmetry of the induced Fgf-4 expression indicates that Sonic polarizes the extended AER, much as a ZPA graft does (Maccabe and Parker, (1979) *J Embryol. Exp. Morph.* 53:67–73). Since FGFs by themselves are mitogenic for limb mesoderm, these results are most consistent with Sonic inducing distal proliferation indirectly, through the induction of mitogens in the overlying AER.

(vi) Reciprocal Regulation of Sonic by Fgf-4

Sonic thus appears to be upstream of Fgf-4 expression in the AER. However, since the AER is required to maintain polarizing activity in the posterior mesoderm (Vogel and Tickle, (1993) *Development* 19:199–206; Niswander et al., (1993) *Cell* 75:579–87), Sonic may also be downstream of the AER. If Sonic is regulated by the AER and the AER by Sonic, this would imply that they are reinforcing one another through a positive feedback loop.

To test whether the AER dependence of ZPA activity is controlled at the level of transcription of the Sonic gene, Sonic expression following removal of the AER from the posterior half of the limb bud was assayed. Sonic expression is reduced in an operated limb compared to the contralateral control limb within ten hours of AER removal, indicating that Sonic expression is indeed AER dependent. The dependence of Sonic expression on signals from the AER suggests that one of the functions of the AER is to constrain Sonic expression to the more distal regions of the posterior mesoderm.

In addition to their mitogenic and competence-inducing properties, FGFs can also substitute for the AER to maintain the ZPA. In order to test whether FGFs can support the expression of Sonic, beads soaked in FGF-4 protein were stapled to the posterior-distal tips of limb buds after posterior AER removal. Embryos were assayed for Sonic expression approximately 24 hours later, when Sonic expression is greatly reduced in operated limb buds which had not received an FGF-4 bead. Strong Sonic expression is detectable in the posterior mesoderm, slightly proximal to the bead implant, and reflecting the normal domain of Sonic expression seen in the contralateral limb. With the finding that FGF-4 can maintain Sonic expression, the elements required for a positive feedback loop between Sonic expression in the posterior mesoderm and Fgf-4 expression in the posterior AER are established (see also Niswander et al. (1994) *Nature* (in press)).

The induction of Bmp-2 expression by Sonic requires signals from the AER, and its domain correlates over time with that of Sonic. Therefore, it was interesting to learn if the continued expression of Bmp-2 also requires signals from the AER, and if so, whether they could be replaced by FGF-4. To test this, Bmp-2 expression following posterior AER removal, and following its substitution with an FGF-4 bead was assayed. Bmp-2 expression fades within hours of AER removal, and can be rescued by FGF-4. These data indicate that the maintenance of Bmp-2 expression in the posterior mesoderm, like that of Sonic, is dependent on signals from the AER, which are likely to be FGFs.

(vii) The Mesodermal Response to Sonic

It has been found that only mesoderm underlying the AER is responsive to Sonic, apparently because the AER is required to provide competence signals to the limb mesoderm. Fgf-4, which is expressed in the AER, can substitute for the AER in this regard, and thus might act in combination with Sonic to promote Hoxd and Bmp-2 gene expression in the mesoderm. FGFs may be permissive factors in a number of instructive pathways, as they are also required for activins to pattern *Xenopus* axial mesoderm (Cornell and Kimelman, (1994) *Development* 120:2187–2198; LaBonne and Whitman, (1994) *Development* 120:463–472).

The induction of Hoxd and Bmp-2 expression in response to Sonic and FGF-4 in the absence of an AER suggests that the mesoderm is a direct target tissue of Sonic protein. Since Sonic can induce Fgf-4 expression in the AER, it follows that Sonic also acts indirectly on the mesoderm through the induction of competence factors in the AER.

(viii) Downstream Targets and a Cascade of Signals Induced by Sonic

The five AbdB-like Hoxd genes, Hoxd-9 through -13, are initially expressed in a nested pattern centered on the posterior of the limb bud, a pattern which suggests they might be controlled by a common mechanism (Dolle, et al., (1989) *Cell* 75:431441; Izpisua-Belmonte, et al., (1991) *Nature* 350:585–9). The analysis of the endogenous and induced domains of Hoxd gene expression suggests that Sonic normally induces expression of Hoxd-11, -12 and -13. In contrast it was found that Hoxd-9 and -10 expression initiate before Sonic mRNA is detectable. This implies that at least two distinct mechanisms control the initiation of Hoxd gene expression in the wing bud, only one of which is dependent on Sonic.

Several observations suggest that the elaboration of the Hoxd expression domains is not controlled directly by Sonic, but rather by signals which are downstream of Sonic. The Hoxd expression domains rapidly diverge from Sonic, and evolve into several distinct subdomains. Moreover these subdomains appear to be separately regulated, as analysis of the murine Hoxd-11 gene promoter suggests that it contains independent posterior and distal elements (Gerard, et al., (1993) *Embo. J.* 12:3539–50). In addition, although initiation of Hoxd-11 through -13 gene expression is dependent on the AER, their expression is maintained following AER removal (Izpisua-Belmonte, et al., (1992) *Embo. J.* 11:1451–7). As Sonic expression fades rapidly under similar conditions, this implies that maintenance of Hoxd gene expression is independent of Sonic. Since ectopic Sonic can induce a recapitulation of the Hoxd expression domains in the limb, it can be concluded that although indirect effectors appear to regulate the proper patterning of the Hoxd expression domains, they are downstream of Sonic. Potential mediators of these indirect effects include Bmp-2 in the mesoderm and Fgf-4 from the AER.

In contrast to the Hoxd genes, Bmp-2 gene expression in the posterior limb mesoderm appears to be continually regulated by Sonic. It was found that both endogenous and ectopic Bmp-2 expression correspond to that of Sonic. Furthermore, continued Bmp-2 expression is dependent on the AER and can be rescued by FGF-4. It is likely that this is an indirect consequence of the fact that Sonic expression is also maintained by the AER and can be rescued by FGF-4. In fact, Bmp-2 expression might be a direct response of cells to secreted Sonic protein. The differences between Bmp-2 and Hoxd gene expression suggest that multiple pathways downstream of Sonic regulate gene expression in the mesoderm.

Bmp-2 itself is a candidate for a secondary signaling molecule in the cascade of patterning events induced by Sonic. Bmp-2 is a secreted molecule of the TGF-$\beta$ family and its expression can be induced by Sonic. This appears to be an evolutionarily conserved pathway, as HH, the *Drosophila* homolog of Sonic, activates the expression of dpp, the homolog of Bmp-2, in the eye and wing imaginal discs (Heberlein, et al., (1993) *Cell* 75:913–26; Ma, et al., (1993) *Cell* 75:927–38; Tabata and Kornberg, (1994) *Cell* 76:89–102). Expression of HH is normally confined to the posterior of the wing disc. Ectopic expression of HH in the anterior of the disc results in ectopic expression of dpp and ultimately in the duplication of wing structure with mirror image symmetry (Bassler and Struhl, (1994) *Nature* 368:208–214). This effect is strikingly parallel to the phenotypic results of ectopic expression of Sonic in the chick limb.

(ix) Regulation of Sonic Expression

Sonic expression is activated in the posterior of the limb bud very early during mesodermal outgrowth (Riddle et al., (1993) *Cell* 75:1401–16). The factors which initiate this localized expression are not yet identified but ectopic expression of Hoxb-8 at the anterior margin of the mouse limb bud results in the activation of a second domain of Sonic expression under the anterior AER (Charité et al., (1994) *Cell* 78:589–601). Since retinoic acid is known to be able to induce the expression of Hoxb-8 and other Hox genes in vitro (Mavilio et al., (1988) *Differentiation* 37:73–79) it is possible that endogenous retinoic acid acts to make cells competent to express Sonic by inducing expression of upstream Hox genes, either in the very early limb bud or in the flank prior to the limb bud formation.

Several lines of evidence suggest that once induced Sonic expression is dependent on signals from the posterior AER. Following its initiation in the posterior limb mesoderm, the Sonic expression domain moves distally as the limb bud grows out, always remaining subjacent to the AER. Similarly, Sonic expression can also be induced on the anterior margin of the limb bud by implantation of a retinoic acid bead, but the induced ectopic expression is limited to the mesoderm directly underlying the AER (Riddle, et al., (1993) *Cell* 75:1401–16). In addition, ZPA activity fades rapidly following removal of the AER (Niswander, et al., (1993) *Cell* 75:579–87; Vogel and Tickle, (1993) *Development* 119:199–206), and ZPA grafts only function when placed in close proximity to the AER (Tabin, (1991) *Cell* 66:199–217; Tickle, (1991) *Development Supp.* 1:113–21). The observation that continued Sonic expression depends on signals from the posterior AER reveals the mechanism underlying these observations.

The reliance of Sonic expression on AER-derived signals suggests an explanation for the distal shift in Sonic expression during limb development (Riddle et al., (1993) *Cell* 75:1401–16). Signals from the AER also promote distal outgrowth of the mesodermal cells of the progress zone, which in turn results in the distal displacement of the AER. Hence, as maintenance of Sonic expression requires signals from the AER, its expression domain will be similarly displaced.

It was found that replacement of the AER with FGF-4 soaked beads results in the maintenance of Sonic expression. This result is consistent with the previous findings that ZPA activity can be maintained in vivo and in vitro by members of the FGF family (Anderson, et al., (1993) *Development* 117:1421–33; Niswander et al., (1993) *Cell* 75:1401–16; Vogel and Tickle, (1993) *Development* 119:199–206). Since Fgf-4 is normally expressed in the posterior AER, these results suggest that Fgf-4 is the signal from the ectoderm involved in maintaining Sonic expression.

(x) Sonic and Regulation and Maintenance of the AER

Sonic can induce anterior extensions of the AER which have an inverted polarity relative to the endogenous AER. This polarity is demonstrated by examining the expression of two markers in the AER. In normal limbs Bmp-2 is expressed throughout the AER, while Fgf-4 is expressed in the posterior two thirds of the AER. In the extended AER resulting from ectopic Sonic expression, Bmp-2 is again found throughout the AER, while Fgf-4 expression is biphasic, found at either end of the AER, overlying the anterior and posterior mesodermal domains expressing Sonic. These results are consistent with previous observations that antero-posterior polarity of the AER appears to be regulated by the underlying mesoderm, and that ZPA grafts lead to the induction of ectopic, polarized AER tissue (Maccabe and Parker, (1979) *J Embryol. Exp. Morph.* 53:67–73). Our results also suggest that the normal AP polarity of the AER is a reflection of endogenous Sonic expression. The induced AER is sufficient to promote complete PD outgrowth of the induced structures (Riddle et al., (1993) *Cell* 75:1401–16). Hence whatever factors are necessary to maintain the AER are also downstream of Sonic.

(xi) A Positive Feedback Loop Between Sonic and Fgf-4

The induction of Fgf-4 expression by Sonic in the ectopic AER, and the maintenance of Sonic expression by FGF-4 suggest that Sonic and Fgf-4 expression are normally sustained by a positive feedback loop. Such a feedback loop would allow the coordination of mesodermal outgrowth and patterning. This coordination is possible because Sonic patterns mesodermal tissue and regulates Fgf-4 expression, while FGF-4 protein induces mesodermal proliferation and maintains Sonic expression. Moreover mesodermal tissue can only be patterned by Sonic in the context of a competence activity provided by F8f-4. Thus patterning is always coincident with proliferation.

It remains possible that exogenously applied Fgf-4 might be mimicking the activity of a different member of the FGF family. For example, Fgf-2 is expressed in the limb mesoderm and the AER (Savage et al., (1993) *Development Dynamics* 198:159–70) and has similar effects on limb tissue as Fgf-4 (Niswander and Martin, (1993) *Nature* 361:68–71; Niswander, et al., (1993) *Cell* 75:579–87; Riley, et al., (1993) *Development* 118:95–104; Fallon, et al., (1994) *Science* 264:104–7).

(xii) Coordinated Regulation of Limb Outgrowth and Patterning

Patterning and outgrowth of the developing limb are known to be regulated by two major signaling centers, the ZPA and AER. The identification of Sonic and FGFs as molecular mediators of the activities of the ZPA and AER has allowed for dissociation of the activities of these signaling centers from their regulation, and investigation of the signaling pathways through which they function.

The results presented above suggest that the ability of cells to respond to Sonic protein is dependent on FGFs produced by the AER. It was also found that Sonic induces a cascade of secondary signals involved in regulating mesodermal gene expression patterns. In addition evidence was found for a positive feedback loop initiated by Sonic, which maintains expression of Sonic in the posterior mesoderm and Fgf-4 in the AER. The feedback loop described suggests a mechanism whereby outgrowth and patterning along the AP and PD axes of the limb can be coordinately regulated.

Figure 13:
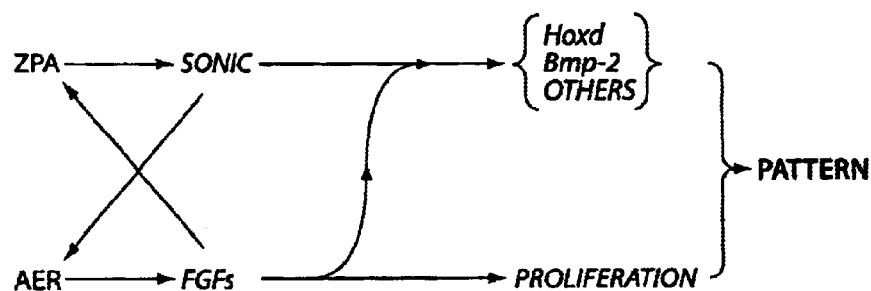
FIG. 13: Schematic diagram of a model for the coordinated growth and patterning of the limb. Sonic is proposed to signal directly to the mesoderm to induce expression of the Hoxd and Bmp-2 genes. The induction of these mesodermal genes requires competence signals from the overlying AER. One such signal is apparently Fgf-4. Expression of Fgf-4 in the AER can be induced by Sonic providing an indirect signaling pathway from Sonic to the mesoderm. FGFs also maintain expression of Sonic in the ZPA, thereby completing a positive feedback loop which controls the relative positions of the signaling centers. While Fgf-4 provides competence signals to the mesoderm, it also promotes mesodermal proliferation. Thus patterning of the mesoderm is dependent on the same signals which promote its proliferation. This mechanism inextricably integrates limb patterning with outgrowth.

The results described above further suggest that Sonic acts as a short range signal which triggers a cascade of secondary signals whose interplay determines the resultant pattern of structures. The data suggest a number of inductive pathways that can be combined to generate a model (FIG. 13) which describes how Sonic, in coordination with the AER, acts to pattern mesodermal tissues along the anterior-posterior limb axis, while simultaneously regulating proximal-distal outgrowth.

Following its induction, Sonic signals to both the limb ectoderm and mesoderm. Sonic imposes a distinct polarity on the forming AER, including the posteriorly biased expression of Fgf-4, and the AER becomes dependent on continued Sonic expression. The mesoderm, as long as it is receiving permissive signals from the overlying ectoderm, responds to the Sonic signal by expressing secondary signaling molecules such as Bmp-2 and by activating Hoxd genes. Bmp-2 expression is directly dependent on continued Sonic expression, while the continued expression of the Hoxd genes, rapidly becomes Sonic independent. In a reciprocal fashion, maintenance of Sonic hedgehog expression in the posterior mesoderm becomes dependent on signals from the AER. Since the factors expressed by the AER are not only required for the maintenance of Sonic expression and activity, but are also mitogenic, growth and patterning become inextricably linked. Coordination of limb development through interdependent signaling centers forces the AP and PD structures to be induced and patterned in tandem. The pathways elucidated herein thus provide a molecular framework for the controls governing limb patterning.

Example 8

Sonic, BMP-4, and Hox Gene Expression Suggest a Conserved Pathway in Patterning the Vertebrate and *Drosophila* Gut (i) Experimental Procedure In Situ Hybridization and Photography BMP probes were isolated using primers designed to amplify members of the TGF- and BMP families (Basler, K. et al., (1993) *Cell* 73:687–702, eight independent 120 bp BMP fragments were amplified from a stage 22 chicken posterior limb bud plasmid cDNA library. These fragments were pooled and used to screen an unamplified stage 22 limb bud lambda zap cDNA library constructed as in Riddle et al., (1993) *Cell* 75:1401–16. Among the BMP related clones isolated were an approximately 1.9 kb cDNA clone corresponding to chicken BMP-2 and an approximately 1.5 kb cDNA clone corresponding to chicken BMP-4. Both clones contain the entire coding regions. The Sonic clone was obtained as described in Riddle et al, (1993) *Cell* 75:1401–16. Digoxigenin-UTP labeled RNA probes were transcribed as per Riddle et al., (1993) *Cell* 75:1401–16. Briefly, harvested chick embryos were fixed overnight in 4% paraformaldehyde, washed in PBS then processed for whole mount in situ hybridization methods as per Riddle et al., (1993) *Cell* 75:1401–16. Embryos were photographed from either ventral or dorsal surfaces under transmitted light using a Nikon zoom stereo microscope with Kodak Ektar 100 ASA film. Whole mount in situ hybridization embryos and viscera were processed for sectioning as described in Riddle et al., (1993)*Cell* 75:1401–16. 15–25 μm transverse sections were air dried and photographed with brightfield or numarski optics using a Zeiss Axiophot microscope and Kodak Ektar 25 ASA film.

Chick Embryos and Recombinant Retroviruses

A retroviral vector engineered to express a full length cDNA of chicken Sonic, as in Riddle et al. (1993) *Cell* 75:1401–16, was injected unilaterally into stage 8–13 chicken embryos targeting the definitive endoderm at the midembryo level. At this stage the CIP has not formed and neither Sonic nor BMP-4 are expressed in the region injected. Injections were performed on the ventral surface on embryos cultured with their ventral surface facing up (New, D. A. T. (1955) *Embryol. Exp. Morph.* 3:320–31. Embryos were harvested 18–28 hours after injection and prepared for whole mount in situ hybridization (see above description of in situ experiment), hybridized with Sonic or BMP-4 digoxigenin labeled probes.

In Situ Hybridization with Hox Genes

Cloned cDNA of the chicken homologues of Hoxa-9,-10,-11,-13; b-9, c-9,-10,-11; d-9,-10,-11,-12, and -13 were used to transcribe digoxigenen-UTP labeled riboprobes for whole mount in situ hybridization. Domestic chick embryos were harvested into PBS and eviscerated. The visceral organ block was fixed in 4% paraformaldehyde overnight and processed for whole mount in situ hybridization. Methods and photographic technique as described above.

(ii) Expression of Sonic and BMP-4 in Stage 13 Chick Embryos Determined by Whole Mount In Situ Hybridization Chick gut morphogenesis begins at stage 8 (Hamberger and Hamilton, (1987) *Nutr.* 6:14–23 with a ventral in-folding of the anterior definitive endoderm to form the anterior intestinal portal (AIP) (Romanoff, A. L., (1960) *The Avian Embryo*, The Macmillan Co., NY. This lengthens posteriorly forming the foregut. A second wave of endodermal invagination is initiated posteriorly at stage 13, creating the caudal intestinal portal (CIP). The CIP extends anteriorly forming the hindgut. Sonic expression, previously noted in the endoderm of the vertebrate gut (Riddle et al., (1993) *Cell* 75:1401–16; Echelard et al., (1993) *Cell* 75:1417–1430), is expressed early in a restricted pattern in the endodermal lips of the AIP and CIP. Sonic expression is detected in the endoderm of the AIP and CIP in pre gut closure stages. At later stages, stage 28 embryos, Sonic is expressed in the gut in all levels (fore-, mid-, and hind-gut) restricted to the endoderm. Sonic is known to be an important inductive signal in other regions of the embryo including the limb bud (Riddle et al., (1993) *Cell* 75:1401–16) and neural tube (Echelard et al., (1993) *Cell* 75:1417–1430; Kraus et al., (1994) *Cell* 75:1437–1444; Roelink et al., (1994) *Cell* 76:761–775). Since primitive gut endoderm is known to cause gut-specific mesodermal differentiation when combined with non-gut mesenchyme (Haffen et al., (1987) *Nutr.* 6:14–23), we speculated that Sonic might function as an inductive signal to the visceral mesoderm. A potential target gene for the action of Sonic was suggested by analogy to the *Drosophila* imaginal discs where HH, the homologue of vertebrate Sonic, activates the expression of the TGF-β related gene dpp in adjacent cells (Tabata abd Komberg, (1994) *Cell* 76:89–102; Heberlein et al., (1993) *Cell* 75:913–926; Ma et al., (1993) *Cell* 75:913–926; Basler et al., (1993) *Cell* 73:687–702). There are two vertebrate homologues of dpp, BMP-2 and BMP-4. The earliest detectable expression of BMP-4 occurs simultaneously with the first observable expression of Sonic in the developing gut. BMP-4 is expressed in a domain abutting Sonic at the AIP and the CIP, but is restricted to the adjacent ventral mesoderm. BMP-4 gut expression persists into later stage embryos, stage 33 embryos, in the visceral mesoderm only. The tissue restricted expression of both genes is maintained in all stages studied. BMP-2 is not expressed in the gut at the AIP or CIP, but is expressed in clusters of cells in the gut mesoderm in later stages, a pattern distinct from that of BMP-4.

(iii) Ectopic Expression of Sonic Induces Ectopic Expression of BMP-4 in Mesodermal Tissues of the Developing Chick To test whether Sonic is capable of inducing BMP-4 in the mesoderm we an ectopic expression system previously used to study the role of Sonic in limb development was utilized (Riddle et al., (1993) *Cell* 75:1401–16). A replication competent retrovirus engineered to express Sonic was injected unilaterally into the presumptive endoderm and visceral mesoderm at mid-embryo positions in stage 8–13 chick embryos in vitro (New, D. A. T. (1955) *Embryol. Exp. Morph.* 3:320–321). When embryos were examined by in situ hybridization 18–26 hours later, the normal wild type expression of Sonic is detected at the AIP, CIP, and in the midline (neural tube and notochord). Ectopic Sonic expression is present unilaterally on the left ventral surface. Also, wild type Sonic expression is seen in the floor plate of the neural tube and notochord. Ectopic expression is seen unilaterally in the visceral endoderm, its underlying splanchnic mesoderm, and somatic mesoderm. BMP-4 expression can be seen induced in the mesoderm at the site of injection, in addition to its normal expression in the mesoderm of the CIP. Wild type BMP-4 expression is seen in the most dorsal aspects of the neural tube and symmetrical lateral regions adjacent to the neural tube. Induced BMP-4 expression is present unilaterally in the splanchnic mesoderm at the site of Sonic viral injection, and not in the visceral endoderm.

Since BMP-4 is, itself, a secreted protein, it could function as a secondary signal in an inductive cascade, similar to the signal cascades from HH to dpp in *Drosophila* imaginal discs (Tabata abd Komberg, (1994) *Cell* 76:89–102; Heberlein et al., (1993) *Cell* 75:913–926; Ma et al., (1993) *Cell* 75:913–926; Basler et al., (1993) *Cell* 73:687–702) and from Sonic to BMP-2 in the limb bud. In the gut, BMP-4 could act as a secondary signal either as part of a feedback loop to the endoderm or within the visceral mesoderm. This latter possibility is consistent with the finding that in mice homozygous for a deletion in the BMP-4 gene, the ventral mesoderm fails to close.

(iv) Expression of Hox Genes in the Developing Chick Gut

There is a striking parallel between the apparent role of Sonic as an endoderm-to-mesoderm signal in early vertebrate gut morphogenesis and that of its *Drosophila* homologue, HH. HH (like Sonic) is expressed in the *Drosophila* gut endoderm from the earliest stages of morphogenesis (Taylor et al., (1993) *Mech. Dev.* 42:89–96). Its putative receptor, patched, is found in the visceral mesoderm implicating HH (like Sonic) in endodermal-mesodermal inductive interactions. This led to consideration whether other genes known to be involved in regulating *Drosophila* gut development might also play a role in regulating chick gut morphogenesis. Regionally specific pattern in *Drosophila* gut endoderm is regulated by a pathway involving restricted expression of homeotic genes in the mesoderm (McGinnis and Krumlauf, (1992) *Cell* 68:283–302). Although the basis for patterning the vertebrate gut is poorly understood, in several other regions of the embryo Hox genes have been implicated as key regulators of patterns. Vertebrate Hox genes are expressed in overlapping anteroposterior domains which correlate with structural boundaries in the developing hindbrain, vertebrae, and limbs (McGinnis and Krumlauf, (1992) *Cell* 68:283–302). Whole mount in situ hybridization was used to test whether these genes are also expressed in the developing vertebrate hindgut and whether their domains of expression correlate with morphologic borders of the chick gut.

Lumenal gut differentiation creates three morphologically and physiologically distinct regions: fore-, mid-, and hind-gut. The fore-gut and hind-gut are the derivatives of the primitive gut tubes initiated at the AIP and CIP respectively. Ultimately these tubes meet and fuse at the yolk stalk around stage 24–28. The midgut is formed from both foregut and hindgut primordia, just anterior and posterior to the yolk stalk.

The most posterior derivative of the hindgut is the cloaca, the common gut-urogenital opening. The rest of the hindgut develops into the large intestine. The midgut/hindgut border is demarcated by a paired tubal structure, the ceca (analogous to the mammalian appendix), which forms as budding expansions at the midgut/hindgut border at stage 19–20. Anterior to the ceca, the midgut forms the small intestine.

The expression pattern of the 5' members of the Hox gene clusters in the chick hindgut by whole mount in situ hybridization was studied. Hox gene expression patterns in the gut are dynamic. They are initially expressed (by stage 10) in broad mesodermal domains extending anteriorly and laterally. Later they become restricted. By stage 25, the Abd-B like genes of the Hoxa and Hoxd cluster are regionally restricted in their expression in hindgut mesoderm. The most anteriorly expressed gene, Hoxa-9, has an anterior border of expression within the mesoderm of the distal midgut (to a point approximating the distal third of the midgut length). Each successive gene within the A and D Hox clusters has a more posterior domain of expression. Hoxa-10, Hoxd-9 and Hoxd-10 are restricted in their expression to the ceca Hoxa-11 and Hoxd-11 have an anterior limit of expression in the mid-ceca at the approximate midgut/hindgut boundary (Romanoff, A. L. (1960) The Avian Embryo, The Macmillan Co. NY). Hoxd-12 has an anterior limit at the posterior border of the ceca and extends posteriorly throughout the hindgut to the cloaca. Hoxa-13 and Hoxd-13 are expressed in the most posteriorly restricted domain, in the ventral mesoderm surrounding the cloaca. Hoxa-13 and Hoxd-13 are the only Abd-B like genes which are also expressed within the gut endoderm, from the ceca to the cloaca.

The only member of the B or C Hox clusters which we found to be expressed in the hindgut is Hoxc-9. The expression of Hoxc-9 overlaps with its paralogues Hoxa-9 and Hoxd-9 in the midgut mesoderm, but has a sharp posterior boundary, complementary to Hoxa-11 and Hoxd-11 in the mid-ceca.

The restricted expression of the Abd-B like Hox genes appear to demarcate the successive regions of the gut which will form the cloaca, the large intestine, the ceca, the mid-ceca at the midgut/hindgut border, and the lower portion of the midgut (perhaps identifying that portion of the midgut derived from the posterior gut tube3). Moreover, these molecular events presage regional distinctions. Expression of all Hox genes could be detected by stage 14, well before the hindgut lumen is closed (by stage 28) and is maintained in subsequent stages studied. Cytodifferentiation of the hindgut mesoderm and epithelium begins later, at stages 29–31 (Romanoff, A. L. (1960) The Avian Embryo, The Macmillan Co. NY).

These results suggest that specific Hox genes might be responsible for regulating morphogenesis of the gut. Consistent with this, there is an apparent homeotic alteration in the gut of a transgenic mouse in which the anterior limit of expression of Hoxc-8 is shifted rostrally: a portion of foregut epithelium mis-differentiates as midgut (Pollock and Bieberich, (1992) *Cell* 71:911–923).

(v) Conservation in the Expression of Regulatory Genes Involved in the Formation of Vertebrate and *Drosophila* Gut There is an intriguing parallel between the expression patterns of Sonic, BMP-4, and the Hox genes in the vertebrate gut and those of their homologues during *Drosophila* gut morphogenesis. This conservation is of particular interest because in *Drosophila* the role played by these genes has been clarified genetically. HH (like its vertebrate homologue, Sonic) is expressed at the earliest stages in the gut endoderm and may be a signal to visceral mesoderm (Taylor et al., (1993) *Mech. Dev.* 42:89–96). Nothing is known directly of the relationship between HH expression and activation of expression of other genes in the *Drosophila* gut. However, in *Drosophila* imaginal discs, HH is known to activate the expression of dpp in a signaling cascade (Kraus et al., (1994) *Cell* 75:1437–1444; Heberlein et al., (1993) *Cell* 75:913–926; Ma et al., (1993) *Cell* 75:913–926; Basler et al., (1993) *Cell* 73:687–702). Later in gut development, the production of dpp in the mesoderm contributes to the regulation of the expression of homeotic genes in both the mesoderm and the endoderm (Bienz, M. (1994) *TIG* 10:22–26). *Drosophila* homeotic genes are expressed in the gut visceral mesoderm and their expression is known to determine the morphologic borders of the midgut. This involves proper induction of gene expression in the adjacent endoderm, one of the mediators of the interaction is dpp (Bienz, M. (1994) *TIG* 10:22–26). If HH is required for the ultimate activation of the homeotic genes in the *Drosophila* midgut, this would parallel the situation in the vertebrate limb bud where Sonic functions as an upstream activator of the Hox genes (Riddle et al., (1993) *Cell* 75:1401–1416), perhaps in a signaling cascade involving BMP-2.

The extraordinary conservation in the expression of regulatory genes in the vertebrate and *Drosophila* gut strongly suggests a conservation of patterning mechanisms. Pathways established by genetic studies in *Drosophila* provide direct insights into the molecular basis for the regionalization and morphogenesis of the vertebrate gut.

Example 9

Bacterially Expressed Hedgehog Proteins Retain Inducing Activity

Various fragments of the mouse Shh gene were cloned into the pET11D vector as fusion proteins with a poly(His) leader sequence to facilitate purification. Briefly, fusion genes encoding the mature M-Shh protein (corresponding to Cys-25 through Ser437 of SEQ ID No. 13) or N-terminal containing fragments, and an N-terminal exogenous leader having the sequence M-G-S-S-H-H-H-H-H-H-L-V-P-R-G-S-H-M were cloned in pET1 ID and introduced into *E. coli*. The poly(His)-Shh fusion proteins were purified using nickel chelate chromatography according to the vendor's instructions (Qiagen catalog 30210), and the poly(His) leader cleaved from the purified proteins by treatment with thrombin.

Preparations of the purified Shh proteins were added to tissue explants (neural tube) obtained from chicken embryos and cultured in a defined media (e.g., no serum). M-Shh protein was added to final concentrations of between 0.5 pM to 5 nM, and differentiation of the embryonic explant tissue to motorneuron phenotype was detected by expression of Islet-1 antigen. The bacterially produced protein was demonstrated to be active in the explant cultures at concentrations as low as 5 to 50 pM. An Shh polypeptide containing all 19 kd of the amino terminal fragment and approximately 9 kd of the carboxyl terminal fragment (see Example 6) displayed both motor neuron inducing activity and weak floor plate inducing activity, indicating that these activities likely reside with the N-terminal fragment.

Example 10

Sonic Hedgehog Induces Bone Formation

The ectopic bone formation assay was essentially done as described in Sampath and Reddi, 1983, PNAS USA 80:6591–6595. The mouse Shh protein was frozen and lyophilized, and the powder was enclosed in no. 5 gelatin capsule. Alternatively, 0.9–2.0 mg of collagen sponge (Collastat) was used as matrix. The Shh protein (12.5 μg) was added directly to the washed sponge, the sponge lyophilized, and the sponge implanted. The capsules or collagen sponges were implanted subcutaneously in the abdominal thoracic area of 21- to 49-day female Long-Evans rats and routinely removed at 11 days. Samples were processed for histological analysis, with 1-lm glycolmethacrylate sections stained with Von Kossa and acid fuschin or toluidine blue. Von Kossa staining shows mineral (hydroxyapatite) formation. The collagen sponge by itself was used as a control in these experiments. The results indicate that the addition of mouse Shh protein induced bone formation in these rats.

Example 11

Patched is a Receptor for Sonic Hedgehog
(i) Experimental Procedures
In vitro Transcription of Chick Patched
Chick patched coding sequences were inserted into the vector pRD67 (kindly provided by J. Cunningham) which contains an SP6 phage promoter and both 5' and 3' untranslated sequences derived from the *Xenopus laevis* β-Globin gene. This vector also contains a flu epitope inserted at the 3' end. After restriction endonuclease digestion with XbaI to generate linear templates, RNA was transcribed in vitro using SP6 RNA polymerase in the presence of 1 mM cap structure analog ($m^7G(5')ppp(5')Gm$ (Ambion Kit for capped mRNAs) Following digestion with RQI DNase I (Ambion) to remove the DNA template, transcripts were purified by phenol:choloroform extraction and ethanol precipitation.

*Xenopus* Oocyte Injection

*Xenopus laevis* oocytes were surgically isolated and enzymatically defolliculated using published techniques (see, for example, Coleman et al., eds., Transcription and Translation: A Practical Approach. IRL Press, pp. 271–302; and Williams et al. (1988) *PNAS* 85:4939–4943). Defolliculated oocytes were incubated at 19° C. in media. Defolliculated oocytes were injected with water (control oocyte) or with 25 ng of in vitro transcribed, capped chick patched or TMM13 cRNAs (prepared as described above). Injected oocytes were incubated for 16 hours at 19° C. in media.

Following a recovery period, healthy injected oocytes and uninjected controls were cultured at 19° C. for 48 hours in Buffer A (50% L-15 medium (Sigma Chemicals), 1 mM L-glutamine, 15 mM HEPES pH 7.5, 100 μg/mL gentamcin).

Binding assays

Recombinant, bacterial human sonic Hedgehog (Shh) (prepared as described in Example 9) was radioiodinated using the commercially available IODO-BEADS Iodination Reagent (Pierce, Product # 28,665) according to the manufacturer's instructions. The reagent used in this system is N-chloro-benzene sulfonamide (sodium salt) immobilized on nonporous, polystyrene beads. (Markwell, M. A. K. (1982) *Anal. Biochem.* 125, 427–43) Reactions were carried out for 1 minute at room temperature before purifying the labeled protein by the manufacturer's protocol.

Binding experiments were performed in oocytes which had been microinjected with patched or TM13 cRNAs, or uninjected controls. Defolliculated oocytes were preincubated in 1% Bovine Serum Albumin (BSA) in a Buffer B (5 mM Tris (pH7.5), 5 mM HEPES, 100 mM NaCl, 1 mM $CaCl_2$, 1 mM $MgCl_2$ and 2 mM KCl) for 1 hour at 4° C. or room temperature (RT). Oocytes were incubated in the presence $^{125}$I-labeled Shh (3 nM) diluted in 5% BSA in Buffer B for 40 minutes allowing for equilibrium to be reached. Incubated oocytes were rinsed with 1% BSA in buffer to remove unbound label. The amount of labeled Shh (cpm) bound to each oocyte was determined using a standard scintillation counter.

Figure 14:
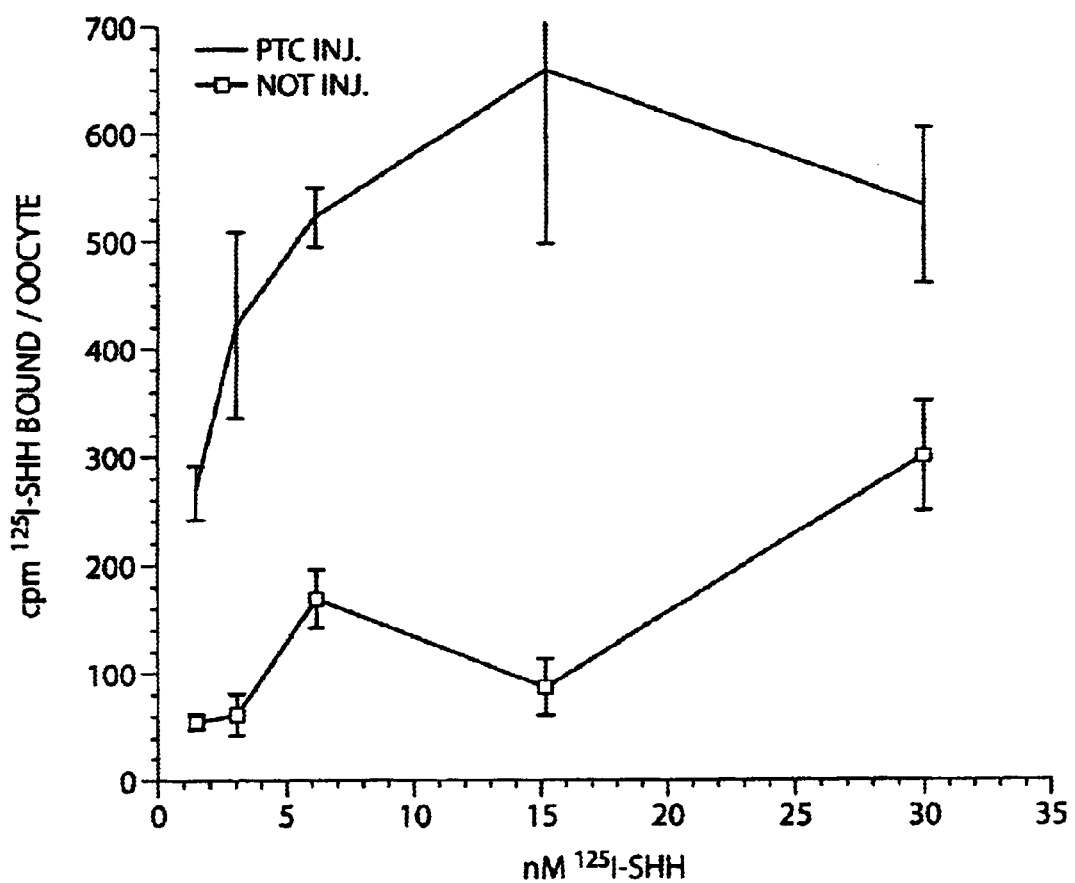
FIG. 14: Graph depicting saturable, concentration-dependent binding of human Shh to chick patched expressed in *Xenopus laevis* oocytes.

As demonstrated by FIG. 14, Shh shows saturable, concentration-dependent binding to the ectopically expressed patched on the oocytes. The amount of $^{125}$I-labeled Shh bound per oocyte (cpm/oocyte) is indicated with respect to the concentration of labeled Shh (nM). The solid line represents binding assays using oocytes which had been microinjected with in vitro transcribed chick patched cRNA. The open squares represent control uninjected oocytes. Saturable, concentration-dependent binding of Shh was detected only in patched-expressing oocytes. Each point represents the mean±standard deviation (SD) from five oocytes for the indicated concentrations of labeled Shh.

Figure 15:
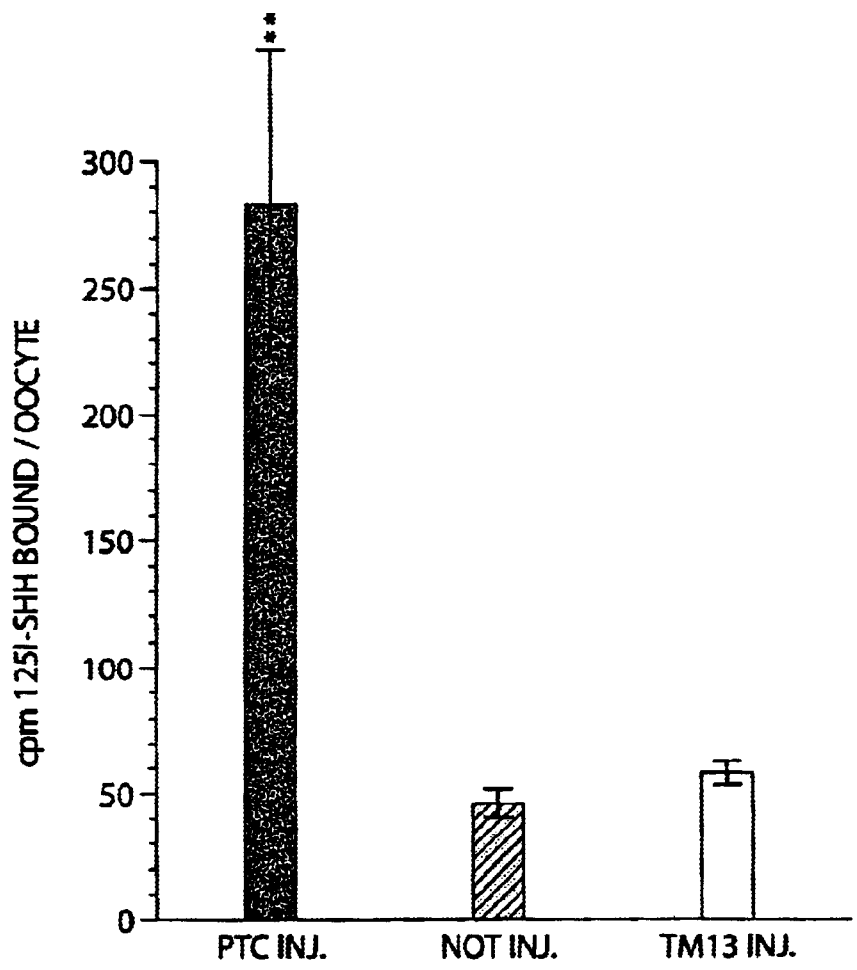
FIG. 15: Bar graph depicting the specificity of human Shh binding to the chick patched.

FIG. 15 shows that Shh binds to the recombinant patched in a specific manner. The amount of bound $^{125}$I-labeled Shh (cpm/oocyte) was determined in *Xenopus laevis* oocytes microinjected with in vitro transcribed patched cRNA (first bar in set), uninjected control (second bar) and in vitro transcribed TM13 cRNA (third bar). TM13 was used as a control since it encodes an amino acid transporter that contains 13 membrane spanning domains. A significant increase in the amount of bound label was detected only in patched-expressing oocytes. The concentration of labeled Shh used was 1.3 nM. Each point represents the mean±SD of bound label (cpm) from five oocytes per condition. Asterisks indicate a statistical significant increase in the amount of bound label.

Figure 16:
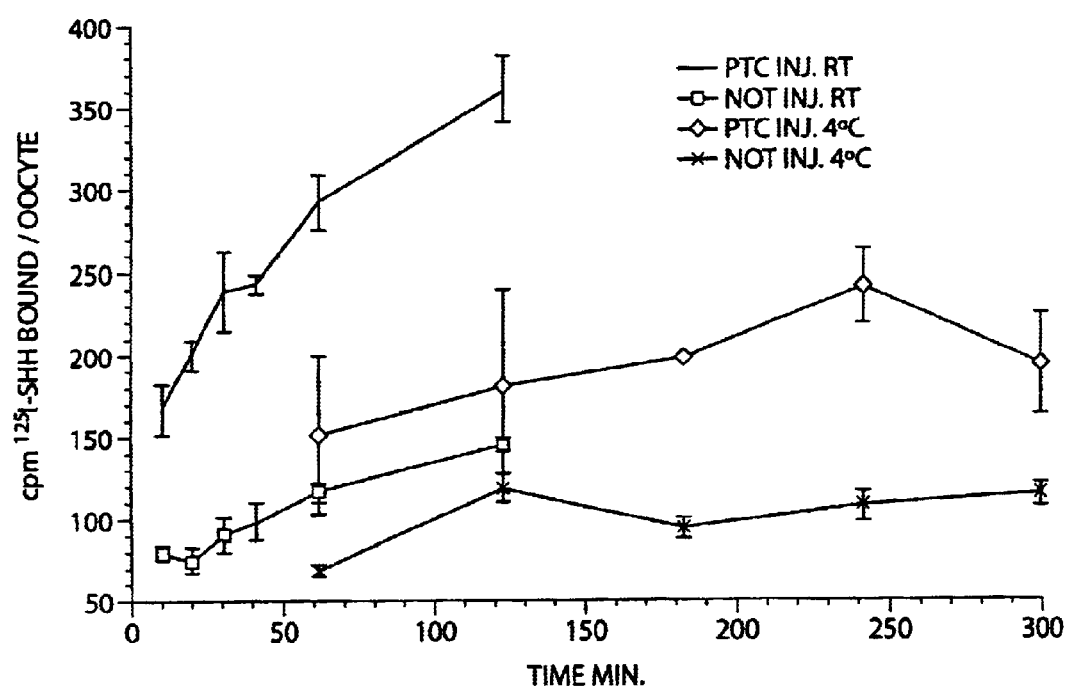
FIG. 16: Graph depicting the timecourse of human Shh binding to chick patched.

FIG. 16 shows the timecourse of human Shh binding to chick patched. The solid line and open triangles represent $^{125}$I-labeled Shh binding to *Xenopus laevis* oocytes which had been microinjected with in vitro transcribed patched cRNA and incubated for the indicated times. Open squares and stars represent labeled Shh bound to control uninjected oocytes. The conditions represented by the solid line and open squares were performed at room temperature (RT). The conditions represented by the open triangles and stars were performed at 4° C. A comparison of the binding curves at these two temperatures suggests that some internalization of the label occurs at RT compared to 4° C. Thus, the lower temperature of 4° C. provides an optimal condition for these assays. Each point represents the mean±SD of bound label (cpm) from five oocytes per condition.

Figure 17:
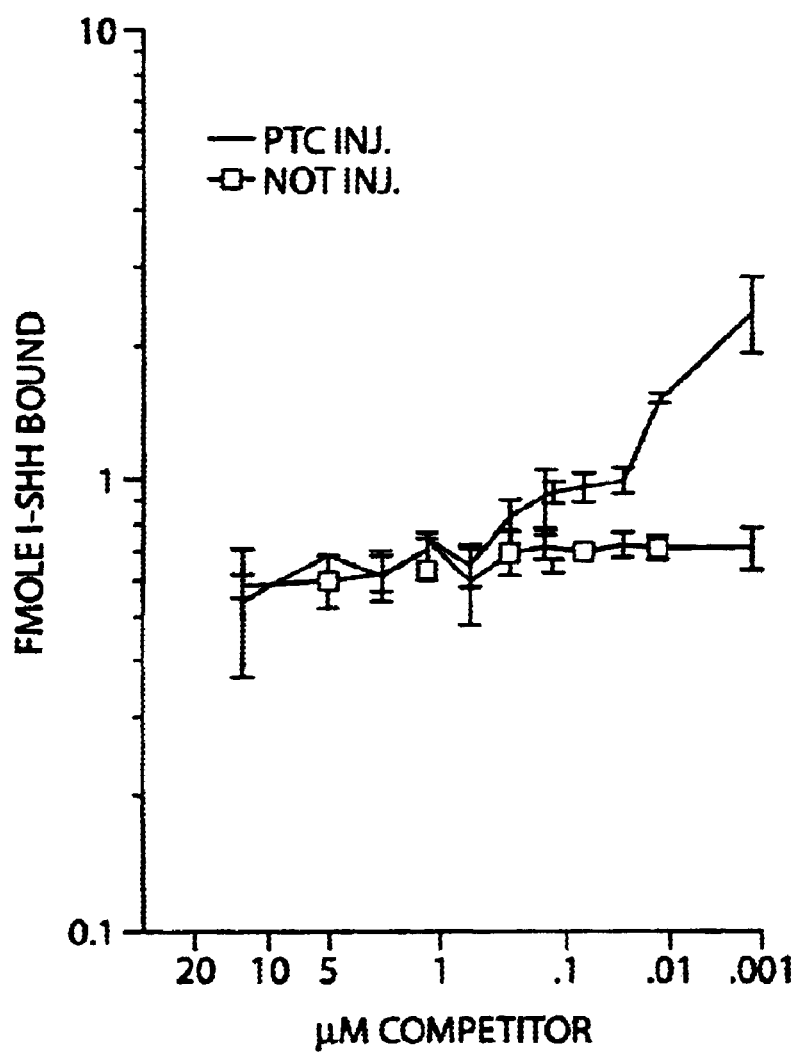
FIG. 17: Graph depicting the dissociation rate of human Shh binding to chick patched.

FIG. 17 shows the dissociation rate of human Shh binding to chick patched. *Xenopus laevis* oocytes incubated in the presence of $^{125}$I-labeled Sh were mixed with the indicated concentrations of unlabeled Shh for 40 minutes at room temperature. The solid line represents labeled Shh binding to *Xenopus laevis* oocytes microinjected with in vitro transcribed patched cRNA. Open squares represent the nonspecific binding of $^{125}$I-Shh to control uninjected oocytes. Displacement of bound labeled Shh was detected by competition with unlabeled protein. Each condition represents the mean bound label (cpm) from five oocytes±standard deviation.

Figure 18:
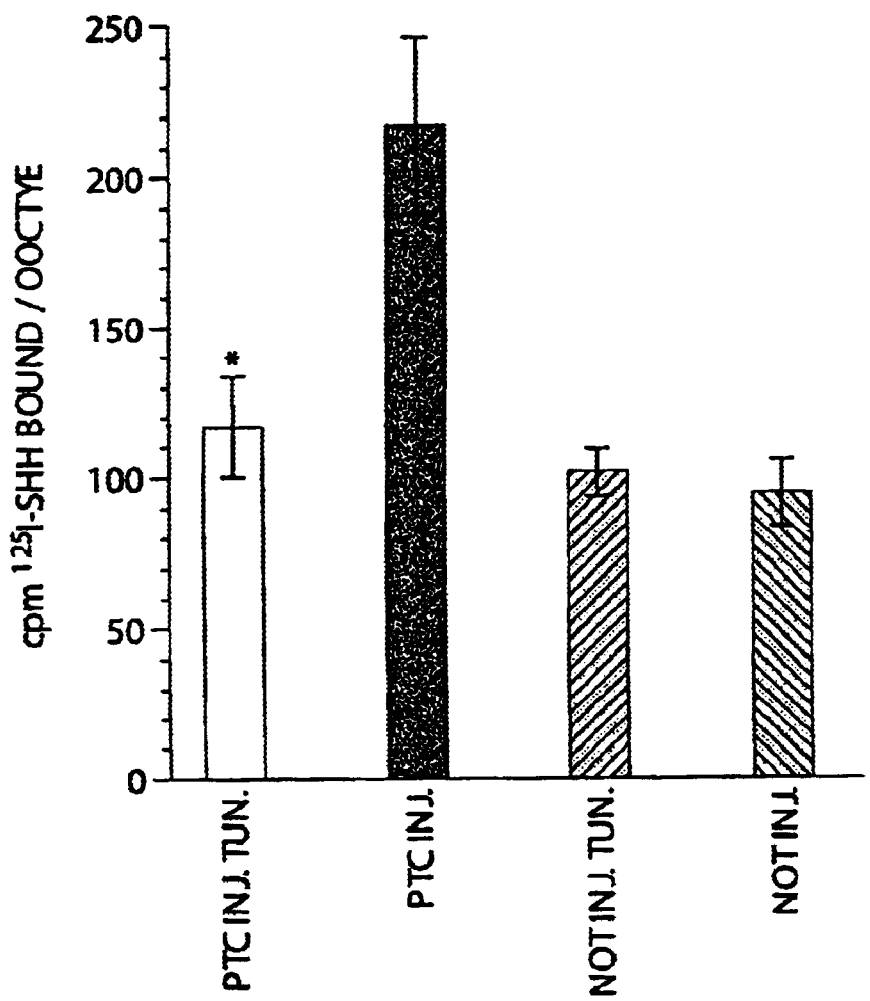
FIG. 18: Bar graph depicting the effect of glycosylation on the binding of Shh to patched.

A comparison of the fly and mouse patched sequences suggests the presence of two potential glycosylated, hydrophilic loops in the extracellular domain of this protein. (Goodrich et al. (1996), *Genes & Development* 10: 301–312) The address the effect of these putative glycosylation sites on Shh binding to patched, oocytes microinjected with chick patched cRNA were incubated with 2 µg/ml tunicamycin (New England Biolabs, Inc.). The expected decrease in the molecular weight of patched was detected in the tunicamycin-treated samples compared to the untreated controls as detected by Western Blot using the flu tag antibody. As shown in FIG. 18, binding of Shh is sensitive to the glycosylation state of patched. This Figure shows bound $^{125}$I-labeled Shh (cpm/oocyte) in *Xenopus laevis* oocytes microinjected with in vitro transcribed patched cRNA (first two bars in set). The last two bars represent uninjected control oocytes. The concentration of labeled Shh used was 3 nM. The conditions shown in the first and third bars represent oocytes treated with tunicamycin (2 µg/ml) for 48 hours. A significant decrease in labeled Shh binding after treatment with tunicamycin was detected only in the patched-expressing oocytes. Each condition represents the mean bound label (cpm) from five oocytes±standard deviation.

Figure 19:
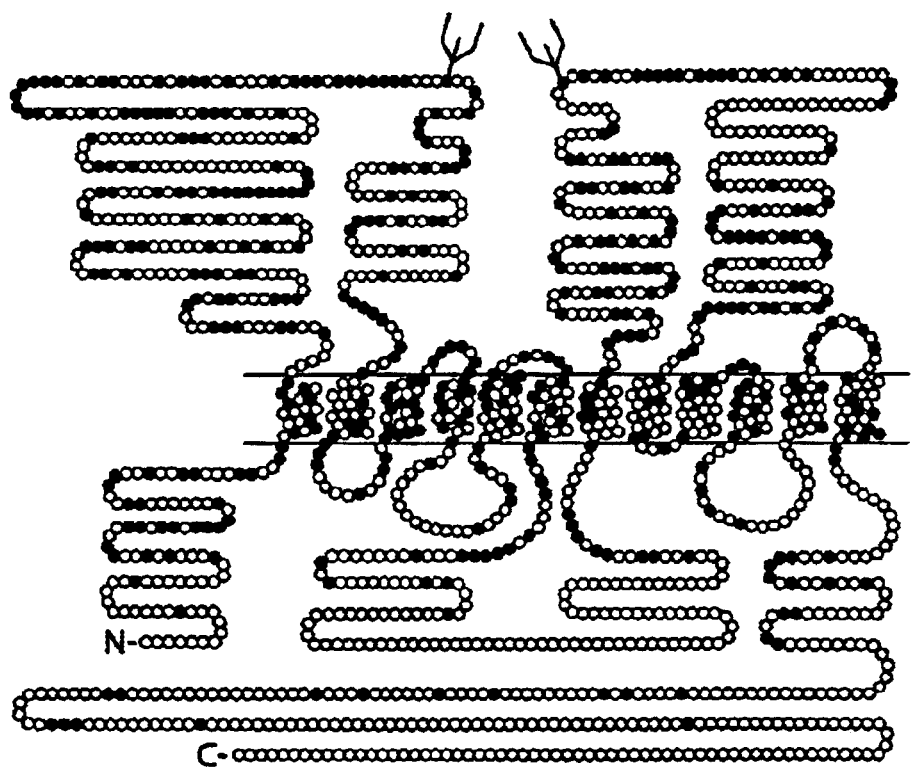
FIG. 19: Schematic diagram of a proposed topological model of the mouse patched protein. (Goodrich et al. (1996), Genes & Development 10(3): 301–10)

FIG. 19 illustrates a proposed topological model of the mouse patched protein. The mouse patched has been proposed to have 12 transmembrane domains and two glycosylated extracellular hydrophilic loops. Black and lightly shaded circles indicate identical and similar amino acids, respectively, shared between the mouse and fly patched proteins. (Goodrich et al. (1996), supra at 310)

Example 12

Regulation of Rate of Cartilage Differentiation by Indian Hedgehog and PTH-Related Protein During vertebrate embryogenesis the first elements of the skeleton to he formed are cartilage templates that are subsequently replaced by bone tissue in a process called endochondral ossification (1, 2). This process begins with the aggregation of undifferentiated mesenchyme. Cells in the core of these condensations differentiate into chondrocytes, whereas spindle-shaped cells at the periphery form a sheath around the cartilage, the perichondrium. These precursors of the skeletal elements elongate by proliferation of the chondrocytes and by matrix deposition. Shortly after the condensations form, chondrocytes in the central region of the cartilage elements cease proliferating, become hypertrophic, and alter their extracellular matrix. The changes in the extracellular matrix allow blood vessels to invade from the perichondrium. Bone marrow cells and osteoblasts appear in association with the vascularization and replace the cartilage with bone (ossification).

In this process, the chondrocytes serve both to drive the growth of the skeletal elements and to form a scaffold for the osteoblasts. Both the zone of hypertrophic cartilage and the ossified region subsequently expand toward the ends of the skeletal elements. Ultimately, the shaft of the bone is mostly mineralized, leaving growth plates—narrow bands of proliferating cartilage and transitional hypertrophic cartilage— at the ends of each hone. Premature ossification of the cartilage is prevented by continued proliferation of the round chondrocytes at the ends of the bone and by careful control of the rate of their differentiation into hypertrophic chondrocytes. Regulation of the rate of endochondral ossification is critical to bone morphogenesis, because it plays a major role in determining the shape and length of the skeletal elements. Whereas the cellular steps in this process are well described (1, 2), little is known about its regulation. Studies of mutant mice suggest roles for FGFs (3–5), IGFs (6), and PTHrP (7, 8), but many other local and systemic factors are likely to be involved. Virtually nothing, however, is known about how the expression and action of these factors are regulated or about their specific functions in the coordination of skeletal formation.

In the mouse embryo, Indian hedgehog is expressed in the developing cartilage elements (9), suggesting that it might play a role in regulating bone formation. Hedgehog proteins constitute a conserved family of secreted molecules that provide key signals in embryonic patterning in many organisms. During *Drosophila* development, the segment polarity gene hedgehog (hh) regulates embryonic segmentation and anterior-posterior patterning of the imaginal disks (10–12). In higher vertebrates, there are at least three hedgehog genes: Sonic hedgehog (Shh), Desert hedgehog (Dhh), and Indian hedgehog (Ihh) (13–15). Shh has multiple functions during embryonic development, including the establishment of left-right asymmetry in the early embryo (16), the induction of ventral cell fates in the neural tube (14, 15, 17), the specification of sclerotomal cell fate in the somites (18, 19), the mediation of epithelial-mesenchymal signaling in the gut (20), and the specification of the anterior-posterior limb axis (13). Dhh functions as a spermatocyte survival factor in the testes (21). In contrast, specific biological roles for Ihh have not yet been determined.

Whereas the various Hedgehog proteins have distinct biological functions, they appear to use the same signal transduction pathway. On the basis of genetic analysis, patched (ptc), which encodes a transmembrane protein (22, 23), and cubitus interruptus (ci), which encodes a putative transcription factor (24), are two key genes in the *Drosophila* Hedgehog transduction pathway (25–27). Both are required for cellular responses to Hedgehog signaling. Their vertebrate homologs, Patched (Ptc) (28, 29) and Gli (30, 31), are also expressed in cells capable of responding to ectopic Hedgehog and are highly up-regulated in all tissues actively responding to Shh or Dhh (21, 28, 29, 31, 32). Transforming growth factor-,8 (TGF beta) family members can act as secondary signals downstream of Hedgehog proteins. In *Drosophila*, decapentaplegic (dpp) mediates aspects of Hedgehog signaling in the imaginal disks (33–35), whereas the vertebrate homologs, Bmp-2 and Bmp-4, are induced in several tissues in response to Shh (9, 20, 36). However, in contrast to ptc/Ptc and ci/Gli, the TGF-g family members are not consistent targets of Hedgehog signaling in either *Drosophila* or vertebrates. Knowledge of these pathways, particularly of the apparently universal targets Ptc and Gli, is useful for evaluating the role of Ihh in developing bone.

Isolation and characterization of a chicken Ihh clone: Ihh and Shh have similar biological activities. To examine the role of Ihh in endochondral bone development, we isolated a cDNA clone containing the chicken Ihh coding sequence of 408 amino acids (37). Like the other Hedgehog proteins, the predicted amino acid sequence of Ihh contains a conserved COOH-terminal protease motif, which has been shown to be responsible for autocatalytic cleavage of other Hedgehog proteins (3840). Ihh also contains the conserved protease cleavage site, indicating that it is likely to be processed in a manner similar to that for Hedgehog and Shh. Whereas the COOH-terminal domain of Ihh is substantially divergent from that of Shh, the NH2-terminal domains of the two proteins are 93% identical. Because the NH2-terminal fragment encodes the functional Hedgehog signal in long- and short-range signaling (41–43), the high extent of NH2-terminal conservation between Shh and Ihh suggests that they might have similar biological properties. However, this cannot be assumed because in zebrafish not all Hedgehog proteins have the same activity (44).

Figure 1B:
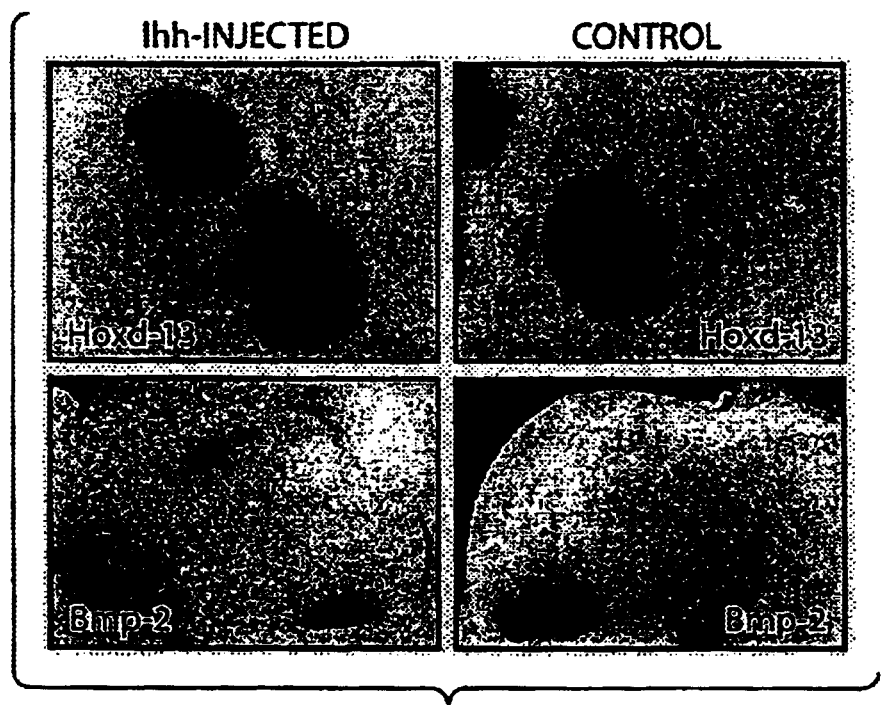
Figure 1C:

To test whether Ihh and Shh can function similarly, we compared their activities in the context of the early limb bud of the chick, a setting in which the role of Shh has been extensively characterized. Anterior misexpression of Shh at early limb stages induces mirror-image duplications of posterior limb structures (13). To test whether ectopic Ihh could induce similar morphological changes, we implanted Ihh-expressing cells in the anterior side of Hamburger Hamilton (HH) (45) stage 21 limb buds (46). After 7 days of incubation, the operated limbs showed duplications of the radius and digits II and III (FIG. 1A) similar to those induced by Shh in a parallel experiment (47). We also examined the ability of Ihh to replicate the effects of ectopic Shh on a molecular level after infection of early limb buds with an Ihh-expressing retrovirus (46). Using whole-mount in situ hybridization (48), we detected ectopic expression of limb-specific patterning genes located downstream of Shh (36), including Hoxd-11, Hoxd-13, and Bmp-2 (FIG. 1B) (47), as well as expression of the universal Hedgehog response genes, Ptc and Gli (FIG. 1C). These results demonstrate that Ihh and Shh proteins have similar biological properties and can stimulate expression of the same downstream genes.

Figure 2:
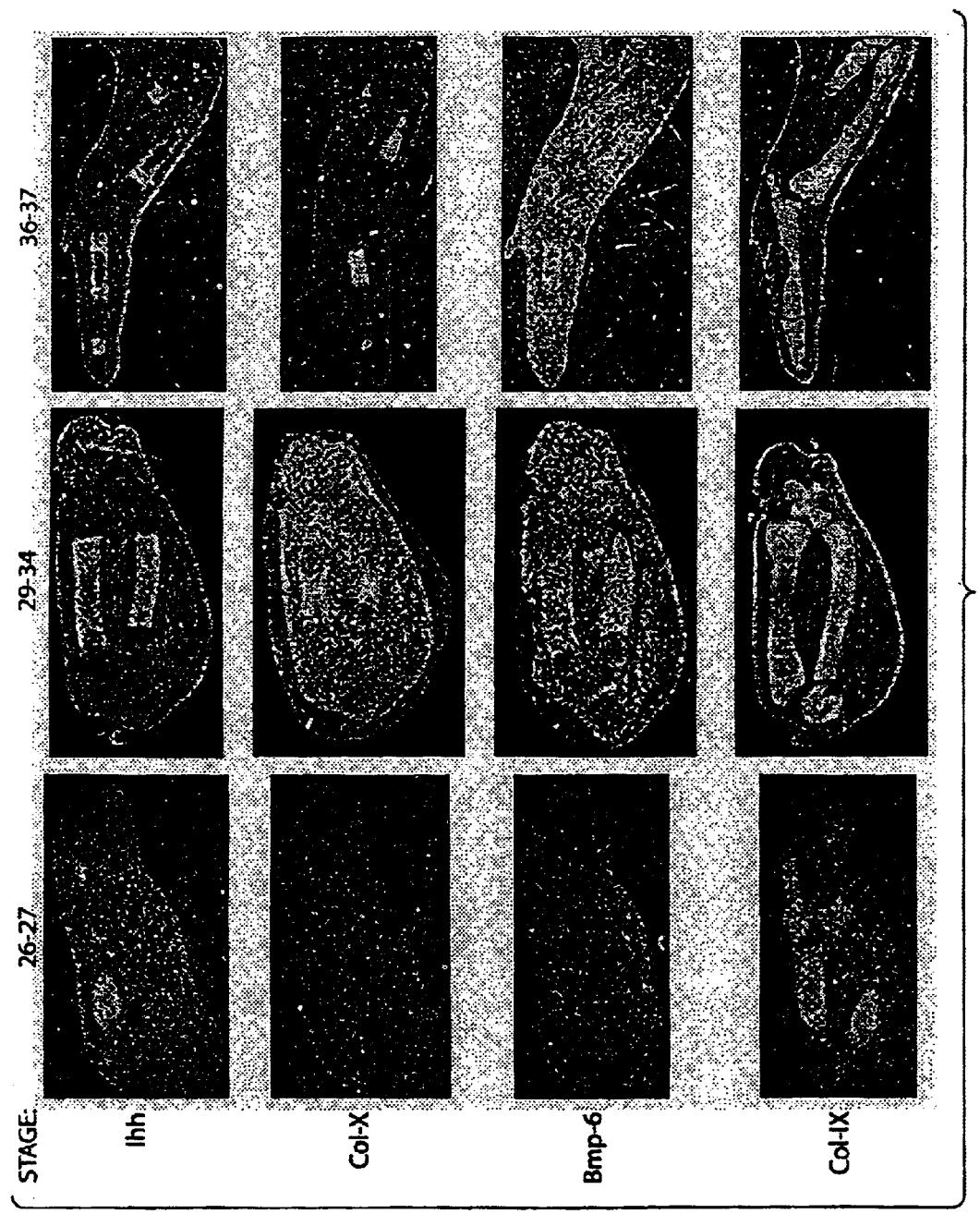
FIG. 2: Ihh expression in prehypertrophic chondrocytes. The expression of Ihh during cartilage development was compared to the expression of the specific cartilage markers Col-IX, Col-X, and Bmp-6 (51). At all stages investigated, Col-IX is expressed throughout the entire cartilage element, whereas Col-X identifies hypertrophic chondrocytes. At stage 26, before the first chondrocytes become hypertrophic, Ihh is already expressed in the middle of the cartilage element overlapping the expression domain of Bmp-6. Between stages 29 and 37, the expression of Ihh expands toward the distal ends of the cartilage elements and fades in their center where the chondrocytes have differentiated into hypertrophic chondrocytes and express Col-X. Bmp-6 expression at this stage overlaps both the Ihh and Col-X expression domains. Radioactive in situ hybridization was carried out on serial sections of limb buds of the different stages (48).

Expression of Ihh during bone development. Because Ihh and Shh appear to have identical signaling capabilities, their distinct embryonic roles are likely to be determined by spatial or temporal differences in their expression patterns. To investigate the developmental processes potentially regulated by Ihh, we analyzed its expression pattern by whole-mount in situ hybridization. Expression of Ihh was detected at two major sites in the embryo: in the endoderm of the developing midgut and lung (47) and in the cartilage of the developing long bones in the limbs (FIG. 2). No expression of Ihh was observed early in limb development (47), when Shh is expressed in the posterior mesenchyme, suggesting that Ihh plays a role distinct from that of Shh, acting later in limb development during the formation of the skeletal elements.

To determine the cell types expressing Ihh in the forming skeletal elements, we compared the expression pattern of Ihh to that of specific cartilage markers (FIG. 2) by in situ hybridization to parallel sections (48). During skeletal development, distinct types of collagen are expressed at different stages of differentiation; thus, they serve as excellent markers for specific cell types. For example, Col-IX is expressed in all cartilage cells, whereas Col-X is specific for hypertrophic chondrocytes (49). In addition to Col-X, Bmp-6 has also been described as a marker for hypertrophic chondrocytes (50, 51).

Patched expression in proliferating chondrocytes was also observed.

At stage 26/27, Col-IX was expressed in all cells of the developing cartilage elements of the wings. Ihh expression was detected ill the middle of the Col-IX expression domain but was excluded from the distal portions of the cartilage elements. At this stage, the entire cartilage consisted of proliferating chondrocytes, and no expression of the hypertrophic cartilage marker Col-X could he detected. Bmp-6, however, was expressed in a region similar to that of the Ihh express ion domain. During the subsequent stages, the expression of Ihh expanded toward the ends of the cartilage elements and was reduced in their central regions. At the same time, these central regions started to express Col-X, indicating their differentiation into hypertrophic chondrocytes. By stage 36, the Ihh expression domain had split into two regions, each distal to and slightly overlapping a central expression domain of Col-X in most of the skeletal elements of the wings (FIG. 2). Histological examination of hematoxylin and eosin (H&E)-stained sections verified that Col-X expression was restricted to morphologically hypertrophic cells, whereas Ihh was expressed in the region of transition from proliferating to hypertrophic chondrocytes and was excluded from hypertrophic cells (47). Ihh expression, therefore, preceded the hypertrophic state. Bmp-6 expression overlapped both the Ihh and the Col-X expression domains at all stages investigated (FIG. 2). Thus, Bmp-6 is expressed not only in hypertrophic cells (50) but also in the prehypertrophic, Ihh-expressing cells, possibly demarcating all cells that leave the proliferating zone.

Figure 3A:
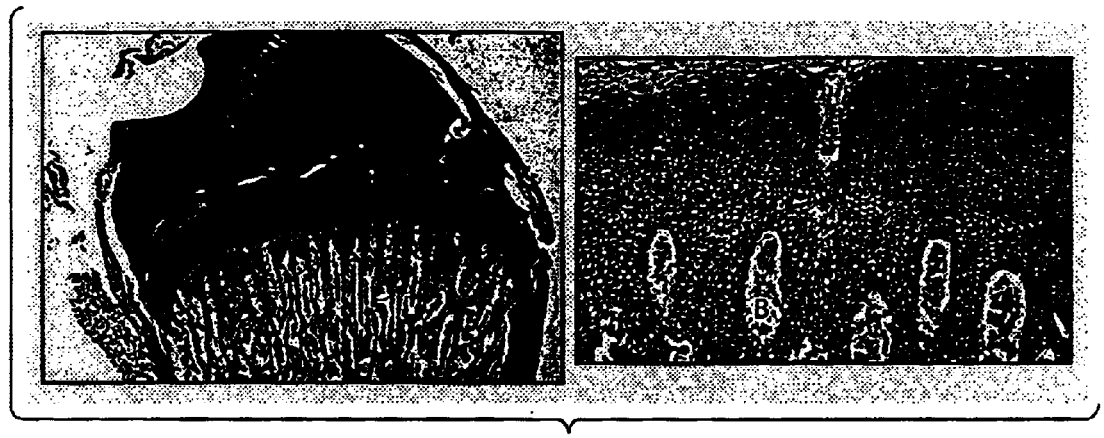
FIG. 3: Expression of Ihh in the growth plate. (A) Morphology of the growth plate of a chicken ulna, shown in low and high magnification. Longitudinal sections of an ulna from a 3-week old chicken were stained with Weigert-Safranin to differentiate between cartilage (red) and bone marrow (blue) and with H & E to visualize the morphology of the growth plate. B, bone and bone marrow; H, hypertrophic chondrocytes; P, proliferating chondrocytes. (B) Relative expression patterns of Ihh, Col-X, and PTH/PTHrP receptor. The three genes are expressed in overlapping domains, with the PTH/PTHrP receptor most distally located, followed by Ihh and Col-X. The PTH/PTHrP receptor and Col-X appear to be expressed in mutually exclusive domains, whereas the Ihh expression domain partially overlaps with both of them.
Figure 3B:
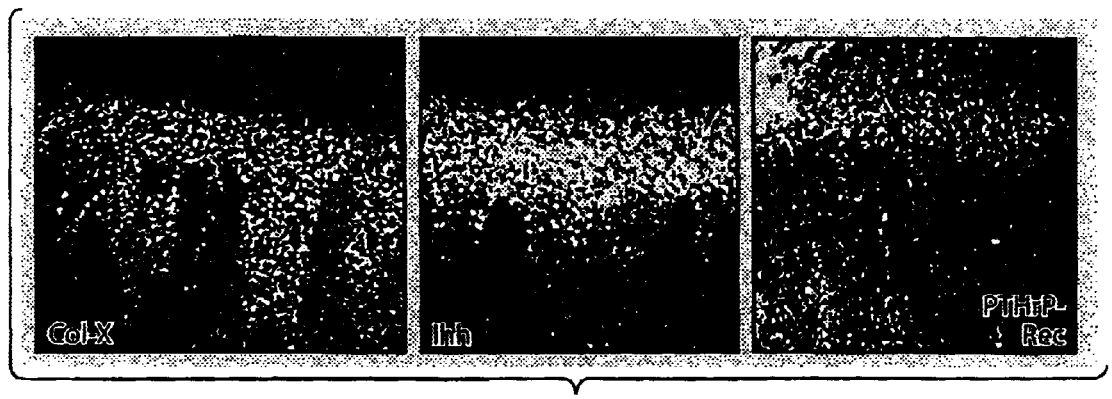

The relative expression patterns of Ihh and Col-X are maintained as long as the bones are growing. At 3 weeks after hatching Ihh was expressed in the prehypertrophic chondrocytes in the growth plates, whereas Col-X was expressed in the adjacent hypertrophic chondrocytes (FIG. 3). Ihh is, therefore, expressed at a specific, critical stage of endochondral bone formation in cells undergoing the transition from proliferating to hypertrophic chondrocytes, suggesting that Ihh may play an important regulatory role in cartilage differentiation.

Figure 4A:
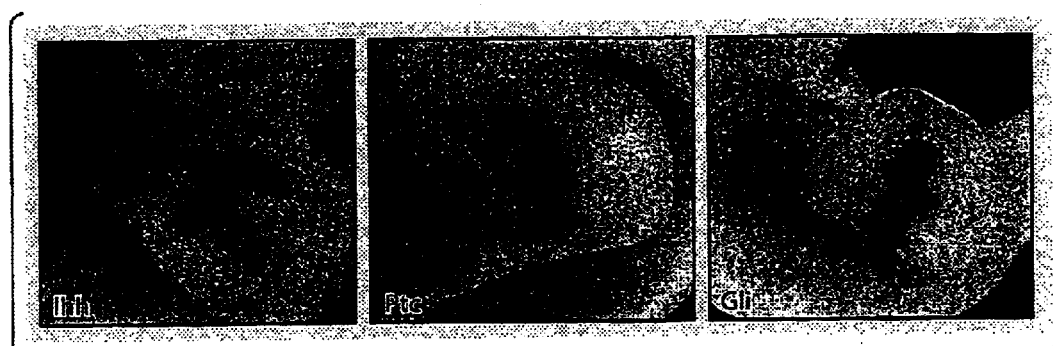
FIG. 4 (panels A and B): The Ihh expression domain in the cartilage is flanked by the expression of Ptc and Gli in the perochondrium. Neither Ptc nor Gli is expr3essed in the cartilage core. (A) Whole-mount in situ hybridization with Ihh, Ptc, and Gli was carried out on HH stage 30 limb buds. (B) Radioactive in situ hybridization was carried out on sections of stage 34 chicken wings.
Figure 4B:

To identify the target tissue of Ihh signaling, we analyzed the expression of Ptc and Gli, which are ectopically induced by Ihh in early limb buds. Whole-mount in situ hybridization showed that both genes were expressed in the perichondrial region flanking the Ihh expression domain but that their expression extended slightly further toward the end of the cartilage elements (FIG. 4A). Hybridization to serial sections confirmed that both genes were expressed in the perichondrial region, and though also at lower levels in the cartilage core. This expression pattern is consistent with Gli and Ptc being targets of Ihh signaling during bone development and strongly suggests that the perichondrium, as well as at least certain chondrocytes of the cartilage, is the natural target of the Ihh signal.

Phenotypic consequences of Ihh misexpression. To analyze the role of Ihh in the development of long bones, we misexpressed Ihh during cartilage formation with a replication-competent retroviral vector. We targeted our injections to restrict the infection to posterior and medial regions of HH stage 22 wing buds, resulting in a high level of infection of the posterior and medial cartilage elements including the ulnae and the humeri. Because the virus fails to spread within the cartilage tissue, infection was often excluded from anterior radii, which could therefore be used as internal controls (FIG. 5A).

To determine the morphological consequences of Ihh misexpression on the skeletal elements, we harvested and sectioned infected wings at late stages of embryonic development and treated them with stains that differentially demarcate hone and cartilage tissue (Weigert-Safranin) (52). On day 10 of development (stage 36), the centers of normal diaphyses consisted of hypertrophic cartilage that had not yet been invaded by blood vessels and was surrounded by a bone collar laid down by cells in the adjacent perichondrium. After this stage, the invasion of the blood vessels into the hypertrophic chondrocytes occurred, which resulted in the replacement of cartilage by bone. By day 16 (HH stage 42), a large part of the diaphysis consisted of bone that was distally flanked by hypertrophic and proliferating cartilage (FIG. 5B).

Figure 5A:
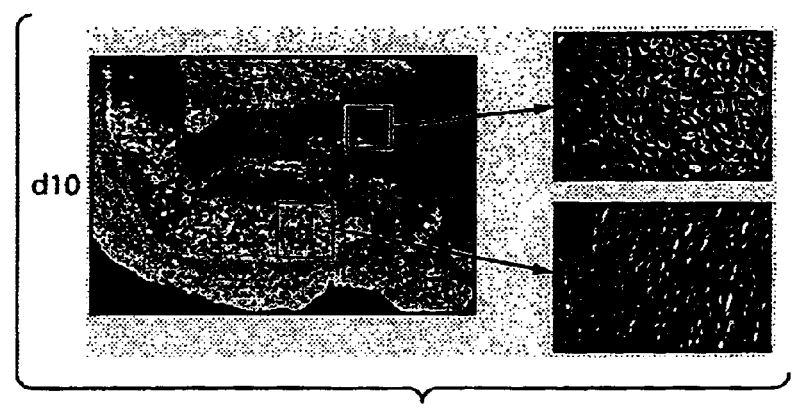
FIG. 5 (panels A–C): Misexpression of Ihh disrupts endochondrial bone development. An Ihh-expressing replication-competent virus (46) was used to infect the posterior and medial region of a HH stage 22 wing bud. Greater than 100 limbs were infected. In every instance, gross morphological alterations were observed. More than 30 of the infected limbs were sectioned and then stained or hybridized (or both) with probes as described, and every one displayed the described alterations. (A) On day 10 (d10) the ulna and the humerus are highly infected, whereas the radius in uninfected. Hybridization of a sectioned wing with an Ihh probe detects the viral transcript in ulna, humerus, and soft tissue and the endogenous Ihh expression (red arrowheads) in the radius above. High magnification of the cartilage, histologically stained with Weigert-Safranin, shows the presence of hypertrophic cells in the noninfected radius but not in the infected ulnae. (B) Infection with Ihh virus delays ossification. Weigert-Safranin-stained sections show that in normal day 10 chicken wings, the central region of the skeletal elements consists of cartilage, surrounded by a bone collar (black arrowhead). The replacement of cartilage by bone starts in this region, and on day 16 a large part of the diaphysis consists of bone (arrowhead) with cartilage distally. After Ihh infection, the cartilage elements on day 10 are shorter and broader than those of noninfected controls. At day 16 the noninfected radius of an infected wing shows normal ossification similar to that of uninfected limbs, whereas the infected ulna is still characterized by a continuous nonhypertrophic cartilage core that is surrounded by a layer of membranous bone. (C) Irregular ossification after Ihh misexpression. Weigert-Safranin staining of an infected chicken wing (day 16) at higher magnification shows the continuous cartilage core surrounded by a thick layer of bone. A replacement of cartilage by bone takes place from the outside at various positions along the cartilage core. Red arrowheads demarcate endogenous Ihh expression, black arrowheads demarcate bone and bone marrow.
Figure 5B:
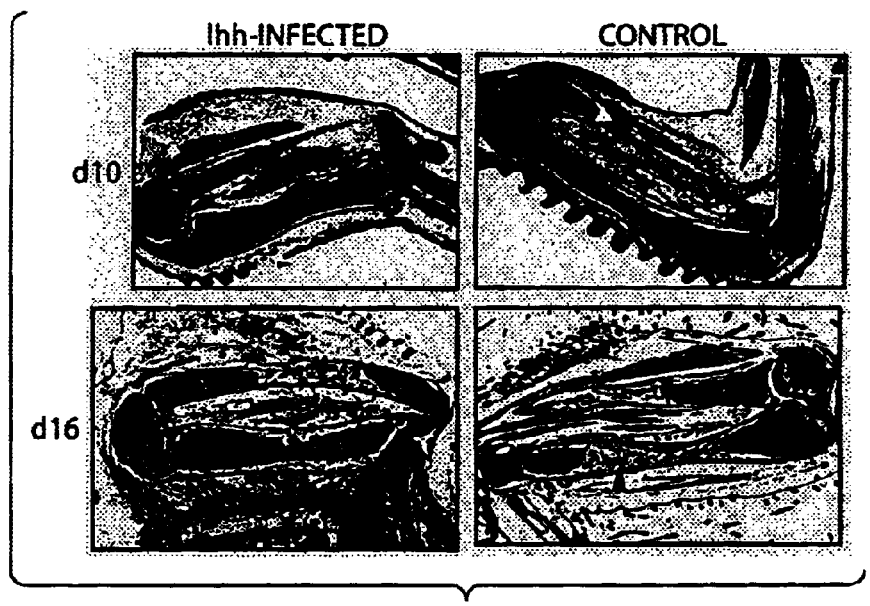

In most of the infected wings harvested on day 10 of development, the cartilage elements appeared broader and shorter than in the noninfected controls (FIG. 5B) and lacked hypertrophic cartilage throughout the cartilage core (FIG. 5A). The effect on bone morphology was more severe by day 16. A continuous cartilage core was still present in the infected limbs, whereas uninfected bones were largely ossified (FIG. 5B). Depending on the extent of infection, the radius was generally less affected and often contained hypertrophic cartilage (FIG. 5A) and showed normal ossification (FIG. 5B).

Figure 5C:
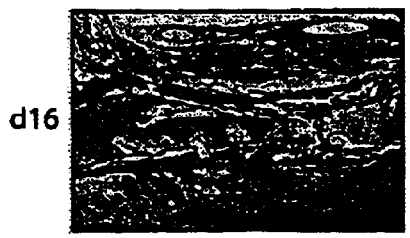

Although on day 16 the cartilage was continuous along the length of most of the infected skeletal elements, an invasion of bone had begun. In contrast to normal development, however, this replacement was not initiated by the invasion of blood vessels at the center of the shaft which would result in the replacement of cartilage by bone tissue from the inside. Rather, the replacement occurred from the outside at multiple locations along the cartilage element, which appeared to be "eaten away" by the invading bone (FIG. 5C). The cartilage cells being replaced were morphologically quite large. However, in contrast to normal hypertrophic cartilage, these cells did not express either the specific hypertrophic marker Col-X or the pan-cartilage marker Col-IX, indicating that they may have been dead (47). At later stages the cartilage continued to be replaced by bone tissue, but the bones were abnormal in shape and did not have normal growth plates at the ends (47). Thus, misexpression of Ihh greatly disrupts the process of endochondral bone formation.

Figure 6A:
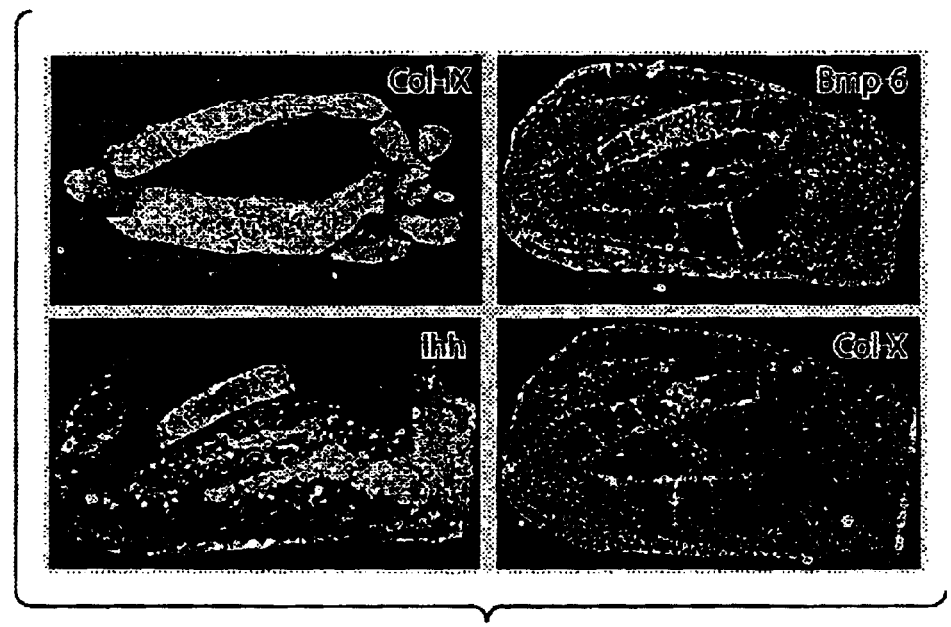
FIG. 6 (panels A–B): Ihh regulates cartilage differentiation. (A) Markers of hypertrophic cartilage are suppressed by Ihh. The expression of the cartilage markers Col-IX, Col-X, and Bmp-6 was analyzed in stage 34 chicken wings that had been infected with the Ihh-expressing retrovirus. Hybridization with an Ihh probe detects the viral transcript in the ulna and soft tissue and the endogenous Ihh expression domain in the noninfected radius. Col-LX is expressed in all cartilage cells, indicating that the infected cells are still viable. Col-X, a marker for hypertrophic cartilage, and Bmp-6 are both expressed (as in noninjected control limbs) in the noninfected radius but not in the infected ulna. Ihh therefore represses the differentiation of hypertrophic cartilage. (B) Ihh misexpression prevents the expression of the endogenous Ihh gene. Serial sections of infected chicken wings of HH stage 30 were hybridized with an Ihh probe that detects both the endogenous and the viral gene transcripts and with an Ihh probe that is specific only for the endogenous Ihh transcript. The nonspecific probe detects a signal in the infected ulna and soft tissue and in the noninfected radius, whereas the endogenous Ihh transcript can be detected only in the radius and is absent from the infected ulna, indicating that misexpression of Ihh represses endogenous Ihh expression.

The role of Ihh in the regulation of cartilage differentiation. To identify the specific steps of bone development affected by Ihh, we analyzed serial sections for changes in the expression of molecular markers after Ihh misexpression. The effects of Ihh misexpression on cartilage differentiation were evident by HH stage 34. Col-IX was still expressed throughout the entire cartilage elements, indicating that the chondrocytes remained viable after Ihh infection. In contrast, the analysis of the hypertrophic cartilage marker Col-X revealed that, whereas Col-X was expressed in the noninfected radii, it was not expressed in highly infected ulnae and humeri (FIG. 6A). Histological analysis of the infected cartilage supported this interpretation. Hypertrophic chondrocytes could easily be identified in the central regions of uninfected cartilage elements. However, they were missing in highly infected cartilage elements, which throughout their length consisted of small chondrocytes, similar in appearance but less organized than those normally found in the proliferative zone (FIG. 5A). Ihh, therefore, appears to block the differentiation pathway from proliferating to Col-X-expressing, hypertrophic chondrocytes. In addition to repressing expression of the hypertrophic cartilage marker Col-X, we could not detect expression of Bmp-6 in infected cartilage elements (FIG. 6A). Our observation that Bmp-6 was expressed in both hypertrophic and prehypertrophic chondrocytes suggests that misexpressed Ihh might act before overt hypertrophic differentiation.

Figure 6B:
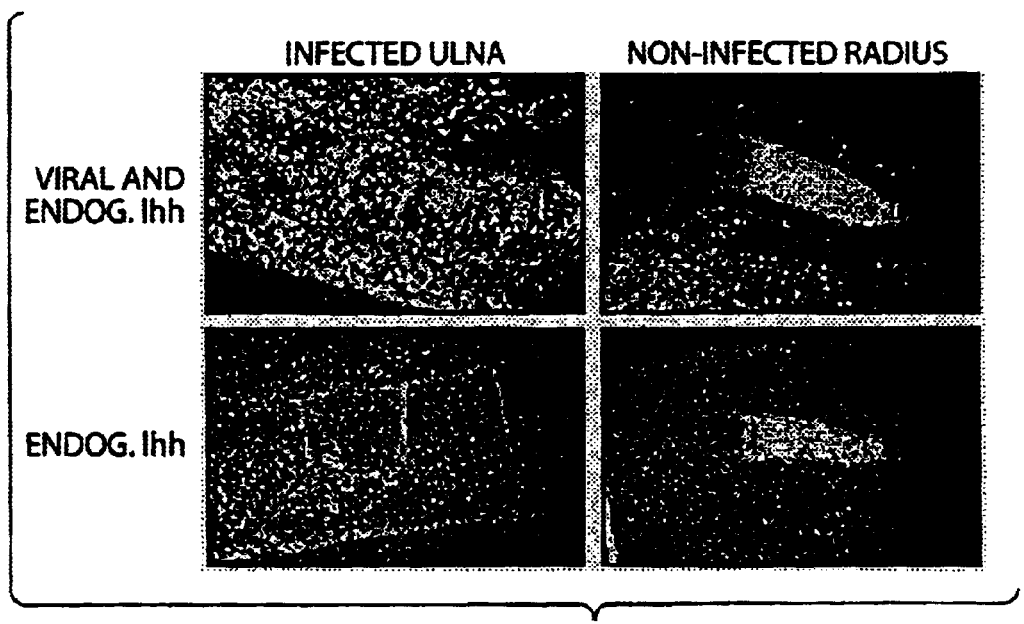

Because Ihh is expressed in cells undergoing differentiation, it could in principle act at either of two steps to repress the hypertrophic cell fate: Ihh could either block the terminal differentiation to the hypertrophic state, which would result in an accumulation of Ihh-expressing cells, or it could prevent proliferating cells from initiating the differentiation process, thus preventing the formation of the Ihh-expressing cell type itself. To distinguish between these possibilities, we analyzed the expression of the endogenous Ihh gene after viral misexpression. Hybridization with a probe specific for the endogenous Ihh transcript revealed that the expression of the gene was normal in noninfected radii. However, no expression was detected in infected cartilage elements, demonstrating that misexpression of Ihh suppressed the endogenous Ihh gene (FIG. 6B). Therefore, ectopic Ihh blocks chondrocyte differentiation before the transition to an Ihh-expressing state.

Although misexpression of Ihh has a profound effect on cartilage differentiation, the expression patterns of Gli and Ptc suggest that the perichondrium is also a target of Ihh activity. To examine whether the morphological effects we observe in response to ectopic Ihh are also mediated by the perichondrium, we analyzed Ptc and Gli expression in infected limbs.

Figure 7:
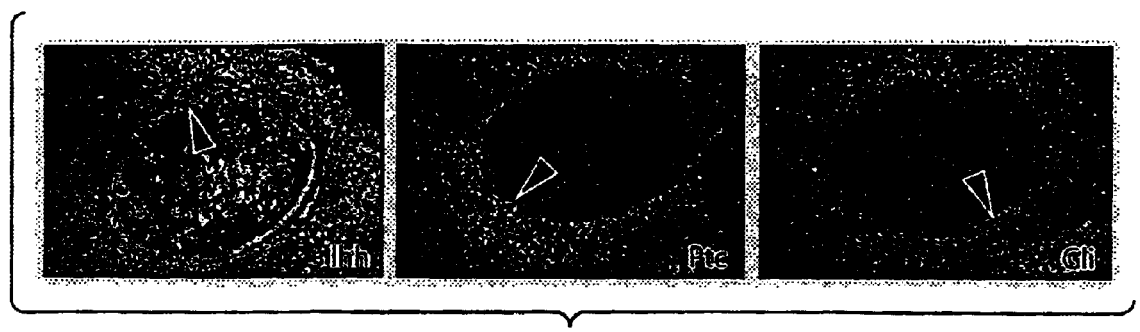
FIG. 7: Ptc and Gi are induced in response to Ihh misexpression. After Ihh infection, serial sections were prepared from a region of HH stage 34 wings where Ihh, Ptc and Gli are normally not expressed. Hybridization with Ptc and Gli probes shows expression in the soft tissue and in the perichondrium of the ulna, but expression is excluded from the cartilage. In contrast, both soft tissue and cartilage express ectopic Ihh after infection. The perichondrium is demarcated by arrowheads.

Both genes were strongly induced in the perichondrium as well as in muscle and soft tissue after Ihh infection (FIG. 7). Their expression was observed in proliferating chondrocytes (not shown). Because there are no known examples in which a Hedgehog signal is mediated without the induction of Ptc and Gli, these misexpression studies imply that the effect of Ihh on the cartilage includes an indirect mechanism e.g., which is mediated by the perichondrium.

Taken together, these results suggest that Ihh normally acts on the perichondrium to initiate a negative feedback loop that regulates the hypertrophic differentiation process. We propose that Ihh is produced by cells that become committed to the hypertrophic cell fate. The expression level of Ihh in this model may serve as a sensor within the skeletal element to regulate the number of cells committed to the process, where a certain threshold level of Ihh indirectly prevents additional cells from leaving the proliferative state. When Ihh-expressing cells undergo the final differentiation steps to become hypertrophic chondrocytes, they turn off the expression of Ihh, thereby attenuating the negative feedback loop and allowing more cells to commit to the differentiation pathway. By controlling the number of cells that differentiate at a given time, Ihh has a fundamental role in regulating the balance between growth and ossification of the developing bones.

PTHrP as a mediator of the Ihh signal. Our results suggest that the negative feedback loop initiated by Ihh is mediated by the perichondrium. Parathyroid hormone-related protein (PTHrP) (53, 54) is expressed in the perichondrium of the developing cartilage elements of mouse and rat limbs, predominantly in the periarticular regions early in bone development (55, 56), and appears to encode another signal that regulates the differentiation of cartilage. Targeted disruption of the PTHrP gene in mice has an effect on bone development opposite that produced by overexpression of Ihh: In PTHrP (−/−) mice the transition of chondrocytes from the proliferative to the hypertrophic phase is accelerated, which results in advanced, premature ossification (7, 8). Although PTHrP itself is expressed at a considerable distance from the expression domain of Ihh, its receptor (PTH/PTHrP receptor) (57) is expressed in the prehypertrophic cartilage zone (as well as in osteoblasts) (55, 56, 58).

Figure 8A:
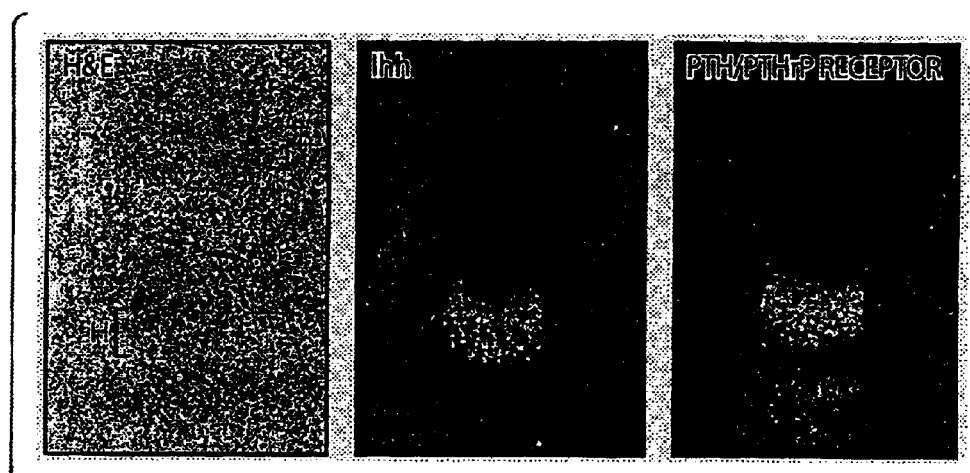
FIG. 8 (panels A–B): Expression of Ihh and PTH/PTHrP receptor in mouse hind limbs. (A) Serial sections of wild-type E16.5 mouse hind limbs were stained with H & E to show cartilage histology or were hybridized with an Ihh or a PTH/PTHrP receptor probe. As in chicken limbs, the expression domain of the PTH/PTHrP receptor overlaps that of Ihh on its distal side. (B) Sections from a PTHrP (–/–) mutant mouse embryo were stained with H & E or were hybridized with an Ihh probe. Similar expression of Ihh can be observed in wild-type and mutant mouse limbs. H, hypertrophic cartilage.

To investigate the possible interactions between Ihh and PTH/PTHrP receptor, we cloned a fragment of the chick PTH/PTHrP receptor (59) and compared its expression to that of Ihh in the prehypertrophic cartilage. In chicken, PTH/PTHrP receptor was strongly expressed in the osteoblastic precursors of the perichondrium from at least day 6, but no signal could be detected in the developing cartilage at this stage (47). However, at later stages of bone development (3 weeks after hatching), PTH/PTHrP receptor was expressed in the prehypertrophic cartilage in a domain distal to and slightly overlapping the Ihh-expression domain (FIG. 3B), consistent with the pattern of rodent expression (55, 58). In rodents, PTH/PTHrP receptor expression was detected at earlier stages of cartilage development (FIG. 8A), suggesting that in limbs of early stage chicken embryos its expression might be present but too weak to be detected. Once they are both detectable, the relative expression domains of Ihh and PTH/PTHrP receptor indicate that cells express PTH/PTHrP receptor before differentiating into an Ihh-expressing cell type. The differentiation block induced by Ihh appears to occur upstream of Ihh expression, which is precisely the putative target cell type for the Ihh feedback loop.

Figure 9:
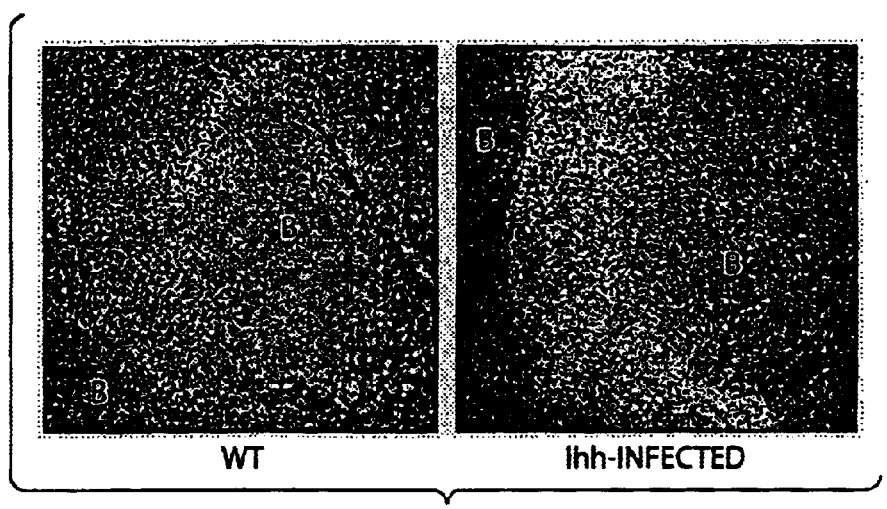
FIG. 9: PTHrP is induced in periarticular joint regions by Ihh. Serial sections of infected and noninfected control chicken wings of HH stage 30 were hybridized with Ihh and PTHrP probes. PTHrP is expressed in the perochondrium of the joint region of the developing cartilage elements and is strongly up-regulated in this area after infection of the wing buds with an Ihh-expressing virus. B, bone.

To test directly whether PTHrP is regulated by Ihh, we examined PTHrP expression in normal and Ihh-infected skeletal elements. As in rodents, PTHrP was normally expressed in the periarticular perichondrium adjacent to the developing chick cartilage elements. In Ihh-infected wings, increased PTHrP expression was detected throughout the periarticular perichondrium (FIG. 9). In contrast to the induction of Gli and Ptc, however, the Ihh-induced PTHrP expression was restricted to the perichondrium in the periarticular regions of infected limbs, indicating that either additional signals, required in concert with Ihh, are present only at the ends of the skeletal elements or that only a specific periarticular cell type is capable of expressing PTHrP in response to Ihh.

Figure 8B:
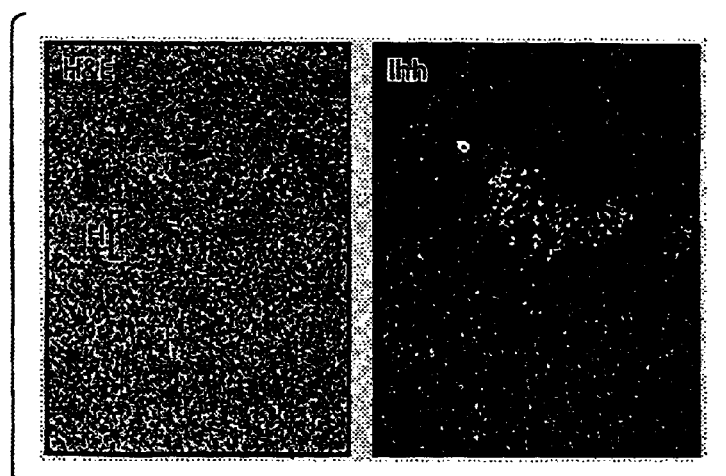

These results place PTHrP downstream of Ihh in regulating cartilage differentiation. To verify this epistatic relation, we compared the expression of Ihh in limbs of wild-type and PTHrP (−/−) mice. In wild-type limbs, Ihh was expressed overlapping with and medial to the PTH/PTHrP receptor (FIG. 8A), as in the chicken, and a similar level of Ihh expression was seen in PTHrP (−/−) limbs (FIG. 8B), excluding the possibility that Ihh expression is reciprocally regulated by PTHrP.

Figure 10A:
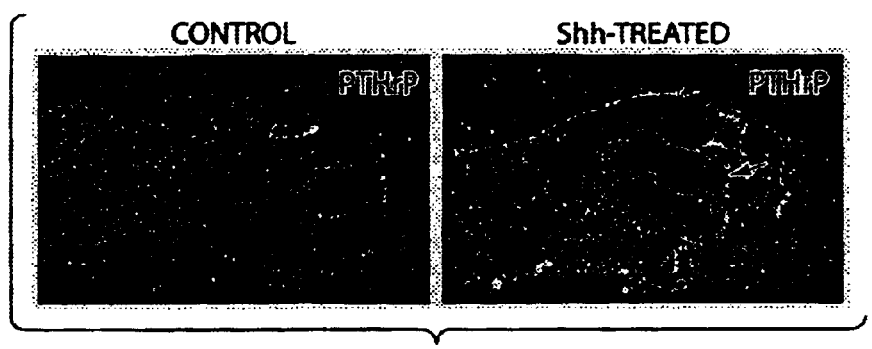
FIG. 10 (panels A–B): Conservation of the Ihh/PTHrP pathway in mouse and chick. (A) Sections of wild-type mouse hind limb explants treated with control or Shh-containing medium were hybridized with the PTHrP probe. Whereas in the control limbs the PTHrP signal can barely be detected, an up-regulation of PTHrP expression (arrow) is seen in the periarticular perichondrium, after Shh treatment. (B) Sections of wild-type mouse hind limbs treated with control or Shh- or PTHrP containing medium were hybridized with an Ihh probe. Ihh expression is seen in the prehypertrophic chondrocytes of control limbs but is repressed by Shh and PTHrP.
Figure 10B:
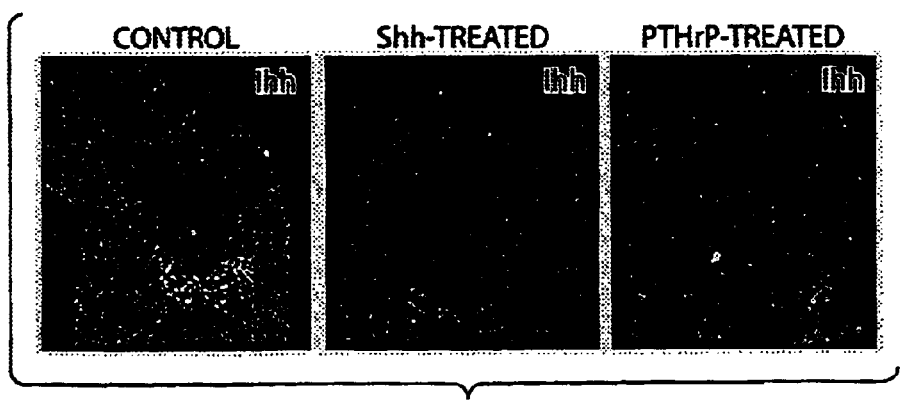

We conclude that both Ihh and PTHrP (on the basis of the murine mutant phenotype) repress hypertrophic cartilage differentiation, and that Ihh can induce PTHrP. This raises the question of whether the induction of PTHrP mediates the effect of Ihh. Assuming that the same signals regulate bone development in mice and in chicken, the existence of PTHrP (−/−) mutant mice provides the opportunity to definitively address this question. Because there is no convenient way to introduce ectopic Ihh into embryonic mouse limbs in utero, we cultured day 16.5 fetal mouse limb explants in vitro (60). Purified Ihh protein was not available for these studies. However, as shown above, Shh has the same biological activities as Ihh in early limb buds, activating the same target genes. Moreover, infection with a Shh-expressing retrovirus has the same effect as Ihh on chondrocyte differentiation and bone growth in chicken (47). We therefore used recombinant Shh protein in the mouse hind limb cultures. To verify that the PTHrP/Ihh feedback loop operates equivalently in the murine and chick systems, we examined PTHrP and Ihh expression in wild-type limb explants treated with control or Shh-containing medium. As in the chick, PTHrP was up-regulated and Ihh was repressed in response to Hedgehog protein in mouse limb explants (FIG. 10, A and B). Consistent with Ihh and PTHrP being in the same regulatory pathway, PTHrP treatment of limb explants also resulted in repression of Ihh expression (FIG. 10B).

Figure 11A:
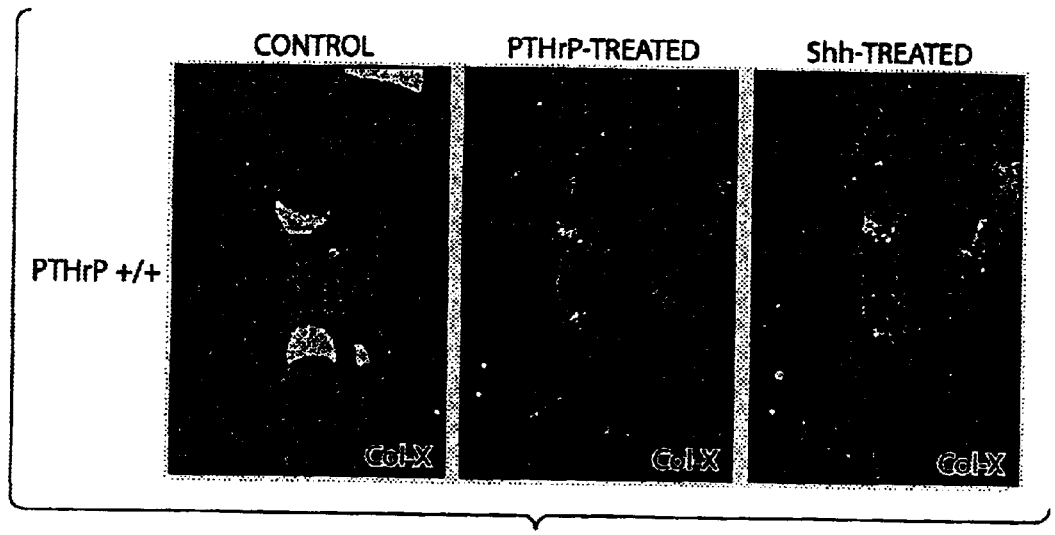
FIG. 11 (panels A–C): Shh acts upstream of PTHrP. E16.5 mouse hind limbs from PTHrP (+/+) and PTHrP (−/−) mice were cultured for 4 days in control, PTHrP-, or Shh-containing medium. (A) Col-X expression is repressed after PTHrP and Shh treatment in PTHrP (+/+) hind limbs. In situ hybridization with a Col-X probe to sections of tibias from the control animals shows a repression of the hypertrophic cartilage marker Col-X after PTHrP or Shh treatment, relative to untreated limbs. (B and C) PTHrP rescues the PTHrP (−/−) phenotype, whereas Shh has no effect on cartilage. In PTHrP (−/−) animals the hypertrophy of the cartilage is advanced in all the bones including the tibia (B) and the digits (C), as shown by Col-X expression (B) and H & E staining (C). Treatment of the cultures with PTHrP not only rescues the wild-type phenotype but also induces the same repression of hypertrophic cartilage as observed in PTHrP treatment of normal limbs: Col-X expression is repressed (B), and morphologically no hypertrophic chondrocytes form during culture (C). In contrast to the rescue of the PTHrP (−/−) phenotype by, Shh treatment does not change the phenotype of the cartilage elements; Col-X expression is still advanced (B), and H & E staining shows the premature hypertrophic cartilage (C).
Figure 11B:
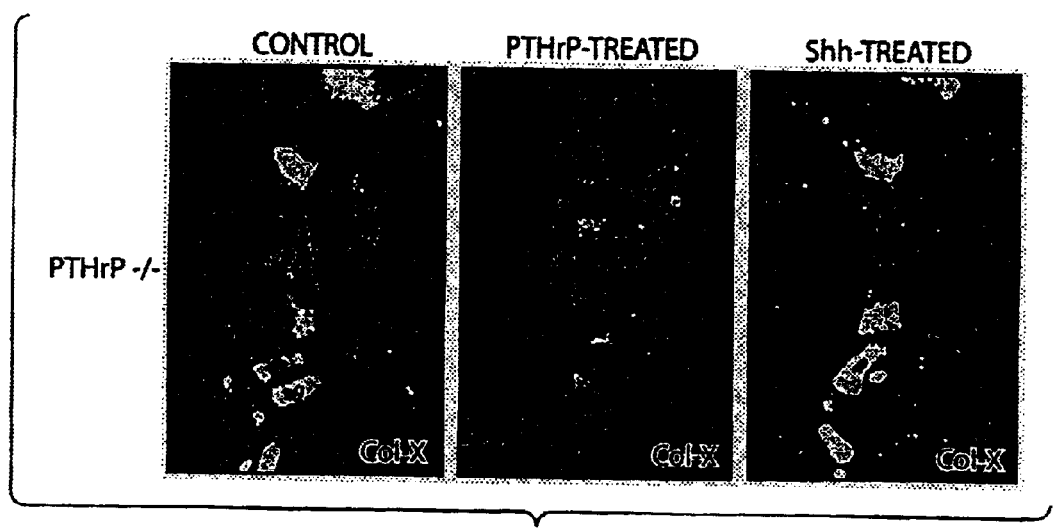
Figure 11C:
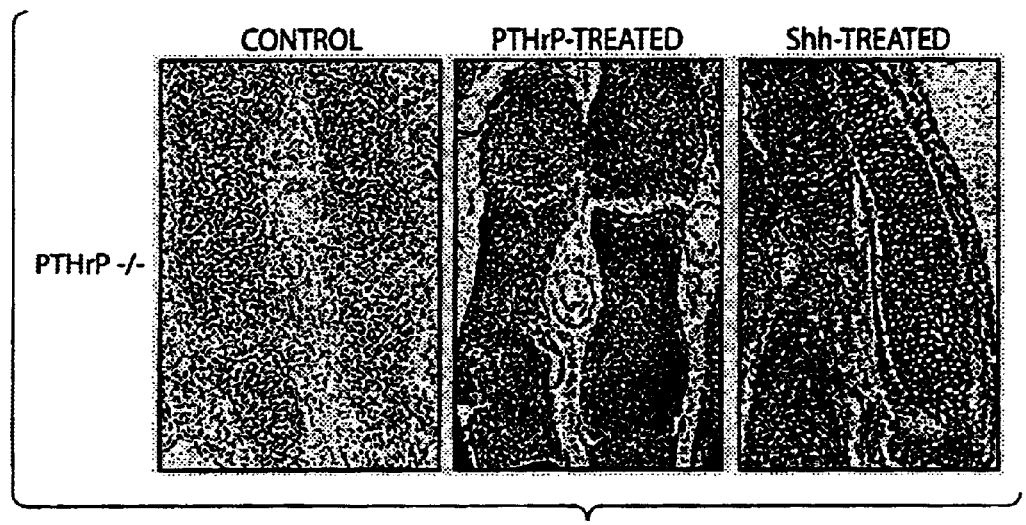

To test whether PTHrP is required for cartilage to respond to Hedgehog protein, we placed explants of PTHrP (+/+) hind limbs embryonic day 16.5 (E16.5) in serum-free culture, treated them with control, PTHrP-containing, or Shh-containing media, and assessed the differentiation of hypertrophic cartilage. Morphologically (47) and as judged by Col-X expression (FIG. 11A), both PTHrP and Shh repressed hypertrophic differentiation in wild-type limbs in vitro, consistent with their effects in vivo. Explants of E16.5 PTHrP (−/−) mutant hind limbs placed in similar culture conditions showed extensive premature hypertrophy in vitro (FIG. 11, B and C), as they did in vivo. For example, hypertrophic changes in the cartilage of the feet progressed over the culture period and became completely hypertrophic after 4 days in culture (FIG. 11C). As expected, this premature hypertrophy could be prevented by addition of PTHrP to the media, which, moreover, blocked even normal hypertrophic differentiation, as it did after addition to wild-type limbs (FIG. 11, B and C). In contrast, Shh, which also blocked hypertrophy in wild-type limbs, had no effect on PTHrP (−/−) limbs. Shh-treated mutant explants were indistinguishable, both morphologically (FIG. 11C) and in their pattern of Col-X expression (FIG. 11B), from untreated mutant limbs. Because ectopic Hedgehog can induce PTHrP expression both in chick limbs and in mouse limb explants, and because Shh has no observable effect on PTHrP (−/−) mutant explants, we conclude that the effect of Hedgehog protein on cartilage differentiation is mediated by the PTHrP pathway. This further substantiates our inference that the perichondrium and not the cartilage is the direct target of Ihh activity and confirms that Ihh acts via the induction of PTHrP. In the feedback loop, PTHrP must act on cells before their activation of Ihh, because this regulation loop prevents Ihh expression. Consistent with this model, we have shown that one receptor of PTHrP, the PTH/PTHrP receptor, is specifically expressed in cells just distal to those expressing Ihh. In an accompanying report (58), we provide functional data demonstrating that not only is the PTH/PTHrP receptor in the right place, but it is absolutely necessary for Ihh and PTHrP to affect chondrocyte differentiation in the mouse. Because the PTH/PTHrP receptor is expressed at a considerable distance from PTHrP itself, this ligand must act across multiple cell diameters.

Figure 12:
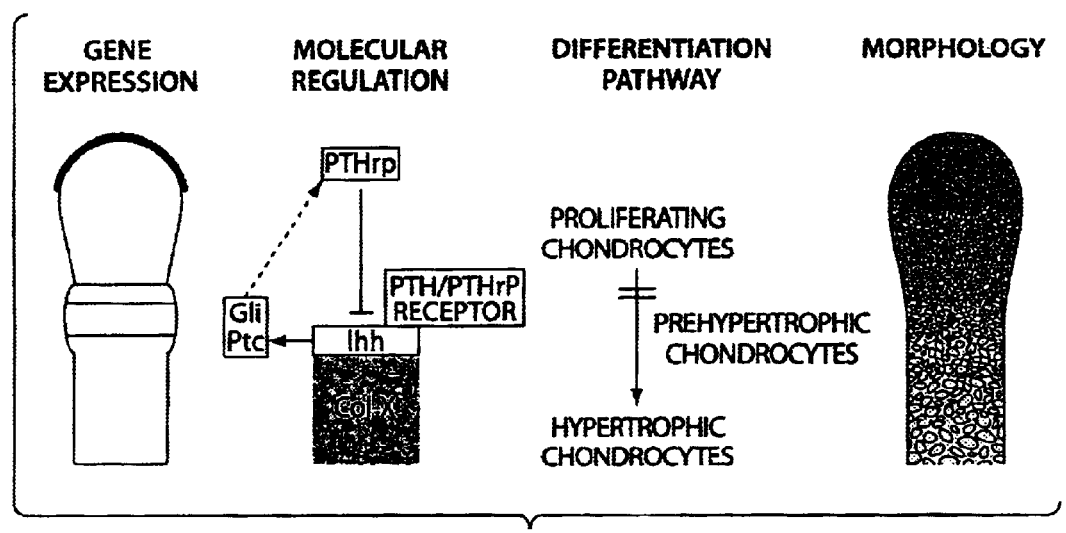
FIG. 12: Molecular regulation of the rate of cartilage differentiation. During cartilage development chondrocytes differentiate from proliferating chondrocytes (white) through an intermediate, prehypertrophic cell type to hypertrophic chondrocytes (expressing Col-X, blue). With the initiation of this differentiation pathway, the prehypertrophic chondrocytes express PTH/PTHrP receptor (yellow) and Ihh (red). PTH/PTHrP receptor is expressed in cells before the onset of Ihh expression. For clarity, the expression domains of the two genes (yellow and red) are shown as distinct regions. However, they actually overlap, both in chick and mouse. The target of the secreted Ihh signal is the perichondrium, which responds by expressing Gli and Ptc (green). This Ihh response in the perichondrium directly or indirectly results in the expression of PTHrP in the periarticular perichondrium (purple). PTHrP then signals back to the PTH/PTHrP receptor in the prehypertrophic cells, preventing additional chondrocytes from moving down the differentiation pathway and from expressing Ihh (73). When the prehypertrophic chondrocytes have fully differentiated into hypertrophic chondrocytes, they turn off Ihh expression. This reduction of the Ihh level attenuates the negative feedback loop and allows new cells to initiate the differentiation pathway. The Ihh level produced by the prehypertrophic chondrocytes, therefore, reflects the number of cells committed to the hypertrophic pathway, providing a mechanism for regulating the rate of hypertrophic differentiation.

We therefore extend our understanding of the feedback regulation of chondrocyte differentiation as follows (FIG. 12): As proliferating chondrocytes decide to undergo hypertrophy, they express high levels of the PTH/PTHrP receptor. When they subsequently become committed to this pathway, they transiently express Ihh, until they become fully hypertrophic. The Ihh signal acts on the perichondrium adjacent to the prehypertrophic zone (Ptc/Gli-expressing cells) and (directly or indirectly) on the more distant periarticular perichondrium, ultimately inducing the expression of PTHrP. PTHrP then signals back to chondrocytes expressing the PTH/PTHrP receptor, thereby preventing nondifferentiated chondrocytes from moving down the hypertrophic pathway.

Ihh and PTHrP function in a common feedback loop that regulates the rate of chondrocyte differentiation and thereby balances the growth and ossification of long bones. The elucidation of this feedback loop provides insight into the molecular mechanisms regulating the formation of long bones and forms a basis for further analysis of these processes.

References for Example 12

(1.) J. R. Hinchliffe and D. R. Johnson, in the Development of the Vertebrate Limb (Oxford Univ. Press, New York, 1980), pp. 76–83.
(2.) A. Erlebacher, E. H. Filvaroff, S. E. Gitelman, R. Derynck, Cell 80, 371 (1995).
(3.) F. Rousseau et al., Nature 371, 252 (1994).
(4.) R. Shiang et al., Cell 78, 335 (1994).
(5.) C. Deng, A. Wyoshaw-Boris, F. Zhou, A. Kuo, P. Leder, ibid. 84, 911 (1996).
(6.) J. Baker, J. P. Liu, E. J. Robertson, A. Efstratiadis, ibid. 75, 73 (1993).
(7.) A. C. Karaplis et al., Genes Dev. 8, 277 (1994).
(8.) N. Amizuka, H. Warshawsky, J. E. Henderson, D. Goltzman, A. C. Karaplis, J. Cell Biol. 126, 1611 (1994).
(9.) M. J. Bitgood and A. P. McMahon, Dev. Biol. 172, 126 (1995).
(10.) C. Nusslein-Volhard and E. Wieschaus, Nature 287, 795 (1980).
(11.) J. J. Lee, K. D. Von, S. Parks, P. A. Beachy, Cell 71, 33 (1992)
(12.) J. Mohler and K. Vani, Development 115, 957 (1992).
(13.) R. D. Riddle, R. L. Johnson, E. Laufer, C. Tabin, Cell 75, 1401 (1993).
(14.) Y. Echelard et al., ibid., p. 1417.
(15.) S. Krauss, J.-P. Concordet, P. W. Ingham, ibid., p. 1431.
(16.) M. Levin, R. L. Johnson, C. D. Stern, M. Kuehn, C. Tabin, ibid. 82, 803 (1995).
(17.) H. Roelink et al., ibid. 76, 761 (1994).
(18.) R. L. Johnson, E. Laufer, R. D. Riddle, C. Tabin, ibid. 79, 1165 (1994).
(19.) C. M. Fan and M. Tessier-Lavigne, ibid., p. 1175.
(20.) D. J. Roberts et al., Development 121, 3163 (1995).
(21.) M. Bitgood, L. Shen, A. McMahon, Curr. Biol. 6, 298 (1996).
(22.) J. E. Hooper and M. P. Scott, Cell 59, 751 (1989).
(23.) Y. Nakano et al., Nature 341, 508 (1989).
(24.) T. Orenic, D. C. Slusarski, K. L. Kroll, R. A. Holmgren, Genes Dev. 124, 50 (1990).
(25.) P. W. Ingham, A. M. Taylor, Y. Nakano, Nature 353, 184 (1991).
(26.) J. Capdevila, M. P. Estrada, E. Sanchez-Herrero, I. Guerrero, EMBO J. 13, 71 (1994).
(27.) A. J. Forbes, Y. Nakano, A. M. Taylor, P. W. Ingham, Dev. Suppl. 115 (1993).
(28.) V. Marigo, M. P. Scott, R. L. Johnson, L. V. Goodrich, C. J. Tabin, Development 122, 1225 (1996).
(29.) L. V. Goodrich, R. L. Johnson, L. Milenkovic, J. A. McMahon, M. P. Scott, Genes Dev. 10, 301 (1996).
(30.) J. M. Ruppert et al., Mol. Cell. Biol. 8, 3104 (1988).
(31.) V. Marigo and C. J. Tabin, unpublished results.
(32.) -, Proc. Natl. Acad. Sci. U.S.A., in press.
(33.) K. Basler and G. Struhil, Nature 368, 208 (1994).
(34.) J. Capdevila and I. Guerrero, EMBO J. 13, 4459 (1994).
(35.) R. Tabata and T. Kornberg, Cell 76, 89 (1994).
(36.) E. Laufer, C. E. Nelson, R. L. Johnson, B. A. Morgan, C. J. Tabin, ibid. 79, 993 (1994).
(37.) Cloning of the chicken Ihh cDNA: Unless otherwise noted, all molecular procedures followed published protocols (61). A random primed cDNA library from embryonic day 7 chicken limbs was constructed in the lambda ZapII vector (Stratagene) with the use of Eco RI-Not I linkers. Clones ($1 \times 10^6$) of the unamplified library were plated and transferred to duplicate sets of nylon filters (Colony Plaque Screen, New England Nuclear). A genomic Ihh DNA probe, plhhex3, homologous to base pairs (bp) 908 to 1180 of the Shh cDNA and containing 400 bp of 3' untranslated sequence, and the Shh cDNA probe pHH2 (13), were mixed and used as a hybridization probe. Hybridization was carried out in 0.5 M phosphate buffer, 7% SDS, 1 mM EDTA, and herring sperm DNA (100 mu g/ml) at 65 degrees C. overnight. Filters were washed in 50 mM phosphate buffer, with 1% SDS at 65 degrees C. as the final stringency (62), and exposed to Kodak XAR-5 films for 16 to 72 hours. After two rounds of subcloning, three positive clones were identified that hybridized strongly to plhhex3 and less strongly to pHH2. Nucleotide sequences of the three clones were determined with Sequenase 2.0 (US Biochemicals) and sequence-specific oligonucleotides as sequencing primers. DNA and amino acid sequences were analyzed with Genetics computer Group (Devreux) and DNA star software. A cDNA contig was assembled, consisting of 1958 bp with an open reading frame encoding a protein of 408 amino acids, flanked by 0.3 kb of untranslated cDNA on the 5' side and 0.4 kb on the 3' side. Comparison of the predicted amino acid sequence with the previously cloned vertebrate Hedgehog proteins showed highest conservation with the predicted mouse (73%) and human (75%) Ihh proteins and less but substantial conservation with the other Hedgehog proteins (55 to 61%), indicating that the isolated cDNA represents the chicken Ihh gene (GenBank accession number U58511).
(38.) J. J. Lee et al., Science 266, 1528 (1994).
(39.) J. A. Porter et al., Nature 374, 363 (1995).
(40.) D. A. Bumcrot, R. Takada, A. P. McMahon, Mol. Cell. Biol. 15, 2294 (1995).
(41.) C. M. Fan et al., Cell 81, 457 (1995). (42.) E. Marti, D. A. Bumcrot, R. Takada, A. P. McMahon, Nature 375, 322 (1995).
(43.) H. Roelink et al., Cell 81, 445 (1995).
(44.) P. Currie and P. Ingham, Nature, in press.
(45.) V. Hamburger and H. L. Hamilton, J. Exp. Morphol. 88, 49 (1951).
(46.) Misexpression of Ihh: The complete Ihh coding region and part of the 3' untranslated cDNA nucleotides (nt) 328 to 1691 were cloned into replication-competent retroviral vectors (RCAS) with various host ranges with the Slacksl3 shuttle vector (13, 63–65). Ihh-expressing RCAS (E)-type virus, which has a limited host range, was used to infect susceptible chicken primary fibroblast, prepared from chick line 15b. The Ihh-expressing cells were pelleted and transplanted into the anterior limb mesenchyme of a virally resistant outbred host strain, which resulted in a localized expression of Ihh and prevented the spread of the virus into the surrounding tissue. All other misexpression experiments were carried out with Ihh-expressing RCAS(A)-type viruses, which directly infected the outbred chicken host strain and spread throughout the surrounding tissue after infection (13), resulting in high Ihh expression in the infected limb tissue. Outbred specific pathogen-free eggs were obtained from SPAFAS (Norwich, Conn.).

(47.) A. Vortkamp and C. J. Tabin, unpublished results.

(48.) In situ hybridization: Whole-mount in situ hybridization was done as described (13), except that embryos older than stage 25 were treated with fourfold higher concentration of proteinase K than in the original protocol. In situ hybridization was done with sup.35 S-uridine 5'-triphosphate (UTP) or sup.33 P-UTP-labeled probes on 6-mu m sections as described (66). Hybridization was done at 52 degrees to 70 degrees C. in 50% formamide, and posthybridization washes were carried out at a final stringency of 55 degrees C. in 50% formamide and 2×SSC (sodium chloride/sodium citrate). For serial sections, three continuous sections were successively collected on six alternating slides. Probes used for hybridizations were as follows: Ihh: pIhh-R1-4sac contains nt 1 to 557 of the cloned Ihh sequence and corresponds to the 5' untranslated region and to exon 1. The probe detects the endogenous and the viral Ihh transcript. Endogenous Ihh: pIhh-R1-4AE contains nt 1 to 276 of the Ihh cDNA, which correspond to the 5' untranslated Ihh message and are not included in the viral construct. This probe detects only the endogenous Ihh transcript. Human Ihh (67), Gli (31), Shh (13), Hoxd-11, Hoxd-13, and Bmp2 (36), Ptc (28), Col-X (68), Col-IX (69), Bmp6 (B. Houston), PTHrP (70), PTH/PTHrP receptor (59), and rat PTH/PTHrP receptor (71).

(49.) T. F. Linsenmayer et al., Development 111, 191 (1991).

(50.) D. M. Kingsley, Trends Genet. 10, 16 (1994).

(51.) BMP expression: Because members of the Bmps/dpp family are often induced by Hedgehog proteins, we also looked at the expression of Bmp-2, Bmp-4, Bmp-5, and Bmp-7. All were expressed in the perichondrium as described (50); however, none of their expression domains correlated with the domain of Ihh expression.

(52.) Weigert-Safranin staining: 16-mu m paraffin sections of chicken wings were fixed in Bouins fixative and stained with a series of Weigert hematoxylin, fast green, and safranin (53.) L. J. Suva et al., Science 237, 893 (1987).

(54.) A. Broadus and A. Stewart, in The Parathyroids, J. Bilezikiaan, M. Levine, R. Marcus, Eds. (Raven, New York, 1994), pp. 259–294.

(55.) K. Lee, J. D. Deeds, G. V. Segre, Endocrinology 136, 453 (1995).

(56.) K. Lee et al., in preparation.

(57.) H. Juppner et al., Science 254, 1024 (1991).

(58.) B. Lanske et al., ibid. 273, 663 (1996).

(59.) PTH/PTHrP receptor probe: pRP—R1/4, corresponding to amino acids 219 to 454 of PTH/PTHrP receptor, was amplified from reverse-transcribed RNA of day 8 chicken limbs and subcloned into pBluescript SK–. Degenerate primers GACGGATCC(CA)GIAA(CT)TA(CT)-AT(CTA)CA(CT)ATGCA and GACGAATTC(TC)TC(AG)TA(AG)TGCAT(TC)TGIAC-(TC)TGCCA were based on the human, mouse, rat, pig, opossum, and Xenopus cDNA sequences. Polymerase chain reaction (PCR) conditions: 5 min at 94 degrees C., 30 cycles of 30 s at 94 degrees C., 30 s at 55 degrees C., and 30 s at 72 degrees C. followed by a final extension of 5 min at 72 degrees C. Sequence analysis revealed that the resulting probe pRP—R1/4 shows highest homology to the opossum PTH/PTHrP receptor cDNA.

(60.) Mouse hind limb cultures: Hind limbs of E16.5 fetuses were severed at mid-femur and stripped of skin. They were then placed on a filter paper (pore size, 0.8 mu m) on a wire mesh in a Falcon organ tissue culture dish, and 1 ml of BGJb (Gibco BRL) medium was added. The hind limbs, which lay at the air-fluid interface, were cultured at 37 degrees C. in a humidified atmosphere of 95% air-5% $CO_2$ with daily changes of medium. The hind limbs were treated with either 10 to 7 M human PTHrP (1–34), recombinant mouse Shh (5 mu g/ml), or vehicle (BGJb) medium containing 0.1% bovine serum albumin) alone from day 2 for 4 days. The samples were never exposed to serum. At the termination of culture, the hind limbs were fixed by 10% formalin in phosphate-buffered saline.

(61.) F. M. Ausubel et al., Current Protocols in Molecular Biology (Greene and Wiley Interscience, New York, 1989).

(62.) G. M. Church and W. Gilbert, Proc. Natl. Acad. Sci. U.S.A. 81, 1991 (1984).

(63.) D. M. Fekete and C. L. Cepko, Mol. Cell. Biol. 13, 2604 (1993).

(64.) Proc. Natl. Acad. Sci. U.S.A. 90, 2350 (1993).

(65.) S. H. Hughes, J. J. Greenhouse, C. J. Petropoulos, P. Suprave, J. Virol. 61, 3004 (1987).

(66.) L. Tessarollo, L. Nagarajan, L. F. Parada, Development 115, 11 (1992).

(67.) V. Marigo et al., Genomics 28, 44 (1995).

(68.) P. LuValle, Y. Ninomiya, N. D. Rosenblum, B. R. Olsen, J. Biol. Chem. 263, 18378 (1988).

(69.) I. Nishimura, Y. Muragaki, B. R. Olsen, ibid. 264, 20033 (1989).

(70.) M. A. Thiede and S. J. Rutledge, Nucleic Acids Res. 18, 3062 (1990).

(71.) A. B. Abou-Samra et al., Adv. Nephrol. Necker Hosp. 23, 247 (1994).

(72.) A. Vortkamp et al., data not shown.

(73.) Our model suggests that PTHrP represses chondrocyte differentiation, acting on prehypertrophic cells just before the onset of Ihh expression. However, the inhibitory PTHrP signal may also act, to some extent, on the proliferating chondrocytes before the prehypertrophic stage. In the mouse, both antibodies to the receptor and PTH-binding studies suggest that a very low level of PTH/PTHrP receptor may be present on the surface of proliferating cartilage cells even though the levels of PTH/PTHrP receptor mRNA are too low to be detected (72).

All of the above-cited references and publications are hereby incorporated by reference.

Equivalents

Those skilled in the art will recognize, or be able to ascertain, by no more than routine experimentation, many equivalents of the specific embodiments of the invention described herein. Such equivalents are intended to be encompassed by the following claims.

We claim:

1. A method for promoting proliferation of a chondrocytic cell comprising contacting the cell with an amount of a hedgehog therapeutic effective to promote proliferation of the cell, wherein said hedgehog therapeutic comprises a polypeptide which includes an amino acid sequence at least 80% identical to at least one of SEQ ID NO: 10, SEQ ID NO: 12, SEQ ID NO: 13, SEQ ID NO: 14, SEQ ID NO: 15, SEQ ID NO: 16, or at least 80% identical to a 19 kDa N-terminal fragment thereof and wherein said polypeptide which includes said amino acid sequence binds to a patched polypeptide and promotes hedgehog signal transduction.

2. The method of claim 1, wherein said hedgehog therapeutic increases the rate of proliferation of the cell.

3. The method of claim 1, wherein the cell is in culture, and said hedgehog therapeutic is provided as a cell culture additive.

4. The method of claim 1, wherein the cell is in an animal and said hedgehog therapeutic is administered to the animal as a therapeutic composition.

5. The method of claim 1, wherein contacting the chondrocytic cell with an effective amount of said hedgehog therapeutic improves the rate of survival of the chondrocytic cell.

6. The method of claim 1, wherein said polypeptide comprises an amino acid sequence encoded by a nucleic acid at least 80% identical to at least one of SEQ ID NO: 1, SEQ ID NO: 3, SEQ ID NO: 4, SEQ ID NO: 5, SEQ ID NO: 6, or SEQ ID NO: 7, and wherein said polypeptide binds to a patched polypeptide and promotes hedgehog signal transduction.

7. The method of claim 1, wherein said polypeptide comprises an amino acid sequence encoded by a nucleic acid at least 90% identical to at least one of SEQ ID NO: 1, SEQ ID NO: 3, SEQ ID NO: 4, SEQ ID NO: 5, SEQ ID NO: 6, or SEQ ID NO: 7, and wherein said polypeptide binds to a patched polypeptide and promotes hedgehog signal transduction.

8. The method of claim 1, wherein said polypeptide comprises an amino acid sequence encoded by a nucleic acid at least 95% identical to at least one of SEQ ID NO: 1, SEQ ID NO: 3, SEQ ID NO: 4, SEQ ID NO: 5, SEQ ID NO: 6, or SEQ ID NO: 7, and wherein said polypeptide binds to a patched polypeptide and promotes hedgehog signal transduction.

9. The method of claim 1, wherein said polypeptide comprises an amino acid sequence encoded by a nucleic acid at least 98% identical to at least one of SEQ ID NO: 1, SEQ ID NO: 3, SEQ ID NO: 4, SEQ ID NO: 5, SEQ ID NO: 6, or SEQ ID NO: 7, and wherein said polypeptide binds to a patched polypeptide and promotes hedgehog signal transduction.

10. The method of claim 1, wherein said polypeptide comprises an amino acid sequence encoded by a nucleic acid identical to SEQ ID NO: 1, SEQ ID NO: 3, SEQ ID NO: 4, SEQ ID NO: 5, SEQ ID NO: 6, or SEQ ID NO: 7, and wherein said polypeptide binds to a patched polypeptide and promotes hedgehog signal transduction.

11. The method of claim 1, wherein said polypeptide is encoded by a nucleic acid which hybridizes under stringent conditions, including a wash step of 0.2×SSC at 65° C., to a nucleic acid sequence designated in at least one of SEQ ID NO: 1, SEQ ID NO: 3, SEQ ID NO: 4, SEQ ID NO: 5, SEQ ID NO: 6, or SEQ ID NO: 7, and wherein said polypeptide binds to a patched polypeptide and promotes hedgehog signal transduction.

12. The method of claim 1, wherein said polypeptide comprises an amino acid sequence at least 90% identical to at least one of SEQ ID NO: 10, SEQ ID NO: 12, SEQ ID NO: 13, SEQ ID NO: 14, SEQ ID NO: 15, SEQ ID NO: 16, or at least 90% identical to a 19 kDa N-terminal fragment thereof, and wherein said polypeptide binds to a patched polypeptide and promotes hedgehog signal transduction.

13. The method of claim 1, wherein said polypeptide comprises an amino acid sequence at least 95% identical to at least one of SEQ ID NO: 10, SEQ ID NO: 12, SEQ ID NO: 13, SEQ ID NO: 14, SEQ ID NO: 15, SEQ ID NO: 16, or at least 95% identical to a 19 kDa N-terminal fragment thereof, and wherein said polypeptide binds to a patched polypeptide and promotes hedgehog signal transduction.

14. The method of claim 1, wherein said polypeptide comprises an amino acid sequence at least 98% identical to at least one of SEQ ID NO: 10, SEQ ID NO: 12, SEQ ID NO: 13, SEQ ID NO: 14, SEQ ID NO: 15, SEQ ID NO: 16, or at least 98% identical to a 19 kDa N-terminal fragment thereof, and wherein said polypeptide binds to a patched polypeptide and promotes hedgehog signal transduction.

15. The method of claim 1, wherein said polypeptide comprises an amino acid sequence identical to SEQ ID NO: 10, SEQ ID NO: 12, SEQ ID NO: 13, SEQ ID NO: 14, SEQ ID NO: 15, SEQ ID NO: 16, or a 19 kDa N-terminal fragment thereof, and wherein said polypeptide binds to a patched polypeptide and promotes hedgehog signal transduction.

16. The method of claim 1, wherein said polypeptide comprises: a) amino acid residues 24–197 of SEQ ID NO: 15 or b) amino acid residues 28–202 of SEQ ID NO: 16.

17. The method of claim 1, wherein said polypeptide comprises: a) amino acid residues 1–168 of SEQ ID NO: 21, b) amino acid residues 24–193 of SEQ ID NO: 15, c) amino acid residues 25–193 of SEQ ID NO: 13, or d) amino acid residues 28–197 of SEQ ID NO: 12.

18. The method of claim 5, wherein said polypeptide comprises an amino acid sequence encoded by a non-synthetic vertebrate hedgehog gene.

19. The method of claim 18, wherein said hedgehog gene is a mammalian hedgehog gene.

20. The method of claim 19, wherein said hedgehog gene is a human hedgehog gene.

21. The method of claim 5, wherein said polypeptide comprises an amino acid sequence represented by the general formula SEQ ID NO: 21.

22. A method for promoting survival of a chondrocytic cell comprising contacting the cell with an amount of a hedgehog therapeutic effective to promote survival of the cell, wherein said hedgehog therapeutic comprises a polypeptide which includes an amino acid sequence at least 80% identical to at least one of SEQ ID NO: 10, SEQ ID NO: 12, SEQ ID NO: 13, SEQ ID NO: 14, SEQ ID NO: 15, SEQ 1) NO 16, or at least 80% identical to a 19 kDa N-terminal fragment thereof, and wherein said polypeptide which includes said amino acid sequence binds to a patched polypeptide and promotes hedgehog signal transduction.

23. The method of claim 22, wherein said polypeptide comprises an amino acid sequence encoded by a nucleic acid at least 80% identical to at least one of SEQ ID NO: 1, SEQ ID NO: 3, SEQ ID NO: 4, SEQ ID NO: 5, SEQ ID NO: 6, or SEQ ID NO: 7, and wherein said polypeptide which includes said amino acid sequence binds to a patched polypeptide and promotes hedgehog signal transduction.

24. The method of claim 22, wherein said polypeptide comprises an amino acid sequence encoded by a nucleic acid at least 90% identical to at least one of SEQ ID NO: 1, SEQ ID NO: 3, SEQ ID NO: 4, SEQ ID NO: 5, SEQ ID NO: 6, or SEQ ID NO: 7, and wherein said polypeptide which includes said amino acid sequence binds to a patched polypeptide and promotes hedgehog signal transduction.

25. The method claim 22, wherein said polypeptide comprises an amino acid sequence encoded by a nucleic acid at least 95% identical to at least one of SEQ ID NO: 1, SEQ ID NO: 3, SEQ ID NO: 4, SEQ ID NO: 5, SEQ ID NO: 6, or SEQ ID NO: 7, and wherein said polypeptide which includes said amino acid sequence binds to a patched polypeptide and promotes hedgehog signal transduction.

26. The method of claim 22, wherein said polypeptide comprises an amino acid sequence encoded by a nucleic acid at least 98% identical to at least one of SEQ ID NO: 1, SEQ ID NO: 3, SEQ ID NO: 4, SEQ ID NO: 5, SEQ ID NO: 6, or SEQ D) NO: 7, and wherein said polypeptide which includes said amino acid sequence binds to a patched polypeptide and promotes hedgehog signal transduction.

27. The method of claim 22, wherein said polypeptide comprises an amino acid sequence encoded by a nucleic acid identical to SEQ ID NO: 1, SEQ ID NO: 3, SEQ ID NO: 4, SEQ ID NO: 5, SEQ ID NO: 6, or SEQ ID NO: 7, and wherein said polypeptide which includes said amino acid sequence binds to a patched polypeptide and promotes hedgehog signal transduction.

28. The method of claim 22, wherein said polypeptide is encoded by a nucleic acid which hybridizes under stringent conditions, including a wash step of 0.2×SSC at 65° C., to a nucleic acid sequence designated in at least one of SEQ ID NO: 1, SEQ ID NO: 3, SEQ ID NO: 4, SEQ ID NO: 5, SEQ ID NO: 6, or SEQ ID NO: 7, and wherein said polypeptide which includes said amino acid sequence binds to a patched polypeptide and promotes hedgehog signal transduction.

29. The method of claim 22, wherein said polypeptide comprises an amino acid sequence at least 90% identical to at least one of SEQ ID NO: 10, SEQ ID NO: 12, SEQ ID NO: 13, SEQ ID NO: 14, SEQ ID NO: 15, SEQ ID NO 16, or at least 90% identical to a 19 kDa N-terminal fragment thereof, and wherein said polypeptide which includes said amino acid sequence binds to a patched polypeptide and promotes hedgehog signal trasduction.

30. The method of claim 22, wherein said polypeptide comprises an amino acid sequence at least 95% identical to at least one of SEQ ID NO: 10, SEQ ID NO: 12, SEQ ID NO: 13, SEQ ID NO: 14, SEQ ID NO: 15, SEQ ID NO 16, or at least 95% identical to a 19 kDa N-terminal fragment thereof, and wherein said polypeptide which includes said amino acid sequence binds to a patched polypeptide and promotes hedgehog signal transduction.

31. The method of claim 22, wherein said polypeptide comprises an amino acid sequence at least 98% identical to at least one of SEQ ID NO: 10, SEQ ID NO: 12, SEQ ID NO: 13, SEQ 1) NO: 14, SEQ ID NO: 15, SEQ ID NO 16, or at least 98% identical to a 19 kDa N-terminal fragment thereof, and wherein said polypeptide which includes said amino acid sequence binds to a patched polypeptide and promotes hedgehog signal transduction.

32. The method of claim 22, wherein said polypeptide comprises an amino acid sequence identical to SEQ ID NO: 10, SEQ ID NO: 12, SEQ ID NO: 13, SEQ ID NO: 14, SEQ ID NO: 15, SEQ ID NO 16, or a 19 kDa N-terminal fragment thereof, and wherein said polypeptide which includes said amino acid sequence binds to a patched polypeptide and promotes hedgehog signal transduction.

33. The method of claim 22, wherein said polypeptide comprises: a) amino acid residues 24–197 of SEQ ID NO: 15 or b) amino acid residues 28–202 of SEQ ID NO: 16.

34. The method of claim 22, wherein said polypeptide comprises: a) amino acid residues 1–168 of SEQ ID NO: 21, b) amino acid residues 24–193 of SEQ ID NO: 15, c) amino acid residues 25–193 of SEQ ID NO: 13, or d) amino acid residues 28–197 of SEQ ID NO: 12.

35. A method for promoting proliferation of a chondrocytic cell comprising contacting the cell with an amount of a hedgehog therapeutic effective to promote proliferation of the cell, wherein said hedgehog therapeutic comprises a polypeptide including an amino acid sequence encoded by a nucleic acid that hybridizes under stringent conditions, including a wash step of 0.2×SSC at 65° C., to at least one of SEQ ID NO: 1, SEQ ID NO: 3, SEQ ID NO: 4, SEQ ID NO: 5, SEQ ID NO: 6, or SEQ ID NO: 7, and wherein said polypeptide which includes said amino acid sequence binds to a patched polypeptide and promotes hedgehog signal transduction.

36. A method of promoting survival of a chondrocytic cell comprising contacting the cell with an amount of a hedgehog therapeutic effective to promote survival of the cell, wherein said hedgehog therapeutic comprises a polypeptide including an amino acid sequence encoded by a nucleic acid that hybridizes under stringent conditions, including a wash step of 0.2×SSC at 65° C., to at least one of SEQ ID NO: 1, SEQ ID NO: 3, SEQ ID NO: 4, SEQ ID NO: 5, SEQ ID NO: 6, or SEQ ID NO: 7, and wherein said polypeptide which includes said amino acid sequence binds to a patched polypeptide and promotes hedgehog signal transduction.

37. A method for promoting proliferation of a chondrocytic cell comprising contacting the cell with an amount of a hedgehog therapeutic effective to promote proliferation of the cell, wherein said hedgehog therapeutic comprises a polypeptide including an amino acid sequence identical to SEQ ID NO: 21, and wherein said polypeptide which includes said amino acid sequence binds to a patched polypeptide and promotes hedgehog signal transduction.

38. A method of promoting survival of a chondrocytic cell comprising contacting the cell with an amount of a hedgehog therapeutic effective to promote survival of the cell, wherein said hedgehog therapeutic comprises a polypeptide including an amino acid sequence identical to SEQ ID NO: 21, and wherein said polypeptide which includes said amino acid sequence binds to a patched polypeptide and promotes hedgehog signal transduction.

* * * * *

UNITED STATES PATENT AND TRADEMARK OFFICE
CERTIFICATE OF CORRECTION

PATENT NO. : 6,884,775 B1
DATED : April 26, 2005
INVENTOR(S) : Tabin et al.

It is certified that error appears in the above-identified patent and that said Letters Patent is hereby corrected as shown below:

Column 191,
Line 61, insert -- , -- after the word "thereof".

Column 193,
Line 17, "polypeptidc" should be -- polypeptide --.

Column 194,
Line 19, "SEQ 1) NO 16" should be -- SEQ ID NO: 16 --.
Line 37, "The method claim 22," should be -- The method of claim 22, --.
Line 48, "SEQ D)" should be -- SEQ ID --.

Column 195,
Lines 2, 10, "SEQ ID NO 16," should be -- SEQ ID NO: 16, --.
Line 6, "trasduction" should be -- transduction --.
Lines 18 and 26, "SEQ ID NO 16" should be -- SEQ ID NO: 16 --.
Line 18, "SEQ 1) NO: 14," should be -- SEQ ID NO: 14, --.

Signed and Sealed this

Eighth Day of November, 2005

JON W. DUDAS
*Director of the United States Patent and Trademark Office*

SEQUENCE LISTING (1) GENERAL INFORMATION:

(iii) NUMBER OF SEQUENCES: 49

(2) INFORMATION FOR SEQ ID NO:1:

(i) SEQUENCE CHARACTERISTICS:
        (A) LENGTH: 1277 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1275

(xi) SEQUENCE DESCRIPTION: SEQ ID NO:1:

```
ATG GTC GAA ATG CTG CTG TTG ACA AGA ATT CTC TTG GTG GGC TTC ATC        48
Met Val Glu Met Leu Leu Leu Thr Arg Ile Leu Leu Val Gly Phe Ile
  1               5                  10                  15

TGC GCT CTT TTA GTC TCC TCT GGG CTG ACT TGT GGA CCA GGC AGG GGC        96
Cys Ala Leu Leu Val Ser Ser Gly Leu Thr Cys Gly Pro Gly Arg Gly
                 20                  25                  30

ATT GGA AAA AGG AGG CAC CCC AAA AAG CTG ACC CCG TTA GCC TAT AAG       144
Ile Gly Lys Arg Arg His Pro Lys Lys Leu Thr Pro Leu Ala Tyr Lys
             35                  40                  45

CAG TTT ATT CCC AAT GTG GCA GAG AAG ACC CTA GGG GCC AGT GGA AGA       192
Gln Phe Ile Pro Asn Val Ala Glu Lys Thr Leu Gly Ala Ser Gly Arg
 50                  55                  60

TAT GAA GGG AAG ATC ACA AGA AAC TCC GAG AGA TTT AAA GAA CTA ACC       240
Tyr Glu Gly Lys Ile Thr Arg Asn Ser Glu Arg Phe Lys Glu Leu Thr
 65                  70                  75                  80

CCA AAT TAC AAC CCT GAC ATT ATT TTT AAG GAT GAA GAG AAC ACG GGA       288
Pro Asn Tyr Asn Pro Asp Ile Ile Phe Lys Asp Glu Glu Asn Thr Gly
                 85                  90                  95

GCT GAC AGA CTG ATG ACT CAG CGC TGC AAG GAC AAG CTG AAT GCC CTG       336
Ala Asp Arg Leu Met Thr Gln Arg Cys Lys Asp Lys Leu Asn Ala Leu
            100                 105                 110

GCG ATC TCG GTG ATG AAC CAG TGG CCC GGG GTG AAG CTG CGG GTG ACC       384
Ala Ile Ser Val Met Asn Gln Trp Pro Gly Val Lys Leu Arg Val Thr
        115                 120                 125

GAG GGC TGG GAC GAG GAT GGC CAT CAC TCC GAG GAA TCG CTG CAC TAC       432
Glu Gly Trp Asp Glu Asp Gly His His Ser Glu Glu Ser Leu His Tyr
    130                 135                 140

GAG GGT CGC GCC GTG GAC ATC ACC ACG TCG GAT CGG GAC CGC AGC AAG       480
Glu Gly Arg Ala Val Asp Ile Thr Thr Ser Asp Arg Asp Arg Ser Lys
145                 150                 155                 160

TAC GGA ATG CTG GCC CGC CTC GCC GTC GAG GCC GGC TTC GAC TGG GTC       528
Tyr Gly Met Leu Ala Arg Leu Ala Val Glu Ala Gly Phe Asp Trp Val
                165                 170                 175

TAC TAC GAG TCC AAG GCG CAC ATC CAC TGC TCC GTC AAA GCA GAA AAC       576
Tyr Tyr Glu Ser Lys Ala His Ile His Cys Ser Val Lys Ala Glu Asn
            180                 185                 190

TCA GTG GCA GCG AAA TCA GGA GGC TGC TTC CCT GGC TCA GCC ACA GTG       624
Ser Val Ala Ala Lys Ser Gly Gly Cys Phe Pro Gly Ser Ala Thr Val
        195                 200                 205

CAC CTG GAG CAT GGA GGC ACC AAG CTG GTG AAG GAC CTG AGC CCT GGG       672
His Leu Glu His Gly Gly Thr Lys Leu Val Lys Asp Leu Ser Pro Gly
    210                 215                 220
```

```
GAC CGC GTG CTG GCT GCT GAC GCG GAC GGC CGG CTG CTC TAC AGT GAC      720
Asp Arg Val Leu Ala Ala Asp Ala Asp Gly Arg Leu Leu Tyr Ser Asp
225                 230                 235                 240

TTC CTC ACC TTC CTC GAC CGG ATG GAC AGC TCC CGA AAG CTC TTC TAC      768
Phe Leu Thr Phe Leu Asp Arg Met Asp Ser Ser Arg Lys Leu Phe Tyr
                245                 250                 255

GTC ATC GAG ACG CGG CAG CCC CGG GCC CGG CTG CTA CTG ACG GCG GCC      816
Val Ile Glu Thr Arg Gln Pro Arg Ala Arg Leu Leu Leu Thr Ala Ala
            260                 265                 270

CAC CTG CTC TTT GTG GCC CCC CAG CAC AAC CAG TCG GAG GCC ACA GGG      864
His Leu Leu Phe Val Ala Pro Gln His Asn Gln Ser Glu Ala Thr Gly
        275                 280                 285

TCC ACC AGT GGC CAG GCG CTC TTC GCC AGC AAC GTG AAG CCT GGC CAA      912
Ser Thr Ser Gly Gln Ala Leu Phe Ala Ser Asn Val Lys Pro Gly Gln
290                 295                 300

CGT GTC TAT GTG CTG GGC GAG GGC GGG CAG CAG CTG CTG CCG GCG TCT      960
Arg Val Tyr Val Leu Gly Glu Gly Gly Gln Gln Leu Leu Pro Ala Ser
305                 310                 315                 320

GTC CAC AGC GTC TCA TTG CGG GAG GAG GCG TCC GGA GCC TAC GCC CCA     1008
Val His Ser Val Ser Leu Arg Glu Glu Ala Ser Gly Ala Tyr Ala Pro
                325                 330                 335

CTC ACC GCC CAG GGC ACC ATC CTC ATC AAC CGG GTG TTG GCC TCC TGC     1056
Leu Thr Ala Gln Gly Thr Ile Leu Ile Asn Arg Val Leu Ala Ser Cys
            340                 345                 350

TAC GCC GTC ATC GAG GAG CAC AGT TGG GCC CAT TGG GCC TTC GCA CCA     1104
Tyr Ala Val Ile Glu Glu His Ser Trp Ala His Trp Ala Phe Ala Pro
        355                 360                 365

TTC CGC TTG GCT CAG GGG CTG CTG GCC GCC CTC TGC CCA GAT GGG GCC     1152
Phe Arg Leu Ala Gln Gly Leu Leu Ala Ala Leu Cys Pro Asp Gly Ala
    370                 375                 380

ATC CCT ACT GCC GCC ACC ACC ACC ACT GGC ATC CAT TGG TAC TCA CGG     1200
Ile Pro Thr Ala Ala Thr Thr Thr Thr Gly Ile His Trp Tyr Ser Arg
385                 390                 395                 400

CTC CTC TAC CGC ATC GGC AGC TGG GTG CTG GAT GGT GAC GCG CTG CAT     1248
Leu Leu Tyr Arg Ile Gly Ser Trp Val Leu Asp Gly Asp Ala Leu His
                405                 410                 415

CCG CTG GGC ATG GTG GCA CCG GCC AGC TG                             1277
Pro Leu Gly Met Val Ala Pro Ala Ser
            420                 425

(2) INFORMATION FOR SEQ ID NO:2:

(i) SEQUENCE CHARACTERISTICS:
        (A) LENGTH: 1190 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1188

(xi) SEQUENCE DESCRIPTION: SEQ ID NO:2:

ATG GCT CTG CCG GCC AGT CTG TTG CCC CTG TGC TGC TTG GCA CTC TTG       48
Met Ala Leu Pro Ala Ser Leu Leu Pro Leu Cys Cys Leu Ala Leu Leu
1               5                   10                  15

GCA CTA TCT GCC CAG AGC TGC GGG CCG GGC CGA GGA CCG GTT GGC CGG       96
Ala Leu Ser Ala Gln Ser Cys Gly Pro Gly Arg Gly Pro Val Gly Arg
            20                  25                  30

CGG CGT TAT GTG CGC AAG CAA CTT GTG CCT CTG CTA TAC AAG CAG TTT      144
```

-continued

```
                Arg Arg Tyr Val Arg Lys Gln Leu Val Pro Leu Leu Tyr Lys Gln Phe
                        35                  40                  45

GTG CCC AGT ATG CCC GAG CGG ACC CTG GGC GCG AGT GGG CCA GCG GAG           192
Val Pro Ser Met Pro Glu Arg Thr Leu Gly Ala Ser Gly Pro Ala Glu
         50                  55                  60

GGG AGG GTA ACA AGG GGG TCG GAG CGC TTC CGG GAC CTC GTA CCC AAC           240
Gly Arg Val Thr Arg Gly Ser Glu Arg Phe Arg Asp Leu Val Pro Asn
 65                  70                  75                  80

TAC AAC CCC GAC ATA ATC TTC AAG GAT GAG GAG AAC AGC GGC GCA GAC           288
Tyr Asn Pro Asp Ile Ile Phe Lys Asp Glu Glu Asn Ser Gly Ala Asp
                     85                  90                  95

CGC CTG ATG ACA GAG CGT TGC AAA GAG CGG GTG AAC GCT CTA GCC ATC           336
Arg Leu Met Thr Glu Arg Cys Lys Glu Arg Val Asn Ala Leu Ala Ile
                100                 105                 110

GCG GTG ATG AAC ATG TGG CCC GGA GTA CGC CTA CGT GTG ACT GAA GGC           384
Ala Val Met Asn Met Trp Pro Gly Val Arg Leu Arg Val Thr Glu Gly
            115                 120                 125

TGG GAC GAG GAC GGC CAC CAC GCA CAG GAT TCA CTC CAC TAC GAA GGC           432
Trp Asp Glu Asp Gly His His Ala Gln Asp Ser Leu His Tyr Glu Gly
        130                 135                 140

CGT GCC TTG GAC ATC ACC ACG TCT GAC CGT GAC CGT AAT AAG TAT GGT           480
Arg Ala Leu Asp Ile Thr Thr Ser Asp Arg Asp Arg Asn Lys Tyr Gly
145                 150                 155                 160

TTG TTG GCG CGC CTA GCT GTG GAA GCC GGA TTC GAC TGG GTC TAC TAC           528
Leu Leu Ala Arg Leu Ala Val Glu Ala Gly Phe Asp Trp Val Tyr Tyr
                    165                 170                 175

GAG TCC CGC AAC CAC ATC CAC GTA TCG GTC AAA GCT GAT AAC TCA CTG           576
Glu Ser Arg Asn His Ile His Val Ser Val Lys Ala Asp Asn Ser Leu
                180                 185                 190

GCG GTC CGA GCC GGA GGC TGC TTT CCG GGA AAT GCC ACG GTG CGC TTG           624
Ala Val Arg Ala Gly Gly Cys Phe Pro Gly Asn Ala Thr Val Arg Leu
            195                 200                 205

CGG AGC GGC GAA CGG AAG GGG CTG AGG GAA CTA CAT CGT GGT GAC TGG           672
Arg Ser Gly Glu Arg Lys Gly Leu Arg Glu Leu His Arg Gly Asp Trp
        210                 215                 220

GTA CTG GCC GCT GAT GCA GCG GGC CGA GTG GTA CCC ACG CCA GTG CTG           720
Val Leu Ala Ala Asp Ala Ala Gly Arg Val Val Pro Thr Pro Val Leu
225                 230                 235                 240

CTC TTC CTG GAC CGG GAT CTG CAG CGC CGC GCC TCG TTC GTG GCT GTG           768
Leu Phe Leu Asp Arg Asp Leu Gln Arg Arg Ala Ser Phe Val Ala Val
                    245                 250                 255

GAG ACC GAG CGG CCT CCG CGC AAA CTG TTG CTC ACA CCC TGG CAT CTG           816
Glu Thr Glu Arg Pro Pro Arg Lys Leu Leu Leu Thr Pro Trp His Leu
                260                 265                 270

GTG TTC GCT GCT CGC GGG CCA GCG CCT GCT CCA GGT GAC TTT GCA CCG           864
Val Phe Ala Ala Arg Gly Pro Ala Pro Ala Pro Gly Asp Phe Ala Pro
            275                 280                 285

GTG TTC GCG CGC CGC TTA CGT GCT GGC GAC TCG GTG CTG GCT CCC GGC           912
Val Phe Ala Arg Arg Leu Arg Ala Gly Asp Ser Val Leu Ala Pro Gly
        290                 295                 300

GGG GAC GCG CTC CAG CCG GCG CGC GTA GCC CGC GTG GCG CGC GAG GAA           960
Gly Asp Ala Leu Gln Pro Ala Arg Val Ala Arg Val Ala Arg Glu Glu
305                 310                 315                 320

GCC GTG GGC GTG TTC GCA CCG CTC ACT GCG CAC GGG ACG CTG CTG GTC          1008
Ala Val Gly Val Phe Ala Pro Leu Thr Ala His Gly Thr Leu Leu Val
                    325                 330                 335

AAC GAC GTC CTC GCC TCC TGC TAC GCG GTT CTA GAG AGT CAC CAG TGG          1056
Asn Asp Val Leu Ala Ser Cys Tyr Ala Val Leu Glu Ser His Gln Trp
                340                 345                 350
```

```
GCC CAC CGC GCC TTC GCC CCT TTG CGG CTG CTG CAC GCG CTC GGG GCT     1104
Ala His Arg Ala Phe Ala Pro Leu Arg Leu Leu His Ala Leu Gly Ala
        355                 360                 365

CTG CTC CCT GGG GGT GCA GTC CAG CCG ACT GGC ATG CAT TGG TAC TCT     1152
Leu Leu Pro Gly Gly Ala Val Gln Pro Thr Gly Met His Trp Tyr Ser
370                 375                 380

CGC CTC CTT TAC CGC TTG GCC GAG GAG TTA ATG GGC TG                  1190
Arg Leu Leu Tyr Arg Leu Ala Glu Glu Leu Met Gly
385                 390                 395
```

(2) INFORMATION FOR SEQ ID NO:3:

(i) SEQUENCE CHARACTERISTICS:
        (A) LENGTH: 1281 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1233

(xi) SEQUENCE DESCRIPTION: SEQ ID NO:3:

```
ATG TCT CCC GCC TGG CTC CGG CCC CGA CTG CGG TTC TGT CTG TTC CTG     48
Met Ser Pro Ala Trp Leu Arg Pro Arg Leu Arg Phe Cys Leu Phe Leu
1               5                   10                  15

CTG CTG CTG CTT CTG GTG CCG GCG GCG CGG GGC TGC GGG CCG GGC CGG     96
Leu Leu Leu Leu Leu Val Pro Ala Ala Arg Gly Cys Gly Pro Gly Arg
            20                  25                  30

GTG GTG GGC AGC CGC CGG AGG CCG CCT CGC AAG CTC GTG CCT CTT GCC    144
Val Val Gly Ser Arg Arg Arg Pro Pro Arg Lys Leu Val Pro Leu Ala
        35                  40                  45

TAC AAG CAG TTC AGC CCC AAC GTG CCG GAG AAG ACC CTG GGC GCC AGC    192
Tyr Lys Gln Phe Ser Pro Asn Val Pro Glu Lys Thr Leu Gly Ala Ser
    50                  55                  60

GGG CGC TAC GAA GGC AAG ATC GCG CGC AGC TCT GAG CGC TTC AAA GAG    240
Gly Arg Tyr Glu Gly Lys Ile Ala Arg Ser Ser Glu Arg Phe Lys Glu
65                  70                  75                  80

CTC ACC CCC AAC TAC AAT CCC GAC ATC ATC TTC AAG GAC GAG GAG AAC    288
Leu Thr Pro Asn Tyr Asn Pro Asp Ile Ile Phe Lys Asp Glu Glu Asn
                85                  90                  95

ACG GGT GCC GAC CGC CTC ATG ACC CAG CGC TGC AAG GAC CGT CTG AAC    336
Thr Gly Ala Asp Arg Leu Met Thr Gln Arg Cys Lys Asp Arg Leu Asn
            100                 105                 110

TCA CTG GCC ATC TCT GTC ATG AAC CAG TGG CCT GGT GTG AAA CTG CGG    384
Ser Leu Ala Ile Ser Val Met Asn Gln Trp Pro Gly Val Lys Leu Arg
        115                 120                 125

GTG ACC GAA GGC TGG GAT GAA GAT GGC CAT CAC TCA GAG GAG TCT TTA    432
Val Thr Glu Gly Trp Asp Glu Asp Gly His His Ser Glu Glu Ser Leu
    130                 135                 140

CAC TAT GAG GGC CGC GCG GTG GAT ATC ACC ACC TCA GAC CGT GAC CGA    480
His Tyr Glu Gly Arg Ala Val Asp Ile Thr Thr Ser Asp Arg Asp Arg
145                 150                 155                 160

AAT AAG TAT GGA CTG CTG GCG CGC TTA GCA GTG GAG GCC GGC TTC GAC    528
Asn Lys Tyr Gly Leu Leu Ala Arg Leu Ala Val Glu Ala Gly Phe Asp
                165                 170                 175

TGG GTG TAT TAC GAG TCC AAG GCC CAC GTG CAT TGC TCT GTC AAG TCT    576
Trp Val Tyr Tyr Glu Ser Lys Ala His Val His Cys Ser Val Lys Ser
            180                 185                 190

GAG CAT TCG GCC GCT GCC AAG ACA GGT GGC TGC TTT CCT GCC GGA GCC    624
Glu His Ser Ala Ala Ala Lys Thr Gly Gly Cys Phe Pro Ala Gly Ala
```

-continued

```
              195                 200                 205
CAG GTG CGC CTA GAG AAC GGG GAG CGT GTG GCC CTG TCA GCT GTA AAG    672
Gln Val Arg Leu Glu Asn Gly Glu Arg Val Ala Leu Ser Ala Val Lys
        210                 215                 220

CCA GGA GAC CGG GTG CTG GCC ATG GGG GAG GAT GGG ACC CCC ACC TTC    720
Pro Gly Asp Arg Val Leu Ala Met Gly Glu Asp Gly Thr Pro Thr Phe
225                 230                 235                 240

AGT GAT GTG CTT ATT TTC CTG GAC CGC GAG CCA AAC CGG CTG AGA GCT    768
Ser Asp Val Leu Ile Phe Leu Asp Arg Glu Pro Asn Arg Leu Arg Ala
            245                 250                 255

TTC CAG GTC ATC GAG ACT CAG GAT CCT CCG CGT CGG CTG GCG CTC ACG    816
Phe Gln Val Ile Glu Thr Gln Asp Pro Pro Arg Arg Leu Ala Leu Thr
                260                 265                 270

CCT GCC CAC CTG CTC TTC ATT GCG GAC AAT CAT ACA GAA CCA GCA GCC    864
Pro Ala His Leu Leu Phe Ile Ala Asp Asn His Thr Glu Pro Ala Ala
                    275                 280                 285

CAC TTC CGG GCC ACA TTT GCC AGC CAT GTG CAA CCA GGC CAA TAT GTG    912
His Phe Arg Ala Thr Phe Ala Ser His Val Gln Pro Gly Gln Tyr Val
    290                 295                 300

CTG GTA TCA GGG GTA CCA GGC CTC CAG CCT GCT CGG GTG GCA GCT GTC    960
Leu Val Ser Gly Val Pro Gly Leu Gln Pro Ala Arg Val Ala Ala Val
305                 310                 315                 320

TCC ACC CAC GTG GCC CTT GGG TCC TAT GCT CCT CTC ACA AGG CAT GGG   1008
Ser Thr His Val Ala Leu Gly Ser Tyr Ala Pro Leu Thr Arg His Gly
            325                 330                 335

ACA CTT GTG GTG GAG GAT GTG GTG GCC TCC TGC TTT GCA GCT GTG GCT   1056
Thr Leu Val Val Glu Asp Val Val Ala Ser Cys Phe Ala Ala Val Ala
                340                 345                 350

GAC CAC CAT CTG GCT CAG TTG GCC TTC TGG CCC CTG CGA CTG TTT CCC   1104
Asp His His Leu Ala Gln Leu Ala Phe Trp Pro Leu Arg Leu Phe Pro
                    355                 360                 365

AGT TTG GCA TGG GGC AGC TGG ACC CCA AGT GAG GGT GTT CAC TCC TAC   1152
Ser Leu Ala Trp Gly Ser Trp Thr Pro Ser Glu Gly Val His Ser Tyr
    370                 375                 380

CCT CAG ATG CTC TAC CGC CTG GGG CGT CTC TTG CTA GAA GAG AGC ACC   1200
Pro Gln Met Leu Tyr Arg Leu Gly Arg Leu Leu Leu Glu Glu Ser Thr
385                 390                 395                 400

TTC CAT CCA CTG GGC ATG TCT GGG GCA GGA AGC TGAAGGGACT CTAACCACTG  1253
Phe His Pro Leu Gly Met Ser Gly Ala Gly Ser
            405                 410

CCCTCCTGGA ACTGCTGTGC GTGGATCC                                     1281

(2) INFORMATION FOR SEQ ID NO:4:

(i) SEQUENCE CHARACTERISTICS:
        (A) LENGTH: 1313 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1311

(xi) SEQUENCE DESCRIPTION: SEQ ID NO:4:

ATG CTG CTG CTG CTG GCC AGA TGT TTT CTG GTG ATC CTT GCT TCC TCG     48
Met Leu Leu Leu Leu Ala Arg Cys Phe Leu Val Ile Leu Ala Ser Ser
  1               5                  10                  15

CTG CTG GTG TGC CCC GGG CTG GCC TGT GGG CCC GGC AGG GGG TTT GGA     96
Leu Leu Val Cys Pro Gly Leu Ala Cys Gly Pro Gly Arg Gly Phe Gly
```

```
                    20                      25                      30
AAG AGG CGG CAC CCC AAA AAG CTG ACC CCT TTA GCC TAC AAG CAG TTT    144
Lys Arg Arg His Pro Lys Lys Leu Thr Pro Leu Ala Tyr Lys Gln Phe
        35                      40                      45

ATT CCC AAC GTA GCC GAG AAG ACC CTA GGG GCC AGC GGC AGA TAT GAA    192
Ile Pro Asn Val Ala Glu Lys Thr Leu Gly Ala Ser Gly Arg Tyr Glu
    50                      55                      60

GGG AAG ATC ACA AGA AAC TCC GAA CGA TTT AAG GAA CTC ACC CCC AAT    240
Gly Lys Ile Thr Arg Asn Ser Glu Arg Phe Lys Glu Leu Thr Pro Asn
 65                      70                      75              80

TAC AAC CCC GAC ATC ATA TTT AAG GAT GAG GAA AAC ACG GGA GCA GAC    288
Tyr Asn Pro Asp Ile Ile Phe Lys Asp Glu Glu Asn Thr Gly Ala Asp
                    85                      90                      95

CGG CTG ATG ACT CAG AGG TGC AAA GAC AAG TTA AAT GCC TTG GCC ATC    336
Arg Leu Met Thr Gln Arg Cys Lys Asp Lys Leu Asn Ala Leu Ala Ile
                100                     105                     110

TCT GTG ATG AAC CAG TGG CCT GGA GTG AGG CTG CGA GTG ACC GAG GGC    384
Ser Val Met Asn Gln Trp Pro Gly Val Arg Leu Arg Val Thr Glu Gly
            115                     120                     125

TGG GAT GAG GAC GGC CAT CAT TCA GAG GAG TCT CTA CAC TAT GAG GGT    432
Trp Asp Glu Asp Gly His His Ser Glu Glu Ser Leu His Tyr Glu Gly
    130                     135                     140

CGA GCA GTG GAC ATC ACC ACG TCC GAC CGG GAC CGC AGC AAG TAC GGC    480
Arg Ala Val Asp Ile Thr Thr Ser Asp Arg Asp Arg Ser Lys Tyr Gly
145                     150                     155                 160

ATG CTG GCT CGC CTG GCT GTG GAA GCA GGT TTC GAC TGG GTC TAC TAT    528
Met Leu Ala Arg Leu Ala Val Glu Ala Gly Phe Asp Trp Val Tyr Tyr
                165                     170                     175

GAA TCC AAA GCT CAC ATC CAC TGT TCT GTG AAA GCA GAG AAC TCC GTG    576
Glu Ser Lys Ala His Ile His Cys Ser Val Lys Ala Glu Asn Ser Val
            180                     185                     190

GCG GCC AAA TCC GGC GGC TGT TTC CCG GGA TCC GCC ACC GTG CAC CTG    624
Ala Ala Lys Ser Gly Gly Cys Phe Pro Gly Ser Ala Thr Val His Leu
        195                     200                     205

GAG CAG GGC GGC ACC AAG CTG GTG AAG GAC TTA CGT CCC GGA GAC CGC    672
Glu Gln Gly Gly Thr Lys Leu Val Lys Asp Leu Arg Pro Gly Asp Arg
    210                     215                     220

GTG CTG GCG GCT GAC GAC CAG GGC CGG CTG CTG TAC AGC GAC TTC CTC    720
Val Leu Ala Ala Asp Asp Gln Gly Arg Leu Leu Tyr Ser Asp Phe Leu
225                     230                     235                 240

ACC TTC CTG GAC CGC GAC GAA GGC GCC AAG AAG GTC TTC TAC GTG ATC    768
Thr Phe Leu Asp Arg Asp Glu Gly Ala Lys Lys Val Phe Tyr Val Ile
                245                     250                     255

GAG ACG CTG GAG CCG CGC GAG CGC CTG CTG CTC ACC GCC GCG CAC CTG    816
Glu Thr Leu Glu Pro Arg Glu Arg Leu Leu Leu Thr Ala Ala His Leu
            260                     265                     270

CTC TTC GTG GCG CCG CAC AAC GAC TCG GGG CCC ACG CCC GGG CCA AGC    864
Leu Phe Val Ala Pro His Asn Asp Ser Gly Pro Thr Pro Gly Pro Ser
        275                     280                     285

GCG CTC TTT GCC AGC CGC GTG CGC CCC GGG CAG CGC GTG TAC GTG GTG    912
Ala Leu Phe Ala Ser Arg Val Arg Pro Gly Gln Arg Val Tyr Val Val
    290                     295                     300

GCT GAA CGC GGC GGG GAC CGC CGG CTG CTG CCC GCC GCG GTG CAC AGC    960
Ala Glu Arg Gly Gly Asp Arg Arg Leu Leu Pro Ala Ala Val His Ser
305                     310                     315                 320

GTG ACG CTG CGA GAG GAG GAG GCG GGC GCG TAC GCG CCG CTC ACG GCG    1008
Val Thr Leu Arg Glu Glu Glu Ala Gly Ala Tyr Ala Pro Leu Thr Ala
                325                     330                     335

CAC GGC ACC ATT CTC ATC AAC CGG GTG CTC GCC TCG TGC TAC GCT GTC    1056
```

```
His Gly Thr Ile Leu Ile Asn Arg Val Leu Ala Ser Cys Tyr Ala Val
            340                 345                 350

ATC GAG GAG CAC AGC TGG GCA CAC CGG GCC TTC GCG CCT TTC CGC CTG      1104
Ile Glu Glu His Ser Trp Ala His Arg Ala Phe Ala Pro Phe Arg Leu
            355                 360                 365

GCG CAC GCG CTG CTG GCC GCG CTG GCA CCC GCC CGC ACG GAC GGC GGG      1152
Ala His Ala Leu Leu Ala Ala Leu Ala Pro Ala Arg Thr Asp Gly Gly
            370                 375                 380

GGC GGG GGC AGC ATC CCT GCA GCG CAA TCT GCA ACG GAA GCG AGG GGC      1200
Gly Gly Gly Ser Ile Pro Ala Ala Gln Ser Ala Thr Glu Ala Arg Gly
385                 390                 395                 400

GCG GAG CCG ACT GCG GGC ATC CAC TGG TAC TCG CAG CTG CTC TAC CAC      1248
Ala Glu Pro Thr Ala Gly Ile His Trp Tyr Ser Gln Leu Leu Tyr His
            405                 410                 415

ATT GGC ACC TGG CTG TTG GAC AGC GAG ACC ATG CAT CCC TTG GGA ATG      1296
Ile Gly Thr Trp Leu Leu Asp Ser Glu Thr Met His Pro Leu Gly Met
            420                 425                 430

GCG GTC AAG TCC AGC TG                                               1313
Ala Val Lys Ser Ser
            435

(2) INFORMATION FOR SEQ ID NO:5:

(i) SEQUENCE CHARACTERISTICS:
        (A) LENGTH: 1256 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1254

(xi) SEQUENCE DESCRIPTION: SEQ ID NO:5:

ATG CGG CTT TTG ACG AGA GTG CTG CTG GTG TCT CTT CTC ACT CTG TCC       48
Met Arg Leu Leu Thr Arg Val Leu Leu Val Ser Leu Leu Thr Leu Ser
1               5                   10                  15

TTG GTG GTG TCC GGA CTG GCC TGC GGT CCT GGC AGA GGC TAC GGC AGA       96
Leu Val Val Ser Gly Leu Ala Cys Gly Pro Gly Arg Gly Tyr Gly Arg
            20                  25                  30

AGA AGA CAT CCG AAG AAG CTG ACA CCT CTC GCC TAC AAG CAG TTC ATA      144
Arg Arg His Pro Lys Lys Leu Thr Pro Leu Ala Tyr Lys Gln Phe Ile
            35                  40                  45

CCT AAT GTC GCG GAG AAG ACC TTA GGG GCC AGC GGC AGA TAC GAG GGC      192
Pro Asn Val Ala Glu Lys Thr Leu Gly Ala Ser Gly Arg Tyr Glu Gly
50                  55                  60

AAG ATA ACG CGC AAT TCG GAG AGA TTT AAA GAA CTT ACT CCA AAT TAC      240
Lys Ile Thr Arg Asn Ser Glu Arg Phe Lys Glu Leu Thr Pro Asn Tyr
65                  70                  75                  80

AAT CCC GAC ATT ATC TTT AAG GAT GAG GAG AAC ACG GGA GCG GAC AGG      288
Asn Pro Asp Ile Ile Phe Lys Asp Glu Glu Asn Thr Gly Ala Asp Arg
                85                  90                  95

CTC ATG ACA CAG AGA TGC AAA GAC AAG CTG AAC TCG CTG GCC ATC TCT      336
Leu Met Thr Gln Arg Cys Lys Asp Lys Leu Asn Ser Leu Ala Ile Ser
            100                 105                 110

GTA ATG AAC CAC TGG CCA GGG GTT AAG CTG CGT GTG ACA GAG GGC TGG      384
Val Met Asn His Trp Pro Gly Val Lys Leu Arg Val Thr Glu Gly Trp
            115                 120                 125

GAT GAG GAC GGT CAC CAT TTT GAA GAA TCA CTC CAC TAC GAG GGA AGA      432
Asp Glu Asp Gly His His Phe Glu Glu Ser Leu His Tyr Glu Gly Arg
130                 135                 140
```

```
GCT GTT GAT ATT ACC ACC TCT GAC CGA GAC AAG AGC AAA TAC GGG ACA    480
Ala Val Asp Ile Thr Thr Ser Asp Arg Asp Lys Ser Lys Tyr Gly Thr
145                 150                 155                 160

CTG TCT CGC CTA GCT GTG GAG GCT GGA TTT GAC TGG GTC TAT TAC GAG    528
Leu Ser Arg Leu Ala Val Glu Ala Gly Phe Asp Trp Val Tyr Tyr Glu
                165                 170                 175

TCC AAA GCC CAC ATT CAT TGC TCT GTC AAA GCA GAA AAT TCG GTT GCT    576
Ser Lys Ala His Ile His Cys Ser Val Lys Ala Glu Asn Ser Val Ala
            180                 185                 190

GCG AAA TCT GGG GGC TGT TTC CCA GGT TCG GCT CTG GTC TCG CTC CAG    624
Ala Lys Ser Gly Gly Cys Phe Pro Gly Ser Ala Leu Val Ser Leu Gln
        195                 200                 205

GAC GGA GGA CAG AAG GCC GTG AAG GAC CTG AAC CCC GGA GAC AAG GTG    672
Asp Gly Gly Gln Lys Ala Val Lys Asp Leu Asn Pro Gly Asp Lys Val
210                 215                 220

CTG GCG GCA GAC AGC GCG GGA AAC CTG GTG TTC AGC GAC TTC ATC ATG    720
Leu Ala Ala Asp Ser Ala Gly Asn Leu Val Phe Ser Asp Phe Ile Met
225                 230                 235                 240

TTC ACA GAC CGA GAC TCC ACG ACG CGA CGT GTG TTT TAC GTC ATA GAA    768
Phe Thr Asp Arg Asp Ser Thr Thr Arg Arg Val Phe Tyr Val Ile Glu
                245                 250                 255

ACG CAA GAA CCC GTT GAA AAG ATC ACC CTC ACC GCC GCT CAC CTC CTT    816
Thr Gln Glu Pro Val Glu Lys Ile Thr Leu Thr Ala Ala His Leu Leu
            260                 265                 270

TTT GTC CTC GAC AAC TCA ACG GAA GAT CTC CAC ACC ATG ACC GCC GCG    864
Phe Val Leu Asp Asn Ser Thr Glu Asp Leu His Thr Met Thr Ala Ala
        275                 280                 285

TAT GCC AGC AGT GTC AGA GCC GGA CAA AAG GTG ATG GTT GTT GAT GAT    912
Tyr Ala Ser Ser Val Arg Ala Gly Gln Lys Val Met Val Val Asp Asp
290                 295                 300

AGC GGT CAG CTT AAA TCT GTC ATC GTG CAG CGG ATA TAC ACG GAG GAG    960
Ser Gly Gln Leu Lys Ser Val Ile Val Gln Arg Ile Tyr Thr Glu Glu
305                 310                 315                 320

CAG CGG GGC TCG TTC GCA CCA GTG ACT GCA CAT GGG ACC ATT GTG GTC   1008
Gln Arg Gly Ser Phe Ala Pro Val Thr Ala His Gly Thr Ile Val Val
                325                 330                 335

GAC AGA ATA CTG GCG TCC TGT TAC GCC GTA ATA GAG GAC CAG GGG CTT   1056
Asp Arg Ile Leu Ala Ser Cys Tyr Ala Val Ile Glu Asp Gln Gly Leu
            340                 345                 350

GCG CAT TTG GCC TTC GCG CCC GCC AGG CTC TAT TAT TAC GTG TCA TCA   1104
Ala His Leu Ala Phe Ala Pro Ala Arg Leu Tyr Tyr Tyr Val Ser Ser
        355                 360                 365

TTC CTG TCC CCC AAA ACT CCA GCA GTC GGT CCA ATG CGA CTT TAC AAC   1152
Phe Leu Ser Pro Lys Thr Pro Ala Val Gly Pro Met Arg Leu Tyr Asn
370                 375                 380

AGG AGG GGG TCC ACT GGT ACT CCA GGC TCC TGT CAT CAA ATG GGA ACG   1200
Arg Arg Gly Ser Thr Gly Thr Pro Gly Ser Cys His Gln Met Gly Thr
385                 390                 395                 400

TGG CTT TTG GAC AGC AAC ATG CTT CAT CCT TTG GGG ATG TCA GTA AAC   1248
Trp Leu Leu Asp Ser Asn Met Leu His Pro Leu Gly Met Ser Val Asn
                405                 410                 415

TCA AGC TG                                                        1256
Ser Ser
```

(2) INFORMATION FOR SEQ ID NO:6:

(i) SEQUENCE CHARACTERISTICS:
        (A) LENGTH: 1425 base pairs
        (B) TYPE: nucleic acid
        (C) STRANDEDNESS: both (D) TOPOLOGY: linear (ii) MOLECULE TYPE: cDNA (ix) FEATURE:
    (A) NAME/KEY: CDS
    (B) LOCATION: 1..1425

(xi) SEQUENCE DESCRIPTION: SEQ ID NO:6:

| | | | | | | | | | | | | | | | | |
|---|---|---|---|---|---|---|---|---|---|---|---|---|---|---|---|---|
| ATG | CTG | CTG | CTG | GCG | AGA | TGT | CTG | CTG | CTA | GTC | CTC | GTC | TCC | TCG | CTG | 48 |
| Met | Leu | Leu | Leu | Ala | Arg | Cys | Leu | Leu | Leu | Val | Leu | Val | Ser | Ser | Leu | |
| 1 | | | | 5 | | | | | 10 | | | | | 15 | | |
| CTG | GTA | TGC | TCG | GGA | CTG | GCG | TGC | GGA | CCG | GGC | AGG | GGG | TTC | GGG | AAG | 96 |
| Leu | Val | Cys | Ser | Gly | Leu | Ala | Cys | Gly | Pro | Gly | Arg | Gly | Phe | Gly | Lys | |
| | | | 20 | | | | | 25 | | | | | 30 | | | |
| AGG | AGG | CAC | CCC | AAA | AAG | CTG | ACC | CCT | TTA | GCC | TAC | AAG | CAG | TTT | ATC | 144 |
| Arg | Arg | His | Pro | Lys | Lys | Leu | Thr | Pro | Leu | Ala | Tyr | Lys | Gln | Phe | Ile | |
| | | | 35 | | | | | 40 | | | | | 45 | | | |
| CCC | AAT | GTG | GCC | GAG | AAG | ACC | CTA | GGC | GCC | AGC | GGA | AGG | TAT | GAA | GGG | 192 |
| Pro | Asn | Val | Ala | Glu | Lys | Thr | Leu | Gly | Ala | Ser | Gly | Arg | Tyr | Glu | Gly | |
| | | 50 | | | | | 55 | | | | | 60 | | | | |
| AAG | ATC | TCC | AGA | AAC | TCC | GAG | CGA | TTT | AAG | GAA | CTC | ACC | CCC | AAT | TAC | 240 |
| Lys | Ile | Ser | Arg | Asn | Ser | Glu | Arg | Phe | Lys | Glu | Leu | Thr | Pro | Asn | Tyr | |
| 65 | | | | | 70 | | | | | 75 | | | | | 80 | |
| AAC | CCC | GAC | ATC | ATA | TTT | AAG | GAT | GAA | GAA | AAC | ACC | GGA | GCG | GAC | AGG | 288 |
| Asn | Pro | Asp | Ile | Ile | Phe | Lys | Asp | Glu | Glu | Asn | Thr | Gly | Ala | Asp | Arg | |
| | | | | 85 | | | | | 90 | | | | | 95 | | |
| CTG | ATG | ACT | CAG | AGG | TGT | AAG | GAC | AAG | TTG | AAC | GCT | TTG | GCC | ATC | TCG | 336 |
| Leu | Met | Thr | Gln | Arg | Cys | Lys | Asp | Lys | Leu | Asn | Ala | Leu | Ala | Ile | Ser | |
| | | | | 100 | | | | | 105 | | | | | 110 | | |
| GTG | ATG | AAC | CAG | TGG | CCA | GGA | GTG | AAA | CTG | CGG | GTG | ACC | GAG | GGC | TGG | 384 |
| Val | Met | Asn | Gln | Trp | Pro | Gly | Val | Lys | Leu | Arg | Val | Thr | Glu | Gly | Trp | |
| | | | 115 | | | | | 120 | | | | | 125 | | | |
| GAC | GAA | GAT | GGC | CAC | CAC | TCA | GAG | GAG | TCT | CTG | CAC | TAC | GAG | GGC | CGC | 432 |
| Asp | Glu | Asp | Gly | His | His | Ser | Glu | Glu | Ser | Leu | His | Tyr | Glu | Gly | Arg | |
| | 130 | | | | | 135 | | | | | 140 | | | | | |
| GCA | GTG | GAC | ATC | ACC | ACG | TCT | GAC | CGC | GAC | CGC | AGC | AAG | TAC | GGC | ATG | 480 |
| Ala | Val | Asp | Ile | Thr | Thr | Ser | Asp | Arg | Asp | Arg | Ser | Lys | Tyr | Gly | Met | |
| 145 | | | | | 150 | | | | | 155 | | | | | 160 | |
| CTG | GCC | CGC | CTG | GCG | GTG | GAG | GCC | GGC | TTC | GAC | TGG | GTG | TAC | TAC | GAG | 528 |
| Leu | Ala | Arg | Leu | Ala | Val | Glu | Ala | Gly | Phe | Asp | Trp | Val | Tyr | Tyr | Glu | |
| | | | 165 | | | | | 170 | | | | | 175 | | | |
| TCC | AAG | GCA | CAT | ATC | CAC | TGC | TCG | GTG | AAA | GCA | GAG | AAC | TCG | GTG | GCG | 576 |
| Ser | Lys | Ala | His | Ile | His | Cys | Ser | Val | Lys | Ala | Glu | Asn | Ser | Val | Ala | |
| | | | 180 | | | | | 185 | | | | | 190 | | | |
| GCC | AAA | TCG | GGA | GGC | TGC | TTC | CCG | GGC | TCG | GCC | ACG | GTG | CAC | CTG | GAG | 624 |
| Ala | Lys | Ser | Gly | Gly | Cys | Phe | Pro | Gly | Ser | Ala | Thr | Val | His | Leu | Glu | |
| | | | 195 | | | | | 200 | | | | | 205 | | | |
| CAG | GGC | GGC | ACC | AAG | CTG | GTG | AAG | GAC | CTG | AGC | CCC | GGG | GAC | CGC | GTG | 672 |
| Gln | Gly | Gly | Thr | Lys | Leu | Val | Lys | Asp | Leu | Ser | Pro | Gly | Asp | Arg | Val | |
| | 210 | | | | | 215 | | | | | 220 | | | | | |
| CTG | GCG | GCG | GAC | GAC | CAG | GGC | CGG | CTG | CTC | TAC | AGC | GAC | TTC | CTC | ACT | 720 |
| Leu | Ala | Ala | Asp | Asp | Gln | Gly | Arg | Leu | Leu | Tyr | Ser | Asp | Phe | Leu | Thr | |
| 225 | | | | | 230 | | | | | 235 | | | | | 240 | |
| TTC | CTG | GAC | CGC | GAC | GAC | GGC | GCC | AAG | AAG | GTC | TTC | TAC | GTG | ATC | GAG | 768 |
| Phe | Leu | Asp | Arg | Asp | Asp | Gly | Ala | Lys | Lys | Val | Phe | Tyr | Val | Ile | Glu | |
| | | | 245 | | | | | 250 | | | | | 255 | | | |
| ACG | CGG | GAG | CCG | CGC | GAG | CGC | CTG | CTG | CTC | ACC | GCC | GCG | CAC | CTG | CTC | 816 |
| Thr | Arg | Glu | Pro | Arg | Glu | Arg | Leu | Leu | Leu | Thr | Ala | Ala | His | Leu | Leu | |
| | | 260 | | | | | 265 | | | | | 270 | | | | |
| TTT | GTG | GCG | CCG | CAC | AAC | GAC | TCG | GCC | ACC | GGG | GAG | CCC | GAG | GCG | TCC | 864 |

```
Phe Val Ala Pro His Asn Asp Ser Ala Thr Gly Glu Pro Glu Ala Ser
        275                 280                 285

TCG GGC TCG GGG CCG CCT TCC GGG GGC GCA CTG GGG CCT CGG GCG CTG         912
Ser Gly Ser Gly Pro Pro Ser Gly Gly Ala Leu Gly Pro Arg Ala Leu
        290                 295                 300

TTC GCC AGC CGC GTG CGC CCG GGC CAG CGC GTG TAC GTG GTG GCC GAG         960
Phe Ala Ser Arg Val Arg Pro Gly Gln Arg Val Tyr Val Val Ala Glu
305                 310                 315                 320

CGT GAC GGG GAC CGC CGG CTC CTG CCC GCC GCT GTG CAC AGC GTG ACC        1008
Arg Asp Gly Asp Arg Arg Leu Leu Pro Ala Ala Val His Ser Val Thr
                325                 330                 335

CTA AGC GAG GAG GCC GCG GGC GCC TAC GCG CCG CTC ACG GCC CAG GGC        1056
Leu Ser Glu Glu Ala Ala Gly Ala Tyr Ala Pro Leu Thr Ala Gln Gly
        340                 345                 350

ACC ATT CTC ATC AAC CGG GTG CTG GCC TCG TGC TAC GCG GTC ATC GAG        1104
Thr Ile Leu Ile Asn Arg Val Leu Ala Ser Cys Tyr Ala Val Ile Glu
        355                 360                 365

GAG CAC AGC TGG GCG CAC CGG GCC TTC GCG CCC TTC CGC CTG GCG CAC        1152
Glu His Ser Trp Ala His Arg Ala Phe Ala Pro Phe Arg Leu Ala His
        370                 375                 380

GCG CTC CTG GCT GCA CTG GCG CCC GCG CGC ACG GAC CGC GGC GGG GAC        1200
Ala Leu Leu Ala Ala Leu Ala Pro Ala Arg Thr Asp Arg Gly Gly Asp
385                 390                 395                 400

AGC GGC GGC GGG GAC CGC GGG GGC GGC GGC GGA AGA GTA GCC CTA ACC        1248
Ser Gly Gly Gly Asp Arg Gly Gly Gly Gly Arg Val Ala Leu Thr
                405                 410                 415

GCT CCA GGT GCT GCC GAC GCT CCG GGT GCG GGG GCC ACC GCG GGC ATC        1296
Ala Pro Gly Ala Ala Asp Ala Pro Gly Ala Gly Ala Thr Ala Gly Ile
        420                 425                 430

CAC TGG TAC TCG CAG CTG CTC TAC CAA ATA GGC ACC TGG CTC CTG GAC        1344
His Trp Tyr Ser Gln Leu Leu Tyr Gln Ile Gly Thr Trp Leu Leu Asp
        435                 440                 445

AGC GAG GCC CTG CAC CCG CTG GGC ATG GCG GTC AAG TCC AGC NNN AGC        1392
Ser Glu Ala Leu His Pro Leu Gly Met Ala Val Lys Ser Ser Xaa Ser
        450                 455                 460

CGG GGG GCC GGG GGA GGG GCG CGG GAG GGG GCC                            1425
Arg Gly Ala Gly Gly Gly Ala Arg Glu Gly Ala
465                 470                 475
```

(2) INFORMATION FOR SEQ ID NO:7:

(i) SEQUENCE CHARACTERISTICS:
        (A) LENGTH: 1622 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 51..1283

(xi) SEQUENCE DESCRIPTION: SEQ ID NO:7:

```
CATCAGCCCA CCAGGAGACC TCGCCCGCCG CTCCCCCGGG CTCCCCGGCC ATG TCT          56
                                                      Met Ser
                                                        1

CCC GCC CGG CTC CGG CCC CGA CTG CAC TTC TGC CTG GTC CTG TTG CTG        104
Pro Ala Arg Leu Arg Pro Arg Leu His Phe Cys Leu Val Leu Leu Leu
        5                   10                  15

CTG CTG GTG GTG CCC GCG GCA TGG GGC TGC GGG CCG GGT CGG GTG GTG        152
Leu Leu Val Val Pro Ala Ala Trp Gly Cys Gly Pro Gly Arg Val Val
        20                  25                  30
```

```
GGC AGC CGC CGG CGA CCG CCA CGC AAA CTC GTG CCG CTC GCC TAC AAG        200
Gly Ser Arg Arg Arg Pro Pro Arg Lys Leu Val Pro Leu Ala Tyr Lys
 35              40                  45                  50

CAG TTC AGC CCC AAT GTG CCC GAG AAG ACC CTG GGC GCC AGC GGA CGC        248
Gln Phe Ser Pro Asn Val Pro Glu Lys Thr Leu Gly Ala Ser Gly Arg
                 55                  60                  65

TAT GAA GGC AAG ATC GCT CGC AGC TCC GAG CGC TTC AAG GAG CTC ACC        296
Tyr Glu Gly Lys Ile Ala Arg Ser Ser Glu Arg Phe Lys Glu Leu Thr
             70                  75                  80

CCC AAT TAC AAT CCA GAC ATC ATC TTC AAG GAC GAG GAG AAC ACA GGC        344
Pro Asn Tyr Asn Pro Asp Ile Ile Phe Lys Asp Glu Glu Asn Thr Gly
         85                  90                  95

GCC GAC CGC CTC ATG ACC CAG CGC TGC AAG GAC CGC CTG AAC TCG CTG        392
Ala Asp Arg Leu Met Thr Gln Arg Cys Lys Asp Arg Leu Asn Ser Leu
100                 105                 110

GCT ATC TCG GTG ATG AAC CAG TGG CCC GGT GTG AAG CTG CGG GTG ACC        440
Ala Ile Ser Val Met Asn Gln Trp Pro Gly Val Lys Leu Arg Val Thr
115                 120                 125                 130

GAG GGC TGG GAC GAG GAC GGC CAC CAC TCA GAG GAG TCC CTG CAT TAT        488
Glu Gly Trp Asp Glu Asp Gly His His Ser Glu Glu Ser Leu His Tyr
                135                 140                 145

GAG GGC CGC GCG GTG GAC ATC ACC ACA TCA GAC CGC GAC CGC AAT AAG        536
Glu Gly Arg Ala Val Asp Ile Thr Thr Ser Asp Arg Asp Arg Asn Lys
            150                 155                 160

TAT GGA CTG CTG GCG CGC TTG GCA GTG GAG GCC GGC TTT GAC TGG GTG        584
Tyr Gly Leu Leu Ala Arg Leu Ala Val Glu Ala Gly Phe Asp Trp Val
        165                 170                 175

TAT TAC GAG TCA AAG GCC CAC GTG CAT TGC TCC GTC AAG TCC GAG CAC        632
Tyr Tyr Glu Ser Lys Ala His Val His Cys Ser Val Lys Ser Glu His
180                 185                 190

TCG GCC GCA GCC AAG ACG GGC GGC TGC TTC CCT GCC GGA GCC CAG GTA        680
Ser Ala Ala Ala Lys Thr Gly Gly Cys Phe Pro Ala Gly Ala Gln Val
195                 200                 205                 210

CGC CTG GAG AGT GGG GCG CGT GTG GCC TTG TCA GCC GTG AGG CCG GGA        728
Arg Leu Glu Ser Gly Ala Arg Val Ala Leu Ser Ala Val Arg Pro Gly
                215                 220                 225

GAC CGT GTG CTG GCC ATG GGG GAG GAT GGG AGC CCC ACC TTC AGC GAT        776
Asp Arg Val Leu Ala Met Gly Glu Asp Gly Ser Pro Thr Phe Ser Asp
            230                 235                 240

GTG CTC ATT TTC CTG GAC CGC GAG CCC CAC AGG CTG AGA GCC TTC CAG        824
Val Leu Ile Phe Leu Asp Arg Glu Pro His Arg Leu Arg Ala Phe Gln
        245                 250                 255

GTC ATC GAG ACT CAG GAC CCC CCA CGC CGC CTG GCA CTC ACA CCC GCT        872
Val Ile Glu Thr Gln Asp Pro Pro Arg Arg Leu Ala Leu Thr Pro Ala
260                 265                 270

CAC CTG CTC TTT ACG GCT GAC AAT CAC ACG GAG CCG GCA GCC CGC TTC        920
His Leu Leu Phe Thr Ala Asp Asn His Thr Glu Pro Ala Ala Arg Phe
275                 280                 285                 290

CGG GCC ACA TTT GCC AGC CAC GTG CAG CCT GGC CAG TAC GTG CTG GTG        968
Arg Ala Thr Phe Ala Ser His Val Gln Pro Gly Gln Tyr Val Leu Val
                295                 300                 305

GCT GGG GTG CCA GGC CTG CAG CCT GCC CGC GTG GCA GCT GTC TCT ACA       1016
Ala Gly Val Pro Gly Leu Gln Pro Ala Arg Val Ala Ala Val Ser Thr
            310                 315                 320

CAC GTG GCC CTC GGG GCC TAC GCC CCG CTC ACA AAG CAT GGG ACA CTG       1064
His Val Ala Leu Gly Ala Tyr Ala Pro Leu Thr Lys His Gly Thr Leu
        325                 330                 335

GTG GTG GAG GAT GTG GTG GCA TCC TGC TTC GCG GCC GTG GCT GAC CAC       1112
Val Val Glu Asp Val Val Ala Ser Cys Phe Ala Ala Val Ala Asp His
```

-continued

```
         340              345            350
CAC CTG GCT CAG TTG GCC TTC TGG CCC CTG AGA CTC TTT CAC AGC TTG      1160
His Leu Ala Gln Leu Ala Phe Trp Pro Leu Arg Leu Phe His Ser Leu
355                 360             365                 370

GCA TGG GGC AGC TGG ACC CCG GGG GAG GGT GTG CAT TGG TAC CCC CAG      1208
Ala Trp Gly Ser Trp Thr Pro Gly Glu Gly Val His Trp Tyr Pro Gln
                375             380             385

CTG CTC TAC CGC CTG GGG CGT CTC CTA GAA GAG GGC AGC TTC CAC          1256
Leu Leu Tyr Arg Leu Gly Arg Leu Leu Glu Glu Gly Ser Phe His
            390             395             400

CCA CTG GGC ATG TCC GGG GCA GGG AGC TGAAAGGACT CCACCGCTGC            1303
Pro Leu Gly Met Ser Gly Ala Gly Ser
        405             410

CCTCCTGGAA CTGCTGTACT GGGTCCAGAA GCCTCTCAGC CAGGAGGGAG CTGGCCCTGG    1363

AAGGGACCTG AGCTGGGGGA CACTGGCTCC TGCCATCTCC TCTGCCATGA AGATACACCA    1423

TTGAGACTTG ACTGGGCAAC ACCAGCGTCC CCCACCCGCG TCGTGGTGTA GTCATAGAGC    1483

TGCAAGCTGA GCTGGCGAGG GGATGGTTGT TGACCCCTCT CTCCTAGAGA CCTTGAGGCT    1543

GGCACGGCGA CTCCCAACTC AGCCTGCTCT CACTACGAGT TTTCATACTC TGCCTCCCCC    1603

ATTGGGAGGG CCCATTCCC                                                 1622
```

(2) INFORMATION FOR SEQ ID NO:8:

(i) SEQUENCE CHARACTERISTICS:
        (A) LENGTH: 1190 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1188

(xi) SEQUENCE DESCRIPTION: SEQ ID NO:8:

```
ATG GCT CTC CTG ACC AAT CTA CTG CCC TTG TGC TGC TTG GCA CTT CTG      48
Met Ala Leu Leu Thr Asn Leu Leu Pro Leu Cys Cys Leu Ala Leu Leu
1               5                   10                  15

GCG CTG CCA GCC CAG AGC TGC GGG CCG GGC CGG GGG CCG GTT GGC CGG      96
Ala Leu Pro Ala Gln Ser Cys Gly Pro Gly Arg Gly Pro Val Gly Arg
                20                  25                  30

CGC CGC TAT GCG CGC AAG CAG CTC GTG CCG CTA CTC TAC AAG CAA TTT     144
Arg Arg Tyr Ala Arg Lys Gln Leu Val Pro Leu Leu Tyr Lys Gln Phe
            35                  40                  45

GTG CCC GGC GTG CCA GAG CGG ACC CTG GGC GCC AGT GGG CCA GCG GAG     192
Val Pro Gly Val Pro Glu Arg Thr Leu Gly Ala Ser Gly Pro Ala Glu
50                  55                  60

GGG AGG GTG GCA AGG GGC TCC GAG CGC TTC CGG GAC CTC GTG CCC AAC     240
Gly Arg Val Ala Arg Gly Ser Glu Arg Phe Arg Asp Leu Val Pro Asn
65                  70                  75                  80

TAC AAC CCC GAC ATC ATC TTC AAG GAT GAG GAG AAC AGT GGA GCC GAC     288
Tyr Asn Pro Asp Ile Ile Phe Lys Asp Glu Glu Asn Ser Gly Ala Asp
                85                  90                  95

CGC CTG ATG ACC GAG CGT TGC AAG GAG AGG GTG AAC GCT TTG GCC ATT     336
Arg Leu Met Thr Glu Arg Cys Lys Glu Arg Val Asn Ala Leu Ala Ile
                100                 105                 110

GCC GTG ATG AAC ATG TGG CCC GGA GTG CGC CTA CGA GTG ACT GAG GGC     384
Ala Val Met Asn Met Trp Pro Gly Val Arg Leu Arg Val Thr Glu Gly
            115                 120                 125
```

```
TGG GAC GAG GAC GGC CAC CAC GCT CAG GAT TCA CTC CAC TAC GAA GGC    432
Trp Asp Glu Asp Gly His His Ala Gln Asp Ser Leu His Tyr Glu Gly
130                 135                 140

CGT GCT TTG GAC ATC ACT ACG TCT GAC CGC GAC CGC AAC AAG TAT GGG    480
Arg Ala Leu Asp Ile Thr Thr Ser Asp Arg Asp Arg Asn Lys Tyr Gly
145                 150                 155                 160

TTG CTG GCG CGC CTC GCA GTG GAA GCC GGC TTC GAC TGG GTC TAC TAC    528
Leu Leu Ala Arg Leu Ala Val Glu Ala Gly Phe Asp Trp Val Tyr Tyr
                165                 170                 175

GAG TCC CGC AAC CAC GTC CAC GTG TCG GTC AAA GCT GAT AAC TCA CTG    576
Glu Ser Arg Asn His Val His Val Ser Val Lys Ala Asp Asn Ser Leu
                180                 185                 190

GCG GTC CGG GCG GGC GGC TGC TTT CCG GGA AAT GCA ACT GTG CGC CTG    624
Ala Val Arg Ala Gly Gly Cys Phe Pro Gly Asn Ala Thr Val Arg Leu
            195                 200                 205

TGG AGC GGC GAG CGG AAA GGG CTG CGG GAA CTG CAC CGC GGA GAC TGG    672
Trp Ser Gly Glu Arg Lys Gly Leu Arg Glu Leu His Arg Gly Asp Trp
210                 215                 220

GTT TTG GCG GCC GAT GCG TCA GGC CGG GTG GTG CCC ACG CCG GTG CTG    720
Val Leu Ala Ala Asp Ala Ser Gly Arg Val Val Pro Thr Pro Val Leu
225                 230                 235                 240

CTC TTC CTG GAC CGG GAC TTG CAG CGC CGG GCT TCA TTT GTG GCT GTG    768
Leu Phe Leu Asp Arg Asp Leu Gln Arg Arg Ala Ser Phe Val Ala Val
                245                 250                 255

GAG ACC GAG TGG CCT CCA CGC AAA CTG TTG CTC ACG CCC TGG CAC CTG    816
Glu Thr Glu Trp Pro Pro Arg Lys Leu Leu Leu Thr Pro Trp His Leu
                260                 265                 270

GTG TTT GCC GCT CGA GGG CCG GCG CCC GCG CCA GGC GAC TTT GCA CCG    864
Val Phe Ala Ala Arg Gly Pro Ala Pro Ala Pro Gly Asp Phe Ala Pro
                275                 280                 285

GTG TTC GCG CGC CGG CTA CGC GCT GGG GAC TCG GTG CTG GCG CCC GGC    912
Val Phe Ala Arg Arg Leu Arg Ala Gly Asp Ser Val Leu Ala Pro Gly
290                 295                 300

GGG GAT GCG CTT CGG CCA GCG CGC GTG GCC CGT GTG GCG CGG GAG GAA    960
Gly Asp Ala Leu Arg Pro Ala Arg Val Ala Arg Val Ala Arg Glu Glu
305                 310                 315                 320

GCC GTG GGC GTG TTC GCG CCG CTC ACC GCG CAC GGG ACG CTG CTG GTG   1008
Ala Val Gly Val Phe Ala Pro Leu Thr Ala His Gly Thr Leu Leu Val
                325                 330                 335

AAC GAT GTC CTG GCC TCT TGC TAC GCG GTT CTG GAG AGT CAC CAG TGG   1056
Asn Asp Val Leu Ala Ser Cys Tyr Ala Val Leu Glu Ser His Gln Trp
                340                 345                 350

GCG CAC CGC GCT TTT GCC CCC TTG AGA CTG CTG CAC GCG CTA GGG GCG   1104
Ala His Arg Ala Phe Ala Pro Leu Arg Leu Leu His Ala Leu Gly Ala
                355                 360                 365

CTG CTC CCC GGC GGG GCC GTC CAG CCG ACT GGC ATG CAT TGG TAC TCT   1152
Leu Leu Pro Gly Gly Ala Val Gln Pro Thr Gly Met His Trp Tyr Ser
370                 375                 380

CGG CTC CTC TAC CGC TTA GCG GAG GAG CTA CTG GGC TG                1190
Arg Leu Leu Tyr Arg Leu Ala Glu Glu Leu Leu Gly
385                 390                 395
```

(2) INFORMATION FOR SEQ ID NO:9:

(i) SEQUENCE CHARACTERISTICS:
        (A) LENGTH: 1251 base pairs
        (B) TYPE: nucleic acid
        (C) STRANDEDNESS: both
        (D) TOPOLOGY: linear (ii) MOLECULE TYPE: cDNA (ix) FEATURE:
    (A) NAME/KEY: CDS
    (B) LOCATION: 1..1248

(xi) SEQUENCE DESCRIPTION: SEQ ID NO:9:

```
ATG GAC GTA AGG CTG CAT CTG AAG CAA TTT GCT TTA CTG TGT TTT ATC         48
Met Asp Val Arg Leu His Leu Lys Gln Phe Ala Leu Leu Cys Phe Ile
 1               5                  10                  15

AGC TTG CTT CTG ACG CCT TGT GGA TTA GCC TGT GGT CCT GGT AGA GGT         96
Ser Leu Leu Leu Thr Pro Cys Gly Leu Ala Cys Gly Pro Gly Arg Gly
                20                  25                  30

TAT GGA AAA CGA AGA CAC CCA AAG AAA TTA ACC CCG TTG GCT TAC AAG        144
Tyr Gly Lys Arg Arg His Pro Lys Lys Leu Thr Pro Leu Ala Tyr Lys
         35                  40                  45

CAA TTC ATC CCC AAC GTT GCT GAG AAA ACG CTT GGA GCC AGC GGC AAA        192
Gln Phe Ile Pro Asn Val Ala Glu Lys Thr Leu Gly Ala Ser Gly Lys
 50                  55                  60

TAC GAA GGC AAA ATC ACA AGG AAT TCA GAG AGA TTT AAA GAG CTG ATT        240
Tyr Glu Gly Lys Ile Thr Arg Asn Ser Glu Arg Phe Lys Glu Leu Ile
 65                  70                  75                  80

CCG AAT TAT AAT CCC GAT ATC ATC TTT AAG GAC GAG GAA AAC ACA AAC        288
Pro Asn Tyr Asn Pro Asp Ile Ile Phe Lys Asp Glu Glu Asn Thr Asn
                 85                  90                  95

GCT GAC AGG CTG ATG ACC AAG CGC TGT AAG GAC AAG TTA AAT TCG TTG        336
Ala Asp Arg Leu Met Thr Lys Arg Cys Lys Asp Lys Leu Asn Ser Leu
            100                 105                 110

GCC ATA TCC GTC ATG AAC CAC TGG CCC GGC GTG AAA CTG CGC GTC ACT        384
Ala Ile Ser Val Met Asn His Trp Pro Gly Val Lys Leu Arg Val Thr
        115                 120                 125

GAA GGC TGG GAT GAG GAT GGT CAC CAT TTA GAA GAA TCT TTG CAC TAT        432
Glu Gly Trp Asp Glu Asp Gly His His Leu Glu Glu Ser Leu His Tyr
130                 135                 140

GAG GGA CGG GCA GTG GAC ATC ACT ACC TCA GAC AGG GAT AAA AGC AAG        480
Glu Gly Arg Ala Val Asp Ile Thr Thr Ser Asp Arg Asp Lys Ser Lys
145                 150                 155                 160

TAT GGG ATG CTA TCC AGG CTT GCA GTG GAG GCA GGA TTC GAC TGG GTC        528
Tyr Gly Met Leu Ser Arg Leu Ala Val Glu Ala Gly Phe Asp Trp Val
                165                 170                 175

TAT TAT GAA TCT AAA GCC CAC ATA CAC TGC TCT GTC AAA GCA GAA AAT        576
Tyr Tyr Glu Ser Lys Ala His Ile His Cys Ser Val Lys Ala Glu Asn
            180                 185                 190

TCA GTG GCT GCT AAA TCA GGA GGA TGT TTT CCT GGG TCT GGG ACG GTG        624
Ser Val Ala Ala Lys Ser Gly Gly Cys Phe Pro Gly Ser Gly Thr Val
        195                 200                 205

ACA CTT GGT GAT GGG ACG AGG AAA CCC ATC AAA GAT CTT AAA GTG GGC        672
Thr Leu Gly Asp Gly Thr Arg Lys Pro Ile Lys Asp Leu Lys Val Gly
210                 215                 220

GAC CGG GTT TTG GCT GCA GAC GAG AAG GGA AAT GTC TTA ATA AGC GAC        720
Asp Arg Val Leu Ala Ala Asp Glu Lys Gly Asn Val Leu Ile Ser Asp
225                 230                 235                 240

TTT ATT ATG TTT ATA GAC CAC GAT CCG ACA ACG AGA AGG CAA TTC ATC        768
Phe Ile Met Phe Ile Asp His Asp Pro Thr Thr Arg Arg Gln Phe Ile
                245                 250                 255

GTC ATC GAG ACG TCA GAA CCT TTC ACC AAG CTC ACC CTC ACT GCC GCG        816
Val Ile Glu Thr Ser Glu Pro Phe Thr Lys Leu Thr Leu Thr Ala Ala
            260                 265                 270

CAC CTA GTT TTC GTT GGA AAC TCT TCA GCA GCT TCG GGT ATA ACA GCA        864
His Leu Val Phe Val Gly Asn Ser Ser Ala Ala Ser Gly Ile Thr Ala
        275                 280                 285

ACA TTT GCC AGC AAC GTG AAG CCT GGA GAT ACA GTT TTA GTG TGG GAA        912
Thr Phe Ala Ser Asn Val Lys Pro Gly Asp Thr Val Leu Val Trp Glu
```

-continued

```
Thr Phe Ala Ser Asn Val Lys Pro Gly Asp Thr Val Leu Val Trp Glu
    290                 295                 300

GAC ACA TGC GAG AGC CTC AAG AGC GTT ACA GTG AAA AGG ATT TAC ACT      960
Asp Thr Cys Glu Ser Leu Lys Ser Val Thr Val Lys Arg Ile Tyr Thr
305                 310                 315                 320

GAG GAG CAC GAG GGC TCT TTT GCG CCA GTC ACC GCG CAC GGA ACC ATA     1008
Glu Glu His Glu Gly Ser Phe Ala Pro Val Thr Ala His Gly Thr Ile
                325                 330                 335

ATA GTG GAT CAG GTG TTG GCA TCG TGC TAC GCG GTC ATT GAG AAC CAC     1056
Ile Val Asp Gln Val Leu Ala Ser Cys Tyr Ala Val Ile Glu Asn His
            340                 345                 350

AAA TGG GCA CAT TGG GCT TTT GCG CCG GTC AGG TTG TGT CAC AAG CTG     1104
Lys Trp Ala His Trp Ala Phe Ala Pro Val Arg Leu Cys His Lys Leu
        355                 360                 365

ATG ACG TGG CTT TTT CCG GCT CGT GAA TCA AAC GTC AAT TTT CAG GAG     1152
Met Thr Trp Leu Phe Pro Ala Arg Glu Ser Asn Val Asn Phe Gln Glu
370                 375                 380

GAT GGT ATC CAC TGG TAC TCA AAT ATG CTG TTT CAC ATC GGC TCT TGG     1200
Asp Gly Ile His Trp Tyr Ser Asn Met Leu Phe His Ile Gly Ser Trp
385                 390                 395                 400

CTG CTG GAC AGA GAC TCT TTC CAT CCA CTC GGG ATT TTA CAC TTA AGT     1248
Leu Leu Asp Arg Asp Ser Phe His Pro Leu Gly Ile Leu His Leu Ser
                405                 410                 415

TGA                                                                 1251
```

(2) INFORMATION FOR SEQ ID NO:10:

(i) SEQUENCE CHARACTERISTICS:
        (A) LENGTH: 425 amino acids
        (B) TYPE: amino acid
        (D) TOPOLOGY: linear (ii) MOLECULE TYPE: protein (xi) SEQUENCE DESCRIPTION: SEQ ID NO:10:

```
Met Val Glu Met Leu Leu Leu Thr Arg Ile Leu Leu Val Gly Phe Ile
1               5                   10                  15

Cys Ala Leu Leu Val Ser Ser Gly Leu Thr Cys Gly Pro Gly Arg Gly
            20                  25                  30

Ile Gly Lys Arg Arg His Pro Lys Lys Leu Thr Pro Leu Ala Tyr Lys
        35                  40                  45

Gln Phe Ile Pro Asn Val Ala Glu Lys Thr Leu Gly Ala Ser Gly Arg
    50                  55                  60

Tyr Glu Gly Lys Ile Thr Arg Asn Ser Glu Arg Phe Lys Glu Leu Thr
65                  70                  75                  80

Pro Asn Tyr Asn Pro Asp Ile Ile Phe Lys Asp Glu Glu Asn Thr Gly
                85                  90                  95

Ala Asp Arg Leu Met Thr Gln Arg Cys Lys Asp Lys Leu Asn Ala Leu
            100                 105                 110

Ala Ile Ser Val Met Asn Gln Trp Pro Gly Val Lys Leu Arg Val Thr
        115                 120                 125

Glu Gly Trp Asp Glu Asp Gly His His Ser Glu Glu Ser Leu His Tyr
    130                 135                 140

Glu Gly Arg Ala Val Asp Ile Thr Thr Ser Asp Arg Asp Arg Ser Lys
145                 150                 155                 160

Tyr Gly Met Leu Ala Arg Leu Ala Val Glu Ala Gly Phe Asp Trp Val
                165                 170                 175

Tyr Tyr Glu Ser Lys Ala His Ile His Cys Ser Val Lys Ala Glu Asn
```

```
                    180                 185                 190
Ser Val Ala Ala Lys Ser Gly Gly Cys Phe Pro Gly Ser Ala Thr Val
                195                 200                 205

His Leu Glu His Gly Gly Thr Lys Leu Val Lys Asp Leu Ser Pro Gly
            210                 215                 220

Asp Arg Val Leu Ala Ala Asp Ala Asp Gly Arg Leu Leu Tyr Ser Asp
225                 230                 235                 240

Phe Leu Thr Phe Leu Asp Arg Met Asp Ser Arg Lys Leu Phe Tyr
                    245                 250                 255

Val Ile Glu Thr Arg Gln Pro Arg Ala Arg Leu Leu Leu Thr Ala Ala
                260                 265                 270

His Leu Leu Phe Val Ala Pro Gln His Asn Gln Ser Glu Ala Thr Gly
            275                 280                 285

Ser Thr Ser Gly Gln Ala Leu Phe Ala Ser Asn Val Lys Pro Gly Gln
        290                 295                 300

Arg Val Tyr Val Leu Gly Glu Gly Gly Gln Leu Leu Pro Ala Ser
305                 310                 315                 320

Val His Ser Val Ser Leu Arg Glu Glu Ala Ser Gly Ala Tyr Ala Pro
                325                 330                 335

Leu Thr Ala Gln Gly Thr Ile Leu Ile Asn Arg Val Leu Ala Ser Cys
            340                 345                 350

Tyr Ala Val Ile Glu Glu His Ser Trp Ala His Trp Ala Phe Ala Pro
                355                 360                 365

Phe Arg Leu Ala Gln Gly Leu Leu Ala Ala Leu Cys Pro Asp Gly Ala
        370                 375                 380

Ile Pro Thr Ala Ala Thr Thr Thr Gly Ile His Trp Tyr Ser Arg
385                 390                 395                 400

Leu Leu Tyr Arg Ile Gly Ser Trp Val Leu Asp Gly Asp Ala Leu His
                405                 410                 415

Pro Leu Gly Met Val Ala Pro Ser
            420                 425

(2) INFORMATION FOR SEQ ID NO:11:

(i) SEQUENCE CHARACTERISTICS:
        (A) LENGTH: 396 amino acids
        (B) TYPE: amino acid
        (D) TOPOLOGY: linear (ii) MOLECULE TYPE: protein (xi) SEQUENCE DESCRIPTION: SEQ ID NO:11:

Met Ala Leu Pro Ala Ser Leu Leu Pro Leu Cys Cys Leu Ala Leu Leu
1               5                   10                  15

Ala Leu Ser Ala Gln Ser Cys Gly Pro Gly Arg Gly Pro Val Gly Arg
            20                  25                  30

Arg Arg Tyr Val Arg Lys Gln Leu Val Pro Leu Leu Tyr Lys Gln Phe
        35                  40                  45

Val Pro Ser Met Pro Glu Arg Thr Leu Gly Ala Ser Gly Pro Ala Glu
    50                  55                  60

Gly Arg Val Thr Arg Gly Ser Glu Arg Phe Arg Asp Leu Val Pro Asn
65                  70                  75                  80

Tyr Asn Pro Asp Ile Ile Phe Lys Asp Glu Glu Asn Ser Gly Ala Asp
                85                  90                  95

Arg Leu Met Thr Glu Arg Cys Lys Glu Arg Val Asn Ala Leu Ala Ile
            100                 105                 110
```

-continued

```
Ala Val Met Asn Met Trp Pro Gly Val Arg Leu Arg Val Thr Glu Gly
        115                 120                 125
Trp Asp Glu Asp Gly His His Ala Gln Asp Ser Leu His Tyr Glu Gly
130                 135                 140
Arg Ala Leu Asp Ile Thr Thr Ser Asp Arg Asp Arg Asn Lys Tyr Gly
145                 150                 155                 160
Leu Leu Ala Arg Leu Ala Val Glu Ala Gly Phe Asp Trp Val Tyr Tyr
                165                 170                 175
Glu Ser Arg Asn His Ile His Val Ser Val Lys Ala Asp Asn Ser Leu
            180                 185                 190
Ala Val Arg Ala Gly Gly Cys Phe Pro Gly Asn Ala Thr Val Arg Leu
        195                 200                 205
Arg Ser Gly Glu Arg Lys Gly Leu Arg Glu Leu His Arg Gly Asp Trp
    210                 215                 220
Val Leu Ala Ala Asp Ala Ala Gly Arg Val Val Pro Thr Pro Val Leu
225                 230                 235                 240
Leu Phe Leu Asp Arg Asp Leu Gln Arg Arg Ala Ser Phe Val Ala Val
                245                 250                 255
Glu Thr Glu Arg Pro Pro Arg Lys Leu Leu Leu Thr Pro Trp His Leu
            260                 265                 270
Val Phe Ala Ala Arg Gly Pro Ala Pro Ala Pro Gly Asp Phe Ala Pro
        275                 280                 285
Val Phe Ala Arg Arg Leu Arg Ala Gly Asp Ser Val Leu Ala Pro Gly
        290                 295                 300
Gly Asp Ala Leu Gln Pro Ala Arg Val Ala Arg Val Ala Arg Glu Glu
305                 310                 315                 320
Ala Val Gly Val Phe Ala Pro Leu Thr Ala His Gly Thr Leu Leu Val
                325                 330                 335
Asn Asp Val Leu Ala Ser Cys Tyr Ala Val Leu Glu Ser His Gln Trp
            340                 345                 350
Ala His Arg Ala Phe Ala Pro Leu Arg Leu Leu His Ala Leu Gly Ala
        355                 360                 365
Leu Leu Pro Gly Gly Ala Val Gln Pro Thr Gly Met His Trp Tyr Ser
370                 375                 380
Arg Leu Leu Tyr Arg Leu Ala Glu Glu Leu Met Gly
385                 390                 395

(2) INFORMATION FOR SEQ ID NO:12:

(i) SEQUENCE CHARACTERISTICS:
        (A) LENGTH: 411 amino acids
        (B) TYPE: amino acid
        (D) TOPOLOGY: linear (ii) MOLECULE TYPE: protein (xi) SEQUENCE DESCRIPTION: SEQ ID NO:12:

Met Ser Pro Ala Trp Leu Arg Pro Arg Leu Arg Phe Cys Leu Phe Leu
1               5                   10                  15
Leu Leu Leu Leu Val Pro Ala Ala Arg Gly Cys Gly Pro Gly Arg
            20                  25                  30
Val Val Gly Ser Arg Arg Arg Pro Arg Lys Leu Val Pro Leu Ala
        35                  40                  45
Tyr Lys Gln Phe Ser Pro Asn Val Pro Glu Lys Thr Leu Gly Ala Ser
    50                  55                  60
```

```
Gly Arg Tyr Glu Gly Lys Ile Ala Arg Ser Ser Glu Arg Phe Lys Glu
 65                  70                  75                  80

Leu Thr Pro Asn Tyr Asn Pro Asp Ile Ile Phe Lys Asp Glu Glu Asn
                 85                  90                  95

Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
        115                 120                 125

Val Thr Glu Gly Arg Asp Glu Asp Gly His His Ser Glu Glu Ser Leu
    130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190

Glu His Ser Ala Ala Lys Thr Gly Gly Cys Phe Pro Ala Gly Ala
        195                 200                 205

Gln Val Arg Leu Glu Asn Gly Glu Arg Val Ala Leu Ser Ala Val Lys
    210                 215                 220

Pro Gly Asp Arg Val Leu Ala Met Gly Glu Asp Gly Thr Pro Thr Phe
225                 230                 235                 240

Ser Asp Val Leu Ile Phe Leu Asp Arg Glu Pro Asn Arg Leu Arg Ala
                245                 250                 255

Phe Gln Val Ile Glu Thr Gln Asp Pro Pro Arg Arg Leu Ala Leu Thr
            260                 265                 270

Pro Ala His Leu Leu Phe Ile Ala Asp Asn His Thr Glu Pro Ala Ala
        275                 280                 285

His Phe Arg Ala Thr Phe Ala Ser His Val Gln Pro Gly Gln Tyr Val
    290                 295                 300

Leu Val Ser Gly Val Pro Gly Leu Gln Pro Ala Arg Val Ala Ala Val
305                 310                 315                 320

Ser Thr His Val Ala Leu Gly Ser Tyr Ala Pro Leu Thr Arg His Gly
                325                 330                 335

Thr Leu Val Val Glu Asp Val Val Ala Ser Cys Phe Ala Ala Val Ala
            340                 345                 350

Asp His His Leu Ala Gln Leu Ala Phe Trp Pro Leu Arg Leu Phe Pro
        355                 360                 365

Ser Leu Ala Trp Gly Ser Trp Thr Pro Ser Glu Gly Val His Ser Tyr
    370                 375                 380

Pro Gln Met Leu Tyr Arg Leu Gly Arg Leu Leu Glu Glu Ser Thr
385                 390                 395                 400

Phe His Pro Leu Gly Met Ser Gly Ala Gly Ser
                405                 410
```

(2) INFORMATION FOR SEQ ID NO:13:

(i) SEQUENCE CHARACTERISTICS:
        (A) LENGTH: 437 amino acids
        (B) TYPE: amino acid
        (D) TOPOLOGY: linear (ii) MOLECULE TYPE: protein (xi) SEQUENCE DESCRIPTION: SEQ ID NO:13:

Met Leu Leu Leu Leu Ala Arg Cys Phe Leu Val Ile Leu Ala Ser Ser

```
              1               5              10              15
Leu Leu Val Cys Pro Gly Leu Ala Cys Gly Pro Gly Arg Gly Phe Gly
                20                      25                      30

Lys Arg Arg His Pro Lys Lys Leu Thr Pro Leu Ala Tyr Lys Gln Phe
                35                      40                      45

Ile Pro Asn Val Ala Glu Lys Thr Leu Gly Ala Ser Gly Arg Tyr Glu
                50                      55                      60

Gly Lys Ile Thr Arg Asn Ser Glu Arg Phe Lys Glu Leu Thr Pro Asn
 65                      70                      75                      80

Tyr Asn Pro Asp Ile Ile Phe Lys Asp Glu Glu Asn Thr Gly Ala Asp
                        85                      90                      95

Arg Leu Met Thr Gln Arg Cys Lys Asp Lys Leu Asn Ala Leu Ala Ile
                       100                     105                     110

Ser Val Met Asn Gln Trp Pro Gly Val Arg Leu Arg Val Thr Glu Gly
                       115                     120                     125

Trp Asp Glu Asp Gly His His Ser Glu Glu Ser Leu His Tyr Glu Gly
                       130                     135                     140

Arg Ala Val Asp Ile Thr Thr Ser Asp Arg Asp Arg Ser Lys Tyr Gly
145                     150                     155                     160

Met Leu Ala Arg Leu Ala Val Glu Ala Gly Phe Asp Trp Val Tyr Tyr
                       165                     170                     175

Glu Ser Lys Ala His Ile His Cys Ser Val Lys Ala Glu Asn Ser Val
                       180                     185                     190

Ala Ala Lys Ser Gly Gly Cys Phe Pro Gly Ser Ala Thr Val His Leu
                       195                     200                     205

Glu Gln Gly Gly Thr Lys Leu Val Lys Asp Leu Arg Pro Gly Asp Arg
                       210                     215                     220

Val Leu Ala Ala Asp Asp Gln Gly Arg Leu Leu Tyr Ser Asp Phe Leu
225                     230                     235                     240

Thr Phe Leu Asp Arg Asp Glu Gly Ala Lys Lys Val Phe Tyr Val Ile
                       245                     250                     255

Glu Thr Leu Glu Pro Arg Glu Arg Leu Leu Leu Thr Ala Ala His Leu
                       260                     265                     270

Leu Phe Val Ala Pro His Asn Asp Ser Gly Pro Thr Pro Gly Pro Ser
                       275                     280                     285

Ala Leu Phe Ala Ser Arg Val Arg Pro Gly Gln Arg Val Tyr Val Val
                       290                     295                     300

Ala Glu Arg Gly Gly Asp Arg Arg Leu Leu Pro Ala Ala Val His Ser
305                     310                     315                     320

Val Thr Leu Arg Glu Glu Glu Ala Gly Ala Tyr Ala Pro Leu Thr Ala
                       325                     330                     335

His Gly Thr Ile Leu Ile Asn Arg Val Leu Ala Ser Cys Tyr Ala Val
                       340                     345                     350

Ile Glu Glu His Ser Trp Ala His Arg Ala Phe Ala Pro Phe Arg Leu
                       355                     360                     365

Ala His Ala Leu Leu Ala Ala Leu Ala Pro Ala Arg Thr Asp Gly Gly
                       370                     375                     380

Gly Gly Gly Ser Ile Pro Ala Ala Gln Ser Ala Thr Glu Ala Arg Gly
385                     390                     395                     400

Ala Glu Pro Thr Ala Gly Ile His Trp Tyr Ser Gln Leu Leu Tyr His
                       405                     410                     415

Ile Gly Thr Trp Leu Leu Asp Ser Glu Thr Met His Pro Leu Gly Met
                       420                     425                     430
```

```
Ala Val Lys Ser Ser
        435
```

(2) INFORMATION FOR SEQ ID NO:14:

(i) SEQUENCE CHARACTERISTICS:
        (A) LENGTH: 418 amino acids
        (B) TYPE: amino acid
        (D) TOPOLOGY: linear (ii) MOLECULE TYPE: protein (xi) SEQUENCE DESCRIPTION: SEQ ID NO:14:

```
Met Arg Leu Leu Thr Arg Val Leu Leu Val Ser Leu Leu Thr Leu Ser
 1               5                  10                  15

Leu Val Val Ser Gly Leu Ala Cys Gly Pro Gly Arg Gly Tyr Gly Arg
            20                  25                  30

Arg Arg His Pro Lys Lys Leu Thr Pro Leu Ala Tyr Lys Gln Phe Ile
        35                  40                  45

Pro Asn Val Ala Glu Lys Thr Leu Gly Ala Ser Gly Arg Tyr Glu Gly
    50                  55                  60

Lys Ile Thr Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ser Leu Ala Ile Ser
            100                 105                 110

Val Met Asn His Trp Pro Gly Val Lys Leu Arg Val Thr Glu Gly Trp
        115                 120                 125

Asp Glu Asp Gly His His Phe Glu Glu Ser Leu His Tyr Glu Gly Arg
    130                 135                 140

Ala Val Asp Ile Thr Thr Ser Asp Arg Asp Lys Ser Lys Tyr Gly Thr
145                 150                 155                 160

Leu Ser Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Leu Val Ser Leu Gln
        195                 200                 205

Asp Gly Gly Gln Lys Ala Val Lys Asp Leu Asn Pro Gly Asp Lys Val
    210                 215                 220

Leu Ala Ala Asp Ser Ala Gly Asn Leu Val Phe Ser Asp Phe Ile Met
225                 230                 235                 240

Phe Thr Asp Arg Asp Ser Thr Thr Arg Arg Val Phe Tyr Val Ile Glu
                245                 250                 255

Thr Gln Glu Pro Val Glu Lys Ile Thr Leu Thr Ala Ala His Leu Leu
            260                 265                 270

Phe Val Leu Asp Asn Ser Thr Glu Asp Leu His Thr Met Thr Ala Ala
        275                 280                 285

Tyr Ala Ser Ser Val Arg Ala Gly Gln Lys Val Met Val Val Asp Asp
    290                 295                 300

Ser Gly Gln Leu Lys Ser Val Ile Val Gln Arg Ile Tyr Thr Glu Glu
305                 310                 315                 320

Gln Arg Gly Ser Phe Ala Pro Val Thr Ala His Gly Thr Ile Val Val
                325                 330                 335
```

Asp Arg Ile Leu Ala Ser Cys Tyr Ala Val Ile Glu Asp Gln Gly Leu
            340                 345                 350

Ala His Leu Ala Phe Ala Pro Ala Arg Leu Tyr Tyr Tyr Val Ser Ser
            355                 360                 365

Phe Leu Ser Pro Lys Thr Pro Ala Val Gly Pro Met Arg Leu Tyr Asn
370                 375                 380

Arg Arg Gly Ser Thr Gly Thr Pro Gly Ser Cys His Gln Met Gly Thr
385                 390                 395                 400

Trp Leu Leu Asp Ser Asn Met Leu His Pro Leu Gly Met Ser Val Asn
                405                 410                 415

Ser Ser (2) INFORMATION FOR SEQ ID NO:15:

(i) SEQUENCE CHARACTERISTICS:
        (A) LENGTH: 475 amino acids
        (B) TYPE: amino acid
        (D) TOPOLOGY: linear (ii) MOLECULE TYPE: protein (xi) SEQUENCE DESCRIPTION: SEQ ID NO:15:

Met Leu Leu Leu Ala Arg Cys Leu Leu Leu Val Leu Ser Ser Leu
1               5                   10                  15

Leu Val Cys Ser Gly Leu Ala Cys Gly Pro Gly Arg Gly Phe Gly Lys
            20                  25                  30

Arg Arg His Pro Lys Lys Leu Thr Pro Leu Ala Tyr Lys Gln Phe Ile
            35                  40                  45

Pro Asn Val Ala Glu Lys Thr Leu Gly Ala Ser Gly Arg Tyr Glu Gly
        50                  55                  60

Lys Ile Ser Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ala Leu Ala Ile Ser
            100                 105                 110

Val Met Asn Gln Trp Pro Gly Val Lys Leu Arg Val Thr Glu Gly Trp
        115                 120                 125

Asp Glu Asp Gly His His Ser Glu Glu Ser Leu His Tyr Glu Gly Arg
    130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
        195                 200                 205

Gln Gly Gly Thr Lys Leu Val Lys Asp Leu Ser Pro Gly Asp Arg Val
    210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

```
Phe Val Ala Pro His Asn Asp Ser Ala Thr Gly Glu Pro Glu Ala Ser
        275                 280                 285

Ser Gly Ser Gly Pro Pro Ser Gly Gly Ala Leu Gly Pro Arg Ala Leu
        290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
                340                 345                 350

Thr Ile Leu Ile Asn Arg Val Leu Ala Ser Cys Tyr Ala Val Ile Glu
                355                 360                 365

Glu His Ser Trp Ala His Arg Ala Phe Ala Pro Phe Arg Leu Ala His
        370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Gly Arg Val Ala Leu Thr
                405                 410                 415

Ala Pro Gly Ala Ala Asp Ala Pro Gly Ala Gly Ala Thr Ala Gly Ile
                420                 425                 430

His Trp Tyr Ser Gln Leu Leu Tyr Gln Ile Gly Thr Trp Leu Leu Asp
                435                 440                 445

Ser Glu Ala Leu His Pro Leu Gly Met Ala Val Lys Ser Ser Xaa Ser
        450                 455                 460

Arg Gly Ala Gly Gly Gly Ala Arg Glu Gly Ala
465                 470                 475

(2) INFORMATION FOR SEQ ID NO:16:

(i) SEQUENCE CHARACTERISTICS:
        (A) LENGTH: 411 amino acids
        (B) TYPE: amino acid
        (D) TOPOLOGY: linear (ii) MOLECULE TYPE: protein (xi) SEQUENCE DESCRIPTION: SEQ ID NO:16:

Met Ser Pro Ala Arg Leu Arg Pro Arg Leu His Phe Cys Leu Val Leu
 1                   5                  10                  15

Leu Leu Leu Leu Val Val Pro Ala Ala Trp Gly Cys Gly Pro Gly Arg
                20                  25                  30

Val Val Gly Ser Arg Arg Arg Pro Pro Arg Lys Leu Val Pro Leu Ala
                35                  40                  45

Tyr Lys Gln Phe Ser Pro Asn Val Pro Glu Lys Thr Leu Gly Ala Ser
        50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                85                  90                  95

Thr Gly Ala Asp Arg Leu Met Thr Gln Arg Cys Lys Asp Arg Leu Asn
                100                 105                 110

Ser Leu Ala Ile Ser Val Met Asn Gln Trp Pro Gly Val Lys Leu Arg
        115                 120                 125

Val Thr Glu Gly Trp Asp Glu Asp Gly His His Ser Glu Glu Ser Leu
130                 135                 140
```

```
His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190

Glu His Ser Ala Ala Ala Lys Thr Gly Gly Cys Phe Pro Ala Gly Ala
        195                 200                 205

Gln Val Arg Leu Glu Ser Gly Ala Arg Val Ala Leu Ser Ala Val Arg
    210                 215                 220

Pro Gly Asp Arg Val Leu Ala Met Gly Glu Asp Gly Ser Pro Thr Phe
225                 230                 235                 240

Ser Asp Val Leu Ile Phe Leu Asp Arg Glu Pro His Arg Leu Arg Ala
                245                 250                 255

Phe Gln Val Ile Glu Thr Gln Asp Pro Pro Arg Arg Leu Ala Leu Thr
            260                 265                 270

Pro Ala His Leu Leu Phe Thr Ala Asp Asn His Thr Glu Pro Ala Ala
        275                 280                 285

Arg Phe Arg Ala Thr Phe Ala Ser His Val Gln Pro Gly Gln Tyr Val
    290                 295                 300

Leu Val Ala Gly Val Pro Gly Leu Gln Pro Ala Arg Val Ala Ala Val
305                 310                 315                 320

Ser Thr His Val Ala Leu Gly Ala Tyr Ala Pro Leu Thr Lys His Gly
                325                 330                 335

Thr Leu Val Val Glu Asp Val Val Ala Ser Cys Phe Ala Ala Val Ala
            340                 345                 350

Asp His His Leu Ala Gln Leu Ala Phe Trp Pro Leu Arg Leu Phe His
        355                 360                 365

Ser Leu Ala Trp Gly Ser Trp Thr Pro Gly Glu Gly Val His Trp Tyr
    370                 375                 380

Pro Gln Leu Leu Tyr Arg Leu Gly Arg Leu Leu Glu Glu Gly Ser
385                 390                 395                 400

Phe His Pro Leu Gly Met Ser Gly Ala Gly Ser
                405                 410

(2) INFORMATION FOR SEQ ID NO:17:

(i) SEQUENCE CHARACTERISTICS:
        (A) LENGTH: 396 amino acids
        (B) TYPE: amino acid
        (D) TOPOLOGY: linear (ii) MOLECULE TYPE: protein (xi) SEQUENCE DESCRIPTION: SEQ ID NO:17:

Met Ala Leu Leu Thr Asn Leu Leu Pro Leu Cys Cys Leu Ala Leu Leu
1               5                   10                  15

Ala Leu Pro Ala Gln Ser Cys Gly Pro Gly Arg Gly Pro Val Gly Arg
                20                  25                  30

Arg Arg Tyr Ala Arg Lys Gln Leu Val Pro Leu Leu Tyr Lys Gln Phe
            35                  40                  45

Val Pro Gly Val Pro Glu Arg Thr Leu Gly Ala Ser Gly Pro Ala Glu
        50                  55                  60

Gly Arg Val Ala Arg Gly Ser Glu Arg Phe Arg Asp Leu Val Pro Asn
65                  70                  75                  80

Tyr Asn Pro Asp Ile Ile Phe Lys Asp Glu Glu Asn Ser Gly Ala Asp
```

```
                    85                  90                  95
Arg Leu Met Thr Glu Arg Cys Lys Glu Arg Val Asn Ala Leu Ala Ile
                100                 105                 110

Ala Val Met Asn Met Trp Pro Gly Val Arg Leu Arg Val Thr Glu Gly
                115                 120                 125

Trp Asp Glu Asp Gly His His Ala Gln Asp Ser Leu His Tyr Glu Gly
                130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Val His Val Ser Val Lys Ala Asp Asn Ser Leu
                180                 185                 190

Ala Val Arg Ala Gly Gly Cys Phe Pro Gly Asn Ala Thr Val Arg Leu
                195                 200                 205

Trp Ser Gly Glu Arg Lys Gly Leu Arg Glu Leu His Arg Gly Asp Trp
                210                 215                 220

Val Leu Ala Ala Asp Ala Ser Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Trp Pro Pro Arg Lys Leu Leu Thr Pro Trp His Leu
                260                 265                 270

Val Phe Ala Ala Arg Gly Pro Ala Pro Ala Pro Gly Asp Phe Ala Pro
                275                 280                 285

Val Phe Ala Arg Arg Leu Arg Ala Gly Asp Ser Val Leu Ala Pro Gly
                290                 295                 300

Gly Asp Ala Leu Arg Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
                340                 345                 350

Ala His Arg Ala Phe Ala Pro Leu Arg Leu Leu His Ala Leu Gly Ala
                355                 360                 365

Leu Leu Pro Gly Gly Ala Val Gln Pro Thr Gly Met His Trp Tyr Ser
                370                 375                 380

Arg Leu Leu Tyr Arg Leu Ala Glu Glu Leu Leu Gly
385                 390                 395

(2) INFORMATION FOR SEQ ID NO:18:

(i) SEQUENCE CHARACTERISTICS:
        (A) LENGTH: 416 amino acids
        (B) TYPE: amino acid
        (D) TOPOLOGY: linear (ii) MOLECULE TYPE: protein (xi) SEQUENCE DESCRIPTION: SEQ ID NO:18:

Met Asp Val Arg Leu His Leu Lys Gln Phe Ala Leu Leu Cys Phe Ile
1                   5                  10                  15

Ser Leu Leu Leu Thr Pro Cys Gly Leu Ala Cys Gly Pro Gly Arg Gly
                20                  25                  30

Tyr Gly Lys Arg Arg His Pro Lys Lys Leu Thr Pro Leu Ala Tyr Lys
                35                  40                  45
```

```
Gln Phe Ile Pro Asn Val Ala Glu Lys Thr Leu Gly Ala Ser Gly Lys
     50                  55                  60

Tyr Glu Gly Lys Ile Thr Arg Asn Ser Glu Arg Phe Lys Glu Leu Ile
 65                  70                  75                  80

Pro Asn Tyr Asn Pro Asp Ile Ile Phe Lys Asp Glu Asn Thr Asn
                 85                  90                  95

Ala Asp Arg Leu Met Thr Lys Arg Cys Lys Asp Lys Leu Asn Ser Leu
             100                 105                 110

Ala Ile Ser Val Met Asn His Trp Pro Gly Val Lys Leu Arg Val Thr
             115                 120                 125

Glu Gly Trp Asp Glu Asp Gly His His Leu Glu Glu Ser Leu His Tyr
             130                 135                 140

Glu Gly Arg Ala Val Asp Ile Thr Thr Ser Asp Arg Asp Lys Ser Lys
145                 150                 155                 160

Tyr Gly Met Leu Ser Arg Leu Ala Val Glu Ala Gly Phe Asp Trp Val
                 165                 170                 175

Tyr Tyr Glu Ser Lys Ala His Ile His Cys Ser Val Lys Ala Glu Asn
                 180                 185                 190

Ser Val Ala Ala Lys Ser Gly Gly Cys Phe Pro Gly Ser Gly Thr Val
             195                 200                 205

Thr Leu Gly Asp Gly Thr Arg Lys Pro Ile Lys Asp Leu Lys Val Gly
             210                 215                 220

Asp Arg Val Leu Ala Ala Asp Glu Lys Gly Asn Val Leu Ile Ser Asp
225                 230                 235                 240

Phe Ile Met Phe Ile Asp His Asp Pro Thr Thr Arg Arg Gln Phe Ile
                 245                 250                 255

Val Ile Glu Thr Ser Glu Pro Phe Thr Lys Leu Thr Leu Thr Ala Ala
             260                 265                 270

His Leu Val Phe Val Gly Asn Ser Ser Ala Ala Ser Gly Ile Thr Ala
             275                 280                 285

Thr Phe Ala Ser Asn Val Lys Pro Gly Asp Thr Val Leu Val Trp Glu
290                 295                 300

Asp Thr Cys Glu Ser Leu Lys Ser Val Thr Val Lys Arg Ile Tyr Thr
305                 310                 315                 320

Glu Glu His Glu Gly Ser Phe Ala Pro Val Thr Ala His Gly Thr Ile
                 325                 330                 335

Ile Val Asp Gln Val Leu Ala Ser Cys Tyr Ala Val Ile Glu Asn His
             340                 345                 350

Lys Trp Ala His Trp Ala Phe Ala Pro Val Arg Leu Cys His Lys Leu
             355                 360                 365

Met Thr Trp Leu Phe Pro Ala Arg Glu Ser Asn Val Asn Phe Gln Glu
370                 375                 380

Asp Gly Ile His Trp Tyr Ser Asn Met Leu Phe His Ile Gly Ser Trp
385                 390                 395                 400

Leu Leu Asp Arg Asp Ser Phe His Pro Leu Gly Ile Leu His Leu Ser
                 405                 410                 415

(2) INFORMATION FOR SEQ ID NO:19:

(i) SEQUENCE CHARACTERISTICS:
        (A) LENGTH: 1416 base pairs
        (B) TYPE: nucleic acid
        (C) STRANDEDNESS: both
        (D) TOPOLOGY: linear
```

(ii) MOLECULE TYPE: cDNA (ix) FEATURE:
 (A) NAME/KEY: CDS
 (B) LOCATION: 1..1413

(xi) SEQUENCE DESCRIPTION: SEQ ID NO:19:

| | | | | | | | | | | | | | | | | |
|---|---|---|---|---|---|---|---|---|---|---|---|---|---|---|---|---|
| ATG | GAT | AAC | CAC | AGC | TCA | GTG | CCT | TGG | GCC | AGT | GCC | GCC | AGT | GTC | ACC | 48 |
| Met | Asp | Asn | His | Ser | Ser | Val | Pro | Trp | Ala | Ser | Ala | Ala | Ser | Val | Thr | |
| 1 | | | | 5 | | | | | 10 | | | | | 15 | | |
| TGT | CTC | TCC | CTG | GGA | TGC | CAA | ATG | CCA | CAG | TTC | CAG | TTC | CAG | TTC | CAG | 96 |
| Cys | Leu | Ser | Leu | Gly | Cys | Gln | Met | Pro | Gln | Phe | Gln | Phe | Gln | Phe | Gln | |
| | | | 20 | | | | | 25 | | | | | 30 | | | |
| CTC | CAA | ATC | CGC | AGC | GAG | CTC | CAT | CTC | CGC | AAG | CCC | GCA | AGA | AGA | ACG | 144 |
| Leu | Gln | Ile | Arg | Ser | Glu | Leu | His | Leu | Arg | Lys | Pro | Ala | Arg | Arg | Thr | |
| | | 35 | | | | | 40 | | | | | 45 | | | | |
| CAA | ACG | ATG | CGC | CAC | ATT | GCG | CAT | ACG | CAG | CGT | TGC | CTC | AGC | AGG | CTG | 192 |
| Gln | Thr | Met | Arg | His | Ile | Ala | His | Thr | Gln | Arg | Cys | Leu | Ser | Arg | Leu | |
| | 50 | | | | | 55 | | | | | 60 | | | | | |
| ACC | TCT | CTG | GTG | GCC | CTG | CTG | CTG | ATC | GTC | TTG | CCG | ATG | GTC | TTT | AGC | 240 |
| Thr | Ser | Leu | Val | Ala | Leu | Leu | Leu | Ile | Val | Leu | Pro | Met | Val | Phe | Ser | |
| 65 | | | | | 70 | | | | | 75 | | | | | 80 | |
| CCG | GCT | CAC | AGC | TGC | GGT | CCT | GGC | CGA | GGA | TTG | GGT | CGT | CAT | AGG | GCG | 288 |
| Pro | Ala | His | Ser | Cys | Gly | Pro | Gly | Arg | Gly | Leu | Gly | Arg | His | Arg | Ala | |
| | | | 85 | | | | | 90 | | | | | 95 | | | |
| CGC | AAC | CTG | TAT | CCG | CTG | GTC | CTC | AAG | CAG | ACA | ATT | CCC | AAT | CTA | TCC | 336 |
| Arg | Asn | Leu | Tyr | Pro | Leu | Val | Leu | Lys | Gln | Thr | Ile | Pro | Asn | Leu | Ser | |
| | | 100 | | | | | 105 | | | | | 110 | | | | |
| GAG | TAC | ACG | AAC | AGC | GCC | TCC | GGA | CCT | CTG | GAG | GGT | GTG | ATC | CGT | CGG | 384 |
| Glu | Tyr | Thr | Asn | Ser | Ala | Ser | Gly | Pro | Leu | Glu | Gly | Val | Ile | Arg | Arg | |
| | | 115 | | | | | 120 | | | | | 125 | | | | |
| GAT | TCG | CCC | AAA | TTC | AAG | GAC | CTC | GTG | CCC | AAC | TAC | AAC | AGG | GAC | ATC | 432 |
| Asp | Ser | Pro | Lys | Phe | Lys | Asp | Leu | Val | Pro | Asn | Tyr | Asn | Arg | Asp | Ile | |
| | 130 | | | | | 135 | | | | | 140 | | | | | |
| CTT | TTC | CGT | GAC | GAG | GAA | GGC | ACC | GGA | GCG | GAT | GGC | TTG | ATG | AGC | AAG | 480 |
| Leu | Phe | Arg | Asp | Glu | Glu | Gly | Thr | Gly | Ala | Asp | Gly | Leu | Met | Ser | Lys | |
| 145 | | | | | 150 | | | | | 155 | | | | | 160 | |
| CGC | TGC | AAG | GAG | AAG | CTA | AAC | GTG | CTG | GCC | TAC | TCG | GTG | ATG | AAC | GAA | 528 |
| Arg | Cys | Lys | Glu | Lys | Leu | Asn | Val | Leu | Ala | Tyr | Ser | Val | Met | Asn | Glu | |
| | | | | 165 | | | | | 170 | | | | | 175 | | |
| TGG | CCC | GGC | ATC | CGG | CTG | CTG | GTC | ACC | GAG | AGC | TGG | GAC | GAG | GAC | TAC | 576 |
| Trp | Pro | Gly | Ile | Arg | Leu | Leu | Val | Thr | Glu | Ser | Trp | Asp | Glu | Asp | Tyr | |
| | | | 180 | | | | | 185 | | | | | 190 | | | |
| CAT | CAC | GGC | CAG | GAG | TCG | CTC | CAC | TAC | GAG | GGC | CGA | GCG | GTG | ACC | ATT | 624 |
| His | His | Gly | Gln | Glu | Ser | Leu | His | Tyr | Glu | Gly | Arg | Ala | Val | Thr | Ile | |
| | | 195 | | | | | 200 | | | | | 205 | | | | |
| GCC | ACC | TCC | GAT | CGC | GAC | CAG | TCC | AAA | TAC | GGC | ATG | CTC | GCT | CGC | CTG | 672 |
| Ala | Thr | Ser | Asp | Arg | Asp | Gln | Ser | Lys | Tyr | Gly | Met | Leu | Ala | Arg | Leu | |
| | 210 | | | | | 215 | | | | | 220 | | | | | |
| GCC | GTC | GAG | GCT | GGA | TTC | GAT | TGG | GTC | TCC | TAC | GTC | AGC | AGG | CGC | CAC | 720 |
| Ala | Val | Glu | Ala | Gly | Phe | Asp | Trp | Val | Ser | Tyr | Val | Ser | Arg | Arg | His | |
| 225 | | | | | 230 | | | | | 235 | | | | | 240 | |
| ATC | TAC | TGC | TCC | GTC | AAG | TCA | GAT | TCG | TCG | ATC | AGT | TCC | CAC | GTG | CAC | 768 |
| Ile | Tyr | Cys | Ser | Val | Lys | Ser | Asp | Ser | Ser | Ile | Ser | Ser | His | Val | His | |
| | | | | 245 | | | | | 250 | | | | | 255 | | |
| GGC | TGC | TTC | ACG | CCG | GAG | AGC | ACA | GCG | CTG | CTG | GAG | AGT | GGA | GTC | CGG | 816 |
| Gly | Cys | Phe | Thr | Pro | Glu | Ser | Thr | Ala | Leu | Leu | Glu | Ser | Gly | Val | Arg | |
| | | | 260 | | | | | 265 | | | | | 270 | | | |
| AAG | CCG | CTC | GGC | GAG | CTC | TCT | ATC | GGA | GAT | CGT | GTT | TTG | AGC | ATG | ACC | 864 |
| Lys | Pro | Leu | Gly | Glu | Leu | Ser | Ile | Gly | Asp | Arg | Val | Leu | Ser | Met | Thr | |
| | | 275 | | | | | 280 | | | | | 285 | | | | |

```
GCC AAC GGA CAG GCC GTC TAC AGC GAA GTG ATC CTC TTC ATG GAC CGC      912
Ala Asn Gly Gln Ala Val Tyr Ser Glu Val Ile Leu Phe Met Asp Arg
    290                 295                 300

AAC CTC GAG CAG ATG CAA AAC TTT GTG CAG CTG CAC ACG GAC GGT GGA      960
Asn Leu Glu Gln Met Gln Asn Phe Val Gln Leu His Thr Asp Gly Gly
305                 310                 315                 320

GCA GTG CTC ACG GTG ACG CCG GCT CAC CTG GTT AGC GTT TGG CAG CCG     1008
Ala Val Leu Thr Val Thr Pro Ala His Leu Val Ser Val Trp Gln Pro
                325                 330                 335

GAG AGC CAG AAG CTC ACG TTT GTG TTT GCG CAT CGC ATC GAG GAG AAG     1056
Glu Ser Gln Lys Leu Thr Phe Val Phe Ala His Arg Ile Glu Glu Lys
            340                 345                 350

AAC CAG GTG CTC GTA CGG GAT GTG GAG ACG GGC GAG CTG AGG CCC CAG     1104
Asn Gln Val Leu Val Arg Asp Val Glu Thr Gly Glu Leu Arg Pro Gln
        355                 360                 365

CGA GTG GTC AAG TTG GGC AGT GTG CGC AGT AAG GGC GTG GTC GCG CCG     1152
Arg Val Val Lys Leu Gly Ser Val Arg Ser Lys Gly Val Val Ala Pro
    370                 375                 380

CTG ACC CGC GAG GGC ACC ATT GTG GTC AAC TCG GTG GCC GCC AGT TGC     1200
Leu Thr Arg Glu Gly Thr Ile Val Val Asn Ser Val Ala Ala Ser Cys
385                 390                 395                 400

TAT GCG GTG ATC AAC AGT CAG TCG CTG GCC CAC TGG GGA CTG GCT CCC     1248
Tyr Ala Val Ile Asn Ser Gln Ser Leu Ala His Trp Gly Leu Ala Pro
                405                 410                 415

ATG CGC CTG CTG TCC ACG CTG GAG GCG TGG CTG CCC GCC AAG GAG CAG     1296
Met Arg Leu Leu Ser Thr Leu Glu Ala Trp Leu Pro Ala Lys Glu Gln
            420                 425                 430

TTG CAC AGT TCG CCG AAG GTG GTG AGC TCG GCG CAG CAG CAG AAT GGC     1344
Leu His Ser Ser Pro Lys Val Val Ser Ser Ala Gln Gln Gln Asn Gly
        435                 440                 445

ATC CAT TGG TAT GCC AAT GCG CTC TAC AAG GTC AAG GAC TAC GTG CTG     1392
Ile His Trp Tyr Ala Asn Ala Leu Tyr Lys Val Lys Asp Tyr Val Leu
    450                 455                 460

CCG CAG AGC TGG CGC CAC GAT TGA                                     1416
Pro Gln Ser Trp Arg His Asp
465                 470
```

(2) INFORMATION FOR SEQ ID NO:20:

(i) SEQUENCE CHARACTERISTICS:
        (A) LENGTH: 471 amino acids
        (B) TYPE: amino acid
        (D) TOPOLOGY: linear (ii) MOLECULE TYPE: protein (xi) SEQUENCE DESCRIPTION: SEQ ID NO:20:

```
Met Asp Asn His Ser Ser Val Pro Trp Ala Ser Ala Ser Val Thr
1               5                   10                  15

Cys Leu Ser Leu Gly Cys Gln Met Pro Gln Phe Gln Phe Gln Phe Gln
                20                  25                  30

Leu Gln Ile Arg Ser Glu Leu His Leu Arg Lys Pro Ala Arg Arg Thr
            35                  40                  45

Gln Thr Met Arg His Ile Ala His Thr Gln Arg Cys Leu Ser Arg Leu
        50                  55                  60

Thr Ser Leu Val Ala Leu Leu Leu Ile Val Leu Pro Met Val Phe Ser
65                  70                  75                  80

Pro Ala His Ser Cys Gly Pro Gly Arg Gly Leu Gly Arg His Arg Ala
                85                  90                  95
```

-continued

```
Arg Asn Leu Tyr Pro Leu Val Leu Lys Gln Thr Ile Pro Asn Leu Ser
            100                 105                 110

Glu Tyr Thr Asn Ser Ala Ser Gly Pro Leu Glu Gly Val Ile Arg Arg
            115                 120                 125

Asp Ser Pro Lys Phe Lys Asp Leu Val Pro Asn Tyr Asn Arg Asp Ile
130                 135                 140

Leu Phe Arg Asp Glu Glu Gly Thr Gly Ala Asp Gly Leu Met Ser Lys
145                 150                 155                 160

Arg Cys Lys Glu Lys Leu Asn Val Leu Ala Tyr Ser Val Met Asn Glu
                165                 170                 175

Trp Pro Gly Ile Arg Leu Leu Val Thr Glu Ser Trp Asp Glu Asp Tyr
                180                 185                 190

His His Gly Gln Glu Ser Leu His Tyr Glu Gly Arg Ala Val Thr Ile
                195                 200                 205

Ala Thr Ser Asp Arg Asp Gln Ser Lys Tyr Gly Met Leu Ala Arg Leu
            210                 215                 220

Ala Val Glu Ala Gly Phe Asp Trp Val Ser Tyr Val Ser Arg Arg His
225                 230                 235                 240

Ile Tyr Cys Ser Val Lys Ser Asp Ser Ser Ile Ser Ser His Val His
                245                 250                 255

Gly Cys Phe Thr Pro Glu Ser Thr Ala Leu Leu Glu Ser Gly Val Arg
            260                 265                 270

Lys Pro Leu Gly Glu Leu Ser Ile Gly Asp Arg Val Leu Ser Met Thr
            275                 280                 285

Ala Asn Gly Gln Ala Val Tyr Ser Glu Val Ile Leu Phe Met Asp Arg
            290                 295                 300

Asn Leu Glu Gln Met Gln Asn Phe Val Gln Leu His Thr Asp Gly Gly
305                 310                 315                 320

Ala Val Leu Thr Val Thr Pro Ala His Leu Val Ser Val Trp Gln Pro
                325                 330                 335

Glu Ser Gln Lys Leu Thr Phe Val Phe Ala His Arg Ile Glu Glu Lys
            340                 345                 350

Asn Gln Val Leu Val Arg Asp Val Glu Thr Gly Glu Leu Arg Pro Gln
            355                 360                 365

Arg Val Val Lys Leu Gly Ser Val Arg Ser Lys Gly Val Val Ala Pro
            370                 375                 380

Leu Thr Arg Glu Gly Thr Ile Val Val Asn Ser Val Ala Ala Ser Cys
385                 390                 395                 400

Tyr Ala Val Ile Asn Ser Gln Ser Leu Ala His Trp Gly Leu Ala Pro
                405                 410                 415

Met Arg Leu Leu Ser Thr Leu Glu Ala Trp Leu Pro Ala Lys Glu Gln
                420                 425                 430

Leu His Ser Ser Pro Lys Val Val Ser Ser Ala Gln Gln Gln Asn Gly
            435                 440                 445

Ile His Trp Tyr Ala Asn Ala Leu Tyr Lys Val Lys Asp Tyr Val Leu
            450                 455                 460

Pro Gln Ser Trp Arg His Asp
465                 470
```

(2) INFORMATION FOR SEQ ID NO:21:

(i) SEQUENCE CHARACTERISTICS:
        (A) LENGTH: 221 amino acids
        (B) TYPE: amino acid
        (C) STRANDEDNESS:

```
       (D) TOPOLOGY: linear (ii) MOLECULE TYPE: peptide (v) FRAGMENT TYPE: internal (xi) SEQUENCE DESCRIPTION: SEQ ID NO:21:

Cys Gly Pro Gly Arg Gly Xaa Gly Xaa Arg Arg His Pro Lys Lys Leu
1               5                  10                  15

Thr Pro Leu Ala Tyr Lys Gln Phe Ile Pro Asn Val Ala Glu Lys Thr
            20                  25                  30

Leu Gly Ala Ser Gly Arg Tyr Glu Gly Lys Ile Xaa Arg Asn Ser Glu
        35                  40                  45

Arg Phe Lys Glu Leu Thr Pro Asn Tyr Asn Pro Asp Ile Ile Phe Lys
    50                  55                  60

Asp Glu Glu Asn Thr Gly Ala Asp Arg Leu Met Thr Gln Arg Cys Lys
65                  70                  75                  80

Asp Lys Leu Asn Xaa Leu Ala Ile Ser Val Met Asn Xaa Trp Pro Gly
                85                  90                  95

Val Xaa Leu Arg Val Thr Glu Gly Trp Asp Glu Asp Gly His His Xaa
            100                 105                 110

Glu Glu Ser Leu His Tyr Glu Gly Arg Ala Val Asp Ile Thr Thr Ser
        115                 120                 125

Asp Arg Asp Xaa Ser Lys Tyr Gly Xaa Leu Xaa Arg Leu Ala Val Glu
    130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly Cys Phe
                165                 170                 175

Pro Gly Ser Ala Xaa Val Xaa Leu Xaa Xaa Gly Gly Xaa Lys Xaa Val
            180                 185                 190

Lys Asp Leu Xaa Pro Gly Asp Xaa Val Leu Ala Ala Asp Xaa Xaa Gly
        195                 200                 205

Xaa Leu Xaa Xaa Ser Asp Phe Xaa Xaa Phe Xaa Asp Arg
210                 215                 220

(2) INFORMATION FOR SEQ ID NO:22:

(i) SEQUENCE CHARACTERISTICS:
        (A) LENGTH: 167 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:22:

Cys Gly Pro Gly Arg Gly Xaa Xaa Xaa Arg Arg Xaa Xaa Xaa Pro Lys
1               5                  10                  15

Xaa Leu Xaa Pro Leu Xaa Tyr Lys Gln Phe Xaa Pro Xaa Xaa Xaa Glu
            20                  25                  30

Xaa Thr Leu Gly Ala Ser Gly Xaa Xaa Glu Gly Xaa Xaa Xaa Arg Xaa
        35                  40                  45

Ser Glu Arg Phe Xaa Xaa Leu Thr Pro Asn Tyr Asn Pro Asp Ile Ile
    50                  55                  60

Phe Lys Asp Glu Glu Asn Xaa Gly Ala Asp Arg Leu Met Thr Xaa Arg
65                  70                  75                  80
```

```
Cys Lys Xaa Xaa Xaa Asn Xaa Leu Ala Ile Ser Val Met Asn Xaa Trp
            85                  90                  95

Pro Gly Val Xaa Leu Arg Val Thr Glu Gly Xaa Asp Glu Asp Gly His
            100                 105                 110

His Xaa Xaa Xaa Ser Leu His Tyr Glu Gly Arg Ala Xaa Asp Ile Thr
            115                 120                 125

Thr Ser Asp Arg Asp Xaa Xaa Lys Tyr Gly Xaa Leu Xaa Arg Leu Ala
            130                 135                 140

Val Glu Ala Gly Phe Asp Trp Val Tyr Glu Ser Xaa Xaa His Xaa
145                 150                 155                 160

His Xaa Ser Val Lys Xaa Xaa
            165
```

(2) INFORMATION FOR SEQ ID NO:23:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

GGAATTCCCA GCAGNTGCTA AAGGAAGCAA GNGCTNAA                               38

(2) INFORMATION FOR SEQ ID NO:24:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

TCATCGATGG ACCCAGATCG AAANCCNGCT CTC                                       33

(2) INFORMATION FOR SEQ ID NO:25:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

GCTCTAGAGC TCNACNGCNA GANCGTNGC                                                 29

(2) INFORMATION FOR SEQ ID NO:26:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

AGCTGTCGAC GCGGCCGCTA CGTAGGTTAC CGACGTCAAG CTTAGATCTC               50

(2) INFORMATION FOR SEQ ID NO:27:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

AGCTGAGATC TAAGCTTGAC GTCGGTAACC TACGTAGCGG CCGCGTCGAC           50

(2) INFORMATION FOR SEQ ID NO:28:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

GATCGGCCAG GCAGGCCTCG CGATATCGTC ACCGCGGTAT TCGAA                45

(2) INFORMATION FOR SEQ ID NO:29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

AGTGCCAGTC GGGGCCCCCA GGGCCGCGCC                                 30

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

TACCACAGCG GATGGTTCGG                                            20

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

GTGGTGGTTA TGCCGATCGC                                            20

(2) INFORMATION FOR SEQ ID NO:32:

(i) SEQUENCE CHARACTERISTICS:

```
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

TAAGAGGCCT ATAAGAGGCG G                                              21

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

AAGTCAGCCC AGAGGAGACT                                                20

(2) INFORMATION FOR SEQ ID NO:34:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:34:

Cys Gly Pro Gly Arg Gly
1               5

(2) INFORMATION FOR SEQ ID NO:35:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

AGCAGNTGCT AAAGGAAGCA AGNGCTNAA                                      29

(2) INFORMATION FOR SEQ ID NO:36:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

CTCNACNGCN AGANCKNGTN GCNA                                           24

(2) INFORMATION FOR SEQ ID NO:37:

(i) SEQUENCE CHARACTERISTICS:
        (A) LENGTH: 32 base pairs
```

```
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:37:

CTGCAGGGAT CCACCATGCG GCTTTTGACG AG                                32

(2) INFORMATION FOR SEQ ID NO:38:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:38:

CTGCAGGGAT CCTTATTCCA CACGAGGGAT T                                 31

(2) INFORMATION FOR SEQ ID NO:39:

(i) SEQUENCE CHARACTERISTICS:
            (A) LENGTH: 65 amino acids
            (B) TYPE: amino acid
            (C) STRANDEDNESS:
            (D) TOPOLOGY: linear (ii) MOLECULE TYPE: peptide (v) FRAGMENT TYPE: internal (xi) SEQUENCE DESCRIPTION: SEQ ID NO:39:

Gln Arg Cys Lys Glu Lys Leu Asn Ser Leu Ala Ile Ser Val Met Asn
1               5                  10                  15

Met Trp Pro Gly Val Lys Leu Arg Val Thr Glu Gly Trp Asp Glu Asp
            20                  25                  30

Gly Asn His Phe Glu Asp Ser Leu His Tyr Glu Gly Arg Ala Val Asp
        35                  40                  45

Ile Thr Thr Ser Ser Asp Arg Asp Arg Asn Lys Tyr Gly Met Phe Ala
    50                  55                  60
Arg
65

(2) INFORMATION FOR SEQ ID NO:40:

(i) SEQUENCE CHARACTERISTICS:
            (A) LENGTH: 64 amino acids
            (B) TYPE: amino acid
            (C) STRANDEDNESS:
            (D) TOPOLOGY: linear (ii) MOLECULE TYPE: peptide (v) FRAGMENT TYPE: internal (xi) SEQUENCE DESCRIPTION: SEQ ID NO:40:

Gln Arg Cys Lys Asp Lys Leu Asn Ser Leu Ala Ile Ser Val Met Asn
1               5                  10                  15

Leu Trp Pro Gly Val Lys Leu Arg Val Thr Glu Gly Trp Asp Glu Asp
            20                  25                  30

Gly Leu His Ser Glu Glu Ser Leu His Tyr Glu Gly Arg Ala Val Asp
        35                  40                  45
```

```
Ile Thr Thr Ser Asp Arg Asp Arg Asn Lys Tyr Arg Met Leu Ala Arg
 50                  55                  60
```

(2) INFORMATION FOR SEQ ID NO:41:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

```
ACCGAGGGCT GGGACGAAGA TGGC                                              24
```

(2) INFORMATION FOR SEQ ID NO:42:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

```
CGCTCGGTCG TACGGCATGA ACGAC                                             25
```

(2) INFORMATION FOR SEQ ID NO:43:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:43:

```
ATGGGGATGT GTGTGTGGTC AAGTGTA                                           27
```

(2) INFORMATION FOR SEQ ID NO:44:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:44:

```
TTCACAGACT CTCAAAGTGT ATTTT                                             25
```

(2) INFORMATION FOR SEQ ID NO:45:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:45:

```
AAAAGCTTTA YTGYTAYGTN GGNATHGG                                          28
```

-continued (2) INFORMATION FOR SEQ ID NO:46:

(i) SEQUENCE CHARACTERISTICS:
  (A) LENGTH: 28 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:46:

AAGAATTCTA NGCRTTRTAR TTRTTNGG  28

(2) INFORMATION FOR SEQ ID NO:47:

(i) SEQUENCE CHARACTERISTICS:
  (A) LENGTH: 26 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:47:

GTCCTGGCGC CGCCGCCGCC GTCGCC  26

(2) INFORMATION FOR SEQ ID NO:48:

(i) SEQUENCE CHARACTERISTICS:
  (A) LENGTH: 25 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:48:

TTCCGATGAC CGGCCTTCGC GGTGA  25

(2) INFORMATION FOR SEQ ID NO:49:

(i) SEQUENCE CHARACTERISTICS:
  (A) LENGTH: 26 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:49:

GTGCACGGAA AGGTGCAGGC CACACT  26